(12) United States Patent
McFarlan et al.

(10) Patent No.: US 8,206,955 B2
(45) Date of Patent: *Jun. 26, 2012

(54) PRODUCTION OF MONATIN AND MONATIN PRECURSORS

(75) Inventors: Sara C. McFarlan, St. Paul, MN (US); Paula M. Hicks, Eden Prairie, MN (US); Mary Jo Zidwick, Wayzata, MN (US); Fernando A. Sanchez-Riera, Eden Prairie, MN (US); Douglas C. Cameron, Plymouth, MN (US); Mervyn L. deSouza, Plymouth, MN (US); John Rosazza, Iowa City, IA (US); Steven J. Gort, Brooklyn Center, MN (US); Timothy W. Abraham, Minnetonka, MN (US)

(73) Assignee: Cargill, Incorporated, Wayzata, MN (US)

( * ) Notice: Subject to any disclaimer, the term of this patent is extended or adjusted under 35 U.S.C. 154(b) by 273 days.

This patent is subject to a terminal disclaimer.

(21) Appl. No.: 10/969,245

(22) Filed: Oct. 21, 2004

(65) Prior Publication Data

US 2005/0221455 A1    Oct. 6, 2005

Related U.S. Application Data

(60) Provisional application No. 60/513,406, filed on Oct. 21, 2003.

(51) Int. Cl.
C12P 17/10     (2006.01)
C12N 1/00      (2006.01)

(52) U.S. Cl. ........................ 435/121; 435/243
(58) Field of Classification Search ................. 435/121, 435/243

See application file for complete search history.

(56) References Cited

U.S. PATENT DOCUMENTS

| | | | |
|---|---|---|---|
| 3,002,889 A | 10/1961 | Kinoshita et al. | |
| 3,128,237 A | 4/1964 | Motozaki et al. | |
| 3,399,114 A | 8/1968 | Ohsawa et al. | |
| 3,751,458 A | 8/1973 | Wiley | |
| 4,371,614 A | 2/1983 | Anderson et al. | |
| 4,975,298 A | 12/1990 | Van Wyk et al. | |
| 5,128,164 A | 7/1992 | Van Wyk et al. | |
| 5,128,482 A | 7/1992 | Olivier et al. | |
| 5,300,437 A | 4/1994 | Stirling et al. | |
| 5,728,555 A | 3/1998 | Fotheringham et al. | |
| 5,756,345 A | 5/1998 | Camakis et al. | |
| 5,985,617 A | 11/1999 | Liao | |
| 5,994,559 A | 11/1999 | Abushanab et al. | |
| 6,207,427 B1 | 3/2001 | Hashimoto et al. | |
| 6,264,999 B1 | 7/2001 | Yatka et al. | |
| 6,489,217 B1 | 12/2002 | Kalnitsky et al. | |
| 7,064,219 B2 | 6/2006 | Kawahara et al. | |
| 7,396,941 B2 | 7/2008 | Mori et al. | |
| 7,534,898 B2 | 5/2009 | Amino et al. | |
| 7,572,607 B2 * | 8/2009 | Hicks et al. | 435/121 |
| 7,781,005 B2 | 8/2010 | Mori | |
| 7,888,081 B2 | 2/2011 | Khare et al. | |
| 8,003,361 B2 | 8/2011 | Brady et al. | |
| 8,076,107 B2 | 12/2011 | Buddoo et al. | |
| 2003/0228403 A1 | 12/2003 | Amino et al. | |
| 2004/0063175 A1 | 4/2004 | Abraham et al. | |
| 2005/0004394 A1 | 1/2005 | Kawahara et al. | |
| 2005/0009153 A1 | 1/2005 | Sugiyama et al. | |
| 2005/0020508 A1 | 1/2005 | Amino et al. | |
| 2005/0095670 A1 | 5/2005 | Ikeda et al. | |
| 2005/0106305 A1 | 5/2005 | Abraham et al. | |
| 2005/0112260 A1 | 5/2005 | Abraham et al. | |
| 2005/0118317 A1 | 6/2005 | Amino et al. | |
| 2005/0137246 A1 | 6/2005 | Amino et al. | |
| 2005/0153405 A1 | 7/2005 | Sugiyama et al. | |
| 2005/0170041 A1 | 8/2005 | Abraham et al. | |
| 2005/0221453 A1 | 10/2005 | Takagi et al. | |
| 2005/0244937 A1 | 11/2005 | Abraham et al. | |
| 2005/0244939 A1 | 11/2005 | Sugiyama et al. | |
| 2005/0272939 A1 | 12/2005 | Amino et al. | |
| 2005/0282260 A1 | 12/2005 | Hicks et al. | |
| 2006/0003411 A1 | 1/2006 | Sugiyama et al. | |
| 2006/0003426 A1 | 1/2006 | Sugiyama et al. | |
| 2006/0009394 A1 | 1/2006 | Amino | |
| 2006/0014819 A1 | 1/2006 | Mori et al. | |
| 2006/0074249 A1 | 4/2006 | Kawahara et al. | |
| 2006/0083695 A1 | 4/2006 | Mori | |
| 2006/0154343 A1 | 7/2006 | Mori et al. | |
| 2006/0172396 A1 | 8/2006 | Sugiyama et al. | |
| 2006/0252135 A1 | 11/2006 | Brazeau et al. | |
| 2007/0099277 A1 | 5/2007 | Anderson et al. | |

(Continued)

FOREIGN PATENT DOCUMENTS

EP          0 438 314 A1      7/1991

(Continued)

OTHER PUBLICATIONS

Witkowski et al., Conversion of b-ketoacyl synthase to a malonyl decarboxylase by replacement of the active-site cysteine with glutamate. Biochemistry, 1999, vol. 38: 11643-11650.*

Seffernick et al., Melamine deaminase and atrazine chlorohydrolase: 98 percent identical but functionally different. J. Bacteriol., 2001, vol. 183 (8): 2405-2410.*

Witkowski et al., Conversion of b-ketoacyl synthase to a malonyl decarboxylase by replacemnt of the active-site cysteine with glutamine. Biochemistry, 1999, vol. 38: 11643-11650.*

Seffernick et al., Melamine deaminase and Atrazine chlorohydrolase: 98 percent identical but functionally different. J. Bacteriol.,2001, vol. 183 (8): 2405-2410.*

(Continued)

Primary Examiner — Ganapathirama Raghu

(57) ABSTRACT

Methods and compositions that can be used to make monatin or salt thereof from glucose, tryptophan, indole-3-lactic acid, indole-3-pyruvate, and 2-hydroxy 2-(indol-3-ylmethyl)-4-keto glutaric acid, are provided. Methods are also disclosed for producing the indole-3-pyruvate and 2-hydroxy 2-(indol-3-ylmethyl)-4-keto glutaric acid intermediates. Compositions provided include nucleic acid molecules, polypeptides, chemical structures, and cells. Methods include in vitro and in vivo processes, and the in vitro methods include chemical reactions.

3 Claims, 13 Drawing Sheets

U.S. PATENT DOCUMENTS

| | | |
|---|---|---|
| 2007/0105938 A1 | 5/2007 | Anderson et al. |
| 2008/0020434 A1 | 1/2008 | Brazeau et al. |
| 2008/0020435 A1 | 1/2008 | Burke et al. |
| 2008/0193984 A1 | 8/2008 | Sugiyama et al. |
| 2008/0274518 A1 | 11/2008 | Hicks et al. |
| 2009/0088577 A1 | 4/2009 | Buddoo et al. |
| 2009/0117625 A1 | 5/2009 | Abraham et al. |
| 2009/0130285 A1 | 5/2009 | Abraham et al. |
| 2009/0198072 A1 | 8/2009 | Khare et al. |
| 2011/0020882 A1 | 1/2011 | de Souza et al. |
| 2011/0045547 A1 | 2/2011 | de Souza et al. |
| 2011/0300828 A1 | 12/2011 | Wass |
| 2012/0009320 A1 | 1/2012 | Evans et al. |
| 2012/0009634 A1 | 1/2012 | Burke et al. |

FOREIGN PATENT DOCUMENTS

| | | |
|---|---|---|
| EP | 0736604 | 10/1996 |
| EP | 1 045 029 A2 | 10/2000 |
| EP | 1 445 323 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 350 791 | 9/2006 |
| EP | 1 719 758 A1 | 11/2006 |
| JP | 2002/060382 | 2/2002 |
| JP | 2003/171365 | 6/2003 |
| JP | 2004/222657 | 8/2004 |
| JP | EP 1445323 A1 * | 8/2004 |
| JP | 2004/331644 | 11/2004 |
| JP | 2004/331650 | 11/2004 |
| WO | WO 87/01130 A1 | 2/1987 |
| WO | WO 89/11212 | 11/1989 |
| WO | WO 99/55877 | 11/1999 |
| WO | WO 99/55877 A1 | 11/1999 |
| WO | WO 02/085293 A2 * | 10/2002 |
| WO | WO 03/000913 A2 | 1/2003 |
| WO | WO 03/045914 | 6/2003 |
| WO | WO 03/056026 * | 7/2003 |
| WO | WO 03/056026 A | 7/2003 |
| WO | WO 03/059865 A1 | 7/2003 |
| WO | WO 03/091396 | 11/2003 |
| WO | WO 2004/018672 | 3/2004 |
| WO | WO 2004/053125 | 6/2004 |
| WO | 2004/085624 | 10/2004 |
| WO | WO 2005/014839 | 2/2005 |
| WO | WO 2005/016022 | 2/2005 |
| WO | WO 2005/020721 | 3/2005 |
| WO | WO 2005/001105 | 4/2005 |
| WO | WO 2005/042756 | 5/2005 |
| WO | WO 2005/082850 A1 | 9/2005 |
| WO | WO 2006/011613 A1 | 2/2006 |
| WO | WO 2006/113897 | 10/2006 |
| WO | WO 2006/116487 | 11/2006 |
| WO | WO 2007/103389 | 9/2007 |
| WO | WO 2007/133183 | 11/2007 |
| WO | WO 2007/133184 | 11/2007 |
| WO | 2010/138513 | 12/2010 |
| WO | 2011/082351 | 7/2011 |
| WO | 2011/082353 | 7/2011 |
| WO | 2011/082363 | 7/2011 |
| WO | 2011/082365 | 7/2011 |

OTHER PUBLICATIONS

Broun et al., Catalytic plasticity of fatty acid modification enzymes underlying chemical diversity of plant lipids. Science, 1998, vol. 282: 1315-1317.*

Devos et al., Practical limits of function prediction: Proteins: Structure, function, and Genetics, 2000, vol. 41: 98-107.*

Whisstock et al., Prediction of protein function from protein sequence. Q. Rev. Biophysics., 2003, vol. 36 (3): 307-340.*

Boom et al., Lipoic acid metabloism in Escherichia coli: Isolation of null mutants defective in lipoic acid biosynthesis, molecular cloning and characterization of E. coli lip locus . . . J. Bacteriol., 1991, vol. 173 (20): 6411-6420.*

Morris et al., Lipoic acid metabolism in Escherichia coli: the IplA and lipB genes define redundant pathways for ligation of lipoyl groups to apoprotein. J. Bacteriol., 1995, vol. 177 (1): 1-10.*

Azuma et al., "Hyper-production of L-tryptophan via fermentation with crystallization," Appl. Microbiol. Biotechnol., 1993, 39:471-476.

Bassoli et al., "General Pseudoreceptor Model for Sweet Compounds: A Semiquantitative Prediction of Binding Affinity for Sweet-Tasting Molecules," J. Med. Chem., 2002, 45:4402-4409.

Bassoli et al., "Monatin and Its Stereoisomers: Chemoenzymatic Synthesis and Taste Properties," Eur. J. Org. Chem., 2005, 8:1652-1658.

Bhatnagar et al., "The Broad-specificity, Membrane-bound Lactate Dehydrogenase of Neisseria gonorrhoeae: Ties to Aromatic Metabolism," J. Gen. Microbiol., 1989, 135:353-360.

Bommarius et al., "Some new developments in reductive amination with cofactor regeneration," Biocatalysis, 1994, 10:37-47.

Brandl and Lindow, "Cloning and characterization of a locus encoding an indolepyruvate decarboxylase involved in indole-3-acetic acid synthesis in Erwinia herbicola," Appl. Environ. Microbiol., 1996, 62:4121-4128.

Camargo (Ediclea Cristina Fregonese Camargo), "Preparation of amino acids not proteinogênicos, structurally related to adoçante natural Monatina" [tranlated by Google], Jan. 2003, Universidade Estadual de Campinas Instituto de Quimica, Dissertation of Masters.

Doolittle et al., "Mutants of Escherichia coli with an Altered Tryptophanyl-Transfer Ribonucleic Acid Synthetase," J. Bacteriol., 1968, 95(4):1283-1294.

Dopheide et al., "Chorismate Mutase-Prephenate Dehydratase from Escherichia coli K-12," J. Biol. Chem., 1972, 247(14):4447-4452.

Eggeling and Sahm, "Amino-acid production: principles of metabolic engineering," Metabolic Engineering, 1999, Lee & Papoutsakis (eds.), Marcel Dekker, Inc., New York.

Eikmanns et al., "Cloning, sequence analysis, and inactivation of the Corynebacterium glutamicum icd gene encoding isocitrate dehydrogenase and biochemical characterization of the enzyme," J. Bacteriol., 1995, 177:774-782.

El-Abyad and Farid, "Optimization of culture conditions for indole-3-pyruvic acid production by Streptomyces griseoflavus," Can. J. Microbio., 1994, 40:754-760.

Fotheringham et al., "The cloning and sequence analysis of the aspC and tyrB genes from Escherichia coli K12," Biochem. J., 1986, 234:593-604.

Fukuda et al., "Production of Substituted $_L$-Tryptophans by Fermentation," Appl. Environ. Microbiol., 1971, 21:841-843.

Furuya et al., "A Novel Enzyme, $_L$-Tryptophan Oxidase, from a Basidiomycete, Coprinus sp. SF-1: Purification and Characterization," Biosci. Biotechnol. Biochem., 2000, 64(7):1486-1493.

Jetten et al., "Metabolic Engineering of Corynebacterium glutamicum," Ann. N.Y. Acad. Sci., 1994, 721:12-29.

Jetten et al., "Recent advances in the physiology and genetics of amino acid-producing bacteria," Crit. Rev. Biotechnol., 1995, 15:73-103.

Kawasaki et al., "$_L$-Tryptophan Production by Pyruvic Acid-Producing Escherichia coli Strain Carrying the Enterobacter aerogenes Tryptophanase Gene," Journal of Fermentation and Bioengineering, 1996, 82(6):604-606.

Koffas et al., "Engineering metabolism and product formation in Corynebacterium glutamicum by coordinated gene overexpression," Metabolic Engineering, 2003, 5:32-41.

Koga et al., "Involvement of $_L$-tryptophan aminotransferase in indole-3-acetic acid biosynthesis in Enterobacter cloacae," Biochim. Biophys. Acta, 1994, 1209:241-247.

Labrou et al., "Oxaloacetate Decarboxylase from Pseudomonas stutzeri: Purification and Characterization," Arch. Biochem. Biophys., 1999, 365(1):17-24.

Liao et al., "Pathway Analysis, Engineering, and Physiological Considerations for Redirecting Central Metabolism," Biotechnology and Bioengineering, 1996, 52:129-140.

Patnaik et al., "Engineering of Escherichia coli Central Metabolism for Aromatic Production with Near Theoretical Yield," Applied and Environmental Microbiology, 1994, 60(11):3903-3908.

Rijnen et al., "Genetic Characterization of the Major Lactococcal Aromatic Aminotransferase and Its Involvement in Conversion of Amino Acids to Aroma Compounds," *Applied Environmental Biology*, 1999, 65(11):4873-4880.

Tamura et al., "Stereoselective Synthesis of 4-Hydroxy 4-Substituted Glutamic Acids," *J. Org. Chem.*, 2005, 70(12):4569-77.

Wolf et al., "A Biocatalytic Route to Enantiomerically Pure Unsaturated -H—Amino Acids," *Adv. Synth. & Catalysis*, 2001, 343:662-674.

Yonaha et al., "$_D$-Amino Acid Aminotransferase of *Bacillus sphaericus*," *J. Biol. Chem.*, 1975, 250(17):6983-6989.

Guo et al., "Protein tolerance to random amino acid charge," *Proc. Natl. Acad. Sci. USA*, 2004, 101(25):9205-9210.

Seo Jeong-Sun et al., "The genome sequence of the ethanologenic bacterium *Zymomonas mobilis* ZM4," *Nature Biotechnology*, 2005, 23(1):63-68.

United States Patent and Trademark Office, non-final Office Action dated Dec. 6, 2010 for U.S. Appl. No. 12/124,014.

Response to Office Action filed Jun. 6, 2011 for U.S. Appl. No. 12/124,014.

ATCC: "Bacteria" Internet Article, 'Online! XP002321015.

Ackerman, L.G., "Structure Elucidation of and Synthetic Approaches to Monatin, a Metabolite from *Schlerochiton illicifolius*," Ph.D. Dissertation, University of Stellenbosch 175 pages (1990).

Ager, D.J., et al., "Commercial, Synthetic Nonnutritive Sweeteners," *Angew. Chem. Int. Ed.* 37:1802-1817, Verlag Chemie (1998).

Ager, D.J., et al., "Novel biosynthetic routes to non-proteinogenic amino acids as chiral pharmaceutical intermediates," *J. Mol. Catal., B: Enzym.* 11:199-205, Elsevier Science (2001).

Bae, H., et al., "Production of aromatic D-amino acids from α-keto acids and ammonia by coupling of four enzyme reactions," *J. Mol. Catal., B: Enzym.* 6:241-247, Elsevier Science (1999).

Bassoli, A., et al., "Design and Synthesis of New Monatin Derivatives," *Abstracts presented at the 13$^{th}$ International Symposium on Olfaction and Taste and 14$^{th}$ European Chemoreception Research Organisation Congress*, Brighton, UK, Jul. 20-24, 2000.

Bassoli, A., "'Chemistry-Nature,' still an open match for the discovery of new intensive sweeteners," *European Journal of Nutraceuticals & Functional Foods* 15:27-29, Tekno Scienze (Jul./Aug. 2004).

Bongaerts, J., et al., "Metabolic Engineering for Microbial Production of Aromatic Amino Acids and Derived Compounds," *Metab. Eng.* 3:289-300, Academic Press (2001).

Buldain, G., et al., "Carbon-13 Nuclear Magnetic Resonance Spectra of the Hydrate, Keto and Enol Forms of Oxalacetic Acid," *Magnetic Resonance in Chemistry* 23:478-481, Wiley Heden Ltd. (1985).

DeLuna, A., et al., "NADP-Glutamate Dehydrogenase Isoenzymes of *Saccharomyces cerevisiae*," *J. Biol. Chem.* 276:43775-43783, The American Society for Biochemistry and Molecular Biology, Inc. (2001).

Flores, N., et al., "Pathway engineering for the production of aromatic compounds in *Escherichia coli*," *Nat. Biotechnol.* 14:620-623, Nature America Publishing (1996).

Floyd, N.C., et al., "A Simple Strategy for obtaining both Enantiomers from an Aldolase Reaction: Preparation of $_L$- and $_D$-4-Hydroxy-2-ketogluterate," *J. Chem. Soc. Perkin Trans.* 19:1085-1086, Chemical Society (1992).

Galkin, A., et al., "Synthesis of Optically Active Amino Acids from α-Keto Acids with *Escherichia coli* Cells Expressing Heterologous Genes," *Appl. Environ. Microbiol.* 63: 4651-4656, American Society for Microbiology (1997).

Gosset, G., et al., "A direct comparison of approaches for increasing carbon flow to aromatic biosynthesis in *Escherichia coli*," *J. Ind. Microbiol.* 17:47-52, Stockton Press on behalf of the Society for Industrial Microbiology (1996).

Hayashi, H., et al., "*Escherichia coli* Aromatic Amino Acid Aminotransferase: Characterization and Comparison with Aspartate Aminotransferase," *Biochemistry* 32:12229-12239, American Chemical Society (1993).

Hibino, S. and Choshi, T., "Simple indole alkaloids and those with a nonrearranged monoterpenoid unit," *Nat. Prod. Rep.* 19:148-180, Royal Society of Chemistry (Apr. 2002).

Holzapfel, C. and Olivier, J., "The Synthesis of aγ-Keto-α-Amino Acid, a Key Intermediate in the Sythesis of Monatin, a New Natural Sweetener," *Synthetic Communications* 23:2511-2526, Marcel Dekker (1993).

Holzapfel, C., et al., "A Simple Cycloaddition Approach to a Racemate of the Natural Sweetener Monatin," *Synthetic Communications* 24:3197-3211, Marcel Dekker (1994).

Izumi, Y., *Amino-san Kogyo—Gosei to Riyo*, Kaneko, T., et al., eds., Kodansha Ltd., pp. 8-9 (1973).

Izumi, Y., *Synthetic production and utilization of amino acids*, Kaneko, T., et al., eds., Kodansha Ltd., pp. 3-16 (1974) (republished English translation that includes NPL18).

Juhl, K., et al., "Catalytic asymmetric homo-aldol reaction of pyruvate-a chiral Lewis acid catalyst that mimics aldolase enzymes," *Chem. Commun.*, No. 22, pp. 2211-2212, Royal Society of Chemistry (2000).

Katsumata, R. and Ikeda, M., "Hyperproduction of Tryptophan in *Corynebacterium glutamicum* by Pathway Engineering," *Bio/Technology* 11:921-925, Nature Publishing Co. (1993).

Koeller, K.M. and Wong, C.-H., "Enzymes for chemical synthesis," *Nature* 409:232-240, Nature Publishing Group (2001).

Kogiso, K., et al., "Control of Lactamization during the Synthesis of the Monatin Analogue," *Peptide Science 2003*, The Proceedings of the 40$^{th}$ Symposium on Japanese Peptide Symposium, pp. 195-198, The Japanese Peptide Society (Mar. 2004).

Koshiba, T. and Mito, N., "Partial Purification and some Properties of L- and D-Tryptophan Aminotransferases form Maize Coleoptiles," Proceedings of the 8$^{th}$ International Symposium on Vitamin B$_6$ and Carbonyl Catalysis, Osaka, Japan, pp. 245-247, Pergamon Press, Oct. 15-19, 1990.

Li, T., et al., "Nonproteinogenic α-Amino Acid Preparation Using Equilibrium Shifted Transamination," *Organic Process Research & Development* 6:533-538, American Chemical Society (Jul./Aug. 2002).

Liao, J.C., et al., "Pathway Analysis, Engineering, and Physiological Considerations for Redirecting Central Metabolism," *Biotechnol. Bioeng.* 52:129-140, John Wiley & Sons, Inc. (1996).

Nakamura, K., et al., "Total Synthesis of Monatin," *Org. Lett.* 2:2967-2970, American Chemical Society (2000).

Nakamura, K., et al., "Total Synthesis of Monatin and the Taste Expression," *Peptide Science 2003*, The Proceedings of the 40$^{th}$ Symposium on Japanese Peptide Symposium, pp. 61-64, The Japanese Peptide Society (Mar. 2004).

Oliveira, D. and Coelho, F., "Highly Diastereoselective Alkylation of a Pyroglutamate Derivative with an Electrophile Obained from Indole. Synthesis of a Potential Intermediate for the Preparation of the Natural Sweetener (−)-Monatin," *Synthetic Communications* 30:2143-2159, Marcel Dekker (2000).

Oliveira, D. and Coelho, F., "Diastereoselective formation of a quanternary center in a pyroglutamate derivative. Formal synthesis of Monatin," *Tetrahedron Lett.* 42:6793-6796, Elsevier Science Ltd. (2001).

Passerat, N. and Bolte, J., "Large-Scale Enzymatic Synthesis of Diastereoisomeric γ-Hydroxy L-Glutamic Acids," *Tetrahedron Lett.* 28:1277-1280, Elsevier (1987).

Patil, R. and Dekker, E., "Cloning Nucleotide Sequence, Overexpression, and Inactivation of the *Escherichia coli* 2-Keto-4-Hydroxyglutarate Aldolase Gene," *J. Bacteriol.* 174:102-107, American Society for Microbiology (1992).

Shelton, M.C., et al., "2-Keto3-deoxy6-phosphogluconate Aldolases as Catalysts for Stereocontrolled Carbon—Carbon Bond Formation," *J. Am. Chem. Soc.* 118:2117-2125, American Chemical Society (1996).

Tamura, O., et al., "Highly stereoselective synthesis of (−)-monatin, a high-intensity sweetener, using chelation-controlled nitrone cycloaddition," *Chem. Commun. (Camb.)* 21:2678-2679, The Royal Society of Chemistry (Nov. 2003).

Vleggaar, R., et al., "Structure Elucidation of Monatin, a High-intensity Sweetener Isolated from the Plant *Schlerochiton ilicifolius*," *J. Chem. Soc. Perkin Trans.I* 22:3095-3098, Royal Society of Chemistry (1992).

Zeman, R., et al., "Enzyme Synthesis of L-Tryptophan," *Folia Microbiol.* 35:200-204, Slovak Academy of Sciences (1990).

Dialog File 351, Accession No. 12442290, Derwent WPI English language abstract for JP 2002/060382 (listed on accompanying PTO/SB/08A as document FP5), Sep. 27, 2006.

Dialog File 351, Accession No. 13655060, Derwent WPI English language abstract for JP 2003/171365 (listed on accompanying PTO/SB/08A as document FP7), Sep. 27, 2006.

Dialog File 351, Accession No. 14386782, Derwent WPI English language abstract for JP 2004/222657 (listed on accompanying PTO/SB/08A as document FP9), Sep. 27, 2006.

Dialog File 351, Accession No. 14644791, Derwent WPI English language abstract for JP 2004/331644 (listed on accompanying PTO/SB/08A as document FP10), Sep. 27, 2006.

Dialog File 351, Accession No. 14655288, Derwent WPI English language abstract for JP 2004/331650 (listed on accompanying PTO/SB/08A as document FP11), Sep. 27, 2006.

Dialog File 351, Accession No. 15288756, Derwent WPI English language abstract for WO 2005/082850 A1 (listed on accompanying PTO/SB/08A as document FP12), Sep. 27, 2006.

Dialog File 351, Accession No. 15581479, Derwent WPI English language abstract for WO 2006/011613 A1 (listed on accompanying PTO/SB/08A as document FP13), Dec. 4, 2006.

Chica et al., "Semi-rational approaches to engineering enzyme activity: combining the benefits of directed evolution and rational design", Curr Opin Biotechnol , Aug. 2005: 16(4):378-84. Review.

Kishimoto at al., "Mutation of Arginine 98, which serves as a substrate-recognition site of D-AminoAcid Aminotransferase, can be partly compensated or by mutaton of tyrosine 88 to an arginyl residue," J. Biochem. 1997, 122, 1182-1189.

Moriya et al., "A facile synthesis of 6-chloro-D-tryptophan", Bulletin of the Chemical Society of Japan, 1975, vol. 48,: 2217-2218 (abstract).

ATCC No. 13058, "Bacteria: *Corynebacterium glutamicum*", available online @www.atcc.org/SearchCatalogs/longview.efm?atccsearch=yes (accessed on Mar. 11, 2005).

* cited by examiner

Indole-3-lactic acid

EC 1.1.1.110 indolelactate dehydrogenase

EC 1.1.1.222 R-4-hydroxyphenyllactate dehydrogenase

EC 1.1.1.237 3-(4)-hydroxyphenylpyruvate reductase

EC 1.1.1.27, 1.1.1.28, 1.1.2.3 lactate dehydrogenase

EC 1.1.1.111 (3-imidazol-5-yl) lactate dehydrogenase

EC 1.1.3.- lactate oxidase

Chemical oxidation

Indole-3-pyruvate

Enolate chemistry $R_1$ = Boc, Cbz, etc.
$R_2$ and $R_3$ = Alkyl, Aryl, etc.

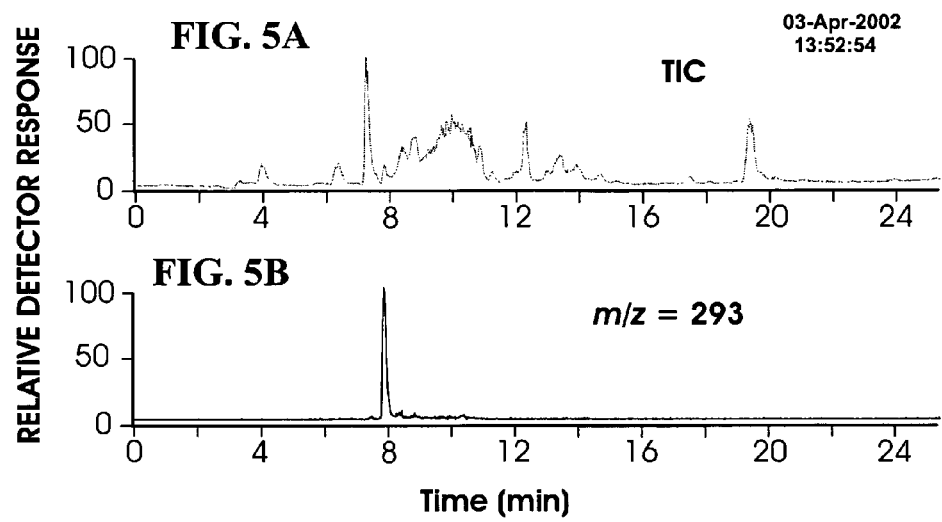
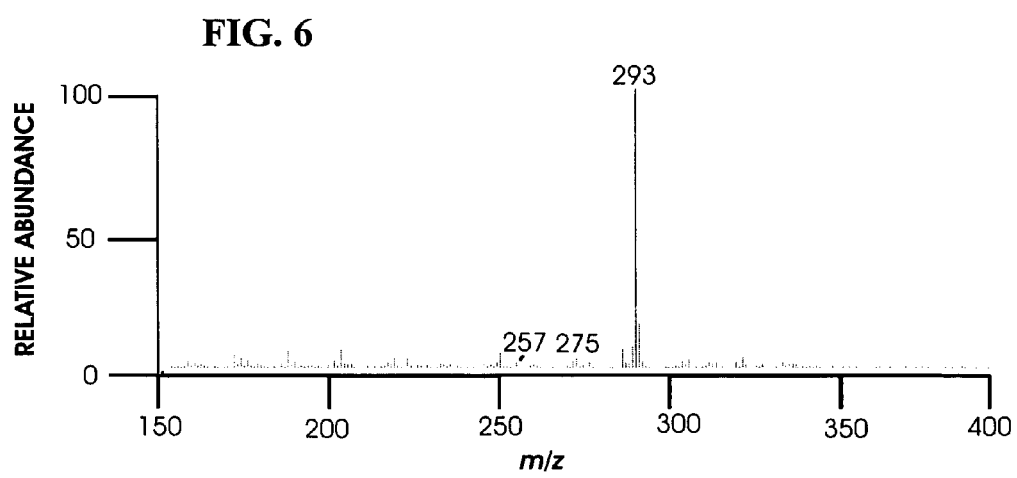

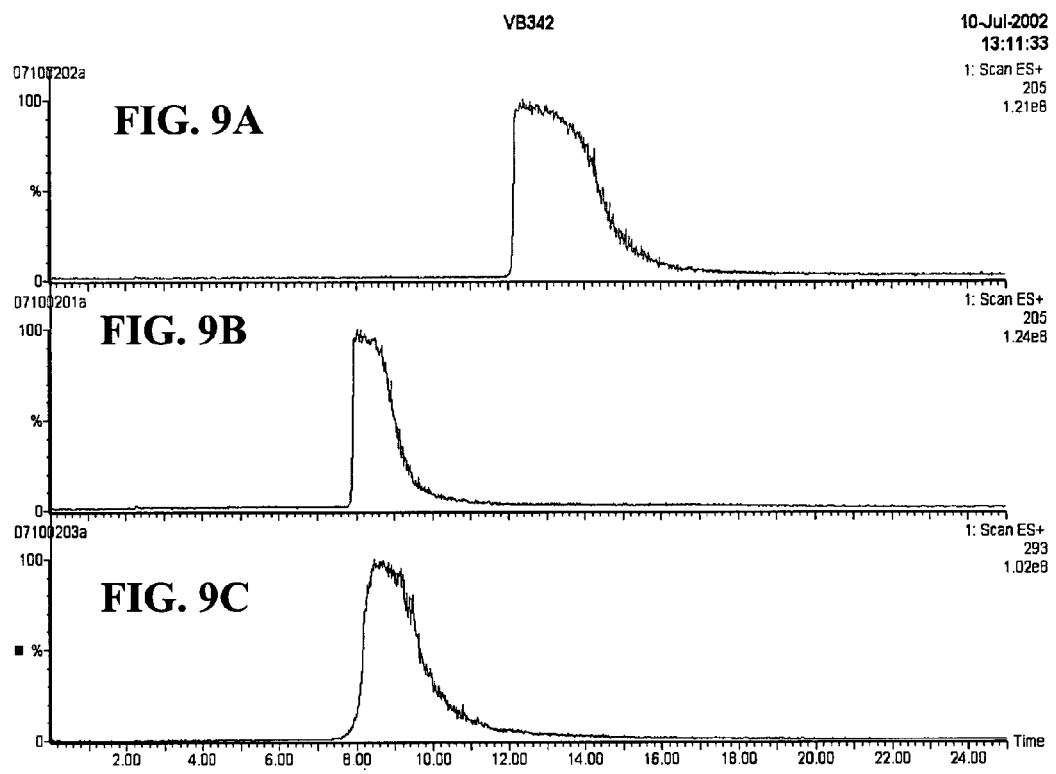
FIG. 9A
FIG. 9B
FIG. 9C
FIG. 10
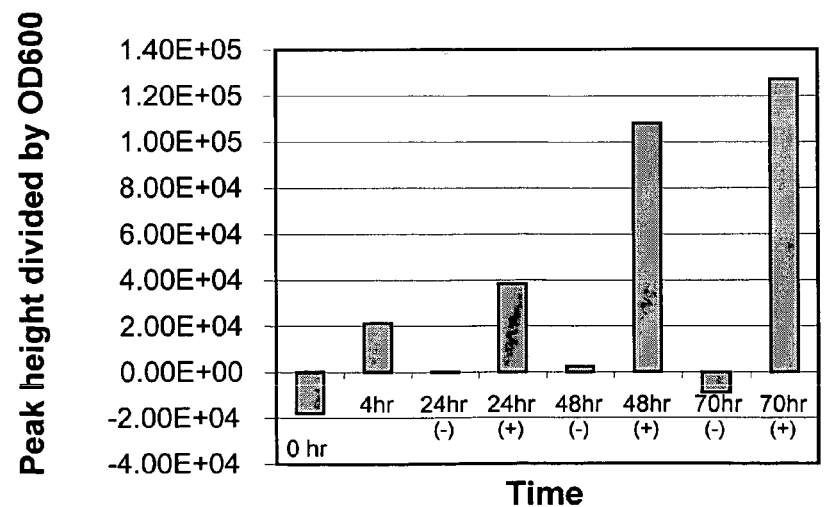

FIG. 16

ATGTACGAACTGGGAGTTGTCTACCGCAATATCCAGCGCGCCGACCGCGC
TGCTGCTGACGGCCTGGCCGCCCTGGGCTCCGCCACCGTGCACGAGGCCA
TGGGCCGCGTCGGTCTGCTCAAGCCCTATATGCGCCCCATCTATGCCGGCA
AGCAGGTCTCGGGCACCGCCGTCACGGTGCTGCTGCAGCCCGGCGACAAC
TGGATGATGCATGTGGCTGCCGAGCAGATTCAGCCCGGCGACATCGTGGT
CGCAGCCGTCACCGCAGAGTGCACCGACGGCTACTTCGGCGATCTGCTGG
CCACCAGCTTCCAGGCGCGCGGCGCACGTGCGCTGATCATCGATGCCGGC
GTGCGCGACGTGAAGACGCTGCAGGAGATGGACTTTCCGGTCTGGAGCAA
GGCCATCTCTTCCAAGGGCACGATCAAGGCCACCCTGGGCTCGGTCAACA
TCCCCATCGTCTGCGCCGGCATGCTGGTCACGCCCGGTGACGTGATCGTGG
CCGACGACGACGGCGTGGTCTGCGTGCCCGCCGCGCGTGCCGTGGAAGTG
CTGGCCGCCGCCCAGAAGCGTGAAAGCTTCGAAGGCGAAAAGCGCGCCA
AGCTGGCCTCGGGCATCCTCGGCCTGGATATGTACAAGATGCGCGAGCCC
CTGGAAAAGGCCGGCCTGAAATATATTGACTAA

FIG. 17

MYELGVVYRNIQRADRAAADGLAALGSATVHEAMGRVGLLKPYMRPIYAG
KQVSGTAVTVLLQPGDNWMMHVAAEQIQPGDIVVAAVTAECTDGYFGDLL
ATSFQARGARALIIDAGVRDVKTLQEMDFPVWSKAISSKGTIKATLGSVNIPIV
CAGMLVTPGDVIVADDDGVVCVPAARAVEVLAAAQKRESFEGEKRAKLASG
ILGLDMYKMREPLEKAGLKYID

PRODUCTION OF MONATIN AND MONATIN PRECURSORS

This application claims priority of U.S. provisional patent application No. 60/513,406, filed Oct. 21, 2003, which is incorporated herein by reference for all purposes.

TECHNICAL FIELD

This disclosure provides methods and materials that are useful in the production of indole-3-pyruvate, 2-hydroxy 2-(indol-3ylmethyl)-4-keto glutaric acid and/or monatin.

BACKGROUND

Indole-3-pyruvate is a strong antioxidant that is believed to counter act oxidative stress in tissues with high oxygen concentrations (Politi et al. "Recent advances in Tryptophan Research", edited by G. A. Filippini et al. Plenum Press, New York, 1996, pp 291-8). Indole pyruvate also is an intermediate in a pathway to produce indole-acetic acid (IAA), the primary plant growth hormone auxin (diffusible growth promoting factor). IAA is active in submicrogram amounts in a range of physiological processes including apical dominance, tropisms, shoot elongation, induction of cambial cell division, and root initiation. Synthetic auxins are used in horticulture to induce rooting and to promote the set and development of fruit. See, e.g., U.S. Pat. Nos. 5,843,782 and 5,952,231. At high concentrations the synthetic auxins are effective herbicides against broad-leafed plants. Natural auxins produced by fermentation may be considered more environmentally friendly than chemically produced herbicides. Growth regulators had world sales in 1999 of 0.4 billion pounds (1.4 billion U.S. dollars). In addition to plant related utilities, indole acetic acid is useful in pharmaceutical applications. For example, U.S. Pat. No. 5,173,497 proposes the use of these compounds in the treatment of memory impairment such as that associated with Alzheimer's disease and senile dementia. The mechanism proposed in U.S. Pat. No. 5,173,497 is that these compounds inhibit acetylcholinesterase and increase acetylcholine levels in the brain.

Indole-3-carbinol is produced from indole-3-acetic acid by peroxidase-catalyzed oxidation, and can easily be converted into-diindolylmethane. Both compounds are reported to eliminate toxins and promote the production of hormones beneficial to women's health. Chlorinated D-tryptophan has been identified as a nonnutritive sweetener, and there is increasing interest in pursuing other derivatives as well.

Monatin (2-hydroxy-2-(indol-3-ylmethyl)-4-aminoglutaric acid) is a naturally-occurring, sweetener that is similar in composition to the amino acid tryptophan. It can be extracted from the bark of the roots of the South African shrub, Sclerochiton ilicifolius, and has promise in the food and beverage industry as a high-intensity sweetener. Some examples of patents on monatin include: U.S. Pat. Nos. 5,994,559; 4,975,298; 5,128,164; and 5,128,482.

SUMMARY

The present invention involves monatin (2-hydroxy-2-(indol-3-ylmethyl)-4-aminoglutaric acid—also known as 4-amino-2-hydroxy-2-(1H-indol-3-ylmethyl)-pentanedioic acid, or alternatively, based on an alternate numbering system, 4-hydroxy-4-(3-indolylmethyl) glutamic acid), a compound having the formula:

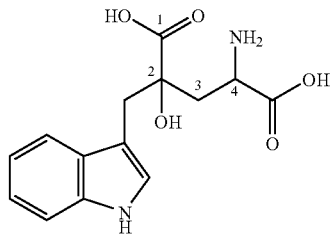

Monatin also has the following chemical names: 3-(1-amino-1,3-dicarboxy-3-hydroxy-but-4-yl)-indole; 4-(indole-3-ylmethyl)-4-hydroxy-glutamic acid; and 3-(1-amino-1,3-dicarboxy-3-hydroxybutane-4-yl)-indole.

Monatin is a naturally-occurring, high intensity sweetener. Monatin has four stereoisomeric forms: 2R, 4R (the "R,R stereoisomer" or "R,R monatin"), 2S, 4S (the "S,S stereoisomer" or "S,S monatin"), 2R, 4S (the "R,S stereoisomer" or "R,S monatin"), and 2S, 4R (the "S,R stereoisomer" or "S,R monatin"). As used herein, unless stated otherwise, "monatin" refers to all four stereoisomers of monatin, as well as any blends of any combination of monatin stereoisomers (e.g., a blend of the R,R and S,S, stereoisomers of monatin).

The invention is based, in part, on the identification of several biosynthetic routes for making monatin from glucose, tryptophan, indole-3-lactic acid, and/or through intermediates such as indole-3-pyruvate and 2-hydroxy 2-(indole-3-ylmethyl)-4-keto glutaric acid (the monatin precursor, MP, the alpha-keto form of monatin). Polypeptides and nucleic acid sequences that can be used to make monatin, indole-3-pyruvate, and MP are disclosed. Because the organic synthesis of monatin requires the resolution of isomers, a biochemical route that can utilize inexpensive raw materials and that can produce only one isomer may be more economically advantageous.

Monatin can be produced through indole-3-pyruvate, MP, indole-3-lactic acid, tryptophan, and/or glucose (FIG. 1). Methods of producing or making monatin or its intermediates shown in FIGS. 1-3 and 11-13 involve converting a substrate to a first product, and then converting the first product to a second product, and so on, until the desired end product is created, are disclosed.

FIGS. 1-3 and 11-13 show potential intermediate products and end products in boxes. For example, a conversion from one product to another, such as glucose to tryptophan, tryptophan to indole-3-pyruvate, indole-3-pyruvate to MP, MP to monatin, or indole-3-lactic acid (indole-lactate) to indole-3-pyruvate, can be performed by using the methods and materials provided herein. These conversions can be facilitated either chemically or biologically. The term "convert" refers to the use of either chemical means or polypeptides in a reaction which changes one product (e.g., a first intermediate) to another product (e.g., a second intermediate). The term "chemical conversion" refers to reactions that are not actively facilitated by polypeptides. The term "biological conversion" refers to reactions that are actively facilitated by polypeptides. Conversions can take place in vivo or in vitro. When biological conversions are used, the polypeptides and/or cells can be immobilized on supports such as by chemical attachment on polymer supports. The conversion can be accomplished using any reactor known to one of ordinary skill in the art, for example in a batch or a continuous reactor.

Methods are also provided that include contacting a first polypeptide with a substrate and making a first product, and then contacting the first product created with a second polypeptide and creating a second product, and then contacting the second product created with a third polypeptide and creating a third product, for example monatin. The polypeptides used and the products produced are shown in FIGS. 1-3 and 11-13.

Polypeptides, and their coding sequences, that can be used to perform the conversions shown in FIGS. 1-3 and 11-13 are disclosed. In some examples, polypeptides having one or more point mutations that allow the substrate specificity and/or activity of the polypeptides to be modified, are used to make monatin.

Isolated and recombinant cells that produce monatin are disclosed. These cells can be any cell, such as a plant, animal, bacterial, yeast, algal, archaeal, or fungal cell.

In a particular example, the disclosed cells include one or more (e.g., two or more, three or more, four or more, or five or more) of the following activities: tryptophan aminotransferase (EC 2.6.1.27), tyrosine (aromatic) aminotransferase (EC 2.6.1.5), multiple substrate aminotransferase (EC 2.6.1.-), aspartate aminotransferase (EC 2.6.1.1), tryptophan dehydrogenase (EC 1.4.1.19), tryptophan-phenylpyruvate transaminase (EC 2.6.1.28), L-amino acid oxidase (EC 1.4.3.2), tryptophan oxidase (no EC number, Hadar et al., *J. Bacteriol* 125:1096-1104, 1976; and Furuya et al., *Biosci Biotechnol Biochem* 64:1486-93, 2000), D-amino acid dehydrogenase (EC 1.4.99.1), D-amino acid oxidase (EC 1.4.3.3), D-alanine aminotransferase (EC 2.6.1.21), synthase/lyase (EC 4.1.3.-), such as 4-hydroxy-4-methyl-2-oxoglutarate aldolase (EC 4.1.3.17) or 4-hydroxy-2-oxoglutarate aldolase (EC 4.1.3.16), synthase/lyase (4.1.2.-), D-tryptophan aminotransferase (Kohiba and Mito, Proceedings of the 8$^{th}$ International Symposium on Vitamin B$_6$ and Carbonyl Catalysis, Osaka, Japan 1990), phenylalanine dehydrogenase (EC 1.4.1.20), and/or glutamate dehydrogenase (EC 1.4.1.2, 1.4.1.3, 1.4.1.4).

In another example, cells include one or more (e.g., two or more, three or more, four or more, or five or more) of the following activities: indolelactate dehydrogenase (EC 1.1.1.10), R-4-hydroxyphenyllactate dehydrogenase (EC 1.1.1.222), 3-(4)-hydroxyphenylpyruvate reductase (EC 1.1.1.237), lactate dehydrogenase (EC 1.1.1.27, 1.1.1.28, 1.1.2.3), (3-imidazol-5-yl) lactate dehydrogenase (EC 1.1.1.111), lactate oxidase (EC 1.1.3.-), synthase/lyase (4.1.3.-) such as 4-hydroxy-4-methyl-2-oxoglutarate aldolase (EC 4.1.3.17) or 4-hydroxy-2-oxoglutarate aldolase (EC 4.1.3.16), synthase/lyase (4.1.2.-), tryptophan dehydrogenase (EC 1.4.1.19), tryptophan-phenylpyruvate transaminase (EC 2.6.1.28), tryptophan aminotransferase (EC 2.6.1.27), tyrosine (aromatic) aminotransferase (EC 2.6.1.5), multiple substrate aminotransferase (EC 2.6.1.-), aspartate aminotransferase (EC 2.6.1.1), phenylalanine dehydrogenase (EC 1.4.1.20), glutamate dehydrogenase (EC 1.4.1.2, 1.4.1.3, 1.4.1.4), D-amino acid dehydrogenase (EC 1.4.99.1), D-tryptophan aminotransferase, and/or D-alanine aminotransferase (EC 2.6.1.21).

In addition, the disclosed cells can include one or more (e.g., two or more, three or more, four or more, or five or more) of the following activities: tryptophan aminotransferase (EC 2.6.1.27), tyrosine (aromatic) aminotransferase (EC 2.6.1.5), multiple substrate aminotransferase (EC 2.6.1.-), aspartate aminotransferase (EC 2.6.1.1), tryptophan dehydrogenase (EC 1.4.1.19), tryptophan-phenylpyruvate transaminase (EC 2.6.1.28), L-amino acid oxidase (EC 1.4.3.2), tryptophan oxidase (no EC number), D-amino acid dehydrogenase (EC 1.4.99.1), D-amino acid oxidase (EC 1.4.3.3), D-alanine aminotransferase (EC 2.6.1.21), indolelactate dehydrogenase (EC 1.1.1.110), R-4-hydroxyphenyllactate dehydrogenase (EC 1.1.1.222), 3-(4)-hydroxyphenylpyruvate reductase (EC 1.1.1.237), lactate dehydrogenase (EC 1.1.1.27, 1.1.1.28, 1.1.2.3), (3-imidazol-5-yl) lactate dehydrogenase (EC 1.1.1.111), lactate oxidase (EC 1.1.3.-), synthase/lyase (4.1.3.-) such as 4-hydroxy-4-methyl-2-oxoglutarate aldolase (EC 4.1.3.17) or 4-hydroxy-2-oxoglutarate aldolase (EC 4.1.3.16), synthase/lyase (4.1.2.-), glutamate dehydrogenase (EC 1.4.1.2, 1.4.1.3, 1.4.1.4), phenylalanine dehydrogenase (EC 1.4.1.20), and/or D-tryptophan aminotransferase.

Monatin can be produced by a method that includes contacting tryptophan and/or indole-3-lactic acid with a first polypeptide, wherein the first polypeptide converts tryptophan and/or indole-3-lactic acid to indole-3-pyruvate (either the D or the L form of tryptophan or indole-3-lactic acid can be used as the substrate that is converted to indole-3-pyruvate; one of skill in the art will appreciate that the polypeptides chosen for this step ideally exhibit the appropriate specificity), contacting the resulting indole-3-pyruvate with a second polypeptide, wherein the second polypeptide converts the indole-3-pyruvate to MP, and contacting the MP with a third polypeptide, wherein the third polypeptide converts MP to monatin. Exemplary polypeptides that can be used for these conversions are shown in FIGS. 2 and 3.

Another aspect of the invention provides compositions such as MP, cells that contain at least two polypeptides, or sometimes at least three or at least four polypeptides, that are encoded on at least one exogenous nucleic acid sequence (e.g., at least two, three, four, five, or more exogenous nucleic acid sequences).

The methods and materials provided herein can be used to make products such as monatin, MP, monatin intermediates, and monatin derivatives. Monatin and some of the intermediates of monatin described herein can be useful as sweeteners or as intermediates in the synthesis of monatin derivatives.

In another aspect, the invention features methods for producing monatin. In certain embodiments, methods of producing monatin or salt thereof comprise: (a) culturing a microorganism in a culture medium, wherein the microorganism comprises at least one nucleic acid encoding an aldolase polypeptide and at least one nucleic acid encoding an aminotransferase polypeptide; and (b) extracting monatin or salt thereof from the culture medium or the cultured microorganism. In certain embodiments, the aldolase polypeptide is chosen from ProA aldolase (4-hydroxy-4-methyl-2-oxoglutarate aldolase, EC 4.1.3.17) and KHG aldolase (4-hydroxy-2-oxoglutarate glyoxylate-lyase, EC 4.1.3.16). In other embodiments, the microorganism is chosen from *Sinorhizobium meliloti, Comamonas testosteroni, Pseudomonas straminea, Corynebacterium glutamicum* and *E. coli*. Alternatively the microorganism may be chosen from the genera *Corynebacterium* and *Brevibacterium*.

In other embodiments, the culture medium comprises a non-ionic detergent, penicillin, a penicillin derivative (such as ampicillin), or a combination thereof. Non-ionic detergents include Tween, Triton X-100 or dodecylammonium acetate. In one embodiment, the culture medium comprises biotin in a concentration less than 5 μg/L. In another embodiment, the pH of the culture medium, before the microorganism is cultured, is from about pH 7 to about pH 8. In addition, the culture medium may include molasses, corn steep liquor or a combination thereof.

In some embodiments, the microorganism is *E. coli*, and the culture medium comprises Trp-1+ glucose medium. In other embodiments, the microorganism requires phenylalanine and tyrosine for growth, and the culture medium comprises phenylalanine and tyrosine. The microorganism may also comprise aspC and proA genes. In addition, the microorganism may be a strain of *Corynebacterium glutamicum* that produces and secretes glutamate. In some embodiments, monatin or salt thereof is secreted from the microorganism (e.g., *Corynebacterium glutamicum*). In another embodiment, the microorganism is cultured in a fermentor.

In some embodiments, the culture medium comprises tryptophan, pyruvic acid, a non-ionic detergent (such as Tween), penicillin, a penicillin derivative or a combination thereof. In other embodiments, the aminotransferase polypeptide is chosen from a tryptophan aminotransferase polypeptide (EC 2.6.1.27), an aspartate aminotransferase polypeptide (EC 2.6.1.1), an aromatic aminotransferase polypeptide (EC 2.6.1.5) and a D-alanine aminotransferase polypeptide (EC 2.6.1.21).

In addition, the invention features methods of producing monatin or salt thereof comprising: (a) culturing *Corynebacterium glutamicum* (ATCC 13058) in a culture medium; and (b) extracting monatin or salt thereof from the culture medium or the cultured microorganism. In some embodiments, the culture medium comprises Tween, penicillin, a penicillin derivative or a combination thereof.

Further, the invention features a microorganism comprising at least one nucleic acid encoding an aldolase polypeptide and at least one nucleic acid encoding an aminotransferase polypeptide, wherein the nucleic acids are chosen from exogenous nucleic acids, recombinant nucleic acids and a combination thereof, and wherein the microorganism produces monatin or salt thereof. In some embodiments, the aldolase polypeptide is chosen from ProA aldolase (4-hydroxy-4-methyl-2-oxoglutarate aldolase, EC 4.1.3.17) and KHG aldolase (4-hydroxy-2-oxoglutarate glyoxylate-lyase, EC 4.1.3.16). In other embodiments, the aminotransferase polypeptide is chosen from a tryptophan aminotransferase polypeptide (EC 2.6.1.27), an aspartate aminotransferase polypeptide (EC 2.6.1.1), an aromatic aminotransferase polypeptide (EC 2.6.1.5) and a D-alanine aminotransferase polypeptide (EC 2.6.1.21). The microorganisms may include those that overproduce pyruvate, and/or are thiamine auxotrophs, phenylalanine and tyrosine auxotrophs or lipoic acid auxotrophs.

In some embodiments, the microorganism is chosen from *Candida glabrata, Trichosporon cutaneum, Candida lipolytica*, and *Saccharomyces cerevisiae*. In other embodiments, the microorganism comprises aspC and proA genes. In certain embodiments, the microorganism comprises aspC and proA genes and at least one tryptophan operon gene. In other embodiments, the microorganism is *E. coli*. In other embodiments, the microorganism comprises a defective F1⁻ ATPase gene, a disruption in an endogenous lipA gene, a disrupted pheA gene, a disrupted endogenous tryptophanase (tna) gene and/or two or more copies of one or more tryptophan biosynthesis genes. In some embodiments, the microorganism overproduces tryptophan. In other embodiments, the microorganism overexpresses a ppsA gene, has an increased amount of 3-deoxy-D-arabino-hepatulosonic 7-phosphate acid (DAHP) synthase activity relative to a corresponding control microorganism, comprises a nucleic acid encoding a polypeptide having phosphoenolpyruvate (PEP) synthase activity, wherein the nucleic acid is chosen from exogenous nucleic acids, recombinant nucleic acids and a combination thereof, and/or a tkt gene. In other embodiments, the microorganism is *E. coli* or *Corynebacterium glutamicum*.

In some embodiments, the microorganism further comprises an exogenous nucleic acid encoding a polypeptide having tryptophanase activity. In other embodiments, the microorganism secretes monatin or salt thereof and/or is a fatty acid auxotroph. In other embodiments, the microorganism is a strain of bacteria comprising a nucleic acid expressing an aldolase, wherein the aldolase expressed from the nucleic acid is capable of producing a stereoisomerically-enriched monatin mixture. In some embodiments, the stereoisomerically-enriched monatin mixture is predominantly S,S monatin or salt thereof. Alternatively, the stereoisomerically-enriched monatin mixture is predominantly R,R monatin or salt thereof. In one embodiment, the microorganism overexpresses at least one nucleic acid encoding a tryptophan uptake polypeptide.

In another aspect, the invention features a method for producing monatin or salt thereof comprising: (a) culturing a microorganism that produces monatin or salt thereof in culture medium under conditions wherein the monatin or salt thereof is produced, and (b) obtaining the monatin or salt thereof from the culture medium or the cultured microorganisms. In some embodiments, the microorganism secretes the monatin or salt thereof and/or is a fatty acid auxotroph.

In addition, the invention also includes a method for identifying a cell capable of synthesizing monatin or salt thereof comprising: (a) culturing a cell in the presence of a carbon/energy source chosen from monatin or salt thereof, 2-hydroxy 2-(indol-3-ylmethyl)-4-keto glutaric acid or salt thereof, an analog of monatin or salt thereof, an analog of 2-hydroxy 2-(indol-3-ylmethyl)-4-keto glutaric acid or salt thereof, and a combination thereof; and (b) testing for growth of the cell, wherein growth of the cell indicates that the cell converts the carbon/energy source to pyruvate, thereby indicating that the cell is capable of synthesizing monatin or salt thereof. In one embodiment, the cell is a pyruvate auxotroph, and pyruvate is produced in the cell by metabolism of the carbon/energy source. In other embodiments, the cell comprises disruptions in the pykA and pykF genes.

Furthermore, the invention features a method for identifying a cell capable of synthesizing monatin or salt thereof or 2-hydroxy-2-(indol-3-ylmethyl)-4-keto-glutaric acid or salt thereof, or a combination thereof from tryptophan, comprising: (a) culturing a cell that is a tryptophan auxotroph in the absence of tryptophan and in the presence of monatin or salt thereof, 2-hydroxy 2-(indol-3-ylmethyl)-4-keto glutaric acid or salt thereof, or a combination thereof; and (b) testing for growth of the cell that is a tryptophan auxotroph, wherein growth of the cell indicates that the cell synthesizes tryptophan from monatin or salt thereof, 2-hydroxy 2-(indol-3-ylmethyl)-4-keto glutaric acid or salt thereof, or a combination thereof, thereby indicating that the cell is capable of synthesizing monatin or salt thereof or 2-hydroxy-2-(indol-3-ylmethyl)-4-keto-glutaric acid or salt thereof, or a combination thereof from tryptophan.

The invention also features a method of producing monatin or salt thereof comprising: (a) culturing a microorganism in a culture medium, wherein the microorganism is chosen from *Sinorhizobium meliloti, Comamonas testosteroni, Pseudomonas straminea* and *Corynebacterium glutamicum*; and (b) extracting monatin or salt thereof from the culture medium or the cultured microorganism. In some embodiments, the microorganism is not genetically modified. In other embodiments, the culture medium comprises PHB Medium. The culture medium may also include tryptophan, pyruvate, a non-ionic detergent, penicillin, a penicillin derivative or a combination thereof. In some embodiments, the microorganism is *Sinorhizobium meliloti* or *Comamonas testosteroni*. In other embodiments, the microorganism is *Comamonas testosteroni*, and/or the culture medium further comprises tryptophan and pyruvate. In other embodiments, the culture medium comprises TY medium. The culture medium may also include tryptophan, pyruvate or a combination thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Compounds shown in boxes are substrates and products produced in the biosynthetic pathways.

Compositions adjacent to the arrows are cofactors, or reactants that can be used during the conversion of a substrate to a product. The cofactor or reactant used will depend upon the polypeptide used for the particular step of the biosynthetic pathway. The cofactor PLP (pyridoxal 5'-phosphate) can catalyze reactions independent of a polypeptide, and therefore, merely providing PLP can allow for the progression from substrate to product.

Figure 2:
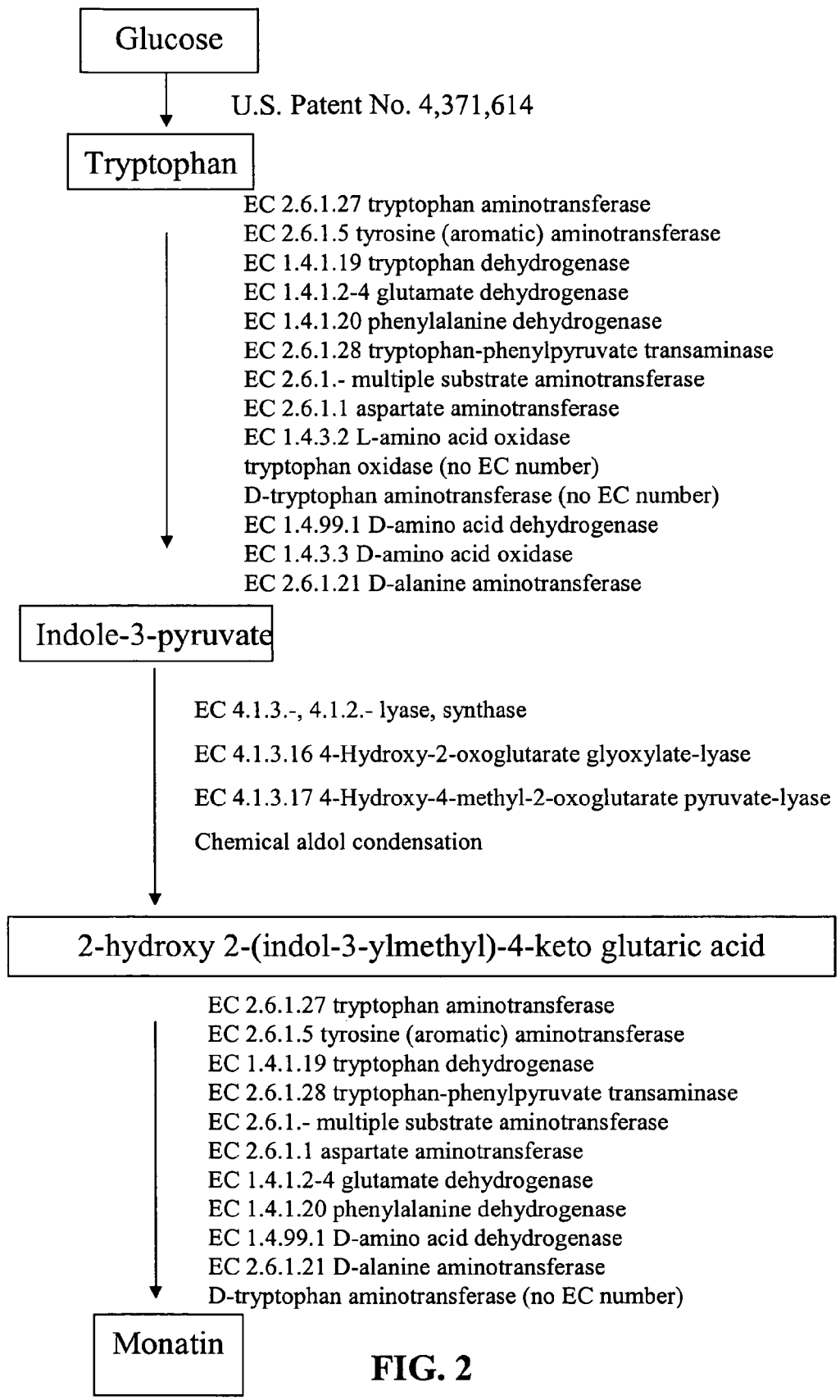

FIG. 2 is a more detailed diagram of the biosynthetic pathway that utilizes the MP intermediate. The substrates for each step in the pathways are shown in boxes. The polypeptides allowing for the conversion between substrates are listed adjacent to the arrows between the substrates. Each polypeptide is described by its common name and an enzymatic class (EC) number.

Figures 3, 4:
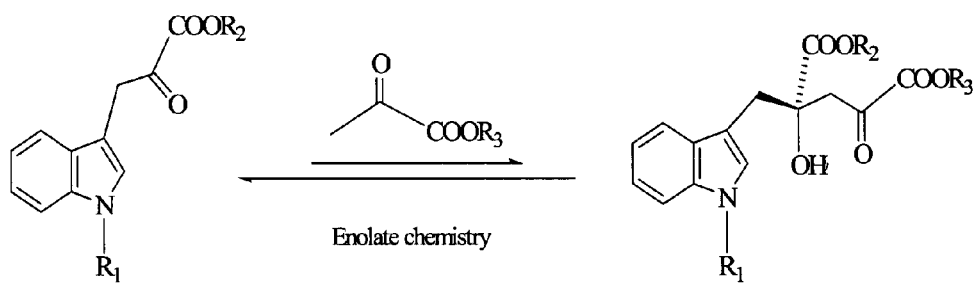

FIG. 3 shows a more detailed diagram of the biosynthetic pathway of the conversion of indole-3-lactic acid to indole-3-pyruvate. The substrates are shown in boxes, and the polypeptides allowing for the conversion between the substrates are listed adjacent to the arrow between the substrates. Each polypeptide is described by its common name and an EC number.

FIG. 4 shows one possible reaction for making MP via chemical means.

FIGS. 5A and 5B are chromatograms showing the LC/MS identification of monatin produced enzymatically.

FIG. 6 is an electrospray mass spectrum of enzymatically synthesized monatin.

Figure 7A:
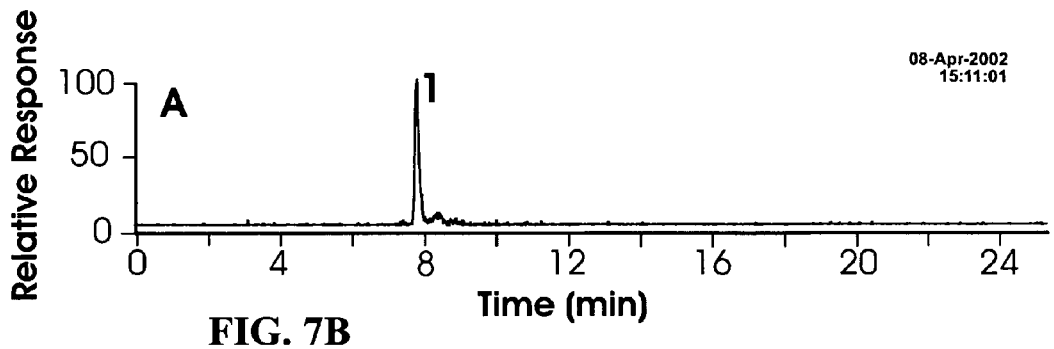
Figure 7B:
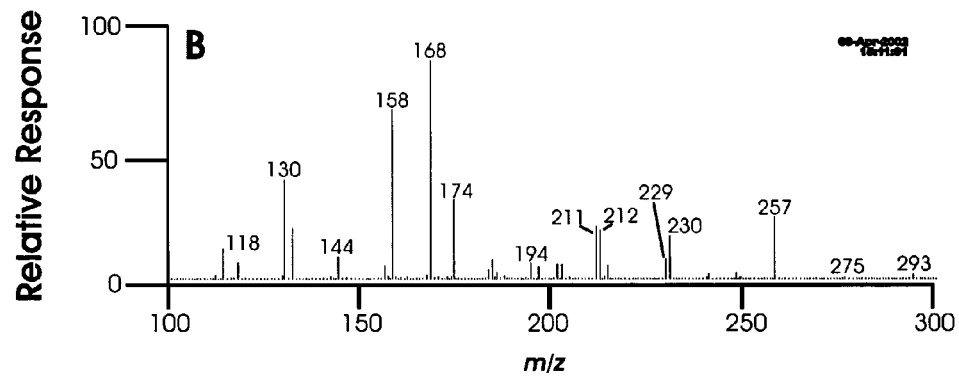

FIGS. 7A and 7B are chromatograms of the LC/MS/MS daughter ion analyses of monatin produced in an enzymatic mixture.

Figure 8:
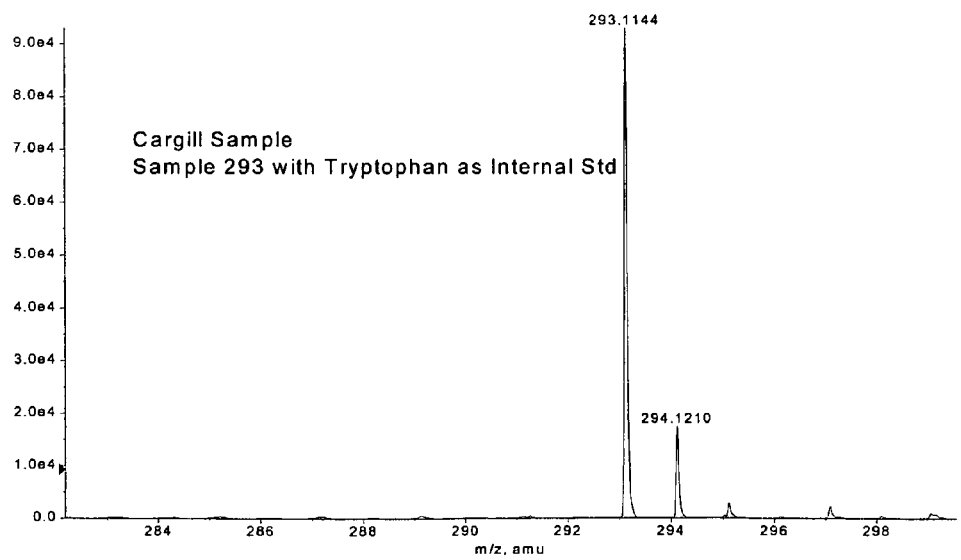

FIG. 8 is a chromatogram showing the high-resolution mass measurement of monatin produced enzymatically.

FIGS. 9A-9C are chromatograms showing the chiral separation of (A) R-tryptophan, (B) S-tryptophan, and (C) monatin produced enzymatically.

FIG. 10 is a bar graph showing the relative amount of monatin produced in bacterial cells following IPTG induction. The (−) indicates a lack of substrate addition (no tryptophan or pyruvate was added).

Figure 11:
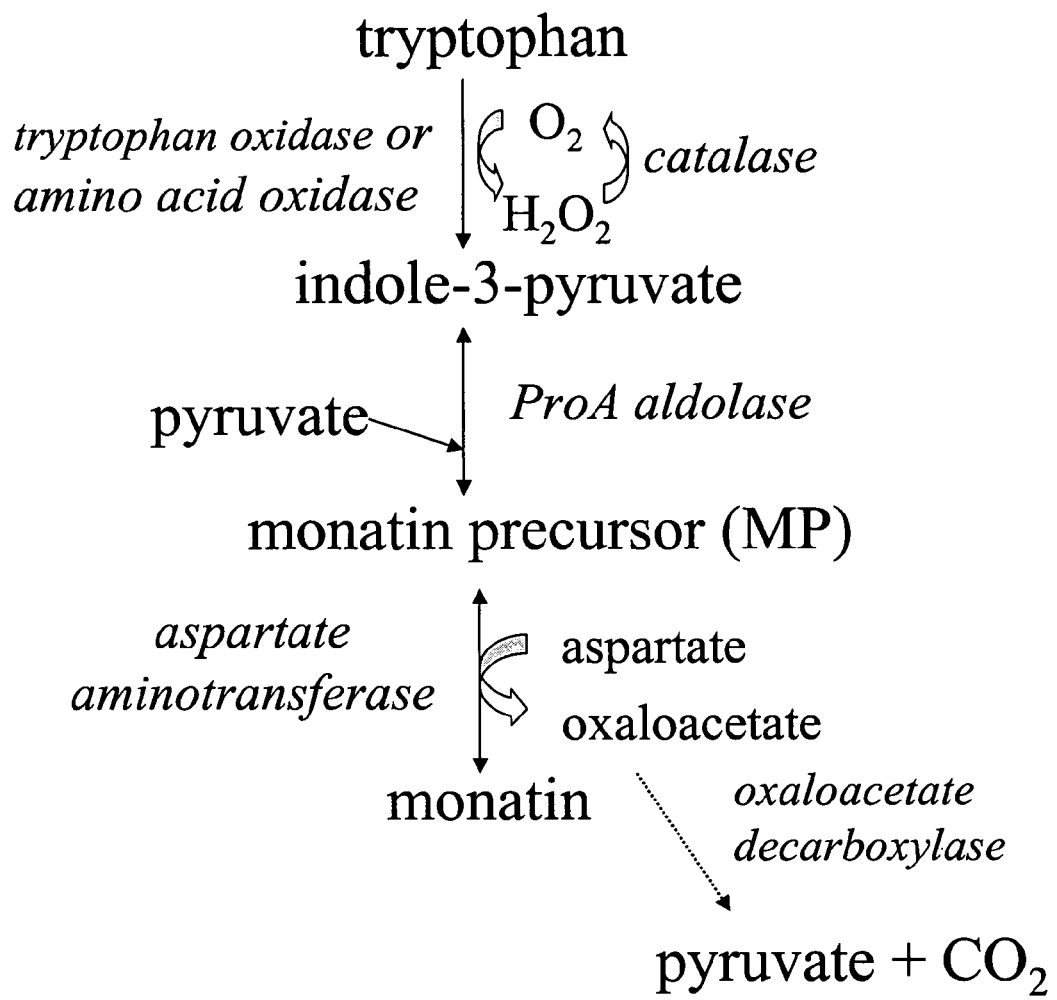
Figure 12:
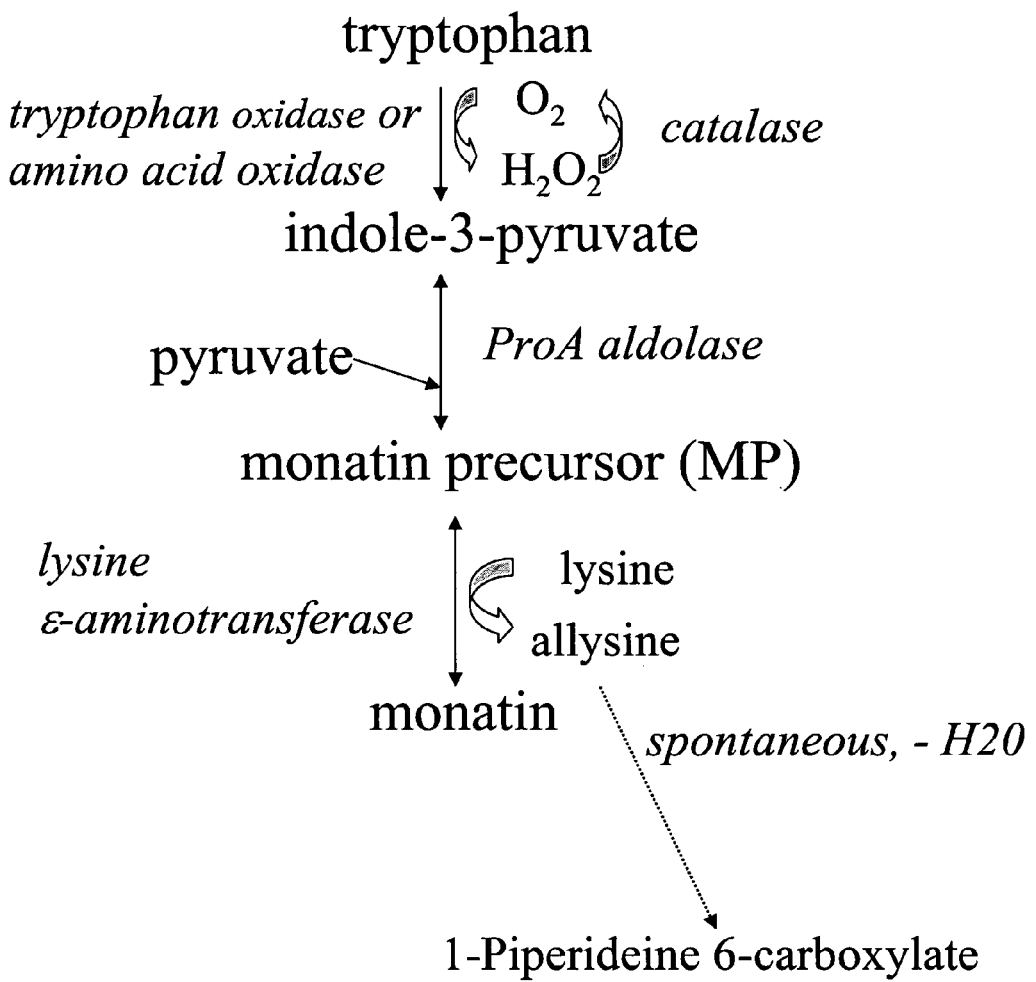

FIGS. 11-12 are schematic diagrams showing pathways used to increase the yield of monatin produced from tryptophan or indole-3-pyruvate.

Figure 13:
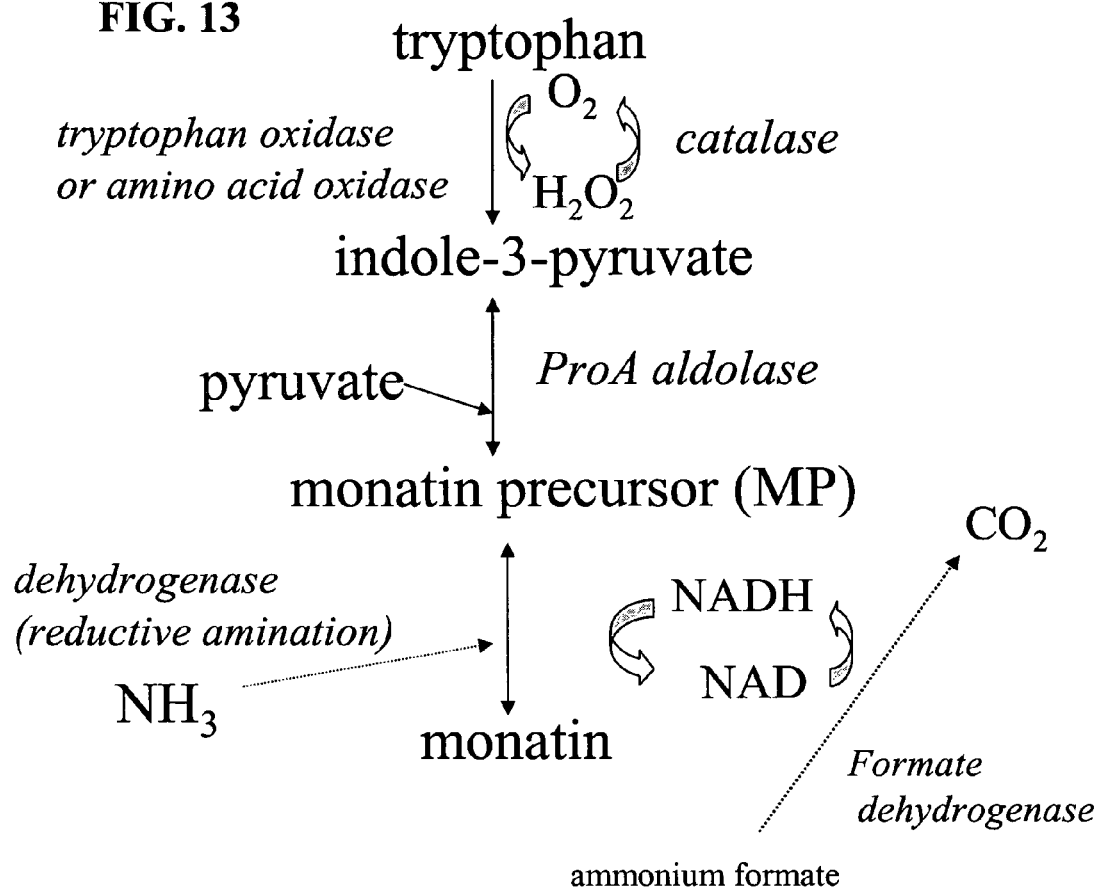

FIG. 13 is a schematic diagram showing a pathway that can be used to increase the yield of monatin produced from tryptophan or indole-3-pyruvate.

Figure 14:
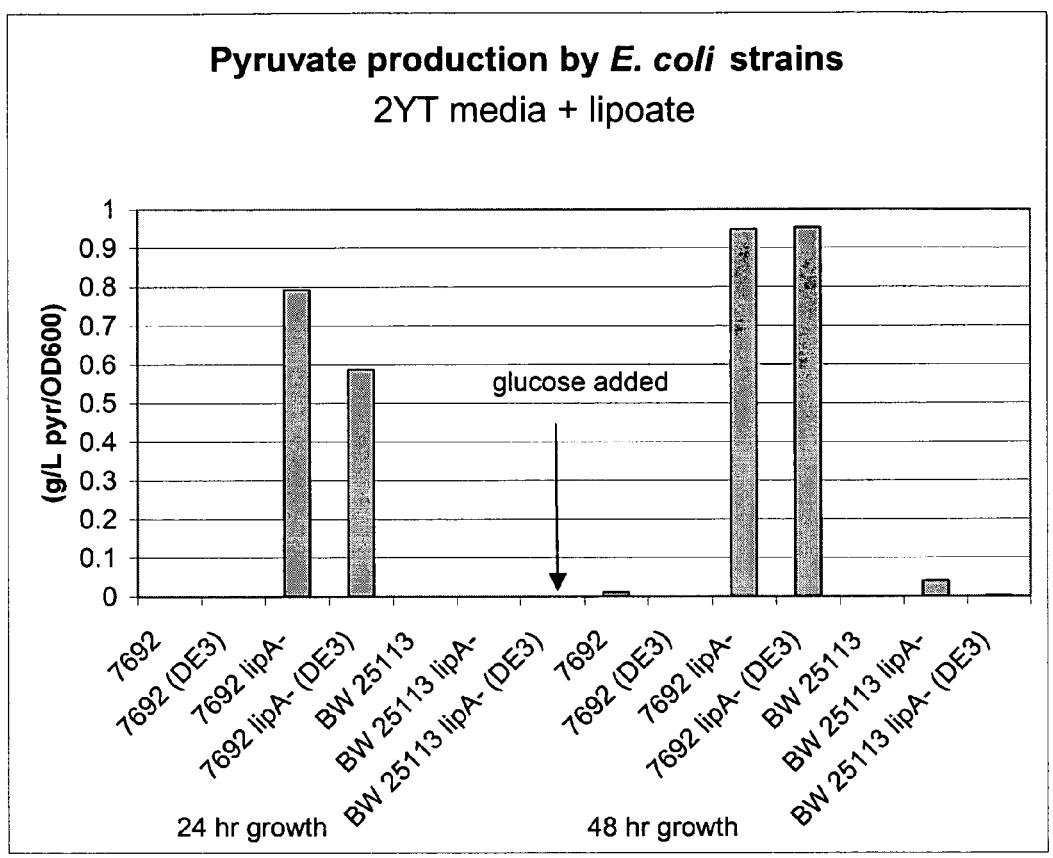

FIG. 14 is a graph depicting an increase in pyruvate production in genetically modified *E. coli* 7692 and BW25113 cells.

Figure 15:
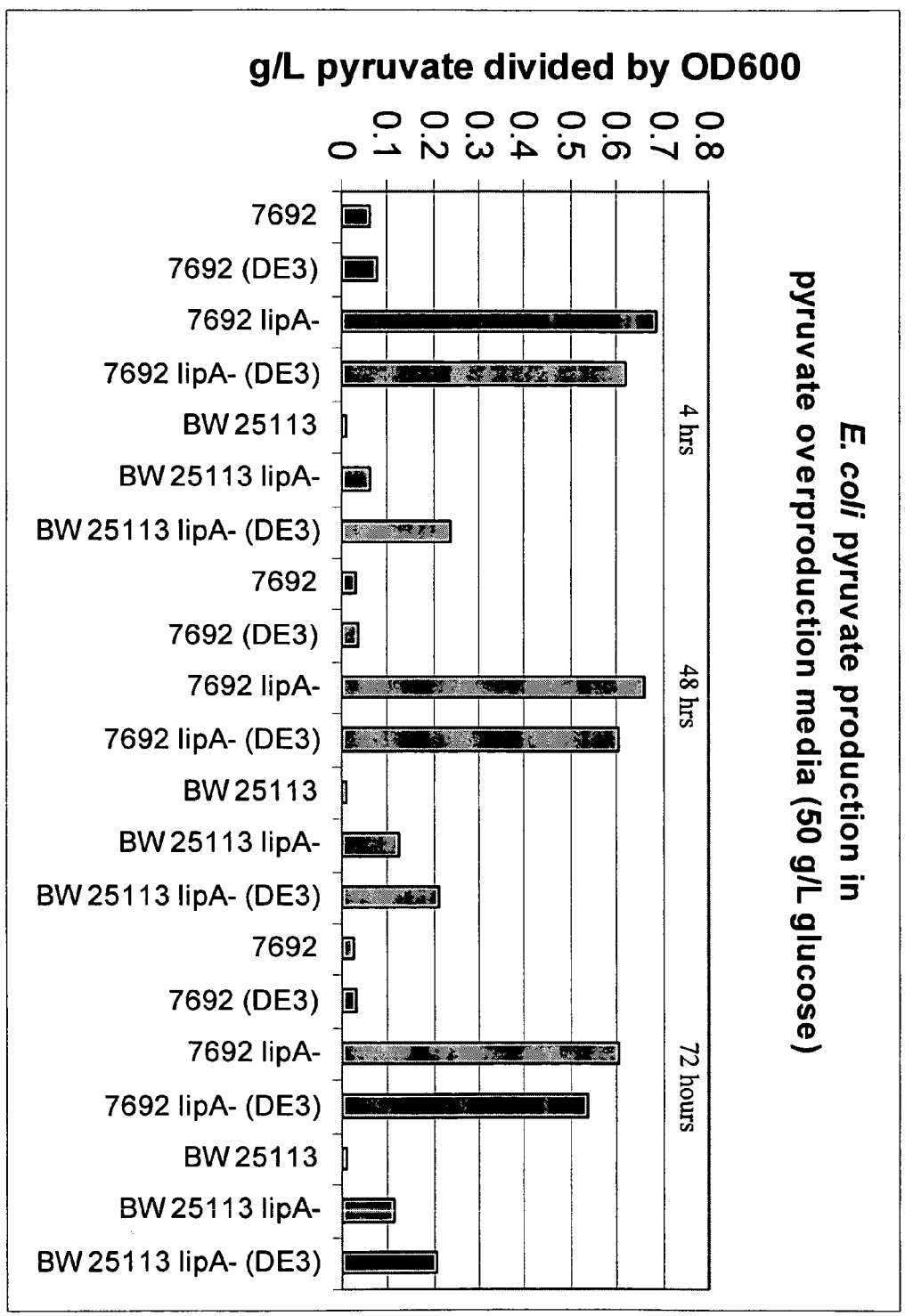

FIG. 15 is a graph depicting an increase in pyruvate production in genetically modified *E. coli* 7692 and BW25113 cells grown in pyruvate overproduction media.

FIG. 16 is a nucleic acid sequence listing (SEQ ID NO: 65) of a proA gene cloned from *Comamonas testosteroni* (ATCC 49249).

FIG. 17 is an amino acid sequence listing (SEQ ID NO: 66) of the ProA aldolase polypeptide encoded by a proA gene from *Comamonas testosteroni* (ATCC 49249).

SEQUENCE LISTING

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NOS: 1 and 2 set forth the nucleic acid and amino acid sequences, respectively, of an aminotransferase from *Sinorhizobium meliloti* (tatA gene, called a tyrosine or aromatic aminotransferase in literature).

SEQ ID NOS: 3 and 4 set forth the nucleic acid and amino acid sequences, respectively, of a tyrosine aminotransferase from *Rhodobacter sphaeroides* (2.4.1) (by homology with tatA (SEQ ID NOS: 1 and 2)).

SEQ ID NOS: 5 and 6 set forth the nucleic acid and amino acid sequences, respectively, of an aminotransferase from *Rhodobacter sphaeroides* (35053) (novel, cloned based on 2.4.1 sequence SEQ ID NOS 3 and 4).

SEQ ID NOS: 7 and 8 set forth the nucleic acid and amino acid sequences, respectively, of a broad substrate aminotransferase (bsat) from *Leishmania major*.

SEQ ID NOS: 9 and 10 set forth the nucleic acid and amino acid sequences, respectively, of an aromatic aminotransferase (araT) from *Bacillus subtilis*.

SEQ ID NOS: 11 and 12 set forth novel nucleic acid and amino acid sequences, respectively, of an aromatic aminotransferase (araT) from *Lactobacillus amylovorus* (identified by homology as an aromatic aminotransferase).

SEQ ID NOS: 13 and 14 set forth the nucleic acid and amino acid sequences, respectively, of a multiple substrate aminotransferase (msa) from *R. sphaeroides* (35053) (identified as a multiple substrate aminotransferase by homology to Accession No. AAAE011000093.1, bp 14743-16155 and Accession No. ZP00005082.1).

SEQ ID NOS: 15 and 16 set forth the nucleic acid sequences of primers used to clone the *B. subtilis* D-alanine aminotransferase (dat) gene sequence.

SEQ ID NOS: 17 and 18 set forth the nucleic acid sequences of primers used to clone the *S. meliloti* tatA sequence.

SEQ ID NOS: 19 and 20 set forth the nucleic acid sequences of primers used to clone the *B. subtilis* araT aminotransferase sequence.

SEQ ID NOS: 21 and 22 set forth the nucleic acid sequences of primers used to clone the *Rhodobacter sphaeroides* (2.4.1 and 35053) multiple substrate aminotransferase sequences.

SEQ ID NOS: 23 and 24 set forth the nucleic acid sequence of primers used to clone the *Leishmania major* bsat sequence.

SEQ ID NOS: 25 and 26 set forth the nucleic acid sequences of primers used to clone the *Lactobacillus amylovorus* araT sequence.

SEQ ID NOS: 27 and 28 set forth the nucleic acid sequences of primers used to clone the *R. sphaeroides* tatA sequences (both 2.4.1 and 35053).

SEQ ID NOS: 29 and 30 set forth the nucleic acid sequences of primers used to clone the *E. coli* aspC sequence (gene sequence Genbank Accession No.: AE000195.1, protein sequence Genbank Accession No.: AAC74014.1).

SEQ ID NOS: 31 and 32 set forth the nucleic acid and amino acid sequences, respectively, of aromatic aminotransferase (tyrB) from *E. coli*.

SEQ ID NOS: 33 and 34 set forth the nucleic acid sequences of primers used to clone the *E. coli* tyrB sequence.

SEQ ID NOS: 35-40 set forth the nucleic acid sequences of primers used to clone polypeptides with 4-hydroxy-2-oxoglutarate aldolase (KHG) (EC 4.1.3.16) activity.

SEQ ID NOS: 41 and 42 set forth the nucleic acid sequences of a tryptophanase (tna) gene from *E. coli* and a tyrosine phenol-lyase (tpl) gene from *Citrobacter freundii*, coding for proteins P00913 (GI:401195) and P31013 (GI:401201), respectively.

SEQ ID NOS: 43-46 set forth the nucleic acid sequences of primers used to clone tryptophanase polypeptides and β-tyrosinase (tyrosine phenol-lyase) polypeptides.

SEQ ID NOS: 47-54 set forth the nucleic acid sequences of primers used to mutate tryptophanase polypeptides and β-tyrosinase polypeptides.

SEQ ID NOS: 55-64 set forth the nucleic acid sequences of primers used to clone polypeptides with 4-hydroxy-4-methyl-2-oxoglutarate aldolase (EC 4.1.3.17) activity.

SEQ ID NOS: 65 and 66 set forth the nucleic acid and amino acid sequences, respectively of 4-hydroxy-4-methyl-2-oxoglutarate aldolase (proA) from *C. testosteroni*.

SEQ ID NOS: 67-68 set forth the nucleic acid sequences of the primers used to clone *C. testosteroni* 4-hydroxy-4-methyl-2-oxoglutarate aldolase (proA) in an operon with *E. coli* aspC in pET30 Xa/LIC.

SEQ ID NOS: 69-72 set forth the nucleic acid sequences of the primers used to clone *E. coli* aspC and *C. testosteroni* proA in pESC-his.

SEQ ID NOS: 73-74 set forth the nucleic acid sequences added to the 5' end of primers used to clone the genes disclosed herein.

SEQ ID NOS: 75 and 76 set forth the nucleic acid sequences of the primers used to shorten the intervening sequence between the aspC and proA genes.

SEQ ID NOS: 77 and 78 set forth the nucleic acid sequences of the primers used to clone *E. coli* tnaA in pPRONco.

SEQ ID NOS: 79 and 80 set forth the nucleic acid sequences of the primers used to clone *E. coli* tryptophan operon (genes trpE, trpD, trpC, trpB, trpA) in pPRONco.

SEQ ID NOS: 81 and 82 set for the nucleic acid and amino acid sequences, respectively, of the trpE gene of plasmid pGX50 (derived from 5-methyltryptophan resistant cells).

SEQ ID NOS: 83 and 84 set forth the nucleic acid sequences of the primers used to clone an operon containing *C. testosteroni* 4-hydroxy-4-methyl-2-oxoglutarate aldolase (proA) and *E. coli* aspC into the *Corynebacterium/E. coli* shuttle vector pEKEX-2.

SEQ ID NOS: 85 and 86 set forth the nucleic acid sequences of the primers used to generate the pykA knockout in *E. coli*.

SEQ ID NOS: 87 and 88 set forth the nucleic acid sequences of the primers used to generate the generate the pykF knockout in *E. coli*.

SEQ ID NO: 89 sets forth the first ten amino acids of an aromatic aminotransferase (araT) from *Lactobacillus amylovorus* (SEQ ID NO: 12).

DETAILED DESCRIPTION

The following explanations of terms and methods are provided to better describe the present disclosure and to guide those of ordinary skill in the art in the practice of the present disclosure. As used herein, "including" means "comprising." In addition, the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth. The term "about" encompasses the range of experimental error that occurs in any measurement. Unless otherwise stated, all measurement numbers are presumed to have the word "about" in front of them even if the word "about" is not expressly used.

cDNA (complementary DNA): A piece of DNA lacking internal, non-coding segments (introns) and regulatory sequences which determine transcription. cDNA can be synthesized in the laboratory by reverse transcription from messenger RNA extracted from cells.

Conservative substitution: One or more amino acid substitutions (for example 2, 5, or 10 residues) for amino acid residues having similar biochemical properties. Typically, conservative substitutions have little to no impact on the activity of a resulting polypeptide. For example, ideally, a tryptophan aminotransferase polypeptide including one or more conservative substitutions retains tryptophan aminotransferase activity. A polypeptide can be produced to contain one or more conservative substitutions by manipulating the nucleotide sequence that encodes that polypeptide using, for example, standard procedures such as site-directed mutagenesis or PCR.

Substitutional variants are those in which at least one residue in the amino acid sequence has been removed and a different residue inserted in its place. Examples of amino acids which can be substituted for an original amino acid in a protein and which are regarded as conservative substitutions include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln lys, or asp; gly substituted with pro; his substituted with asn, lys, gin, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu. See, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (Bio/Technology 6:1321-5, 1988), WO 00/67796 (Curd et al.), or standard textbooks of genetics and molecular biology for further information about conservative substitutions.

Exogenous: The term "exogenous" as used herein with reference to nucleic acid and a particular cell refers to any nucleic acid that does not originate from that particular cell as found in nature. Thus, non-naturally-occurring nucleic acid is considered to be exogenous to a cell once introduced into the cell. Nucleic acid that is naturally-occurring also can be exogenous to a particular cell. For example, an entire chromosome isolated from a cell of person X is an exogenous nucleic acid with respect to a cell of person Y once that chromosome is introduced into Y's cell. An "exogenous" protein results from the expression of an exogenous nucleic acid in a cell.

Functionally Equivalent: Having an equivalent function. In the context of an enzyme, functionally equivalent molecules include different molecules that retain the function of the enzyme. For example, functional equivalents can be provided by sequence alterations in an enzyme sequence, wherein the polypeptide with one or more sequence alterations retains a function of the unaltered polypeptide (e.g., enzymatic activity). In a particular example, a tryptophan aminotransferase functional equivalent retains the ability to convert tryptophan to indole-3-pyruvate.

Examples of sequence alterations include, but are not limited to, conservative substitutions, deletions, mutations, frameshifts, and insertions. In one example, a given polypeptide binds an antibody, and a functional equivalent is a polypeptide that binds the same antibody. Thus a functional equivalent includes peptides that have the same binding specificity as a polypeptide, and that can be used as a reagent in place of the polypeptide. In one example, a functional equivalent includes a polypeptide wherein the binding sequence is discontinuous, wherein the antibody binds a linear epitope. Thus, if the peptide sequence is MPELANDLGL (amino acids 1-10 of SEQ ID NO: 12) (SEQ ID NO: 89), a functional equivalent includes discontinuous epitopes, which can appear as follows (=any number of intervening amino acids): NH2--MPELANDLG**L-COOH. In this example, the polypeptide is functionally equivalent to amino acids 1-10 of SEQ ID NO: 12 if the three dimensional structure of the polypeptide is such that it can bind a monoclonal antibody that binds amino acids 1-10 of SEQ ID NO: 12.

Hybridization: The term "hybridization" as used herein refers to a method of testing for complementarity in the nucleotide sequence of two nucleic acid molecules, based on the ability of complementary single-stranded DNA and/or RNA to form a duplex molecule. Nucleic acid hybridization techniques can be used to obtain an isolated nucleic acid within the scope of the disclosure. Briefly, any nucleic acid having homology to the sequence set forth in SEQ ID NO: 11 or a portion thereof can be used as a probe to identify a similar nucleic acid by hybridization under conditions of moderate to high stringency. Once identified, the nucleic acid then can be purified, sequenced, and analyzed to determine whether it is within the scope of the present disclosure.

Hybridization can be done by Southern or Northern analysis to identify a DNA or RNA sequence, respectively, that hybridizes to a probe. The probe can be labeled with a biotin, digoxygenin, a polypeptide, or a radioisotope such as $^{32}P$. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y. Typically, a probe is at least about 20 nucleotides in length. For example, a probe corresponding to a contiguous 20 nucleotide sequence set forth in SEQ ID NO: 11 can be used to identify an identical or similar nucleic acid. In addition, probes longer or shorter than 20 nucleotides can be used.

The disclosure also provides isolated nucleic acid sequences that are at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid having the sequence set forth in SEQ ID NO: 11. The hybridization conditions can be moderately or highly stringent hybridization conditions. For the purpose of this disclosure, moderately stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5\times10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5\times10^7$ cpm/µg), while the washes are performed at about 65° C. with a wash solution containing 0.2×SSC and 0.1% sodium dodecyl sulfate.

Isolated: The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence. The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

A nucleic acid existing among hundreds to millions of other nucleic acid molecules within, for example, cDNA or genomic libraries, or gel slices containing a genomic DNA restriction digest is not to be considered an isolated nucleic acid.

The term "isolated" as used herein with reference to a polypeptide refers to a polypeptide that is isolated in some way, for example, from a cell, or otherwise separated from a previous environment. An isolated polypeptide can also refer to a polypeptide that has been purified in some way.

Nucleic acid: The term "nucleic acid" as used herein encompasses both RNA and DNA including, without limitation, cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear. One or more nucleic acids can be present within a larger nucleic acid. For example, a nucleic acid encoding an aldolase polypeptide and a nucleic acid encoding an aminotransferase polypeptide can be present within in a larger single nucleic acid, such as genomic DNA or a plasmid vector. Alternatively, a nucleic acid encoding an aldolase polypeptide and a nucleic acid encoding an aminotransferase polypeptide can be present on two different nucleic acids, such as two different plasmid vectors.

Operably linked: A first nucleic acid sequence is "operably linked" with a second nucleic acid sequence when the first nucleic acid sequence is placed in a functional relationship with the second nucleic acid sequence. For instance, a promoter is operably linked to a coding sequence if the promoter affects the transcription of the coding sequence. Generally, operably linked DNA sequences are contiguous and, where necessary to join two polypeptide-coding regions, in the same reading frame.

Overexpress: A cell "overexpresses" a particular nucleic acid or gene if the polypeptide encoded by that nucleic acid or gene is produced in a cell and/or microorganism at a higher concentration than that produced in a corresponding wild-type or native cell and/or microorganism. Cells can overexpress exogenous, recombinant or naturally occurring (i.e., native) nucleic acids or genes in a cell. For example, a polypeptide may be produced at a higher level in a cell by overexpressing a naturally occurring nucleic acid in the cell, where the nucleic acid encoding the polypeptide itself is not genetically modified, but a promoter directing transcription of the nucleic acid sequence is modified or added. The term "overexpress" can also relate to an overexpressed protein, i.e., one present in a cell and/or microorganism at a higher concentration than that present in a corresponding wild-type or native cell and/or microorganism.

Polypeptide: A polypeptide refers to a chain of amino acids, regardless of post-translation modification.

Polypeptide Modifications: The present disclosure includes enzymes, as well as synthetic embodiments thereof. In addition, analogues (non-peptide organic molecules), derivatives (chemically functionalized polypeptide molecules obtained starting with the disclosed polypeptide sequences) and variants (homologs) having the desired enzymatic activity can be utilized in the methods described herein. The polypeptides disclosed herein include a sequence of amino acids, that can be either L- and/or D-amino acids, naturally occurring and otherwise.

Polypeptides can be modified by a variety of chemical techniques to produce derivatives having essentially the same activity as the unmodified polypeptides, and optionally having other desirable properties. For example, carboxylic acid groups of the polypeptide, whether carboxyl-terminal or side chain, can be provided in the form of a salt of a pharmaceutically-acceptable cation or esterified to form a C1-C16 ester, or converted to an amide of formula $NR_1R_2$ wherein $R_1$ and $R_2$ are each independently H or C1-C16 alkyl, or combined to form a heterocyclic ring, such as a 5- or 6-membered ring. Amino groups of the polypeptide, whether amino-terminal or side chain, can be in the form of a pharmaceutically-acceptable acid addition salt, such as HCl, HBr, acetic, benzoic, toluene sulfonic, maleic, tartaric, and other organic salts, or can be modified to C1-C16 alkyl or dialkyl amino or further converted to an amide.

Hydroxyl groups of the amino acid side chains can be converted to C1-C16 alkoxy or to a C1-C16 ester using well-recognized techniques. Phenyl and phenolic rings of the amino acid side chains can be substituted with one or more halogen atoms, such as F, Cl, Br or I, or with C1-C16 alkyl, C1-C16 alkoxy, carboxylic acids and esters thereof, or amides of such carboxylic acids. Methylene groups of the amino acid side chains can be extended to homologous C2-C4 alkylenes. Thiols can be protected with any one of a number of well-recognized protecting groups, such as acetamide groups. Those skilled in the art will also recognize methods for introducing cyclic structures into the polypeptides of this disclosure to select and provide conformational constraints to the structure that result in enhanced stability. For example, a C- or N-terminal cysteine can be added to the polypeptide, so that when oxidized, the polypeptide will contain a disulfide bond, generating a cyclic polypeptide. Other polypeptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the polypeptides of this disclosure having detectable enzyme activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See, e.g., Walters, "Computer-Assisted Modeling of Drugs", in Klegerman & Groves (eds.), Pharmaceutical Biotechnology, 1993, Interpharm Press: Buffalo Grove, Ill., pp. 165-74 and Ch. 102 in Munson (ed.), Principles of Pharmacology, 1995, Chapman & Hall, for descriptions of techniques used in CADD. Also included within the scope of the disclosure are mimetics prepared using such techniques. In one example, a mimetic mimics the enzyme activity generated by an enzyme or a variant, fragment, or fusion thereof.

Probes and primers: Nucleic acid probes and primers can be prepared readily based on the amino acid sequences and nucleic acid sequences provided herein. A "probe" includes an isolated nucleic acid containing a detectable label or reporter molecule. Exemplary labels include, but are not limited to, radioactive isotopes, ligands, chemiluminescent agents, and polypeptides (e.g., enzymes). Methods for labeling and guidance in the choice of labels appropriate for various purposes are discussed in, for example, Sambrook et al. (ed.), Molecular Cloning: A Laboratory Manual 2nd ed., vol. 1-3, Cold Spring Harbor Laboratory Press, Cold Spring Harbor, N.Y., 1989, and Ausubel et al. (ed.) Current Protocols in Molecular Biology, Greene Publishing and Wiley-Interscience, New York (with periodic updates), 1987.

"Primers" are typically nucleic acid molecules having ten or more nucleotides (e.g., nucleic acid molecules having between about 10 nucleotides and about 100 nucleotides). A primer can be annealed to a complementary target nucleic acid strand by nucleic acid hybridization to form a hybrid between the primer and the target nucleic acid strand, and then extended along the target nucleic acid strand by, for example, a DNA polymerase polypeptide. Primer pairs can be used for amplification of a nucleic acid sequence, for example, by the polymerase chain reaction (PCR) or other nucleic-acid amplification methods known in the art.

Methods for preparing and using probes and primers are described, for example, in references such as Sambrook et al. (ed.), Molecular Cloning: A Laboratory Manual, 2nd ed., vol. 1-3, Cold Spring Harbor Laboratory Press, Cold Spring Harbor, N.Y., 1989; Ausubel et al. (ed.), Current Protocols in Molecular Biology, Greene Publishing and Wiley-Interscience, New York (with periodic updates), 1987; and Innis et al. (eds.), PCR Protocols: A Guide to Methods and Applications, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with the length, but that a probe or primer can range in size from a full-length sequence to sequences as short as five consecutive nucleotides. Thus, for example, a primer of 20 consecutive nucleotides can anneal to a target with a higher specificity than a corresponding primer of only 15 nucleotides. Thus, in order to obtain greater specificity, probes and primers can be selected that comprise, for example, 10, 20, 25, 30, 35, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 2000, 2050, 2100, 2150, 2200, 2250, 2300, 2350, 2400, 2450, 2500, 2550, 2600, 2650, 2700, 2750, 2800, 2850, 2900, 3000, 3050, 3100, 3150, 3200, 3250, 3300, 3350, 3400, 3450, 3500, 3550, 3600, 3650, 3700, 3750, 3800, 3850, 3900, 4000, 4050, 4100, 4150, 4200, 4250, 4300, 4350, 4400, 4450, 4500, 4550, 4600, 4650, 4700, 4750, 4800, 4850, 4900, 5000, 5050, 5100, 5150, 5200, 5250, 5300, 5350, 5400, 5450, or more consecutive nucleotides.

Promoter: A nucleic acid control sequence that directs transcription of a nucleic acid sequence. A promoter includes necessary nucleic acid sequences near the start site of transcription, such as, in the case of a polymerase II type promoter, a TATA element. A promoter can include distal enhancer or repressor elements which can be located as much as several thousand base pairs from the start site of transcription.

Purified: The term "purified" as used herein does not require absolute purity; rather, it is intended as a relative term. Thus, for example, a purified polypeptide or nucleic acid preparation can be one in which the subject polypeptide or nucleic acid, respectively, is at a higher concentration than the polypeptide or nucleic acid would be in its natural environment within an organism. For example, a polypeptide preparation can be considered purified if the polypeptide content in the preparation represents at least 50%, 60%, 70%, 80%, 85%, 90%, 92%, 95%, 98%, or 99% of the total soluble protein content of the preparation.

Recombinant: A "recombinant" nucleic acid is one having (1) a sequence that is not naturally occurring in the organism in which it is expressed or (2) a sequence made by an artificial combination of two otherwise-separated, shorter sequences. This artificial combination is often accomplished by chemical synthesis or, more commonly, by the artificial manipulation of isolated segments of nucleic acids, e.g., by genetic engineering techniques. "Recombinant" is also used to describe nucleic acid molecules that have been artificially manipulated, but contain the same regulatory sequences and coding regions that are found in the organism from which the nucleic acid was isolated. A "recombinant" polypeptide is one that is expressed from a recombinant nucleic acid.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide, such as SEQ ID NO: 12, possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443-53, 1970; Pearson and Lipman, *Proc. Natl. Acad. Sci. U.S.A.* 85:2444-8, 1988; Higgins and Sharp, *Gene* 73:237-44, 1988; Higgins and Sharp, *CABIOS* 5:151-3, 1989; Corpet et al., *Nucleic Acids Research* 16:10881-90, 1988; and Altschul et al., *Nature Genet.* 6:119-29, 1994.

The NCBI Basic Local Alignment Search Tool (BLAST™) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of a polypeptide are typically characterized by possession of at least 50% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short polypeptides (fewer than around 30 amino acids), the alignment is performed using the Blast 2 sequences function, employing the PAM30 matrix set to default parameters (open gap 9, extension gap 1 penalties). Polypeptides with even greater similarity to the reference sequences will show increasing percentage identities when assessed by this method, such as at least 80%, at least 90%, at least 95%, at least 98%, or even at least 99% sequence identity. When less than the entire sequence is being compared for sequence identity, homologs and variants will typically possess at least 80% sequence identity over short windows of 10-20 amino acids, and can possess sequence identities of at least 85%, at least 90%, at least 95%, or 98% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

Similar methods can be used to determine the percent sequence identity of a nucleic acid sequence. In a particular example, a homologous sequence is aligned to a native sequence, and the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO: 11), or by an articulated length (e.g., 100 consecutive nucleotides or amino acid residues from a sequence set forth in an identified sequence), followed by multiplying the resulting value by 100. For example, a nucleic acid sequence that has 882 matches when aligned with the sequence set forth in SEQ ID NO: 11 is 75.0 percent identical to the sequence set forth in SEQ ID NO: 11 (i.e., (882÷1176)*100=75.0). It is noted that the percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. It is also noted that the length value will always be an integer.

Specific binding agent: An agent that is capable of specifically binding to any of the polypeptides described herein. Examples include, but are not limited to, polyclonal antibodies, monoclonal antibodies (including humanized monoclonal antibodies), and fragments of monoclonal antibodies such as Fab, F(ab')$_2$, and Fv fragments as well as any other agent capable of specifically binding to an epitope of such polypeptides.

Antibodies to the polypeptides provided herein can be used to purify or identify such polypeptides. The amino acid and nucleic acid sequences provided herein allow for the production of specific antibody-based binding agents that recognize the polypeptides described herein.

Monoclonal or polyclonal antibodies can be produced to the polypeptides, portions of the polypeptides, or variants thereof. Optimally, antibodies raised against one or more epitopes on a polypeptide antigen will specifically detect that polypeptide. That is, antibodies raised against one particular polypeptide would recognize and bind that particular polypeptide, and would not substantially recognize or bind to other polypeptides. The determination that an antibody specifically binds to a particular polypeptide is made by any one of a number of standard immunoassay methods; for instance, Western blotting (See, e.g., Sambrook et al. (ed.), Molecular Cloning: A Laboratory Manual, 2nd ed., vol. 1-3, Cold Spring Harbor Laboratory Press, Cold Spring Harbor, N.Y., 1989).

To determine that a given antibody preparation (such as a preparation produced in a mouse against a polypeptide having the amino acid sequence set forth in SEQ ID NO: 12) specifically detects the appropriate polypeptide (e.g., a polypeptide having the amino acid sequence set forth in SEQ ID NO: 12) by Western blotting, total cellular protein can be extracted from cells and separated by SDS-polyacrylamide gel electrophoresis.

The separated total cellular protein then can be transferred to a membrane (e.g., nitrocellulose), and the antibody preparation incubated with the membrane. After washing the membrane to remove non-specifically bound antibodies, the presence of specifically bound antibodies can be detected using an appropriate secondary antibody (e.g., an anti-mouse antibody) conjugated to a polypeptide such as alkaline phosphatase since application of 5-bromo-4-chloro-3-indolyl phosphate/nitro blue tetrazolium results in the production of a densely blue-colored compound by immuno-localized alkaline phosphatase.

Substantially pure polypeptides suitable for use as an immunogen can be obtained from transfected cells, transformed cells, or wild-type cells. Polypeptide concentrations in the final preparation can be adjusted, for example, by concentration on an Amicon filter device, to the level of a few micrograms per milliliter. In addition, polypeptides ranging in size from full-length polypeptides to polypeptides having as few as nine amino acid residues can be utilized as immunogens. Such polypeptides can be produced in cell culture, can be chemically synthesized using standard methods, or can be obtained by cleaving large polypeptides into smaller polypeptides that can be purified. Polypeptides having as few as nine amino acid residues in length can be immunogenic when presented to an immune system in the context of a Major Histocompatibility Complex (MHC) molecule such as an MHC class I or MHC class II molecule. Accordingly, polypeptides having at least 9, 10, 11, 12, 13, 14, 15, 20, 25, 30, 35, 40, 45, 50, 55, 60, 70, 80, 90, 100, 150, 200, 250, 300, 350, 400, 450, 500, 550, 600, 650, 700, 750, 800, 900, 1000, 1050, 1100, 1150, 1200, 1250, 1300, 1350, or more consecutive amino acid residues of any amino acid sequence disclosed herein can be used as immunogens for producing antibodies.

Monoclonal antibodies to any of the polypeptides disclosed herein can be prepared from murine hybridomas according to the classic method of Kohler & Milstein (Nature 256:495-7, 1975) or a derivative method thereof.

Polyclonal antiserum containing antibodies to the heterogeneous epitopes of any polypeptide disclosed herein can be prepared by immunizing suitable animals with the polypeptide (or fragment thereof), which can be unmodified or modified to enhance immunogenicity. An effective immunization protocol for rabbits can be found in Vaitukaitis et al. (*J. Clin. Endocrinol. Metab.* 33:988-91, 1971).

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (*Methods Enzymol.* 178:476-96, 1989), Glockshuber et al. (*Biochemistry* 29:1362-7, 1990), U.S. Pat. No. 5,648,237 ("Expression of Functional Antibody Fragments"), U.S. Pat. No. 4,946,778 ("Single Polypeptide Chain Binding Molecules"), U.S. Pat. No. 5,455,030 ("Immunotherapy Using Single Chain Polypeptide Binding Molecules"), and references cited therein.

Transformed: A "transformed" cell is a cell into which a nucleic acid molecule has been introduced by, for example, molecular biology techniques. Transformation encompasses all techniques by which a nucleic acid molecule can be introduced into a cell including, without limitation, transfection with a viral vector, conjugation, transformation with a plasmid vector, and introduction of naked DNA by electroporation, lipofection, and particle gun acceleration.

Variants, fragments, or fusion polypeptides: The disclosed polypeptides, include variants, fragments, and fusions thereof. DNA sequences (for example SEQ ID NO: 11) which encode for a polypeptide (for example SEQ ID NO: 12), fusion polypeptide, or a fragment or variant of a polypeptide, can be engineered to allow the polypeptide to be expressed in eukaryotic cells, bacteria, insects, and/or plants. To obtain expression, the DNA sequence can be altered and operably linked to other regulatory sequences. The final product, which contains the regulatory sequences and the polypeptide-encoding sequence, is referred to as a vector. This vector can be introduced into eukaryotic, bacteria, insect, and/or plant cells. Once inside the cell the vector allows the polypeptide to be produced.

A fusion polypeptide can include a polypeptide, such as an aromatic aminotransferase (for example, SEQ ID NO: 12), linked to other amino acid sequences that do not inhibit the desired activity of the polypeptide (for example, the ability to convert tryptophan to indole-3-pyruvate). In one example, the other amino acid sequences are no more than about 10, 12, 15, 20, 25, 30, or 50 amino acids in length.

One of ordinary skill in the art will appreciate that a DNA sequence can be altered in numerous ways without affecting the biological activity of the encoded polypeptide. For example, PCR can be used to produce variations in the DNA sequence which encodes a polypeptide. Such variants can be variants optimized for codon preference in a host cell used to express the polypeptide, or other sequence changes that facilitate expression.

Vector: A nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art.

Overview of Biosynthetic Pathways

As shown in FIGS. 1-3 and 11-13, many biosynthetic pathways can be used to produce monatin or its intermediates such as indole-3-pyruvate or MP. For the conversion of each substrate (e.g., glucose, tryptophan, indole-3-lactic acid, indole-3-pyruvate, and MP) to each product (e.g., tryptophan, indole-3-pyruvate, MP and monatin), several different polypeptides can be used. Moreover, these reactions can be carried out in vivo, in vitro, or through a combination of in vivo reactions and in vitro reactions, such as in vitro reactions that include non-enzymatic chemical reactions. Therefore, FIGS. 1-3 and 11-13 are exemplary, and show multiple different pathways that can be used to obtain desired products.

Glucose to Tryptophan

Many organisms can synthesize tryptophan from glucose. The construct(s) containing the gene(s) necessary to produce monatin, MP, and/or indole-3-pyruvate from glucose and/or tryptophan can be cloned into such organisms. It is shown herein that tryptophan can be converted into monatin.

In other examples, an organism can be engineered using known polypeptides to produce tryptophan, or overproduce tryptophan. For example, U.S. Pat. No. 4,371,614 describes an *E. coli* strain transformed with a plasmid containing a wild type tryptophan operon. Tryptophan operon genes include tryptophan biosynthesis genes encoding the polypeptides anthranilate synthase component I (EC4.1.3.27), anthranilate synthase component II (EC4.1.3.27), N-(5'-phosphoribosyl) anthranilate isomerase (EC5.3.1.24)/indole-3-glycerol phosphate synthase (EC4.1.1.48), tryptophan synthase, alpha subunit (EC4.2.1.20) and tryptophan synthase, beta subunit (EC4.2.1.20), all of which are involved in producing tryptophan from chorismate.

Maximum titers of tryptophan disclosed in U.S. Pat. No. 4,371,614 are about 230 ppm. Similarly, WO 8701130 describes an *E. coli* strain that has been genetically engineered to produce tryptophan and discusses increasing fermentative production of L-tryptophan. Those skilled in the art will recognize that organisms capable of producing tryptophan from glucose are also capable of utilizing other carbon and energy sources that can be converted to glucose or fructose-6-phosphate, with similar results. Exemplary carbon and energy sources include, but are not limited to, sucrose, fructose, starch, cellulose, or glycerol.

Increasing Tryptophan Production

Tryptophan production is regulated in most organisms. One mechanism is via feedback inhibition of certain enzymes in the pathway. For example, increasing the level of tryptophan can result in a decrease of the production rate of tryptophan. Thus, when using a host cell engineered to produce monatin via a tryptophan intermediate, an organism can be used that is not sensitive to tryptophan concentrations. For example, a strain of *Catharanthus roseus* that is resistant to growth inhibition by various tryptophan analogs can be selected by repeated exposure to high concentrations of 5-methyltryptophan as described elsewhere (Schallenberg and Berlin, *Z. Naturforsch*, 34:541-5, 1979). The resulting tryptophan synthase activity of the strain can be less affected by product inhibition due to mutations in the gene.

Similar methods can be used to select for strains that have feedback resistance. For example, *E. coli* strain #7692 (from the *E. coli* Genetic Stock Center, W3110tnaA2trpEfbr19 (Yanofsky et al., *J. Bacteriol.*, 158: 1018-1024, 1984; and Doolittle and Yanofsky, *J. Bacteriol.*, 95:1253, 1968)) can be grown on phenylalanine analogs, beta-2-thienylalanine, m-fluoro-D,L-phenylalanine, and p-fluoro-D,L-phenylalanine to select for mutants with a feedback resistant aroG DAHP (3-deoxy-D-arabinoheptulosonic 7-phosphate acid) synthase. This *E. coli* strain #7692 can produce measurable amounts of tryptophan, and can be used as a starting host for introducing exogenous nucleic acids such as the nucleic acids encoding an aldolase and an aminotransferase. E971, another *E. coli* strain (ATCC15491), is a prototrophic strain that exhibits elevated levels of DAHP synthase as well as higher levels of indole and tryptophan than the parent strain (Lim and Mateles, 1964 *J. Bacteriol.*, 87: 1051-1055). This strain can be used to obtain anthranilate synthase (EC5.3.1.24) mutants where the feedback resistance has been reduced using a 5-methyltryptophan analog in the growth medium. This strain also can serve as a host to which the exogenous nucleic acids encoding the aldolase and aminotransferase are introduced.

Tryptophan production can be optimized through the use of directed evolution to evolve polypeptides that are less sensitive to product inhibition. For example, screening can be performed on plates containing no tryptophan in the medium, but with high levels of non-metabolizable tryptophan analogs. U.S. Pat. Nos. 5,756,345; 4,742,007; and 4,371,614 describe methods used to increase tryptophan productivity in a fermentation organism. The last step of tryptophan biosynthesis is the addition of serine to indole. Thus, the availability of serine can be increased to enhance tryptophan production.

A control point for tryptophan biosynthesis is the enzyme DAHP synthase. Three isozymes of this polypeptide are encoded by the following genes: aroF, aroG, and aroH, which can be feedback inhibited by tyrosine, phenylalanine, and tryptophan, respectively. The L-tyrosine feedback inhibited DAHP synthase contributes about 20% of the total enzyme activity, the L-phenylalanine feedback inhibited DAHP synthase contributes 80% of the total enzyme activity, and the L-tryptophan inhibited DAHP synthase provides very little contribution to the overall enzyme activity. Obtaining mutants whose enzymes are feedback resistant can provide strains where this control point is deregulated. In general, the major feedback resistant targets are aroG and aroF.

One approach to isolate feedback resistant mutants is to use chemical or ultraviolet mutagenesis and select for organisms that can grow on amino acid analogs. Feedback insensitive aroG can be obtained using the analog beta-2-thienylalanine (Duda and Sasvari-Szekely, (1973) *Acta. Biochim. Biophys. Acad. Sci. Hung.* 8(2):81-90). The analog m-fluoro-D,L-phenylalanine also can be used to generate feedback insensitive aroG (Ito et al., (1990) *Agric. Biol. Chem.*, 54(3):707-713) as well as p-fluorophenylalanine (Hagino and Nakayama, (1974) *Agr. Biol. Chem.*, 38(1): 157-161).

One approach for obtaining feedback resistant DAHP synthases is to use the amino acid analogs and create a strain where the native gene has been mutated. Another approach is to clone the gene encoding the feedback resistant enzyme, which provides more flexibility and, with the use of a different promoter, can reduce the possibility of transcriptional regulation (Ito et al., (1990) *Agric. Biol. Chem.*, 54(3):707-713).

Another regulatory point in tryptophan biosynthesis is the branch point enzyme, anthranilate synthase, which is a two component protein coded for by trpE and trpD in *E. coli*. Mutants which are released from feedback inhibition by tryptophan can be obtained using the amino acid analogs 5-fluorotryptophan and 5-methyltryptophan (Shiio et al., (1975) *Agr. Biol. Chem.*, 39(3):627-635).

In addition, feedback inhibition of anthranilate phosphoribosyltransferases and tryptophan synthases by tryptophan can occur in *Brevibacterium lactofermentum*. Desensitization of these enzymes to inhibition, however, can be accomplished (Matsui et al., (1987) *J. Bacteriol.*, 169: 5330-5332). Such mutants can exhibit elevated tryptophan levels and, therefore, would be expected to have increased monatin levels.

Cells use other methods of controlling the levels of tryptophan they synthesize, including regulation at the level of transcription. In *Corynebacterium glutamicum*, DAHP synthase is regulated at the level of transcription by tyrosine, and relief of this regulation by manipulation of the 5' regulatory region can improve tryptophan biosynthesis (Shiio, 1986 in Biotechnology of Amino Acid Production, Aida, K., Chibita, L., Nakayama, K., Takinami, K. and Yamada, H. Eds. Elsevier). In *E. coli*, the tryptophan (trp) operon is regulated at the level of transcription by both repression and attenuation, with repression responsible for an 80-fold variation and attenuation for a 6 to 8-fold variation. Inactivation of the TrpR polypeptide, which is the repressor protein, can increase levels of trp operon mRNA. The leader peptide forms an mRNA secondary structure that responds to levels of charged tRNA$^{trp}$. Deletion of the 5'-regulatory attenuation region can help to overcome this additional level of regulation (Yanofsky et al., *J. Bacteriol.*, 158: 1018-1024, 1984). An attenuation mechanism with a trp-RNA-Binding Attenuation Protein (TRAP) is also observed in *B. subtilis*, and relief of attenuation by down-regulation or deletion of the gene encoding it can improve tryptophan synthesis in this host organism (Babitzke and Gollnick, 2001, *J. Bacteriol.*, 183: 5795-5802). Alternatively, expression of an anti-TRAP polypeptide can be upregulated.

Tryptophan production can be increased by overexpressing polypeptides in a tryptophan pathway, which can improve monatin levels. For example, overexpression of nucleic acids encoding transketolase, of aroF$^{fbr}$, and of aroL (encodes shikimate kinase) can improve tryptophan production. Overexpression of these sequences, however, can cause a metabolic burden on the cells, and in minimal media, the cells can excrete various intermediates. A more nutrient rich media can be used to increase the levels of tryptophan (Kim et al., 2000, *J. Microbiol. Biotechnol.*, 10(6):789-796). In addition, *C. glutamicum* cells containing deregulated DAHP synthase expression, deregulated anthranilate synthase expression, and a multicopy plasmid encoding a phosphoribosyl transferase can exhibit increased tryptophan production to 43 g/L (Katsumata and Ikeda, (1993) *Bio/Technology*, 11:921-9250).

Other enzymes in the aromatic amino acid pathways that are subject to feedback and/or transcriptional control include shikimate dehydrogenase (encoded by aroE) and shikimate kinaseI/II (encoded by aroK, aroL). Mutagenesis of the aroE gene can provide feedback resistant enzymes. AroK and aroL are subject to negative transcriptional control by tyrosine. Genetic manipulation of the promoter region or deletion of regulatory genes (trpR and tyrR) can alleviate the control by tyrosine.

Phenylalanine and tyrosine are aromatic amino acids whose biosynthesis can divert carbon from tryptophan, due to the fact that chorismate is a common precursor for all three aromatic amino acids, and is a branch point between tryptophan metabolism and phenylalanine/tyrosine metabolism. The biosynthetic phenylalanine and tyrosine pathways can be deleted or disrupted to reduce the consumption of chorismate, this can be accomplished by genetic knockout of the pheA or tyrA genes coding for chorismate mutase/prephanate dehydrogenase. The chorismate mutase enzymes compete with anthranilate synthase (trpD and trpE gene product) for available chorismate. Exemplary strains that disruption or deletion of competing aromatic amino acid pathways include *E. coli* NRRL B 12262 (see Example 15), *E. coli* NRRL B 12258, *E. coli* SR250 (Rothman and Kirsch, *J. Mol Biol.* (2003) 327, 593-603), *C. glutamicum* ATCC21847 (see Example 17), *C. glutamicum* ATCC 21850, *C. glutamicum* ATCC21851. Alternatively, rather than deleting the phenylalanine and tyrosine pathways and requiring amino acid additions to the medium, the trpE gene (or the entire tryptophan operon) can be cloned and overexpressed using a heterologous promoter since anthranilate synthase has a higher affinity for chorismate than pheA or tyrA (Dopheide et al., (1972) *J. Biol. Chem.*, 247: 4447-4452). Another method of reducing the carbon flow to phenylalanine and tyrosine is to modify their transcriptional control. Further, reducing expression of a tryptophanase polypeptide, an enzyme that catalyzes the conversion of tryptophan to indole and pyruvate, can help prevent loss of tryptophan (Aiba et al., *Appl. Environ. Microbiol.*, 1982, 43:289-297).

In one embodiment, the central metabolism can be engineered to increase monatin production. As described herein, to obtain adequate monatin production, the selected or obtained organisms should have the capacity to produce tryptophan at a rate than is increased over wildtype organisms. Given that tryptophan is not an end product, but an intermediate in the pathway to monatin, it can be important to develop strains that not only have the ability to accumulate higher concentrations of tryptophan, but also have an increased flux to it. Multiple strategies can be used to engineer the central carbon metabolism to divert carbon into the shikimate and chorismate pathway such that high levels of monatin can be produced.

The first step in the biosynthesis of aromatic compounds such as tryptophan, tyrosine, and phenylalanine is the condensation of phophoenolpyruvate (PEP) and erythrose 4-phosphate (E4P) to form DAHP. Various methods can be used to increase the availability of each precursor and improve the performance of this first reaction. The following five methods are possible examples of procedures that can be used to increase PEP availability.

First, consumption of PEP through glucose uptake by the phosphotransferase system (PTS) can be eliminated. Inactivation of the glucose transport system can result in glucose negative mutants. PTS$^-$ glucose$^+$ mutants have been isolated. Some of them transport and phosphorylate glucose via galactose permease, glucokinase, and ATP, and do not consume PEP (Flores et al., (1996) *Nat. Biotechnol.*, 14:620-623; and Chen et al., (1997) *Biotechnol. Prog.*, 13:768-775). The glucose permease system requires higher amounts of ATP to phosphorylate glucose. A different glucose transport and phosphorylation system, which also can result in increased levels of PEP, can be introduced by the addition of genes encoding a glucose facilitator (encoded by glf), a glucose dehydrogenase (encoded by gdhIV), and a gluconate kinase (encoded by glk) (WO 99/55877). This mechanism can produce gluconate 6-phosphate, which is an intermediate in the pentose phosphate pathway, and therefore can increase the carbon flux in this pathway and result in increased levels of E4P.

Second, PEP consuming enzymes, PEP carboxylase (Ppc), and pyruvate kinases (e.g., PykA and PykB) can be inactivated to increase the pool of PEP available (Bongaerts et al., (2001) *Met. Eng.*, 3, 289-300).

Third, the pyruvate formed by either the PTS or pyruvate kinases can be recycled back to PEP by enhancing expression of PEP synthase (Pps) (Patnaik et al., (1995) *Biotechnol. Bioeng.*, 46:361-370; and Yi et al., (2002) *Biotechnol. Prog.*, 18:1141-1148).

Fourth, the gluconeogenesis regulation can be modified by disrupting the csrA gene, (carbon storage regulator) which can increase gluconeogenesis, influence the regulation of several enzymes that participate in PEP metabolism, decrease glycolysis, and elevate PEP levels. (Tatarko et al., (2001) *Current Microbiol.*, 43(1):26-32).

Fifth, PEP consumption can be lessened by feeding sugars such as xylose that, unlike glucose, circumvent the PTS system for transport into the cell.

To increase the availability of E4P, the tktA gene encoding transketolase and/or the talB gene encoding transaldolase can be overexpressed. Expression of a tranketolase can be more effective in directing carbon flux into the aromatic pathway (Liao at al., (1996) *Biotechnol. Bioeng.*, 52:129-140). For example, a *Corynebacterium glutamicum* strain with a modified pentose phosphate pathway can be used to produce tryptophan (KY9218 carrying pKW9901; Ikeda and Katsumata, *Appl. Environ. Microbiol.*, 1999, 65(6):2497-502).

Any combination of these methods can be used. For example, a combination of several of these modifications can be applied to *E. coli* strains. In a PTS⁻ glucose⁺, pykA, pykB strain that overexpressed tktA, an almost 20 fold increase in carbon flux to the aromatic pathway can be achieved (Gosset et al., (1996) *J. Ind. Microbiol.*, 17:47-52). In addition, these methods can be combined with other modifications to reduce bottlenecks that occur later in the tryptophan biosynthetic pathway (e.g., overexpressing genes in the tryptophan branch of the aromatic pathway, deleting pheA and tyrA genes to avoid consumption of chorismate, overexpressing trpE and trpD to increase the synthesis of anthranilic acid) to increase tryptophan production. The produced tryptophan need not accumulate in the cells since it can be further converted to products such as monatin.

The production of tryptophan, and subsequently that of monatin, can benefit from alterations in the pathway leading to the production of serine. Serine is required in the last step of production of tryptophan, which encompasses the reaction of serine with indole-3-glycerolphosphate. This reaction is catalyzed by a tryptophan synthase polypeptide. Increases in the carbon flow through the tryptophan pathway can result in imbalances in some reactions with the appearances of new bottlenecks. As serine is produced by a separate pathway, its production rate can become a limiting factor in the production of tryptophan. The carbon flow through the serine pathway can be increased by overexpression of the first gene in the pathway, which encodes for 3-phosphoglycerate dehydrogenase (PDG; Ikeda et al., (1994) *Biosci. Biotech. Biochem.*, 58(4):674-678).

Increasing Pyruvate Production

The amount of monatin produced by an organism can be enhanced by increasing the amount of pyruvate produced by the host organism. One pathway for the production of monatin relies on the reaction of indole-3-pyruvate with pyruvate to form the 4-keto acid derivative of monatin. To push this reaction forward, an organism capable of diverting large quantities of carbon to pyruvate is useful as a host for the production of monatin. Pyruvate overproducers can be selected, which do not need to be tolerant to high concentrations of the acid, but rather are deregulated in their metabolic pathway so that more carbon is diverted to pyruvate. Certain yeasts, such as *Trichosporon cutaneum* (Wang et al., *Lett. Appl. Microbiol.*, 35:338-42, 2002), *Candida lypolitica*, *Saccharomyces cerevisiae*, and *Candida glabrata* (formerly known as *Torulopsis glabrata*) (Li et al., *Appl. Microbiol. Biotechnol.*, 57:451-9, 2001) overproduce pyruvate from glucose (up to 50 g/L) and can be used to produce the products described herein.

Thiamine auxotrophs of these different strains accumulate pyruvate under thiamine limitation, because the oxidative decarboxylation of pyruvate is impaired by a decrease in the activity of the thiamine dependent pyruvate dehydrogenase (PDH). Lipoic acid is a cofactor of PDH. As such, lipoic acid auxotrophs, such as *E. coli* strain W1485lip2 (ATCC25645; Kawasaki et al., *J. Ferment. Bioeng.*, 82:604-6, 1996) can accumulate pyruvate to a significant extent (>25 g/L) (Yokota et al., *Appl. Microbiol. Biotechnol.*, 41:638-643, 1994). The rate and amount of pyruvate production can be further increased by introducing a F1-ATPase defective gene into the W1485lip2 strain. This mutation results in a cell deficient in energy production, which tends to compensate by increasing the carbon flux through glycolysis and, thus, generating larger amounts of pyruvic acid (Yokota et al., *J. Ferment. Bioeng.*, 83:132-138, 1997). A double mutant strain can be used to generate host strains that overproduce several amino acids including tryptophan (Kawasaki et al., 1996 supra), leucine and valine (U.S. Pat. Nos. 5,888,783 and 6,214,591).

In addition to mutations in the pyruvate-dehydrogenase complex, further improvements in pyruvate production can be obtained by deleting or reducing the expression of pyruvate decarboxylase, pyruvate ferredoxin-oxidoreductase, pyruvate flavodoxin oxidoreductase, pyruvate-formiate lyase, pyruvate carboxylase, phosphoenolpyruvate synthetase, and/or pyruvate oxidase. See, for example, WO 03/000913.

Overexpression of a tryptophanase gene in a pyruvate overproducing strain can be used to produce tryptophan from indole (Kawasaki et al., 1996, supra). The overproduction of pyruvate can improve the production of tryptophan and also provide increased substrate levels (both pyruvate and indole-3-pyruvate) for the formation of the monatin precursor. Alternatively, when using the tryptophanase gene one can simultaneously feed both pyruvate and indole in the presence of excess ammonium. Detergents can be utilized to increase the solubility of indole, or indole can be fed sequentially to minimize toxicity and precipitation.

Tryptophan to Indole-3-pyruvate

Several polypeptides can be used to convert tryptophan to indole-3-pyruvate. Exemplary polypeptides include, without limitation, members of the enzyme classes (EC) 2.6.1.27, 1.4.1.19, 1.4.99.1, 2.6.1.28, 1.4.3.2, 1.4.3.3, 2.6.1.5, 2.6.1.-, 2.6.1.1, and 2.6.1.21. These classes include, without limitation, polypeptides termed tryptophan aminotransferase (also termed L-phenylalanine-2-oxoglutarate aminotransferase, tryptophan transaminase, 5-hydroxytryptophan-ketoglutaric transaminase, hydroxytryptophan aminotransferase, L-tryptophan aminotransferase, L-tryptophan transaminase, and L-tryptophan:2-oxoglutarate aminotransferase) which converts L-tryptophan and 2-oxoglutarate to indole-3-pyruvate and L-glutamate; D-tryptophan aminotransferase which converts D-tryptophan and a 2-oxo acid to indole-3-pyruvate and an amino acid; tryptophan dehydrogenase (also termed NAD(P)-L-tryptophan dehydrogenase, L-tryptophan dehydrogenase, L-Trp-dehydrogenase, TDH and L-tryptophan:NAD(P) oxidoreductase (deaminating)) which converts L-tryptophan and NAD(P) to indole-3-pyruvate and $NH_3$ and NAD(P)H; D-amino acid dehydrogenase, which converts D-amino acids and FAD to indole-3-pyruvate and $NH_3$ and $FADH_2$; tryptophan-phenylpyruvate transaminase (also termed L-tryptophan-α-ketoisocaproate aminotransferase and L-tryptophan:phenylpyruvate aminotransferase) which converts L-tryptophan and phenylpyruvate to indole-3-pyruvate and L-phenylalanine; L-amino acid oxidase (also termed ophio-amino-acid oxidase and L-amino-acid:oxygen oxidoreductase (deaminating)) which converts an L-amino acid and $H_2O$ and $O_2$ to a 2-oxo acid and $NH_3$ and $H_2O_2$; D-amino acid oxidase (also termed ophio-amino-acid oxidase and D-amino-acid:oxygen oxidoreductase (deaminating)) which converts a D-amino acid and $H_2O$ and $O_2$ to a 2-oxo acid and $NH_3$ and $H_2O_2$; and tryptophan oxidase which converts L-tryptophan and $H_2O$ and $O_2$ to indole-3-pyruvate and $NH_3$ and $H_2O_2$. These classes also contain tyrosine (aromatic) aminotransferase, aspartate aminotransferase, D-amino acid (or D-alanine) aminotransferase, and broad (multiple substrate) aminotransferase which have multiple aminotransferase activities, some of which can convert tryptophan and a 2-oxo acid to indole-3-pyruvate and an amino acid.

Eleven members of the aminotransferase class that have such activity are described below in Example 1, including a novel aminotransferase shown in SEQ ID NOS: 11 and 12. Therefore, this disclosure provides isolated nucleic acid and amino acid sequences having at least 80%, at least 85%, at least 90%, at least 95%, at least 98%, or even at least 99% sequence identity to the sequences set forth in SEQ ID NOS: 11 and 12, respectively. Also encompassed by this disclosure are fragments and fusions of the sequences set forth in SEQ ID NOS: 11 and 12 that encode a polypeptide having aminotransferase activity or retaining aminotransferase activity. Exemplary fragments include, but are not limited to, at least 10, 12, 15, 20, 25, 50, 100, 200, 500, or 1000 contiguous nucleotides of SEQ ID NO: 11 or at least 6, 10, 15, 20, 25, 50, 75, 100, 200, 300 or 350 contiguous amino acids of SEQ ID NO: 12. The disclosed sequences (and variants, fragments, and fusions thereof) can be part of a vector. The vector can be used to transform host cells, thereby producing recombinant cells which can produce indole-3-pyruvate from tryptophan, and in some examples can further produce MP and/or monatin.

L-amino acid oxidases (1.4.3.2) are known, and sequences can be isolated from several different sources, such as *Vipera lebetine* (sp P81375), *Ophiophagus hannah* (sp P81383), *Agkistrodon rhodostoma* (spP81382), *Crotalus atrox* (sp P56742), *Burkholderia cepacia*, *Arabidopsis thaliana*, *Caulobacter cresentus*, *Chlamydomonas reinhardtii*, *Mus musculus*, *Pseudomonas syringae*, and *Rhodococcus* str. In addition, tryptophan oxidases are described in the literature and can be isolated, for example, from *Coprinus* sp. SF-1, Chinese cabbage with club root disease, *Arabidopsis thaliana*, and mammalian liver.

Tryptophan dehydrogenases are known, and can be isolated, for example, from spinach, *Pisum sativum*, *Prosopis juliflora*, pea, mesquite, wheat, maize, tomato, tobacco, *Chromobacterium violaceum*, and *Lactobacilli*. Many D-amino acid dehydrogenase gene sequences are known.

As shown in FIGS. 11-13, if an amino acid oxidase, such as tryptophan oxidase, is used to convert tryptophan to indole-3-pyruvate, catalase can be added to reduce or even eliminate the presence of hydrogen peroxide.

Indole-3-lactate to Indole-3-pyruvate

The reaction that converts indole-3-lactate to indole-3-pyruvate can be catalyzed by a variety of polypeptides, such as members of the 1.1.1.110, 1.1.1.27, 1.1.1.28, 1.1.2.3, 1.1.1.222, 1.1.1.237, 1.1.3.-, or 1.1.1.111 classes of polypeptides. The 1.1.1.110 class of polypeptides includes indolelactate dehydrogenases (also termed indolelactic acid: $NAD^+$ oxidoreductase). The 1.1.1.27, 1.1.1.28, and 1.1.2.3 classes include lactate dehydrogenases (also termed lactic acid dehydrogenases, lactate: $NAD^+$ oxidoreductase). The 1.1.1.222 class contains (R)-4-hydroxyphenyllactate dehydrogenase (also termed D-aromatic lactate dehydrogenase, R-aromatic lactate dehydrogenase, and R-3-(4-hydroxyphenyl)lactate: $NAD(P)^+$2-oxidoreductase) and the 1.1.1.237 class contains 3-(4-hydroxyphenylpyruvate) reductase (also termed hydroxyphenylpyruvate reductase and 4-hydroxyphenyllactate: $NAD^+$ oxidoreductase). The 1.1.3.- class contains lactate oxidases, and the 1.1.1.111 class contains (3-imidazol-5-yl) lactate dehydrogenases (also termed (S)-3-(imidazol-5-yl) lactate:$NAD(P)^+$ oxidoreductase). It is likely that several of the polypeptides in these classes allow for the production of indole-3-pyruvate from indole-3-lactic acid.

Chemical reactions can also be used to convert indole-3-lactic acid to indole-3-pyruvate. Such chemical reactions include an oxidation step that can be accomplished using several methods, for example: air oxidation using a B2 catalyst (China Chemical Reporter, vol. 13, no. 28, pg. 18(1), 2002), dilute permanganate and perchlorate, or hydrogen peroxide in the presence of metal catalysts.

Indole-3-pyruvate to 2-hydroxy 2-(indol-3ylmethyl)-4-keto glutaric acid (MP)

Several known polypeptides can be used to convert indole-3-pyruvate plus a three-carbon source, such as pyruvate, to MP. Exemplary polypeptide classes include 4.1.3.-, 4.1.3.16, 4.1.3.17, and 4.1.2.-. These classes include carbon-carbon synthases/lyases, such as aldolases that catalyze the condensation of two carboxylic acid substrates. Polypeptide class EC4.1.3.- are synthases/lyases that form carbon-carbon bonds utilizing oxo-acid substrates (such as indole-3-pyruvate) as the electrophile, while EC4.1.2.- are synthases/lyases that form carbon-carbon bonds utilizing aldehyde substrates (such as benzaldehyde) as the electrophile.

For example, the polypeptide described in EP 1045-029 (EC4.1.3.16, 4-hydroxy-2-oxoglutarate glyoxylate-lyase also termed 4-hydroxy-2-oxoglutarate aldolase, 2-oxo-4-hydroxyglutarate aldolase or KHG aldolase) converts glyoxylic acid and pyruvate to 4-hydroxy-2-ketoglutaric acid, and the polypeptide 4-hydroxy-4-methyl-2-oxoglutarate aldolase (EC4.1.3.17, also termed 4-hydroxy-4-methyl-2-oxoglutarate pyruvate-lyase or ProA aldolase), condenses two keto-acids such as two pyruvates to 4-hydroxy-4-methyl-2-oxo-glutarate. Reactions utilizing these lyases are described herein.

FIGS. 1-2 and 11-13 show schematic diagrams of these reactions in which a 3-carbon (C3) molecule is combined with indole-3-pyruvate. Many members of EC 4.1.2.- and 4.1.3.-, particularly PLP-utilizing polypeptides, can utilize C3 molecules that are amino acids such as serine, cysteine, and alanine, or derivatives thereof. Aldol condensations catalyzed by representatives of EC4.1.2.- and 4.1.3.- require the three carbon molecule of this pathway to be pyruvate or a derivative of pyruvate. However, other compounds can serve as a C3 carbon source and be converted to pyruvate. Alanine can be transaminated by many PLP-utilizing transaminases, including many of those mentioned above, to yield pyruvate. Pyruvate and ammonia can be obtained by beta-elimination reactions (such as those catalyzed by, tryptophanase or β-tyrosinase) of L-serine, L-cysteine, and derivatives of serine and cysteine with sufficient leaving groups, such as O-methyl-L-serine, O-benzyl-L-serine, S-methylcysteine, S-benzylcysteine, S-alkyl-L-cysteine, O-acyl-L-serine, and 3-chloro-L-alanine. Aspartate can serve as a source of pyruvate in PLP-mediated beta-lyase reactions such as those catalyzed by tryptophanase (EC4.1.99.1) and/or β-tyrosinase (EC4.1.99.2, also termed tyrosine-phenol lyase). The rate of beta-lyase reactions can be increased by performing site-directed mutagenesis on the (4.1.99.1-2) polypeptides as described by Mouratou et al. (*J. Biol. Chem* 274:1320-5, 1999) and in Example 5. These modifications allow the polypeptides to accept dicarboxylic amino acid substrates. Lactate can also serve as a source of pyruvate, and is oxidized to pyruvate by the addition of lactate dehydrogenase and an oxidized cofactor or lactate oxidase and oxygen. Examples of these reactions are described below. For example, as shown in FIG. 2 and FIGS. 11-13, ProA aldolase can be contacted with indole-3-pyruvate when pyruvate is used as the C3 molecule.

MP to Monatin

Conversion of MP to monatin can be catalyzed by one or more of: tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (EC1.4.1.20), tryptophan-phenylpyruvate transaminases (2.6.1.28), or more generally members of the aminotransferase family (2.6.1.-) such as aspartate aminotransferase (EC2.6.1.1), tyrosine (aromatic) aminotransferase (2.6.1.5), D-tryptophan aminotransferase, or D-alanine (2.6.1.21) aminotransferase (FIG. 2). Eleven members of the aminotransferase class are described below (Example 1), including a novel member of the class shown in SEQ ID NOS: 11 and 12, and reactions demonstrating the activity of aminotransferase and dehydrogenase enzymes are provided in Example 4.

This reaction can also be performed using chemical reactions. Amination of the keto acid (MP) is performed by reductive amination using ammonia and sodium cyanoborohydride.

FIGS. 11-13 show additional polypeptides that can be used to convert MP to monatin, as well as providing increased yields of monatin from indole-3-pyruvate or tryptophan. For example, if aspartate is used as the amino donor, aspartate aminotransferase can be used to convert the aspartate to oxaloacetate (FIG. 11). The oxaloacetate is converted to pyruvate and carbon dioxide by a decarboxylase, such as oxaloacetate decarboxylase (FIG. 11). In addition, if lysine is used as the amino donor, lysine epsilon aminotransferase can be used to convert the lysine to allysine (FIG. 12). The allysine is spontaneously converted to 1-piperidine 6-carboxylate (FIG. 12). If a polypeptide capable of catalyzing reductive amination reactions (e.g., glutamate dehydrogenase) is used to convert MP to monatin, a polypeptide that can recycle NAD(P)H and/or produce a volatile product (FIG. 13) can be used, such as formate dehydrogenase.

Further Methods for Increasing Monatin Production

Other examples of strains with genetic modifications that can be used to increase monatin production include:

1) *E. coli* AGX1757 can be isolated from W3110 (trpAE1, trpR, tnaA with plasmid pSC101+trpI). NTG mutagenesis can be performed and 6-fluorotryptophan or 5-methyltryptophan resistance selected. The addition of Pluronic L-61 can be used to crystallize tryptophan or monatin in media to increase productivity.

2) *C. glutamicum* KY9225, which was derived from Px-115-97, exhibits phenylalanine and tyrosine double auxotrophy and has an anthranilate synthase resistant to tryptophan inhibition.

3) *Brevibacterium lactofermentum* 1041 trpE was mutagenized and desensitized to tryptophan feedback inhibition. The gene was found to have a serine residue replaced by an arginine. A mutation of guanine to adenine in the terminator structure within the putative attenuator was found to relieve transcriptional regulation as well (Matsui et al., (1987) *J. Bacteriology*, 16:5330-5332).

Additional modifications that can be useful in optimizing availability of precursors and maximizing monatin production include, without limitation, (1) deleting genes that encode polypeptides that can facilitate monatin uptake, (2) deleting or down-regulating genes that encode polypeptides involved in competing pathways, (3) upregulating aldolase and aminotransferase polypeptide expression, (4) deleting genes that encode aminotransferase polypeptides that produce an incorrect form of monatin, and (5) increasing PLP availability. Genes that encode polypeptides that can facilitate monatin uptake can include the *Bacillus subtilis* aspartate uptake transporter (YveA; Lorca et al., 2003, *J. Bacteriol.*, 185(10):3218-22), the Glt-1 L-glutamate/L-aspartate/D-aspartate uptake polypeptides (symporters), and the *C. glutamicum* gluA,B,C,D glutamate uptake genes. A gene that encodes a polypeptide involved in a competing pathway can be a tnaA gene (encodes a tryptophanase polypeptide), unless indole is utilized as a substrate for tryptophan production.

Additional Considerations in the Design of the Biosynthetic Pathways

Depending on which polypeptides are used to generate indole-3-pyruvate, MP, and/or monatin, cofactors, substrates, and/or additional polypeptides can be provided to the production cell to enhance product formation. In addition, genetic modification can be designed to enhance production of products such as indole-3-pyruvate, MP, and/or monatin. Similarly, a host cell used for monatin production can be optimized.

As described herein, any organism such as *E. coli* and other Enterobacteriaceae (such as *Klebsiella*, *Pantoea*, and *Erwinia* strains), *Corynebacterium glutamicum*, *Brevibacterium* strains, *Bacillus* strains, and *Saccharomyces* strains can be used to produce a product such as indole-3-pyruvate, MP, and/or monatin. For example, *Bacillus amyloliquefaciens* and *B. subtilis*, which have been engineered to overproduce tryptophan from anthranilic acid (resulting in many problematic byproducts), can be modified to produce products efficiently. Additionally, there are wild-type *Brevibacterium flavum* and *Corynebacterium glutamicum* strains that produce glutamate, and have been modified to efficiently produce other amino acids such as lysine. T. Oka, "Amino Acids, Production Processes" in Encyclopedia of Bioprocess Technology: Fermentation, Biocatalysis, and Bioseparation. M. C. Flickinger and S. W. Drew, eds. John Wiley & Sons, Inc. New York, pp. 89-100. In addition, the organisms described herein can be selected or designed to (1) have favorable growth kinetics such that they can grow on low-cost substrates, (2) secrete products such as monatin, and/or (3) produce increased levels of precursors to monatin such as tryptophan and pyruvate. Such organisms can be from well-characterized species with readily available genetics tools and/or a history of safe use in producing food ingredients.

1. Removal of Hydrogen Peroxide

Hydrogen peroxide ($H_2O_2$) is a product that, if generated, can be toxic to production cells and can damage polypeptides or products (e.g., intermediates) produced. The L-amino acid oxidase described above generates $H_2O_2$ as a product. Therefore, if L-amino acid oxidase is used, the resulting $H_2O_2$ can be removed or its levels decreased to reduce potential injury to the cell or product.

Catalases can be used to reduce the level of $H_2O_2$ in the cell (FIGS. 11-13). The production cell can express a gene or cDNA sequence that encodes a catalase (EC 1.11.1.6), which catalyzes the decomposition of hydrogen peroxide into water and oxygen gas. For example, a catalase can be expressed from a vector transfected into the production cell. Examples of catalases that can be used include, but are not limited to: tr|Q9EV50 (*Staphylococcus xylosus*), tr|Q9KBE8 (*Bacillus halodurans*), tr|Q9URJ7 (*Candida albicans*), tr|P77948 (*Streptomyces coelicolor*), tr|Q9RBJ5 (*Xanthomonas campestris*) (SwissProt Accession Nos.). Biocatalytic reactors utilizing L-amino acid oxidase, D-amino acid oxidase, or tryptophan oxidase can also contain a catalase polypeptide.

2. Modulation of pyridoxal-5'-phosphate (PLP) Availability

Figure 1:
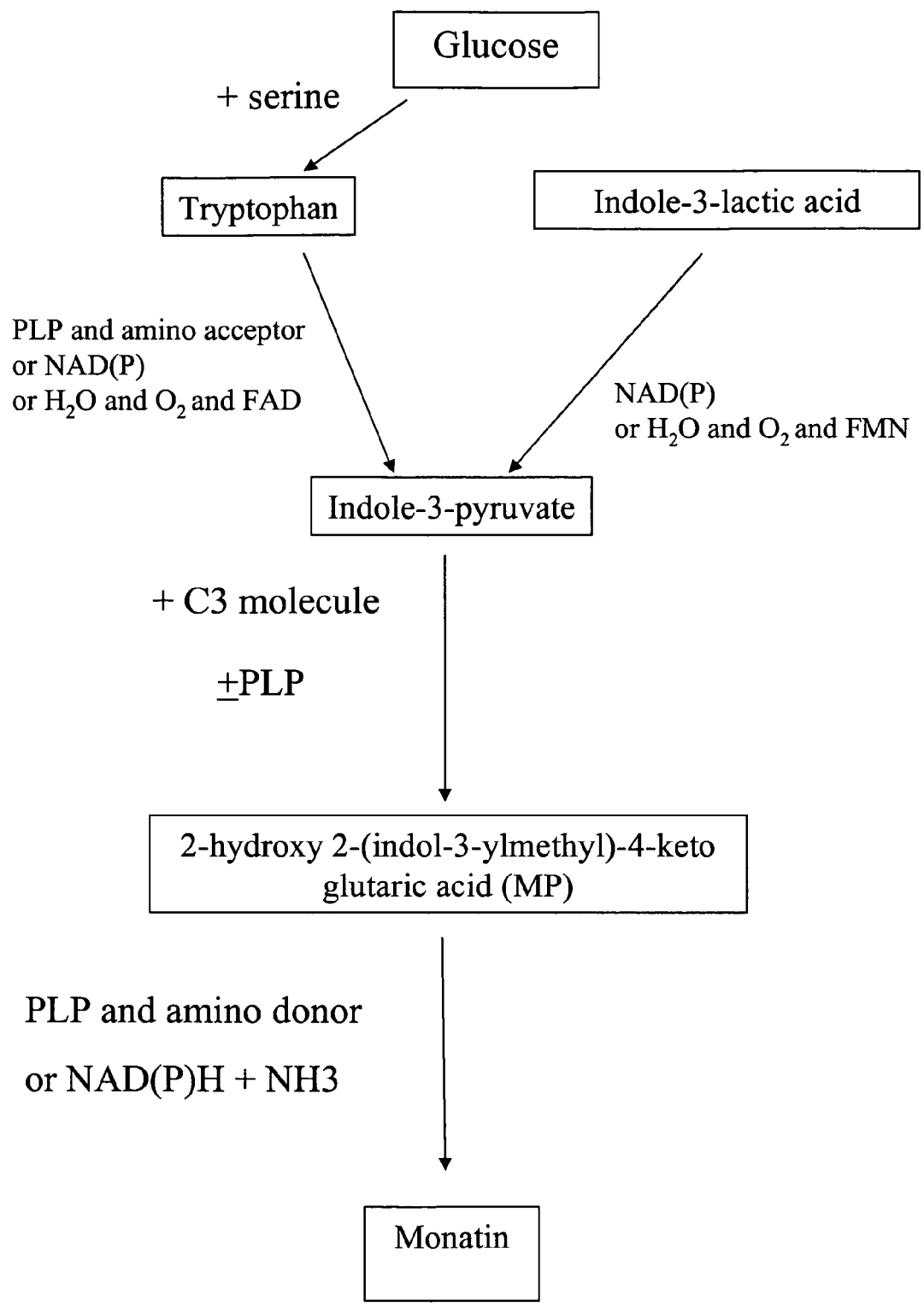
FIG. 1 shows biosynthetic pathways used to produce monatin and/or indole-3-pyruvate. One pathway produces indole-3-pyruvate via tryptophan, while another produces indole-3-pyruvate via indole-3-lactic acid. Monatin is subsequently produced via a MP intermediate.

As shown in FIG. 1, PLP can be utilized in one or more of the biosynthetic steps described herein. The concentration of PLP can be supplemented so that PLP does not become a limitation on the overall efficiency of the reaction.

The biosynthetic pathway for vitamin $B_6$ (the precursor of PLP) has been thoroughly studied in *E. coli*, and some of the proteins have been crystallized (Laber et al., *FEBS Letters*, 449:45-8, 1999). Two of the genes (epd or gapB and serC) are required in other metabolic pathways, while three genes (pdxA, pdxB, and pdxJ) are unique to pyridoxal phosphate biosynthesis. One of the starting materials in the *E. coli* pathway is 1-deoxy-D-xylulose-5-phosphate (DXP). Synthesis of this precursor from common 2 and 3 carbon central metabolites is catalyzed by the polypeptide 1-deoxy-D-xylulose-5-phosphate synthase (DXS). The other precursor is a threonine derivative formed from the 4-carbon sugar, D-erythrose 4-phosphate. The genes required for the conversion to phospho-4-hydroxyl-L threonine (HTP) are epd, pdxB, and serC. The last reaction for the formation of PLP is a complex intramolecular condensation and ring-closure reaction between DXP and HTP, catalyzed by the gene products of pdxA and pdxJ.

If PLP becomes a limiting nutrient during the fermentation to produce monatin, increased expression of one or more of the pathway genes in a production host cell can be used to increase the yield of monatin. A host organism can contain multiple copies of its native pathway genes or copies of non-native pathway genes can be incorporated into the organism's genome. Additionally, multiple copies of the salvage pathway genes can be cloned into the host organism.

One salvage pathway that is conserved in all organisms recycles the various derivatives of vitamin $B_6$ to the active PLP form. The polypeptides involved in this pathway are pdxK kinase, pdxH oxidase, and pdxY kinase. Over-expression of one or more of these genes can increase PLP availability.

Vitamin $B_6$ levels can be elevated by elimination or repression of the metabolic regulation of the native biosynthetic pathway genes in the host organism. PLP represses polypeptides involved in the biosynthesis of the precursor threonine derivative in the bacterium *Flavobacterium* sp. strain 238-7. This bacterial strain, freed of metabolic control, overproduces pyridoxal derivatives and can excrete up to 20 mg/L of PLP. Genetic manipulation of the host organism producing monatin in a similar fashion will allow the increased production PLP without over-expression of the biosynthetic pathway genes.

3. Ammonium Utilization

Tryptophanase reactions can be driven toward the synthetic direction (production of tryptophan from indole) by making ammonia more available or by removal of water. Reductive amination reactions, such as those catalyzed by glutamate dehydrogenase, can also be driven forward by an excess of ammonium.

Ammonia can be made available as an ammonium carbonate or ammonium phosphate salt in a carbonate or phosphate buffered system. Ammonia can also be provided as ammonium pyruvate or ammonium formate. Alternatively, ammonia can be supplied if the reaction is coupled with a reaction that generates ammonia, such as glutamate dehydrogenase or tryptophan dehydrogenase. Ammonia can be generated by addition of the natural substrates of EC4.1.99.-(tyrosine or tryptophan), which will be hydrolyzed to phenol or indole, pyruvate and $NH_3$. This also allows for an increased yield of synthetic product over the normal equilibrium amount by allowing the enzyme to hydrolyze its preferred substrate.

4. Removal of Products and Byproducts

The conversion of tryptophan to indole-3-pyruvate via a tryptophan aminotransferase can adversely affect the production rate of indole-3-pyruvate because the reaction produces glutamate and requires the co-substrate 2-oxoglutarate (α-ketoglutarate). Glutamate can cause inhibition of the aminotransferase, and the reaction can consume large amounts of the co-substrate. Moreover, high glutamate concentrations can be detrimental to downstream separation processes.

The polypeptide glutamate dehydrogenase (GLDH) converts glutamate to 2-oxoglutarate, thereby recycling the co-substrate in the reaction catalyzed by tryptophan aminotransferase. GLDH also generates reducing equivalents (NADH or NADPH) that can be used to generate energy for the cell (ATP) under aerobic conditions. The utilization of glutamate by GLDH also reduces byproduct formation. Additionally, the reaction generates ammonia, which can serve as a nitrogen source for the cell or as a substrate in a reductive amination for the final step shown in FIG. 1. Therefore, a production cell that over-expresses a GLDH polypeptide can be used to increase the yield and reduce the cost of media and/or separation processes.

In the tryptophan to monatin pathway, the amino donor of step three (e.g., glutamate or aspartate) can be converted back to the amino acceptor required for step 1 (e.g., 2-oxo-glutarate or oxaloacetate), if an aminotransferase from the appropriate enzyme classes is used. Utilization of two separate transaminases for this pathway, in which the substrate of one transaminase does not competitively inhibit the activity of the other transaminase, can increase the efficiency of this pathway.

Many of the reactions in the described pathways are reversible and can, therefore, reach an equilibrium between substrates and products. The yield of the pathway can be increased by continuous removal of the products from the polypeptides. For example, secretion of monatin into the fermentation broth using a permease or other transport protein, or selective crystallization of monatin from a biocatalytic reactor stream with concomitant recycle of substrates will increase the reaction yield.

Removal of byproducts via additional enzymatic reactions or via substitution of amino donor groups is another way to increase the reaction yield. For example, a byproduct can be produced that is unavailable to react in the reverse direction, either by phase change (for example, the precipitation of the end product) or by spontaneous conversion to a volatile end product, such as carbon dioxide.

5. Modulation of the Substrate Pools

The indole pool can be modulated by increasing production of tryptophan precursors and/or altering catabolic pathways involving indole-3-pyruvate and/or tryptophan. For example, the production of indole-3-acetic acid from indole-3-pyruvate can be reduced or eliminated by functionally deleting the gene coding for EC4.1.1.74 in the host cell. Production of indole from tryptophan can be reduced or eliminated by functionally deleting the gene coding for EC4.1.99.1 in the host cell. Alternatively, an excess of indole can be utilized as a substrate in an in vitro or in vivo process in combination with increased amounts of the gene coding for EC4.1.99.1 (Kawasaki et al., *J. Ferm. and Bioeng.*, 82:604-6, 1996).

In addition, genetic modifications can be made to increase the level of intermediates such as D-erythrose-4-phosphate and chorismate.

6. Controlling Chirality

The taste profile of monatin can be altered by controlling its stereochemistry (chirality). For example, different monatin isomers may be desired in different blends of concentrations for different food systems. Chirality can be controlled via a combination of pH and polypeptides.

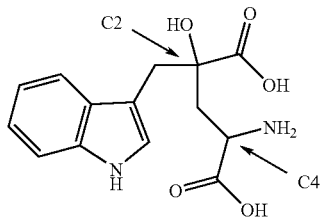

Racemization at the C-4 position of monatin (see numbered molecule above) can occur by deprotonation and reprotonation of the alpha carbon, which can occur by a shift in pH or by reaction with the cofactor PLP bound to an enzyme such as a racemase or free in solution. In a microorganism, the pH is unlikely to shift enough to cause the racemization, but PLP is abundant. Methods to control the chirality with polypeptides depend upon the biosynthetic route utilized for monatin production.

When monatin is formed using the pathway shown in FIG. 2, the following can be considered. In a biocatalytic reaction, the chirality of carbon-2 can be determined by an enzyme that converts indole-3-pyruvate to MP. Multiple enzymes (e.g., from EC4.1.2.-, 4.1.3.-) can convert indole-3-pyruvate to MN, thus, the enzyme that forms the desired isomer can be chosen. Alternatively, the enantiospecificity of the enzyme that converts indole-3-pyruvate to MP can be modified through the use of directed evolution, or catalytic antibodies can be engineered to catalyze the desired reaction. Once MP is produced (either enzymatically or by chemical condensation), the amino group can be added stereospecifically using a transaminase, such as those described herein. Either the R or S configuration of carbon-4 can be generated depending on whether a D- or L-aromatic acid aminotransferase is used. Most aminotransferases react preferentially with the L-isomer of the substrate; however, D-tryptophan aminotransferases exist in certain plants (Kohiba and Mito, Proceedings of the 8th International Symposium on Vitamin $B_6$ and Carbonyl Catalysis, Osaka, Japan 1990). Moreover, D-alanine aminotransferases (2.6.1.21), D-methionine-pyruvate aminotransferases (2.6.1.41), and both (R)-3-amino-2-methylpropanoate aminotransferase (2.6.1.61) and (S)-3-amino-2-methylpropanoate aminotransferase (2.6.1.22) have been identified. Certain aminotransferases may preferentially react with a substrate having a particular configuration at the C2 carbon. Therefore, even if the conversion to MP is not stereospecific, the stereochemistry of the final product can be controlled through the appropriate selection of a transaminase. Since the reactions are reversible, the unreacted MP (undesired isomer) can be recycled back to its constituents, and a racemic mixture of MP can be reformed.

In fermentation or whole cell biocatalysis production routes (in vivo), the production of S,S or R,S monatin will be favored due to the large number of native L-aminotransferases in comparison to D-aminotransferases. If R,R and/or S,R monatin are the desired stereoisomers, broad specificity and aromatic L-aminotransferases such as AspC and TyrB may have to be knocked out as in the strain SR250 (Rothman and Kirsch, *J. Mol Biol.* (2003) 327, 593-603). In doing so, phenylalanine and tyrosine may be required in the growth medium. An L-tryptophan aminotransferase which preferentially reacts with the L-isomer of tryptophan can be substituted for indole-3-pyruvate production in the pathway to produce monatin, while a D-aminotransferase that preferentially reacts with D-amino acids (such as D-alanine aminotransferase) will most likely need to be present in higher amounts than in the wildtype organism to facilitate production of R,R or S,R monatin.

In one embodiment, a stereoisomerically-enriched monatin mixture is produced in a biosynthetic pathway and/or in a cell. "Stereoisomerically-enriched monatin mixture" means that the mixture includes more than one monatin stereoisomer and at least 60% of the monatin stereoisomers in the mixture is a particular stereoisomer, such as R,R, S,S, S,R or R,S. In other embodiments, the mixture includes greater than 65%, 70%, 75%, 80%, 85%, 90%, 95%, 98% or 99% of a particular monatin stereoisomer. "Stereoisomerically-enriched" R,R monatin means that the monatin comprises at least 60% R,R monatin. "Stereoisomerically-enriched" S,S monatin means that the monatin comprises at least 60% S,S monatin. In other embodiments, "stereoisomerically-enriched" monatin comprises greater than 65%, 70%, 75%, 80%, 85%, 90%, 95%, 98% or 99% of R,R or S,S monatin.

In other embodiments, predominantly S,S or R,R monatin is produced in a biosynthetic pathway and/or in a cell. "Predominantly" means that of the monatin stereoisomers produced in a biosynthetic pathway and/or in a cell, the monatin contains greater than 90% of a particular stereoisomer. In some embodiments, the monatin produced is substantially free of R,S or S,R monatin. "Substantially free" means that of the monatin stereoisomers produced in a biosynthetic pathway and/or in a cell, the monatin stereoisomers include less than 2% of a particular stereoisomer. Additionally or alternatively, when used to describe monatin produced in a biosynthetic pathway and/or in a cell, "substantially free" encompasses the amount of a stereoisomer (e.g., R,S monatin) produced as a by-product in a biosynthetic pathway involving chiral-specific enzymes (e.g., D-amino acid dehydrogenases or D-amino acid aminotransferases) and/or chiral-specific substrates (e.g., one having a carbon in the R-stereoconfiguration) to produce a different specific stereoisomer (e.g., R,R monatin).

7. Activating Substrates

Phosphorylated substrates, such as phosphoenolpyruvate (PEP), can be used in the reactions disclosed herein. Phosphorylated substrates can be more energetically favorable and, therefore, can be used to increase the reaction rates and/or yields. In aldol condensations, the addition of a phosphate group stabilizes the enol tautomer of the nucleophilic substrate, making it more reactive. In other reactions, a phosphorylated substrate can provide a better leaving group. Similarly, substrates can be activated by conversion to CoA derivatives or pyrophosphate derivatives.

8. Secreting Products

Microorganisms can produce amino acids. For example, *Corynebacteria* and *Brevibacteria* can produce a variety of amino acids such as glutamate, histidine, tryptophan, phenylalanine, tyrosine, serine, threonine, lysine, methionine, valine, isoleucine, and leucine, while *Pantoea, Erwinia, Klebsiella, Enterobacter agglomerans*, and *Serratia liquefacience* can produce glutamate. In addition, microorganisms can secrete organic acids and amino acids. For example, *Bacillus* and *Lactobacillus* organisms can secrete organic acids such as lactic acid and acetic acid, while *Corynebacteria* and *Brevibacteria* organisms can secrete many, if not all, the amino acids they produce.

The organisms that can secrete amino acids usually do so for one of two reasons: (1) they utilize polypeptides as a carbon and energy source but cannot catabolize a particular amino acid, or (2), the charged amino acids can be secreted as a stress response in order to control pH or osmolytic pressure. Glutamate, for instance, is not constitutively excreted by wildtype *Corynebacteria*. Several conditions are likely to be involved in triggering export of glutamate such as the level of oxoglutarate dehydrogenase activity, the presence of a specific exporter, the status of the cell envelope, the inversion of the uptake process by changes in chemical potential or regulation, and stress.

The cell envelope status can be influenced by the composition of the media and growth conditions. In general, peptidoglycan (cell wall and murein) is not a barrier to transport, but in the case of *Corynebacteria* and glutamate there can be an exception. The addition of penicillin or penicillin derivatives such as ampicillin or carbenicillin appear to aid in glutamate efflux, especially in *Corynebacteria*. Penicillin and penicillin derivatives, such as ampicillin and carbenicillin, are beta-lactam antibiotics that inhibit the final stage of synthesis of cell wall cross-links that is catalyzed by a transpeptidase. They also inhibit enzymes, called penicillin binding proteins, necessary for the rod-like structure of *E. coli* and for septum formation during division.

The fluidity of the cell membrane can be involved as well. For example, the presence of more saturated fatty acids can decrease the fluidity and the efflux. Fluidity can be influenced by limiting biotin, and adding surfactants. Increased temperature, addition of dodecylammonium acetate, oleic acid auxotrophs, glycerol deficiency in glycerol auxotrophs, addition of detergents such as Tween 60, addition of local anaesthetics, fatty acid mutants, use of lysozyme-sensitive mutants, and application of electrical potential can affect the permeability of the cell membrane/wall. For example, the proton motive force can be important for secretion of charged molecules and can be largely affected by the pH of the media in comparison to intracellular pH.

Any method can be used to increase membrane fluidity and product secretion. For example, isonicotinic acid hydrazide (INH) can be added to cultures to inhibit mycolic acid synthesis activity, which can result in increased membrane fluidity and product secretion. In addition, inactivation of csp1 (PS 1-mycolyltransferase) can decrease the cell-wall bound mycolic acid content by 50%, and increase the transport of hydrophilic substrates through the cellular envelope. Since overexpression of the acp gene (involved in mycolic acid synthesis) can counteract the benefits of adding Tween 60 to the media, methods that downregulate this gene can be used to increase monatin secretion from *Corynebacteria* strains.

The major fatty acids of *C. glutamicum*'s cell membrane are oleate (18:1) and palmitate (16:0), fatty acids with little or no unsaturation. Different fatty acid synthases from the *Brevibacteria* and *Corynebacteria* have different properties in terms of the ratio of saturated to unsaturated fatty acids and the length of the fatty acid. *Corynebacteria* have both the FAS I (yeast and mammalian system) and FAS II (*E. coli* and plant system) enzymes for fatty acid synthesis. In fact, *Corynebacterium glutamicum* has two fatty acid synthase I enzymes. Manipulation of these genes or the expression of these genes can alter membrane fluidity.

Biotin can be required for fatty acid synthesis and cell growth. Limiting biotin levels can lower the oleic acid (or other fatty acids with little or no unsaturation) level even more than it affects the highly unsaturated fatty acids, making the cell membrane more fluid. To improve secretion, acetyl-CoA-carboxylase polypeptides, which contain biotin and are necessary for synthesizing phospholipids, can be downregulated or inhibited. In addition, biotin antagonists can be used rather than limiting biotin. For example, temperature sensitive biotin inhibitory polypeptides (dtsR gene products) can confer surfactant resistance and improve secretion. In addition, nucleic acids encoding temperature sensitive biotin inhibitory polypeptides can be transformed into *Corynebacteria*, which can be used to produce glutamic acid and lysine (See, e.g., U.S. patent application Publication No. 20030077765).

Genes encoding desaturase polypeptides can be added to organisms to increase membrane fluidity. In *C. glutamicum*, overexpression of genes encoding phospholipid biosynthetic polypeptides such as plsC, cma, and cls can be used to improve glutamate secretion.

Eicosapentaenoic acid (EPA) is known to play a significant role in membrane fluidity (Hashimoto et al., 1999, *Lipids*, 34:1297-1304), and so overproduction of this polyunsaturated fatty acid can aid in overall fluidity/transport properties of the host organism. A 38 kbp genome DNA fragment has been successfully cloned from a marine bacterium (*Shewanella*) and expressed in *E. coli* resulting in the production of EPA (Yazawa, 1996, *Lipids*, 31:S297-S300). *Shewanella* sp. genes for EPA synthesis are available commercially. Polyketide synthase enzymes are also known to produce polyunsaturated fatty acids, and enzyme domains for these enzymes are present in the same open reading frames as are the above-described FAS-related genes used for EPA production. Cloning of these gene clusters into the host organism can have a significant effect on membrane fluidity and subsequent product efflux.

The medium can have an effect on the amount of byproducts and rate of transport. In *C. glutamicum*, increased amounts of minerals can favor glutamate production over acetate and lactate byproducts in a manner that correlates with an increase in NADPH, $H^+$ production rates. The choice of carbon source also can influence the ratio of NADPH to $NADP^+$ resulting in changes in byproduct formation and transport rate. The presence of high $H^+$ or other positively charged ions in the media such as sodium and potassium can influence the rate of antiport (efflux) or symport (uptake).

Glutamate/glutamine ratios are often an indication of the availability of nitrogen (ammonia) in the cells. Glutamine is utilized in some organisms as an ammonia donor for asparagine production from aspartate. High levels of glutamate can accumulate, and this can signal the cells to secrete glutamate. Also, glutamate and other anionic molecules can be transported in and out of the cells under different conditions of stress.

The aromatic amino acids can share a common transport system in *C. glutamicum*. Finding strains with a defect in uptake of these amino acids can be used to yield strains with increased production of amino acids (Ikeda and Katsumata, (1995) *Biosci. Biotech. Biochem.*, 59:1600-1602).

In one embodiment, the following steps can be performed to identify an organism exhibiting glutamate efflux. Strains such as ATCC 13655 and 13058, which have both been reclassified as *Corynebacterium glutamicum*, can be obtained. See, e.g., U.S. Pat. Nos. 3,128,237 and 3,002,889. Organisms can be assessed to determine the levels of glutamic acid produced. Then, the effects of various conditions such as the use of Tween, ampicillin (or penicillin or carbenicillin), and reduced biotin can be measured to determine the most effective treatment for glutamate efflux. If glutamate efflux is detected, then the organism can be used obtain a gene that encodes a polypeptide having transport activity.

Amino acid efflux polypeptides in bacteria are mainly proton-motive force driven. Generally, these are proton antiporters, but other positively charged molecules can be imported when the amino acid is secreted. Export of negatively charged molecules should not require a proton to be imported, since it is already going in the direction of the charge gradient. Therefore, a glutamate transporter can be a uniporter rather than an antiporter.

Any organism can be screened for polypeptides that transport monatin or glutamate. For example, the following organisms can be examined for monatin or glutamate transporters: (1) organisms having a high number of predicted secondary transporters such as *E. coli*, *B. subtilis*, and *Ricksettia*, (2) organisms that secrete glutamate such as *Corynebacteria* and *Brevibacteria*, (3) plants and legume containing plants such as soybean, peas, peanuts, and beans, (4) *Rhizobium* species, and (5) organisms that have a high resistance to acids such as lactic acid bacteria, *Acetobacter* strains, *Kluyveromyces*, *Saccharomyces cerevisiae*, and *Aspergillus niger*. Organisms also can be screened for the ability to utilize glutamate rich synthetic or natural polypeptides (e.g., GLURP, the glutamate-rich polypeptide from *Plasmodium falciparum* or polyglutamate) as sole nitrogen sources. Such organisms can have the ability to secrete glutamate, allowing them to survive in the presence of high levels of intracellular glutamate, which may be toxic or may adversely affect cellular osmotic potential.

Transporter polypeptides that do not recognize monatin can be manipulated to produce transporter polypeptides that recognize monatin. In particular, techniques such as selection processes can be used to obtain a transporter polypeptide that recognizes monatin as a substrate. For example, mutation of phenylalanine and tyrosine regulatory genes via classical mutagenesis and screening in *E. coli* has been shown to result in increased production and secretion of phenylalanine.

If polypeptides that facilitate tryptophan secretion are detected, then the genes encoding these polypeptide can be knocked out such that tryptophan is readily available inside the cell for production of monatin and to increase yield. In addition, genes encoding tryptophan uptake polypeptide can be expressed in host cells overproducing tryptophan such that tryptophan can be utilized for monatin production rather than being secreted. Such genes include MTR permease (tryptophan specific transport protein), TyrP (tyrosine specific transport protein), TnaB (tryptophan specific transport protein) (*E. coli* designations) and AroP (aromatic amino acid uptake protein).

9. Genetic Tools

In the last two decades, general molecular biology tools such as cloning vectors and DNA transfer methods have been developed for amino acid producing *Corynebacterium* and *Brevibacterium* strains. Several of these tools can be used to manipulate the glutamate and/or tryptophan producing strains of *Corynebacterium glutamicum* such that they produce products such as monatin. For example, monatin can be produced and secreted at high levels when the proA and aspC genes are overexpressed in a *C. glutamicum* strain.

The research laboratories within Kyowa Hakko Kogyo Co. have genetically manipulated *C. glutamicum* strains to increase the production of tryptophan by overexpressing several genes involved in aromatic amino acid biosynthesis. One of the shuttle vectors developed by this company, pCE54, is available from ATCC (catalog number 39019). It has a multiple cloning site, 3 antibiotic markers, and the pCG2 replicon for *Corynbebacterium/Brevibacterium* and pMB 1 replicon for *E. coli*. Several other shuttle vectors with different selectable markers developed at Kyowa Hakko including pCB101, pEthr1, pCG11, and pCE53 (U.S. Pat. No. 4,710,471; and Ikeda and Katsumata, (1999) *App. Env. Microbiology*, 65:2497-2502).

The groups of Eikmanns and Sahm have constructed a family of shuttle and expression vectors for *C. glutamicum/E. coli* (Eikmanns et al., (1991) *Gene*, 102:93-98). These are based on the replication origins of corynbactarial pBL 1 and *E. coli* ColE1, have multiple restriction sites, and carry kanamycin- or chloramphenicol-resistance genes. Two of these, the 8.2 kb pEKEx1 or pEKEx2 vector are inducible with isopropyl-β-D-thiogalactoside. Promoter probe vectors also exist to assay the promoter strengths.

Sinskey and colleagues have developed vectors for metabolic engineering in *Corynebacterium*. Their shuttle vectors are based on the pSR1 (broad host range), pBL1, and pNG2 plasmids originally isolated from *C. glutamicum* and *C. lactofermentum*. They include a conjugation vector, a vector for transcription analysis, two expression vectors containing the *E. coli* tac promoter or both the tac promoter and a *Corynebacaterium* promoter obtained from the fda-gene, and a promoter probe vector (Jetten et al., (1994) *Ann. NY Acad. Sci.*, 721:12-29; and Jetten and Sinskey, (1995) *Crit. Rev. Biotechnology*, 15:73-103).

Genetic tools are available for fungal species as well. See, e.g., Zhou et al., (1994) *Gene*, 142:135-40; Willins et al., (2002) *Gene*, 292:141-9; Hanic-Joyce and Joyce, (1998) *Gene*, 211:395-400; and Barkani et al., (2000) *Gene*, 246:151-5. Briefly, most *Torulopsis* species have been renamed *Candida*, including *T. glabrata*. *Candida glabrata* is an asexual haploid Ascomycete fungus. It is in the same order as *Saccharomyces cerevisiae*, but not all of the cloning tools are compatible. For instance, the common mu autonomous replication sequence (ARS) does not replicate in *C. glabrata*. Nevertheless, pRS316, a centromere (CEN)-based *S. cerevisiae* plasmid, can be used in *C. glabrata*. In addition, URA3 can be used in *C. glabrata* as an auxotrophic selection marker, and integrative plasmids exist for inserting sequences at the URA3 locus via homologous recombination.

An expression vector that functions in *C. glabrata* has been designed by researchers at Genome Therapeutics Corp. (Willins et al., (2002) *Gene* 292:141-149), and contains HIS3, ADE2, and LEU2 auxotrophies. This vector also has *S. cerevisiae* CEN and ARS regions. The copper-inducible metallothionein I (MT-1) promoter of *C. glabrata* and standard neomycin and kanamycin resistance genes can be used in *C. glabrata*. Likewise, a high copy-number vector with the ADE2 gene is functional in *C. glabrata* and contains a fragment of *S. cerevisiae* mitochondrial (mt) DNA that serves as the ARS (Hanic-Joyce and Joyce, (1998) *Gene* 11:395-400).

An *E. coli* shuttle vector for *C. glabrata* has been constructed, containing both the *C. glabrata* CEN-ARS cassette and the lacZ coding sequence of *E. coli* (El Barkani et al., (2000) *Gene* 246:151-155). The HIS3 gene promoter and ribosome binding site was used to express lacZ. A MTII gene:lacZ reporter fusion was also made for differential induction with copper.

Methods developed for other *Candida strains*, such as FLP recombinase of *S. cerevisiae*, isolation of promoters and selection markers, UV mutagenesis techniques, and cell permeabilization methods can be applied to *C. glabrata*. In addition, lithium acetate or electroporation techniques can be used to transform *Candida species*.

Monatin Production in Non-Recombinant Organisms and Screening Methods for Isolation of Organisms Capable of Monatin Production.

*Sinorhizobium meliloti, Comamonas testosteroni*, and *Pseudomonas straminea* are prokaryotes that have 4-hydroxy-4-methyl-2-oxoglutarate aldolase as well as aromatic aminotransferase activities. Because these organisms contain the enzymes necessary to produce monatin from tryptophan, they do not require genetic modification for its biosynthesis. The genes that encode the aldolase and aromatic aminotransferases are inducible and appropriate growth conditions (for example, growth in the presence of p-hydroxybenzoate) are required to ensure that they are induced. The 4-hydroxy-4-methyl-2-oxoglutarate aldolase is part of a protocatechuate degradation pathway in *Pseudomonas* and related species. *Corynebacterium glutamicum* is also capable of producing monatin. Although 4-hydroxy-4-methyl-2-oxoglutarate aldolase has not yet been identified in this organism, it contains other enzymes involved in protocatechuate degradation.

Other organisms that carry these genes or can synthesize monatin by an alternative pathway can be detected by screening for growth on monatin or the monatin precursor (MP) as the sole carbon source. The reactions that produce monatin or the monatin precursor (MP) from tryptophan and pyruvate are all reversible. Therefore, screening for cells that can convert monatin or monatin precursor (MP) to tryptophan or pyruvate is a tool that can be employed to test for cells with enzymes useful for monatin production. The test can be accomplished by using a tryptophan auxotroph (a cell that is incapable of producing tryptophan and requires its addition to the medium for growth) and determining if the cell can grow on monatin or MP, which would indicate that the cell converted monatin or MP to tryptophan. Alternatively, the cells can be plated onto minimal medium where monatin, MP, a monatin analog and/or a MP analog is/are the primary carbon/energy source (as described below). In order to survive (and grow into visible colonies), these cells would have to convert the monatin, MP, monatin analog and/or MP analog into pyruvate or another component of central metabolism. Growth of a cell can be tested, for example, by looking for colony formation on an agar plate, or by looking for evidence of growth in liquid culture as compared to a negative control (e.g., by looking for differences in optical density of the liquids). The test cells can be a pyruvate auxotroph (a cell that is incapable of producing pyruvate and requires a pyruvate source in the medium for growth) and determining if the cell can grow on monatin, MP, monatin analog and/or MP analog. The test cells can be wild-type organisms that naturally contain enzymes useful for monatin production. Once identified as positive test cells by their ability to grow on a plate, for example, aldolases and/or aminotransferases can be purified from the positive test cell.

The test cells can also be recombinant cells that contain genes that will be expressed to test for the gene product's ability to convert monatin or MP to tryptophan and/or pyruvate. A cell that is capable of growth indicates that the exogenous genes encode enzymes that can convert monatin or MP to tryptophan and/or pyruvate. Screening by this method requires (1) that the synthetic pathway be reversible, allowing the product, monatin, to be metabolized by this route and (2) that the organism has a transport system that is able to import monatin or MP (or analogs). Titer improvement in these organisms can be afforded using classical mutagenesis techniques.

The invention will be further described in the following examples, which do not limit the scope of the invention described in the claims.

EXAMPLES

Example 1

Cloning and Expression of Tryptophan Aminotransferases

This example describes methods that were used to clone tryptophan aminotransferases, which can be used to convert tryptophan to indole-3-pyruvate. The genes were cloned into the pET 30 Xa/LIC vector to generate fusion proteins with cleavable N-terminal $HIS_6$-Tag/7-Tags (6×HIS tag disclosed as SEQ ID NO: 90). The resulting proteins were purified using immobilized metal affinity chromatography.

Experimental Overview

Eleven genes encoding aminotransferases were cloned into *E. coli*. These genes were *Bacillus subtilis* D-alanine aminotransferase (dat, Genbank Accession No. Y14082.1 bp 28622-29470 and Genbank Accession No. NP_388848.1, nucleic acid sequence and amino acid sequence, respectively), *Sinorhizobium meliloti* (also termed *Rhizobium meliloti*) tyrosine aminotransferase (tatA, SEQ ID NOS: 1 and 2, nucleic acid sequence and amino acid sequence, respectively), *Rhodobacter sphaeroides* strain 2.4.1 tyrosine aminotransferase (tatA asserted by homology, SEQ ID NOS: 3 and 4, nucleic acid sequence and amino acid sequence, respectively), *R. sphaeroides* 35053 tyrosine aminotransferase (asserted by homology, SEQ ID NOS: 5 and 6, nucleic acid sequence and amino acid sequence, respectively), *Leishmania major* broad substrate aminotransferase (bsat, asserted by homology to peptide fragments from *L. mexicana*, SEQ ID NOS: 7 and 8, nucleic acid sequence and amino acid sequence, respectively), *Bacillus subtilis* aromatic aminotransferase (araT, asserted by homology, SEQ ID NOS: 9 and 10, nucleic acid sequence and amino acid sequence, respectively), *Lactobacillus amylovorus* aromatic aminotransferase (araT asserted by homology, SEQ ID NOS: 11 and 12, nucleic acid sequence and amino acid sequence, respectively), *R. sphaeroides* 35053 multiple substrate aminotransferase (asserted by homology, SEQ ID NOS: 13 and 14, nucleic acid sequence and amino acid sequence, respectively), *Rhodobacter sphaeroides* strain 2.4.1 multiple substrate aminotransferase (msa asserted by homology, Genbank Accession No. NZ_AAAE01000093.1, bp 14743-16155 and Genbank Accession No. ZP_00005082.1, nucleic acid sequence and amino acid sequence, respectively), *Escherichia coli* aspartate aminotransferase (aspC, Genbank Accession No. AE000195.1 bp 2755-1565 and Genbank Accession No. AAC74014.1, nucleic acid sequence and amino acid sequence, respectively), and *E. coli* tyrosine aminotransferase (tyrB, SEQ ID NOS: 31 and 32, nucleic acid sequence and amino acid sequence, respectively).

The genes were cloned, expressed, and tested for activity in conversion of tryptophan to indole-3-pyruvate, along with commercially available enzymes. All eleven clones had activity.

Identification of Bacterial Strains that can Contain Polypeptides with the Desired Activity No genes in the NCBI (National Center for Biotechnology Information) database were designated as tryptophan aminotransferases. However, organisms having this enzymatic activity have been identified. L-tryptophan aminotransferase (TAT) activity has been measured in cell extracts or from purified protein from the following sources: Rhizobacterial isolate from *Festuca octoflora*, pea mitochondria and cytosol, sunflower crown gall cells, *Rhizobium leguminosarum* biovar *trifoli*, *Erwinia herbicola* pv gypsophilae, *Pseudomonas syringae* pv. savastanoi, *Agrobacterium tumefaciens*, *Azospirillum lipferum* & *brasilense*, *Enterobacter cloacae*, *Enterobacter agglomerans*, *Bradyrhizobium elkanii*, *Candida maltosa*, *Azotobacter vinelandii*, rat brain, rat liver, *Sinorhizobium meliloti*, *Pseudomonas fluorescens* CHA0, *Lactococcus lactis*, *Lactobacillus casei*, *Lactobacillus helveticus*, wheat seedlings, barley, *Phaseolus aureus* (mung bean), *Saccharomyces uvarum* (carlsbergensis), *Leishmania* sp., maize, tomato shoots, pea plants, tobacco, pig, *Clostridium sporogenes*, and *Streptomyces griseus*.

Isolation of Genomic DNA for Cloning

*S. meliloti* (ATCC number 9930) was grown in TY media at 25° C., pH 7.2. Cells were grown to an optical density at 600 nm ($OD_{600}$) of 1.85 and a 2% inoculum was used for genomic DNA preparations. The Qiagen genomic tip 20/G kit (Valencia, Calif.) was used for genomic DNA isolation.

*Bacillus subtilis* 6051 (ATCC) was grown at 30° C. in Bereto Nutrient Broth (Difco; Detroit, Mich.). The Qiagen genomic tip 20/G protocol was used to isolate the genomic DNA with the following changes: the concentrations of proteinase K and lysozyme were doubled and incubation times were increased 2-3 fold.

*Leishmania major* ATCC 50122 genomic DNA was supplied by IDI, Inc. (Quebec, Canada) in TE buffer pH 8.0, 17 ng/μL.

*Rhodobacter sphaeroides* 2.4.1 (provided by Professor Sam Kaplan, University of Texas, Houston), *R. sphaeroides* 35053 (ATCC number), and *L. amylovorus* genomic DNA was prepared by standard phenol extraction. Cells were harvested in late log phase, resuspended in TEN buffer (10 mM Tris-HCl, pH 7.5, 1 mM EDTA, 100 mM NaCl), and lysed by the addition of 0.024 mL sodium lauryl sarcosine per mL cell suspension. After extracting at least three times with an equal volume of phenol saturated with TE buffer (10 mM Tris-HCl, pH 7.5, 1 mM EDTA), the DNA solution was extracted once with 9:1 chloroform:octanol and three times with chloroform. The DNA was precipitated by the addition of 0.1 volume of 3 M sodium acetate, pH 6.8 and 2 volumes ethanol. The precipitate was collected by centrifugation and washed once with 70% ethanol. Finally the DNA was dissolved in 0.10 mL distilled water.

*Escherichia coli* genomic DNA was isolated from strain DH10B (Invitrogen) and prepared using the Qiagen Genomic-tip™ (500/G) kit. From 30 mL of this strain grown in LB to an $OD_{650}$ of 1.87, 0.3 mg of purified DNA was obtained. The purified DNA was dissolved in Qiagen elution buffer (EB) at a concentration of 0.37 □g/μL.

Polymerase Chain Reaction Protocol

Primers were designed with compatible overhangs for the pET 30 Xa/LIC vector (Novagen, Madison, Wis.). The pET vector has a 12 base single stranded overhang on the 5' side of the Xa/LIC site and a 15-base single stranded overhang on the 3' side of the Xa/LIC site. The plasmid is designed for ligation independent cloning, with N-terminal His and S-tags and an optional C-terminal His-tag. The Xa protease recognition site (IEGR) sits directly in front of the start codon of the gene of interest, such that the fusion protein tags can be removed.

The following sequences were added to the 5' ends of the organism specific sequences when designing primers: forward primer, 5' GGTATTGAGGGTCGC (SEQ ID NO: 73); reverse primer: 5' AGAGGAGAGTTAGAGCC (SEQ ID NO: 74).

*Bacillus subtilis* dat primers: N term: 5'-

```
                                   (SEQ ID NOS: 15 and 16)
N term: 5'-GGTATTGAGGGTCGCATGAAGGTTTTAGTCAATGG-3'
and C term: 5'-AGAGGAGAGTTAGAGCCTTATGAAATGCTAGCAGCCT-
3.'
```

*Sinorhizobium meliloti* tatA primers: N term: 5'-

```
                                   (SEQ ID NOS: 17 and 18)
N term: 5'-GGTATTGAGGGTCGCATGTTCGACGCCCTCGCCCG
and C term: 5'-AGAGGAGAGTTAGAGCCTCAGAGACTGGTGAACTTGC.
```

*Bacillus subtilis* araT primers: N term: 5'-

```
                                   (SEQ ID NOS: 19 and 20)
N term: 5'-GGTATTGAGGGTCGCATGGAACATTTGCTGAATCC
and C term: 5'-AGAGGAGAGTTAGAGCCTTAAACGCCGTTGTTTATCG.
```

*Rhodobacter sphaeroides* msa (both 2.4.1 and 35053): N term: 5'-

```
                                   (SEQ ID NOS: 21 and 22)
N term: 5'-GGTATTGAGGGTCGCATGCGCGAGCCTCTTGCCCT
and C term: 5'-AGAGGAGAGTTAGAGCCTCAGCCGGGGAAGCTCCGGG.
```

*Leishmania major* bsat: N term: 5'-

```
                                   (SEQ ID NOS: 23 and 24)
N term: 5'-GGTATTQAGGGTCGCATGTCCACGCAGGCGGCCAT
and C term: 5'-AGAGGAGAGTTAGAGCCTCACTCACGATTCACATTGC.
```

*Lactobacillus amylovorus* araT: N term: 5'-

```
                                   (SEQ ID NOS: 25 and 26)
N term: 5'-GGTATTGAGGGTCGCATGCCAGAATTAGCTAATGA
and C term: 5'-AGAGGAGAGTTAGAGCCTTATTCGTCCTCTTGTAAAA.
```

*Rhodobacter sphaeroides* tatA (both 2.4.1 and 35053 strains): N term: 5'-

```
                                               (SEQ ID NOS: 27 and 28)
N term: 5'-GGTATTGAGGGTCGCATGCGCTCTACGACGGCTCC
and C term: 5'-AGAGGAGAGTTAGAGCCTCAGCCGCGCAGCACCTTGG.
```

*Escherichia coli* aspC: N term: 5'-

```
                                               (SEQ ID NOS: 29 and 30)
N term: 5'-GGTATTGAGGGTCGCATGTTTGAGAACATTACCGC-3'
and C term: 5'-AGAGGAGAGTTAGAGCCTTACAGCACTGCCACAATCG-
3'.
```

*Escherichia coli* tyrB: N term: 5'-

```
                                               (SEQ ID NOS: 33 and 34)
N term: 5'-GGTATTGAGGGTCGCGTGTTTCAAAAAGTTGACGC
and C term: 5'-AGAGGAGAGTTAGAGCCTTACATCACCGCAGCAAACG-
3'.
```

The gene derived from *S. meliloti* (tatA) was amplified using the following PCR protocol. In a 50 µL reaction 0.1-0.5 µg template, 1.5 µM of each primer, 0.4 mM each dNTP, 3.5 U Expand High Fidelity Polymerase (Roche, Indianapolis, Ind.), and 1× Expand™ buffer with Mg were used. The thermocycler program used included a hot start at 96° C. for 5 minutes, followed by 29 repetitions of the following steps: 94° C. for 30 seconds, 55° C. for 2 minutes, and 72° C. for 2.5 minutes. After the 29 repetitions the sample was maintained at 72° C. for 10 minutes and then stored at 4° C. This PCR protocol produced a product of 1199 bp.

The sequences of the genes derived from *R. sphaeroides* (msa and tatA), *L. amylovorus* araT, and *Bacillus* araT were amplified using the following PCR protocol. In a 50 µL reaction, 0.1-0.5 µg template, 1.5 µM of each primer, 0.4 mM each dNTP, 3.5 U Expand High Fidelity™ Polymerase, and 1× Expand™ buffer with Mg were added. The thermocycler program used included a hot start at 96° C. for 5 minutes, followed by 29 repetitions of the following steps: 94° C. for 30 seconds, 40-60° C. for 1 minute, 45 seconds (gradient thermocycler) and 72° C. for 2 minutes, 15 seconds. After the 29 repetitions the sample was maintained at 72° C. for 10 minutes and then stored at 4° C.

For each *R. sphaeroides* msa gene, the 42° C. and 48° C. annealing temperatures produced multiple products, but a distinct band at approximately 1464 bp. For *L. amylovorus* araT, the 42° C., 48° C., and 56° C. annealing temperatures yielded single products with intense bands at 1173 bp. For *B. subtilis* araT, the 40° C., 45° C., 50° C., 55° C. annealing temperatures generated single intense products (1173 bp), from both genomic DNA and colonies. For *L. major* bsat, the 55° C. annealing temperature gave the cleanest product (1239 bp). For *Rhodobacter* tatA genes, the 50-55° C. annealing temperatures gave clean products at the correct size (1260 bp). For both *E. coli* genes and the *B. subtilis* dat gene, an annealing temperature of 55-60° C. was used, and the annealing time was shortened to 45 seconds. Clean products of the correct sizes were obtained (approximately 1.3 kb for the *E. coli* genes, 850 bp for the dat gene).

Cloning

The PCR products were gel purified from 0.8 or 1% TAE-agarose gels using the Qiagen gel extraction kit (Valencia, Calif.). The PCR products were quantified by comparison to standards on an agarose gel, and then treated with T4 DNA polymerase following the manufacturer's recommended protocols for Ligation Independent Cloning (Novagen, Madison, Wis.).

Briefly, approximately 0.2 pmol of purified PCR product was treated with 1 U T4 DNA polymerase in the presence of dGTP for 30 minutes at 22° C. The polymerase removes successive bases from the 3' ends of the PCR product. When the polymerase encounters a guanine residue, the 5' to 3' polymerase activity of the enzyme counteracts the exonuclease activity to effectively prevent further excision. This creates single stranded overhangs that are compatible with the pET Xa/LIC vector. The polymerase is inactivated by incubating at 75° C. for 20 minutes.

The vector and treated insert were annealed as recommended by Novagen. Approximately 0.02 pmol of treated insert and 0.01 pmol vector were incubated for 5 minutes at 22° C., 6.25 mM EDTA (final concentration) was added, and the incubation at 22° C. was repeated. The annealing reaction (1 µL) was added to NovaBlue™ singles competent cells (Novagen, Madison, Wis.), and incubated on ice for 5 minutes. After mixing, the cells were transformed by heat shock for 30 seconds at 42° C. The cells were placed on ice for 2 minutes, and allowed to recover in 250 µL of room temperature SOC for 30 minutes at 37° C. with shaking at 225 rpm. Cells were plated on LB plates containing kanamycin (25-50 µg/mL).

Plasmid DNA was purified using the Qiagen spin miniprep kit and screened for the correct inserts by restriction digest with XhoI and XbaI. The sequences of plasmids that appeared to have the correct insert were verified by dideoxy chain termination DNA sequencing.

SEQ ID NOS:1-14 and 31-32 show nucleotide and corresponding amino acid sequences of the recombinant aminotransferases, any changes from the Genbank sequences were either silent or generated conservative substitutions in the protein sequence. SEQ ID NOS: 11 and 12 are novel sequences.

Gene Expression and Assays

Plasmid DNA, verified by sequence analysis, was subcloned into *E. coli* expression hosts BLR(DE3) or BL21 (DE3) (Novagen, Madison, Wis.). The cultures were grown and the plasmids were isolated using Qiagen miniprep kit, and analyzed by restriction digest to confirm identity.

Induction was initially performed with *L. amylovorus* araT, *B. subtilis* araT, and *S. meliloti* tatA in both BLR(DE3) and BL21(DE3) cells. A time course study was performed with cultures grown in LB containing kanamycin (30 mg/L) to an $OD_{600}$ of 0.5-0.8 and induced with 1 mM IPTG (isopropyl thiogalactoside) and sampled at 0, 1, 2, and 4 hours post induction. Cells from 2.0 mL were resuspended in 0.10 mL 120 mM Tris-HCl, pH 6.8 containing 10% sodium dodecyl sulfate, 10% 2-mercaptoethanol, and 20% glycerol, heated at 95° C. for 10 min, and cooled, and diluted with 0.10 mL $H_2O$. Aliquots of these total cellular protein samples were analyzed by SDS-PAGE using a 4-15% gradient gel. There were no significant differences in the amount of protein expressed between the 2 hour and 4 hour induction, nor between the BLR(DE3) and BL21(DE3) cells.

Cell extracts were also prepared from the 4 hour samples by suspending cell pellets from 2 mL of culture in 0.25 mL Novagen BugBuster™ reagent containing 0.25 µL benzonase nuclease, incubating at room temperature for 20 minutes with gentle shaking, and centrifuging at 16,000×g to remove cell debris. The supernatants (cell extracts) were loaded onto 4-15% gradient gels for analysis of the cellular soluble proteins.

The three clones, (*L. amylovorus* araT (SEQ ID NOS: 11 and 12), *B. subtilis* araT (SEQ ID NOS: 9 and 10), and *S. meliloti* tatA (SEQ ID NOS: 1 and 2) showed soluble protein that corresponded to the correct size (approximately 45 kDa). The *B. subtilis* araT gene product was over-expressed at the highest level and/or was more soluble than the other two gene products.

In subsequent expression methods, plasmid DNA from positive clones was subcloned into BL21(DE3) due to the better growth characteristics of this host. Induction was repeated using 1 mM IPTG with cultures grown in LB containing kanamycin at 50 mg/L, inducing when the $OD_{600}$ reached approximately 0.8. Cells were harvested after 4 hours of growth at 37° C., centrifuged at 3000 rpm for 10 minutes (4° C.), washed with TEGGP buffer (50 mM Tris-HCl (pH 7.0), 0.5 mM EDTA, 100 mg/L glutathione, 5% glycerol, with Roche complete protease inhibitor cocktail), and flash frozen in −80° C. ethanol.

Samples were resuspended in 5 mL/g wet cell weight of BugBuster™ (Novagen) reagent containing 5 µL/mL protease inhibitor cocktail set #3 (Calbiochem-Novabiochem Corp., San Diego, Calif.) and 1 µL/mL benzonase nuclease. Samples were incubated at room temperature for 20 minutes on an orbital shaker. Insoluble cell debris was removed by centrifugation at 16,000×g for 20 minutes at 4° C.

Cell extracts were analyzed by SDS-PAGE, and assayed for tryptophan aminotransferase activity by following production of indole-pyruvic acid using the following protocol. One mL reactions were carried out in 50 mM sodium tetraborate (pH 8.5), 0.5 mM EDTA, 0.5 mM sodium arsenate, 50 µM pyridoxal phosphate, 5 mM α-ketoglutarate, and 5 mM L-tryptophan. The reactions were initiated by the addition of cell free extracts or purified enzyme and were incubated 30 minutes at 30° C. 20% TCA (200 µL) was added to stop the reaction, and the precipitated protein was removed by centrifugation. The absorbance at 327 nm was measured and compared to a standard curve of freshly prepared indole-3-pyruvate in the assay buffer. Control reactions without the substrate tryptophan or using cell-free extracts from clones transformed with pET30a alone were also performed.

Due to background from the native *E. coli* aminotransferases in cell extracts, the recombinant fusion proteins each containing an aminotransferase protein fused to the pET30 amino terminal $HIS_6$-Tag/S-Tag (6×HIS tag disclosed as SEQ ID NO: 90) were purified using immobilized metal affinity chromatography with His-Bind cartridges following manufacturer's protocols (Novagen, Madison, Wis.). The $HIS_6$-Tag sequence (SEQ ID NO: 90) of the fusion proteins binds to the divalent $Ni^{2+}$ cations immobilized on IDA-based His-Bind resin. The eluent fractions were desalted on PD-10 (Amersham Biosciences, Piscataway, N.J.) columns and eluted in 50 mM Tris, pH 7.0. Purified proteins were analyzed by SDS-PAGE and assayed for aminotransferase activity.

Results from the 37° C. induction with 1 mM IPTG (4 hours) demonstrate that *L. major* bsat, *S. meliloti* tatA, *E. coli* aspC, and both *R. sphaeroides* tatA clones have significant levels of tryptophan aminotransferase activity. The araT protein from *B. subtilis* was over-expressed and soluble, but showed little enzymatic activity. The *L. amylovorus* araT gene product appeared to be soluble in the cell extract, but purification using a His-Bind cartridge resulted in only small amounts of protein with the correct molecular weight. The msa gene products were insoluble and further expression experiments were done at 24° C. to minimize inclusion body formation. Several concentrations of IPTG between 10 µM and 1 mM were used to maximize the amount of soluble protein.

Table 1 lists the specific activities measured in micrograms of indole-3-pyruvate (I3P) formed per milligram protein per minute. In some cases, very small amounts of recombinant protein showed high levels of activity above the effective linear range of the assay. In these cases a '>' precedes the specific activity number.

TABLE 1

Specific Activities of Clones in Cell Extracts (CE) and Purified (P) and Commercial Enzyme

| Enzyme | Specific Activity (µg I3P/mg protein/min) | Note |
| --- | --- | --- |
| *L. major* bsat CE | >49.3 | |
| *L. major* bsat P | >4280 | |
| *S. meliloti* tatA CE | >28.6 | |
| *S. meliloti* tatA P | >931 | |
| *R. sphaeroides* 2.4.1 tatA CE | >41.2 | |
| *R. sphaeroides* 2.4.1 tatA P | 1086 | |
| *R. sphaeroides* 35053 tatA CE | >62.3 | |
| *R. sphaeroides* 35053 tatA P | >486 | |
| *L. amylovorus* araT CE | 1.26 | |
| *L. amylovorus* araT P | 0 | little protein after His-Bind cartridge |
| *B. subtilis* araT CE | 0 | undetectable |
| *B. subtilis* araT P | 1.5–4.5 | |
| *R. sphaeroides* 2.4.1 msa CE | 2.05 | very little soluble protein |
| *R. sphaeroides* 2.4.1 msa P | 0 | no protein after His-Bind cartridge |
| *R. sphaeroides* 35053 msa CE | 3.97 | very little soluble protein |
| *R. sphaeroides* 35053 msa P | 0 | no protein after His-Bind cartridge |
| *E. coli* aspC (P) | 800 | |
| *E. coli* tyrB (P) | 1 | not very soluble |
| *B. subtilis* D-aminotransf.(P) | 2.7 | using D-tryptophan as substrate |
| broad range transaminase | 22 | Sigma cat # T 7684 |
| Porcine type II-A | 1.5 | Sigma G7005 |
| Porcine type I | 1 | Sigma G2751 |

An alignment comparing all of the recombinant proteins cloned illustrates that there are not many highly conserved areas between the araT, tatA, bsat, and msa sequences. An alignment of highest activity recombinant proteins: *Rhodobacter* tatA gene product homologs, *L. major* broad substrate aminotransferase, and the *Sinorhizobium meliloti* tyrosine aminotransferase showed several conserved regions, however they are only approximately 30-43% identical at the protein level. The availability of the broad range, D-specific (D-alanine) aminotransferase can be useful in the production of other stereoisomers of monatin (see Examples 3 and 4).

Example 2

Converting Indole-3-pyruvate to 2-hydroxy 2-(indol-3-ylmethyl)-4-keto glutaric acid with an Aldolase This example describes methods that can be used to convert indole-3-pyruvate to MP using an aldolase (lyase) (FIG. 2). Aldol condensations are reactions that form carbon-carbon bonds between the β-carbon of an aldehyde or ketone and the carbonyl carbon of another aldehyde or ketone. A carbanion is formed on the carbon adjacent to the carbonyl group of one substrate, and serves as a nucleophile attacking the carbonyl carbon of the second substrate (the electrophilic carbon). Most commonly, the electrophilic substrate is an aldehyde, so most aldolases fall into the EC 4.1.2.- category. Quite often, the nucleophilic substrate is pyruvate. It is less common for aldolases to catalyze the condensation between two keto-acids or two aldehydes.

However, aldolases that catalyze the condensation of two carboxylic acids have been identified. For example, EP 1045-029 describes the production of L-4-hydroxy-2-ketoglutaric acid from glyoxylic acid and pyruvate using a *Pseudomonas* culture (EC 4.1.3.16). In addition, 4-hydroxy-4-methyl-2-oxoglutarate aldolase (4-hydroxy-4-methyl-2-oxoglutarate pyruvate lyase, EC 4.1.3.17) can catalyze the condensation of two keto acids. Therefore, similar aldolase polypeptides were used to catalyze the condensation of indole-3-pyruvate with pyruvate. The activity or enantiospecificity of these enzymes can be modified for production of a specific stereoisomer of monatin and screened using the method described in Example 9 below.

Cloning

4-Hydroxy-4-methyl-2-oxoglutarate pyruvate lyases (ProA aldolase, EC 4.1.3.17) and 4-hydroxy-2-oxoglutarate glyoxylate-lyase (KHG aldolase, EC 4.1.3.16) catalyze reactions very similar to the aldolase reaction of FIG. 2. Primers were designed with compatible overhangs for the pET30 Xa/LIC vector (Novagen, Madison, Wis.). The design of these primers is described above in Example 1.

The following primers were designed for pET30 Xa/LIC cloning:

1. *Pseudomonas straminea* proA gene (Genbank Accession No.: 12964663 Version: 12964663; alternatively designated AB050935.2 GI:12964663) and *Comamonas testosteroni* proA gene (SEQ ID NOS: 65-66, nucleic acid sequence and amino acid sequence, respectively) forward 5'-

(SEQ ID NOS: 55 and 56)
    forward 5'-GGTATTGAGGGTCGCATGTACGAACTGGGAGTTGT-3'
    and reverse 5'-AGAGGAGAGTTAGAGCCTTAGTCAATATATTTCAGGC-3'.

2. *Sinorhizobium meliloti* 1021 SMc00502 gene (homologous to proA, Genbank Accession Nos.: 15074579 or alternatively AL591788.1 GI:15074579 and CAC46344.1, nucleic acid sequence and amino acid sequence, respectively) forward (SEQ ID NO: 61 and 62)
    forward 5'-GGTATTGAGGGTCGCATGAGCGTGGTTCACCGGAA-3'
    and reverse 5'-AGAGGAGAGTTAGAGCCTCAATCGATATATTTCAGTC-3'.

3. *Sphingomonas* sp. LB 126 fldZ gene (Genbank Accession No.: 7573247 Version: 7573247 or alternatively AJ277295.1 GI:7573247, codes for a putative acyl transferase GenBank Accession No.: CAB87566.1 GI:7573254) forward 5'-

(SEQ ID NOS: 57 and 58)
    forward 5'-GGTATTGAGGGTCGCATGTCCGGCATCGTTGTCCA-3'
    and reverse 5'-AGAGGAGAGTTAGAGCCTCAGACATATTTCAGTCCA-3'.

4. *Arthrobacter keyseri* pcmE gene (Genbank Accession No.: AF331043 Version: AF331043.1, codes for an oxalocitramalate aldolase GenBank Accession No.: AAK16525.1 GI:13242045) forward 5'-

(SEQ ID NOS: 59 and 60)
    forward 5'-GGTATTGAGGGTCGCATGCGACTGAACAACCTCGG-3'
    and reverse 5'-AGAGGAGAGTTAGAGCCTCAGTTCTCCACGTATTCCA-3'.

5. *Yersinia pestis* strain CO92 YPO0082 gene (Genbank Accession No.: 15978115 Version: 15978115 or alternatively AJ414141.1 GI:15978115, codes for a possible transferase GenBank Accession No.: CAC88948.1 GI:15978195) forward (SEQ ID NOS: 63 and 64)
    forward 5'-GGTATTGAGGGTCGCATGAGCCTGGTTAATATGAA-3'
    and reverse 5'-AGAGGAGAGTTAGAGCCTTATGACTTTAACGCGTTGA-3'.

6. *Bacillus subtilis* khg gene (Genbank Accession Nos. Z99115.1 GI:2634478, 126711-127301 or alternatively Z99115.1 GI:2634478, 126711-127301 and CAB14127.1, nucleic acid sequence and amino acid sequence, respectively)

(SEQ ID NOS: 35 and 36)
    forward 5'-GGTATTGAGGGTCGCATGGAGTCCAAAGTCGTTGA-3'
    and reverse 5'-AGAGGAGAGTTAGAGCCTTACACTTGGAAACAGCCT-3'.

7. *E. coli* khg gene (Genbank Accession Nos. AE000279.1 1331-1972 and AAC74920.1, nucleic acid and amino acid sequence, respectively)

(SEQ ID NOS: 37 and 38)
    forward 5'-GGTATTGAGGGTCGCATGAAAAACTGGAAAACAAG-3'
    and
    reverse 5'-AGAGGAGAGTTAGAGCCTTACAGCTTAGCGCCTTCTA-3'.

8. *S. meliloti* khg or SMc03153 gene (Genbank Accession Nos. AL591792.1 GI:15075850 or alternatively AL591792.1 GI:15075850, 64673 . . . 65311 and CAC47463.1, nucleic acid and amino acid sequence, respectively)

(SEQ ID NOS: 39 and 40)
    forward 5'-GGTATTGAGGGTCGCATGCGAGGGGCATTATTCAA-3'
    and
    reverse 5'-AGAGGAGAGTTAGAGCCTCAGCCCTTGAGCGCGAAG-3'

Genomic DNA from the organisms described in 1-2 and 6-8, above, was purified using the Qiagen Genomic-tip™ (Valencia, Calif.) protocol. Using similar techniques the genomic DNA from organisms described in 3-5 can be purified.

*Pseudomonas straminea* (ATCC 33636) was grown at 30° C. in Nutrient Broth and hydroxybenzoate medium. *Comamonas testosteroni* (ATCC 49249) was grown at 26° C. in Nutrient Broth and hydroxybenzoate medium. *Sphingomonas* sp. LB 126 (Flemish Institute for Technological Research, VITO, B-2400 Mol, Belgium) is grown according to the method described by Wattiau et al. (*Research in Microbiol.* 152:861-72, 2001). *Arthrobacter keyseri* (Gulf Ecology Division, National Health and Environmental Effects Research Laboratory, U.S. Environmental Protection Agency, Gulf Breeze, Fla. 32561, USA) is grown according to the protocol described by Eaton (*J. Bacteriol.* 183:3689-3703, 2001). *Sinorhizobium meliloti* 1021 (ATCC 51124) was grown at 26° C. in ATCC TY medium and hydroxybenzoate medium. *Yersinia pestis* strain CO92 (ATCC) is grown at 26° C. in ATCC medium 739 Horse blood agar. *Bacillus subtilis* 6051 (ATCC) was grown at 30° C. in Bereto Nutrient Broth (Difco; Detroit, Mich.). *E. coli* genomic DNA was isolated from strain DH10B (Invitrogen) as described in Example 1.

The PCR, cloning, and screening protocols described in Example 1 were used to clone the *C. testosteroni* and the *S. meliloti* proA sequences, as well as the *E. coli, B. subtilis*, and *S. meliloti* khg sequences. The same methods can be used to clone the other sequences described above. For the *C. testosteroni* proA gene, the annealing and extension conditions for PCR were 40-60° C. for 1 minute, 45 seconds (gradient thermocycler) and 72° C. for 2 minutes, 15 seconds.

Positive clones were sequenced using dideoxy chain termination sequencing (Seqwright, Houston, Tex.) with S-tag and T7 terminator primers (Novagen), and internal primers from Integrated DNA Technologies, Inc. (Coralville, Iowa).

Expression and Activity Assays

Plasmid DNA (verified by sequence analysis) was subcloned into expression host BL21(DE3) (Novagen). The cultures were grown in LB medium with 50 mg/L kanamycin, the plasmids isolated using a Qiagen spin plasmid miniprep kit and subsequently analyzed by restriction digest to confirm identity. Induction experiments were done with the BL21 (DE3) constructs grown in LB medium containing 50 mg/L kanamycin at 37° C. Protein expression was induced using 0.1 mM IPTG after the $OD_{600}$ reached approximately 0.6. The cells were grown for 4 hours at 30° C. and harvested by centrifugation. The cells were then lysed using Bugbuster™ reagent (Novagen) and the His-tag recombinant proteins were purified using His-Bind cartridges as described above (Example 1). Purified proteins were desalted on PD-10 disposable columns and eluted in 50 mM Tris-HCl buffer, pH 7.3 with 2 mM $MgCl_2$.

The proteins were analyzed by SDS-PAGE on 4-15% gradient gels to detect soluble protein levels at the predicted MW of the recombinant fusion protein.

The proteins were assayed for activity using indole-3-pyruvate and sodium pyruvate as substrates. The assay mixture contained 100 mM Tris-HCl (pH 7-pH 8.9), 0-8 mM $MgCl_2$, 3 mM potassium phosphate (pH 8), and 6 mM of each substrate in 1 mL. The reaction was started by adding varying amounts of polypeptide (for example from 10 to 100 µg), and was incubated at 25° C.-37° C. for 30 minutes, filtered, and then frozen at −80° C.

Activity Results with proA Gene Products

Both the *C. testosteroni* proA and *S. meliloti* SMc00502 gene constructs had high levels of expression when induced with IPTG. The recombinant proteins were highly soluble, as determined by SDS-PAGE analysis of total protein and cellular extract samples. The *C. testosteroni* gene product was purified to >95% purity. Because the yield of the *S. meliloti* gene product was very low after affinity purification using a His-Bind cartridge, cellular extract was used for the enzymatic assays.

Both recombinant aldolases catalyzed the formation of MP from indole-3-pyruvate and pyruvate. The presence of both divalent magnesium and potassium phosphate were required for enzymatic activity. No product was apparent when indole-3-pyruvate, pyruvate, or potassium phosphate was absent. A small amount of the product was also formed in the absence of enzyme (typically one order of magnitude less than when enzyme was present).

Using the LC/MS method described in Example 6, the product peak eluted from the reverse phase C18 column slightly later than the indole-3-pyruvate standard, the mass spectrum of this peak showed a collisionally-induced parent ion ([M+H]+) of 292.1, the parent ion expected for the product MP. The major daughter fragments present in the mass spectrum included those with m/z=158 (1H-indole-3-carbaldehyde carbonium ion), 168 (3-buta-1,3-dienyl-1H-indole carbonium ion), 274 (292—$H_2O$), 256 (292—2 $H_2O$), 238 (292—3 H2O), 228 (292—$CH_4O_3$), and 204 (loss of pyruvate). The product also exhibited a UV spectrum characteristic of other indole-containing compounds such as tryptophan, with the $\lambda_{max}$ of 279-280 and a small shoulder at approximately 290 nm.

The amount of MP produced by the *C. testosteroni* aldolase increased with an increase in reaction temperature from room temperature to 37° C., amount of substrate, and amount of magnesium. The synthetic activity of the enzyme decreased with increasing pH, the maximum product observed was at pH 7. Based on tryptophan standards, the amount of MP produced under a standard assay using 20 µg of purified protein was approximately 10-40 µg per one mL reaction.

Due to the high degree of homology of the *S. meliloti* and *C. testosteroni* ProA aldolase coding sequences with the other genes described above, it is expected that all of the recombinant gene products can catalyze this reaction. Moreover, it is expected that aldolases that have threonine (T) at positions 59 and 87, arginine (R) at 119, aspartate (D) at 120, and histidine (H) at 31 and 71, (based on the numbering system of *C. testosteroni*) will have similar activity.

Activity Results with khg Gene Products

Both the *B. subtilis* and *E. coli* khg gene constructs had high levels of expression of protein when induced with IPTG, while the *S. meliloti* khg had a lower level of expression. The recombinant proteins were highly soluble, as judged by SDS-PAGE analysis of total proteins and cellular extracts. The *B. subtilis* and *E. coli* khg gene products were purified to >95% purity; the yield of the *S. meliloti* gene product was not as high after affinity purification using a His-Bind cartridge.

There is no evidence that magnesium and phosphate are required for activity for this enzyme. However, the literature reports performing the assays in sodium phosphate buffer, and the enzyme reportedly is bifunctional and has activity on phosphorylated substrates such as 2-keto-3-deoxy-6-phosphogluconate (KDPG). The enzymatic assays were performed as described above, and in some instances the phosphate was omitted. The results indicate that the recombinant KHG aldolases produced MP, but were not as active as the ProA aldolases. In some cases the level of MP produced by KHG was almost identical to the amount produced by magnesium and phosphate alone. Phosphate did not appear to increase the KHG activities. The *Bacillus* enzyme had the highest activity, approximately 20-25% higher activity than the magnesium and phosphate alone, as determined by LC/MS/MS (see Example 6). The *Sinorhizobium* enzyme had the least amount of activity, which can be associated with folding and solubility problems noted in the expression. All three enzymes have the active site glutamate (position 43 in *B. subtilis* numbering system) as well as the lysine required for Shiff base formation with pyruvate (position 130); however, the *B. subtilis* enzyme contains a threonine in position 47, an active site residue, rather than arginine. The *B. subtilis* KHG is smaller and appears to be in a cluster distinct from the *S. meliloti* and *E. coli* enzymes, with other enzymes having the active site threonine. The differences in the active site may be the reason for the increased activity of the *B. subtilis* enzyme.

Improvement of Aldolase Activity

Catalytic antibodies can be as efficient as natural aldolases, accept a broad range of substrates, and can be used to catalyze the reaction shown in FIG. 2.

Aldolases can also be improved by directed evolution, for example as previously described for a KDPG aldolase (highly homologous to KHG described above) evolved by DNA shuffling and error-prone PCR to remove the requirement for phosphate and to invert the enantioselectivity. The KDPG aldolase polypeptides are useful in biochemical reactions since they are highly specific for the donor substrate (herein, pyruvate), but are relatively flexible with respect to the acceptor substrate (i.e. indole-3-pyruvate) (Koeller & Wong, *Nature* 409:232-9, 2001). KHG aldolase has activity for condensation of pyruvate with a number of carboxylic acids and aldehydes. Mammalian versions of the KHG aldolase are thought to have broader enantiospecificity than many bacterial versions, including higher activity on 4-hydroxy 4-methyl 2-oxoglutarate and acceptance of both stereoisomers of 4-hydroxy-2-ketoglutarate. Bacterial sources appear to have a 10-fold preference for the R isomer. There are nearly 100 KHG homologs available in genomic databases, and activity has been demonstrated in *Pseudomonas, Paracoccus, Providencia, Sinorhizobium, Morganella, E. coli,* and mammalian tissues. These enzymes can be used as a starting point for tailoring the enantiospecificity that is desired for monatin production.

Aldolases that utilize pyruvate and another substrate that is either a keto acid and/or has a bulky hydrophobic group like indole can be "evolved" to tailor the polypeptide's specificity, speed, and selectivity. In addition to KHG and ProA aldolases demonstrated herein, examples of these enzymes include, but are not limited to: KDPG aldolase and related polypeptides (KDPH); transcarboxybenzalpyruvate hydratase-aldolase from *Nocardioides* st; 4-(2-carboxyphenyl)-2-oxobut-3-enoate aldolase (2'-carboxybenzalpyruvate aldolase) which condenses pyruvate and 2-carboxybenzaldehyde (an aromatic ring-containing substrate); trans-O-hydroxybenzylidenepyruvate hydratase-aldolase from *Pseudomonas putida* and *Sphingomonas aromaticivorans*, which also utilizes pyruvate and an aromatic-containing aldehyde as substrates; 3-hydroxyaspartate aldolase (erythro-3-hydroxy-L-aspartate glyoxylate lyase), which uses 2-oxo acids as the substrates and is thought to be in the organism *Micrococcus denitrificans*; benzoin aldolase (benzaldehyde lyase), which utilizes substrates containing benzyl groups; dihydroneopterin aldolase; L-threo-3-phenylserine benzaldehyde-lyase (phenylserine aldolase) which condenses glycine with benzaldehyde; 4-hydroxy-2-oxovalerate aldolase; 1,2-dihydroxybenzylpyruvate aldolase; and 2-hydroxybenzalpyruvate aldolase.

Using assays similar to those described above, and the detection methods described in Example 6, isocitrate lyase, N-acetyl neuraminic acid synthase, citrate lyase, tryptophanase and certain mutants, beta-tyrosinase and certain mutants, PLP, catalytic aldolase antibodies, tryptophan synthase(s) did not appear to detectably convert indole-3-pyruvate to MP under the conditions tested.

A polypeptide having the desired activity can be selected by screening clones of interest using the following methods. Tryptophan auxotrophs are transformed with vectors carrying the clones of interest on an expression cassette and are grown on a medium containing small amounts of monatin or MP. Since aminotransferases and aldolase reactions are reversible, the cells are able to produce tryptophan from a racemic mixture of monatin. Similarly, organisms (both recombinant and wildtype) can be screened by ability to utilize MP or monatin as a carbon and energy source. One source of target aldolases is expression libraries of various *Pseudomonas* and rhizobacterial strains. Pseudomonads have many unusual catabolic pathways for degradation of aromatic molecules and they also contain many aldolases; whereas the rhizobacteria contain aldolases, are known to grow in the plant rhizosphere, and have many of the genes described for construction of a biosynthetic pathway for monatin.

Example 3

Conversion of Tryptophan or Indole-3-Pyruvate to Monatin

An in vitro process utilizing two enzymes, an aminotransferase and an aldolase, produced monatin from tryptophan and pyruvate. In the first step alpha-ketoglutarate was the acceptor of the amino group from tryptophan in a transamination reaction generating indole-3-pyruvate and glutamate. An aldolase catalyzed the second reaction in which pyruvate was reacted with indole-3-pyruvate, in the presence of $Mg^{2+}$ and phosphate, generating the alpha-keto derivative of monatin (MP), 2-hydroxy-2-(indol-3-ylmethyl)-4-ketoglutaric acid. Transfer of the amino group from the glutamate formed in the first reaction produced the desired product, monatin. Purification and characterization of the product established that the isomer formed was S,S-monatin. Alternative substrates, enzymes, and conditions are described as well as improvements that were made to this process.

Enzymes

The aldolase, 4-hydroxy-4-methyl-2-oxoglutarate pyruvate lyase (ProA aldolase, proA gene) (EC 4.1.3.17) from *Comamonas testosteroni* was cloned, expressed and purified as described in Example 2. The 4-hydroxy-2-oxoglutarate glyoxylate lyases (KHG aldolases) (EC 4.1.3.16) from *B. subtilis, E. coli,* and *S. meliloti* were cloned, expressed and purified as described in Example 2.

The aminotransferases used in conjunction with the aldolases to produce monatin were L-aspartate aminotransferase encoded by the *E. coli* aspC gene, the tyrosine aminotransferase encoded by the *E. coli* tyrB gene, the *S. meliloti* TatA enzyme, the broad substrate aminotransferase encoded by the *L. major* bsat gene, or the glutamic-oxaloacetic transaminase from pig heart (Type IIa). The cloning, expression and purification of the non-mammalian proteins are described in Example 1. Glutamic-oxaloacetic transaminase from pig heart (type IIa) was obtained from Sigma (# G7005).

Method Using ProA Aldolase and L-Aspartate Aminotransferase

The reaction mixture contained 50 mM ammonium acetate, pH 8.0, 4 mM $MgCl_2$, 3 mM potassium phosphate, 0.05 mM pyridoxal phosphate, 100 mM ammonium pyruvate, 50 mM tryptophan, 10 mM alpha-ketoglutarate, 160 mg of recombinant *C. testosteroni* ProA aldolase (unpurified cell extract, ~30% aldolase), 233 mg of recombinant *E. coli* L-aspartate aminotransferase (unpurified cell extract, ~40% aminotransferase) in one liter. All components except the enzymes were mixed together and incubated at 30° C. until the tryptophan dissolved. The enzymes were then added and the reaction solution was incubated at 30° C. with gentle shaking (100 rpm) for 3.5 hours. At 0.5 and 1 hour after the addition of the enzymes aliquots of solid tryptophan (50 mmoles each) were added to the reaction. All of the added tryptophan did not dissolve, but the concentration was maintained at 50 mM or higher. After 3.5 hours, the solid tryptophan was filtered off. Analysis of the reaction mixture by LC/MS using a defined amount of tryptophan as a standard showed that the concentration of tryptophan in the solution was 60.5 mM and the concentration of monatin was 5.81 mM (1.05 g).

The following methods were used to purify the final product. Ninety percent of the clear solution was applied to a column of BioRad AG50W-X8 resin (225 mL; binding capacity of 1.7 meq/mL). The column was washed with water, collecting 300 mL fractions, until the absorbance at 280 nm was <5% of the first flow through fraction. The column was then eluted with 1 M ammonium acetate, pH 8.4, collecting 4 300-mL fractions. All 4 fractions contained monatin and were evaporated to 105 mL using a roto-evaporator with a tepid water bath. A precipitate formed as the volume reduced and was filtered off over the course of the evaporation process.

Analysis of the column fractions by LC/MS showed that 99% of the tryptophan and monatin bound to the column. The precipitate that formed during the evaporation process contained >97% tryptophan and <2% of monatin. The ratio of tryptophan to product in the supernatant was approximately 2:1.

The supernatant (7 ml) was applied to a 100 mL Fast Flow DEAE Sepharose (Amersham Biosciences) column previously converted to the acetate form by washing with 0.5 L 1 M NaOH, 0.2 L water, 1.0 L of 1.0 M ammonium acetate, pH 8.4, and 0.5 L water. The supernatant was loaded at <2 mL/min and the column was washed with water at 3-4 mL/min until the absorbance at 280 nm was ~0. Monatin was eluted with 100 mM ammonium acetate, pH 8.4, collecting 4 100-mL fractions.

Analysis of the fractions showed that the ratio of tryptophan to monatin in the flow through fractions was 85:15 and the ratio in the eluent fractions was 7:93. Assuming the extinction coefficient at 280 nm of monatin is the same as tryptophan, the eluent fractions contained 0.146 mmole of product. Extrapolation to the total 1 L reaction would produce ~2.4 mmoles (~710 mg) of monatin, for a recovery of 68%.

The eluent fractions from the DEAE Sepharose column were evaporated to <20 mL. An aliquot of the product was further purified by application to a $C_8$ preparative reversed-phase column using the same chromatographic conditions as those described in Example 6 for the analytical-scale monatin characterization. Waters Fractionlynx™ software was employed to trigger automated fraction collection of monatin based on detection of the m/z=293 ion. The fraction from the $C_8$ column with the corresponding protonated molecular ion for monatin was collected, evaporated to dryness, and then dissolved in a small volume of water. This fraction was used for characterization of the product.

The resulting product was characterized using the following methods.

UV/Visible Spectroscopy. UV/visible spectroscopic measurements of monatin produced enzymatically were carried out using a Cary 100 Bio UV/visible spectrophotometer. The purified product, dissolved in water, showed an absorption maximum of 280 nm with a shoulder at 288 nm, characteristics typical of indole containing compounds.

LC/MS Analysis. Analyses of mixtures for monatin derived from the in vitro biochemical reactions were carried out as described in Example 6. A typical LC/MS analysis of monatin in an in vitro enzymatic synthetic mixture is illustrated in FIG. 5. The lower panel of FIG. 5 illustrates a selected ion chromatogram for the protonated molecular ion of monatin at m/z=293. This identification of monatin in the mixture was corroborated by the mass spectrum illustrated in FIG. 6. Analysis of the purified product by LC/MS showed a single peak with a molecular ion of 293 and absorbance at 280 nm. The mass spectrum was identical to that shown in FIG. 6.

MS/MS Analysis. LC/MS/MS daughter ion experiments, as described in Example 6, were also performed on monatin. A daughter ion mass spectrum of monatin is illustrated in FIG. 7. Tentative structural assignments of all fragment ions labeled in FIG. 7 were made. These include fragment ions of m/z=275 (293—$H_2O$), 257 (293—(2×$H_2O$)), 230 (275—COOH), 212 (257—COOH), 168 (3-buta-1,3-dienyl-1H-indole carbonium ion), 158 (1H-indole-3-carbaldehyde carbonium ion), 144 (3-ethyl-1H-indole carbonium ion), 130 (3-methylene-1H-indole carbonium ion), and 118 (indole carbonium ion). Many of these are the same as those obtained for MP (Example 2), as expected if derived from the indole portion of the molecule. Some are 1 mass unit higher than those seen for MP, due to the presence of an amino group instead of a ketone.

Accurate Mass Measurement of Monatin. FIG. 8 illustrates the mass spectrum obtained for purified monatin employing an Applied Biosystems-Perkin Elmer Q-Star hybrid quadrupole/time-of-flight mass spectrometer. The measured mass for protonated monatin using tryptophan as an internal mass calibration standard was 293.1144. The calculated mass of protonated monatin, based on the elemental composition $C_{14}H_{17}N_2O_5$ is 293.1137. This is a mass measurement error of less than 2 parts per million (ppm), providing conclusive evidence of the elemental composition of monatin produced enzymatically.

NMR Spectroscopy. The NMR experiments were performed on a Varian Inova 500 MHz instrument. The sample of monatin (~3 mg) was dissolved in 0.5 ml of $D_2O$. Initially, the solvent ($D_2O$) was used as the internal reference at 4.78 ppm. Since the peak for water was large, the $^1$H-NMR was run with suppression of the peak for water. Subsequently, due to the broadness of the water peak, the C-2 proton of monatin was used as the reference peak, and set at the published value of 7.192 ppm.

For $^{13}$C-NMR, an initial run of several hundred scans indicated that the sample was too dilute to obtain an adequate $^{13}$C spectrum in the allotted time. Therefore, a heteronuclear multiple quantum coherence (HMQC) experiment was performed, which enabled the correlation of the hydrogens and the carbons to which they were attached, and also providing information on the chemical shifts of the carbons.

A summary of the $^1$H and HMQC data is shown in Tables 2 and 3. By comparison to published values, the NMR data indicated that the enzymatically produced monatin was either (S,S), (R,R), or a mixture of both.

Chiral LC/MS Analysis. To establish that the monatin produced in vitro was one isomer, and not a mixture of the (R,R) and (S,S) enantiomers, chiral LC/MS analyses were carried out using the instrumentation described in Example 6.

Chiral LC separations were made using an Chirobiotic T (Advanced Separations Technology) chiral chromatography column at room temperature. Separation and detection, based on published protocols from the vendor, were optimized for the R-(D) and S-(L) isomers of tryptophan. The LC mobile phase consisted of A) water containing 0.05% (v/v) trifluoroacetic acid; B) Methanol containing 0.05% (v/v) trifluoroacetic acid. The elution was isocratic at 70% A and 30% B. The flow rate was 1.0 mL/min, and PDA absorbance was monitored from 200 nm to 400 nm. The instrumental parameters used for chiral LC/MS analysis of tryptophan and monatin are identical to those described in Example 6 for LC/MS analysis. Collection of mass spectra for the region m/z 150-400 was utilized. Selected ion chromatograms for protonated molecular ions ([M+H]$^+$=205 for both R- and S-tryptophan and [M+H]$^+$=293 for monatin) allowed direct identification of these analytes in the mixtures.

The chromatograms of R- and S-tryptophan and monatin, separated by chiral chromatography and monitored by MS, are shown in FIG. 9. The single peak in the chromatogram of monatin indicates that the compound is one isomer, with a retention time almost identical to S-tryptophan.

TABLE 2

1H NMR data

[Structure of monatin with numbered atoms: indole ring with positions 2-9, N1-H, connected via C3 to C12-C11(OH)(COOH at C15)-C10, and C12-C13(NH2)-C14(COOH)]

| | Cargill | | Vleggaar et al.[1] | | Takeshi et al.[2] | |
|---|---|---|---|---|---|---|
| Atom | $\delta_H$ | J(HH) Hz | $\delta_H$ | J(HH) Hz | $\delta_H$ | J(HH) Hz |
| 2 | 7.192 (1H, s) | | 7.192 (s) | | 7.18 (s) | |
| 4 | 7.671 (d) | 7.99 | 7.686 (d) | 7.9 | 7.67 (d) | 8.0 |
| 5 | 7.104 (dd) | 7.99 | 7.102 (dd) | 8.0, 8.0 | 7.11 (dd) | 7.5, 7.5 |
| 6 | 7.178 (dd) | * | 7.176 (dd) | 8.0, 8.0 | 7.17 (dd) | 7.5, 7.5 |
| 7 | 7.439 (dd) | 7.99 | 7.439 (d) | 8.1 | 7.43 (d) | 8.0 |
| 10a | 3.242 (d) | 14.5 | 3.243 (d) | 14.3 | 3.24 (d) | 14.5 |
| 10b | 3.033 (d) | 14.5 | 3.051 (d) | 14.3 | 3.05 (d) | 14.5 |
| 12 | 2.626 (dd) | 15.5, 1.5 | 2.651 (dd) | 15.3, 1.7 | 2.62 (dd) | 15.5, 1.8 |
| | 2.015 (dd) | 15.0, 12.0 | 2.006 (dd) | 15.3, 11.7 | 2.01 (dd) | 15.5, 12.0 |
| 13 | 3.571 (dd) | 10.75*, 1.5 | 3.168 (dd) | 11.6, 1.8 | 3.57 (dd) | 12.0, 1.8 |

[1]Vleggaar et al. (J.C.S. Perkin Trans. 1:3095-8, 1992).
[2]Takeshi and Shusuke (JP 2002060382, 2002-02-26).

TABLE 3

13C NMR data (from HMQC spectrum)

| | Cargill | Vleggaar et al.[1] |
|---|---|---|
| Atom | $\delta_C$ | $\delta_C$ |
| 2 | 126.1 | 126.03 |
| 3 | * | 110.31 |
| 4 | 120.4 | 120.46 |
| 5 | 120.2 | 120.25 |
| 6 | 122.8 | 122.74 |
| 7 | 112.8 | 112.79 |
| 8 | * | 137.06 |
| 9 | * | 129.23 |
| 10a | 36.4 | 36.53 |
| 12 | 39.5 | 39.31 |
| 13 | 54.9 | 54.89 |
| 14 | * | 175.30 |
| 15 | * | 181.18 |

[1]Vleggaar et al. (J.C.S. Perkin Trans. 1: 3095–8, 1992).

Polarimetry. The optical rotation was measured on a Rudolph Autopol III polarimeter. The monatin was prepared as a 14.6 mg/mL solution in water. The expected specific rotation ($[\alpha]_D^{20}$) for S,S monatin (salt form) is −49.6 for a 1 g/mL solution in water (Vleggaar et al). The observed $[\alpha]_D^{20}$ was −28.1 for the purified, enzymatically produced monatin indicating that it was the S, S isomer.

Improvements

The reaction conditions, including reagent and enzyme concentrations, were optimized and yields 5-10 mg/mL were produced using the following reagent mix: 50 mM ammonium acetate pH 8.3, 2 mM MgCl$_2$, 200 mM pyruvate (sodium or ammonium salt), 5 mM alpha-ketoglutarate (sodium salt), 0.05 mM pyridoxal phosphate, deaerated water to achieve a final volume of 1 mL after the addition of the enzymes, 3 mM potassium phosphate, 50 µg/mL of recombinant ProA aldolase (cell extract; total protein concentration of 167 µg/mL), 1000 µg/mL of L-aspartate aminotransferase encoded by the E. coli aspC gene (cell extract; total protein concentration of 2500 µg/mL), and solid tryptophan to afford a concentration of >60 mM (saturated; some undissolved throughout the reaction). The mixture was incubated at 30° C. for 4 hours with gentle stirring or mixing.

Substitutions

The concentration of alpha-ketoglutarate can be reduced to 1 mM and supplemented with 9 mM aspartate with an equivalent yield of monatin. Alternative amino acid acceptors can be utilized in the first step, such as oxaloacetate.

When recombinant L. major broad substrate aminotransferase was used in place of the E. coli L-aspartate aminotransferase, similar yields of monatin were achieved. However, a second unidentified product (3-10% of the major product) with a molecular mass of 292 was also detected by LC-MS analysis. Monatin concentrations of 0.1-0.5 mg/mL were produced when the E. coli tyrB encoded enzyme, the S. meliloti tatA encoded enzyme or the glutamic-oxaloacetic transaminase from pig heart (type IIa) was added as the aminotransferase. When starting the reaction from indole-3-pyruvate, a reductive amination can be done for the last step with glutamate dehydrogenase and NADH (as in Example 4).

The KHG aldolases from B. subtilis, E. coli, and S. meliloti were also used with the E. coli L-aspartate aminotransferase to produce monatin enzymatically. The following reaction conditions were used: 50 mM NH$_4$—OAc pH 8.3, 2 mM MgCl$_2$, 200 mM pyruvate, 5 mM glutamate, 0.05 mM pyridoxal phosphate, deaerated water to achieve a final volume of 0.5 mL after the addition of the enzymes, 3 mM potassium phosphate, 20 µg/mL of recombinant B. subtilis KHG aldolase (purified), ca. 400 µg/mL of E. coli L-aspartate aminotransferase (AspC) unpurified from cell extract, and 12 mM indole-3-pyruvate. The reactions were incubated at 30° C. for 30 minutes with shaking. The amount of monatin produced using the B. subtilis enzyme was 80 ng/mL, and increased with increasing amounts of aldolase. If indole-3-pyruvate and glutamate were replaced by saturating amounts of tryptophan and 5 mM alpha-ketoglutarate, the production of monatin was increased to 360 ng/mL. Reactions were repeated with 30 µg/mL of each of the three KHG enzymes in 50 mM Tris pH 8.3, with saturating amounts of tryptophan, and were allowed to proceed for an hour in order to increase detection. The *Bacillus* enzyme had the highest activity as in Example 2, producing approximately 4000 ng/mL monatin. The *E. coli* KHG produced 3000 ng/mL monatin, and the *S. meliloti* enzyme produced 2300 ng/mL.

Example 4

Interconversion Between MP and Monatin

The amination of MP to form monatin can be catalyzed by aminotransferases such as those identified in Examples 1 and 3, or by dehydrogenases that require a reducing cofactor such as NADH or NADPH. These reactions are reversible and can be measured in either direction. The directionality, when using a dehydrogenase enzyme, can be largely controlled by the concentration of ammonium salts.

Dehydrogenase activity. The oxidative deamination of monatin was monitored by following the increase in absorbance at 340 nm as NAD(P)+ was converted to the more chromophoric NAD(P)H. Monatin was enzymatically produced and purified as described in Example 3.

A typical assay mixture contained 50 mM Tris-HCl, pH 8.0 to 8.9, 0.33 mM NAD$^+$ or NADP$^+$, 2 to 22 units of glutamate dehydrogenase (Sigma), and 10-15 mM substrate in 0.2 mL. The assay was performed in duplicate in a UV-transparent microtiter plate, on a Molecular Devices SpectraMax Plus platereader. A mix of the enzyme, buffer, and NAD(P)$^+$ were pipetted into wells containing the substrate and the increase in absorbance at 340 nm was monitored at 10 second intervals after brief mixing. The reaction was incubated at 25° C. for 10 minutes. Negative controls were carried out without the addition of substrate, and glutamate was utilized as a positive control. The type III glutamate dehydrogenase from bovine liver (Sigma # G-7882) catalyzed the conversion of the monatin to the monatin precursor at a rate of conversion approximately one-hundredth the rate of the conversion of glutamate to alpha-ketoglutarate.

Transamination activity. Monatin aminotransferase assays were conducted with the aspartate aminotransferase (AspC) from *E. coli*, the tyrosine aminotransferase (TyrB) from *E. coli*, the broad substrate aminotransferase (BSAT) from *L. major*, and the two commercially available porcine glutamate-oxaloacetate aminotransferases described in Example 1. Both oxaloacetate and alpha-ketoglutarate were tested as the amino acceptor. The assay mixture contained (in 0.5 mL) 50 mM Tris-HCl, pH 8.0, 0.05 mM PLP, 5 mM amino acceptor, 5 mM monatin, and 25 μg of aminotransferase. The assays were incubated at 30° C. for 30 minutes, and the reactions were stopped by addition of 0.5 mL isopropyl alcohol. The loss of monatin was monitored by LC/MS (Example 6). The highest amount of activity was noted with *L. major* BSAT with oxaloacetate as the amino acceptor, followed by the same enzyme with alpha-ketoglutarate as the amino acceptor. The relative activity with oxaloacetate was: BSAT>AspC>porcine type IIa>porcine type I=TyrB. The relative activity with alpha-ketoglutarate was: BSAT>AspC>porcine type I>porcine type IIa>TyrB.

Using assays similar to those described above, and the detection methods described in Example 6, two enzymes, *S. meliloti* tatA and *R. sphaeroides* tatA, did not appear to detectably convert monatin to MP under the conditions tested. This lack of detectable activity, however, may be due to the fact that MP is sometimes difficult to detect because it is unstable in an aqueous solution.

Example 5

Production of Monatin from Tryptophan and C3 Sources Other than Pyruvate

As described above in Example 3, indole-3-pyruvate or tryptophan can be converted to monatin using pyruvate as the C3 molecule. However, in some circumstances, pyruvate may not be a desirable raw material. For example, pyruvate may be more expensive than other C3 carbon sources, or may have adverse effects on fermentations if added to the medium. Alanine can be transaminated by many PLP-enzymes to produce pyruvate.

Tryptophanase-like enzymes perform beta-elimination reactions at faster rates than other PLP enzymes such as aminotransferases. Enzymes from this class (4.1.99.-) can produce ammonia and pyruvate from amino acids such as L-serine, L-cysteine, and derivatives of serine and cysteine with good leaving groups such as O-methyl-L-serine, O-benzyl-L-serine, S-methylcysteine, S-benzylcysteine, S-alkyl-L-cysteine, O-acyl-L-serine, 3-chloro-L-alanine.

Processes to produce monatin using EC 4.1.99.- polypeptides can be improved by mutating the β-tyrosinase (TPL) or tryptophanase according to the method of Mouratou et al. (*J. Biol. Chem* 274:1320-5, 1999). Mouratou et al. describe the ability to covert the β-tyrosinase into a dicarboxylic amino acid β-lyase, which has not been reported to occur in nature. The change in specificity was accomplished by converting valine (V) 283 to arginine (R) and arginine (R) 100 to threonine (T). These amino acid changes allow for the lyase to accept a dicarboxylic amino acid for the hydrolytic deamination reaction (such as aspartate). Aspartate, therefore, can also be used as a source of pyruvate for subsequent aldol condensation reactions.

Additionally, cells or enzymatic reactors can be supplied with lactate and an enzyme that converts lactate to pyruvate. Examples of enzymes capable of catalyzing this reaction include lactate dehydrogenase and lactate oxidase.

Isolation of Genomic DNA

Tryptophanase polypeptides have previously been reported in, for example, Mouratou et al. (*JBC* 274:1320-5, 1999). To isolate genes that encode tryptophanase polypeptides, genomic DNA from *E. coli* DH10B was used as a template for PCR as described in Example 1.

The gene for tyrosine-phenol lyase was isolated from *C. freundii* (ATCC catalog number 8090, Designation ATCC 13316; NCTC 9750) and grown on Nutrient agar (Difco 0001) and nutrient broth (Difco 0003) at 37° C. to an OD of 2.0. The genomic DNA was purified using a Qiagen Genomic-tip™ 100/G kit.

PCR Amplification of Coding Sequences

Primers were designed with compatible overhangs for the pET 30 Xa/LIC vector (Novagen, Madison, Wis.) as described above in Example 1.

*E. coli* tna (SEQ ID NO: 41). N-terminal primer for pET30 Xa/LIC cloning: 5'-GGT ATT GAG GGT CGC ATG GAA AAC TTT AAA CAT CT-3' (SEQ ID NO: 43). C-terminal primer for pET30 Xa/LIC cloning: 5'-AGA GGA GAG TTA GAG CCT TAA ACT TCT TTA AGT TTT G-3' (SEQ ID NO: 44).

*C. freundii* tpl (SEQ ID NO: 42). N-terminal primer for pET30 Xa/LIC cloning: 5'-GGT ATT GAG GGT CGC ATGAATTATCCGGCAGAACC-3' (SEQ ID NO: 45). C-terminal primer for pET 30 Xa/LIC cloning: 5'-AGA GGA GAG TTA GAG CCTTAGATGTAATCAAAGCGTG-3' (SEQ ID NO: 46).

The Eppendorf Mastercycler™ Gradient 5331 Thermal Cycler was used for all PCR reactions. In 50 μL was added 0.5 μg template (genomic DNA), 1.0 μM of each primer, 0.4 mM each dNTP, 3.5 U Expand High Fidelity Polymerase (Roche), 1× Expand buffer with Mg, and 5% DMSO (final concentration). The thermocycler PCR program used was as follows: 96° C. hot start (5 minutes), 94° C.—30 seconds, 40-60° C.—1 minute 45 seconds, 72° C.—2 minutes 15 seconds; 30 repetitions. The final polymerization step was for 7 minutes, and the samples were then stored at 4° C.

Cloning

Cloning and positive clone identification procedures detailed above in Example 1 were used to identify the appropriate clones.

Gene Expression and Activity Assays

Plasmid DNA (verified by sequence analysis) was subcloned into the expression host BL21(DE3)(Novagen). The cultures were grown in LB medium with 30 mg/L kanamycin, the plasmids were isolated using a Qiagen miniprep kit, and analyzed by restriction digest to confirm identity.

Induction experiments were done with the BL21(DE3) expression host, the constructs were grown in LB medium containing 50 mg/L kanamycin at 37° C. Protein expression was induced using 0.1 mM IPTG after the $OD_{600}$ of the culture reached approximately 0.6. The cells were grown for 4 hours at 30° C. and harvested by centrifugation. The cells were then lysed in 5 mL/g wet cell weight BugBuster™ (Novagen) reagent containing 5 μL/mL protease inhibitor cocktail set #III (Calbiochem) and 1 μL/mL benzonase nuclease (Novagen), and the His-tagged recombinant proteins were purified using the His-Bind cartridges as described above in Example 1. Purified proteins were desalted on a PD-10 (G25 Sephadex, Amersham Biosciences) column and eluted in 100 mM Tris-Cl buffer, pH 8.0. The proteins were analyzed by SDS-PAGE on 4-15% gradient gels to check for soluble protein levels at the predicted MW of the recombinant fusion protein.

Mutagenesis

Some members of polypeptide class 4.1.99.- (tryptophanase and β-tyrosinase) will perform the beta-lyase reaction with aspartate or similar amino acids without any modification. However, some members of the class may need to be mutagenized to allow for the use of the substrates and/or the creation of the product. Moreover, in some cases polypeptides that can perform the conversion can be further optimized by mutagenesis.

Site directed mutagenesis was performed based on 3D structure analysis of PLP-binding polypeptides. Two examples for changing the substrate specificity of the polypeptides are shown below.

Mutagenesis of Tryptophanase Example A

The mutagenesis protocol provided below introduced two point mutations in the amino acid sequence. The first point mutation changed arginine (R) at position 103 to threonine (T) and the second point mutation changed valine (V) at position 299 to arginine (R) (numbering system for *E. coli* mature protein). Mutagenesis experiments were performed by ATG Laboratories (Eden Prairie, Minn.). Mutations were introduced sequentially by PCR of gene fragments and reassembly of the fragments was accomplished by PCR as well.

Primers for converting arginine (R)103 to threonine (T):

```
                                   (SEQ ID NO: 47)
5'-CCAGGGCACCGGCGCAGAGCAAATCTATATT-3'
and
                                   (SEQ ID NO: 48)
5'-TGCGCCGGTGCCCTGGTGAGTCGGAATGGT-3'.
```

Primers for converting valine (V)299 to arginine (R):

```
                                   (SEQ ID NO: 49)
5'-TCCTGCACGCGGCAAAGGGTTCTGCACTCGGT-3'
and
                                   (SEQ ID NO: 50)
5'-CTTTGCCGCGTGCAGGAAGGCTTCCCGACA-3'.
```

Mutants were screened by restriction digest with Xba I/HindIII and SphI, and verified by sequencing.

Mutagenesis of Tyrosine Phenol Lyase (β-tyrosinase)
Example B

Two point mutations were made to the tyrosine phenol lyase amino acid sequence. These mutations converted arginine (R) at position 100 to threonine (T) and valine (V) at position 283 to arginine (R) (in *C. freundii* mature protein sequence).

Primers for the R100T conversion were:

```
                                   (SEQ ID NO: 51)
5'-AGGGGACCGGCGCAGAAAACCTGTTATCG-3'
and
                                   (SEQ ID NO: 52)
5'-TCTGCGCCGGTCCCCTGGTGAGTCGGAACAAT-3'.
```

Primers for the V283R conversion were:

```
                                   (SEQ ID NO: 53)
5'-GTTAGTCCGCGTCTACGAAGGGATGCCAT-3'
and
                                   (SEQ ID NO: 54)
5'-GTAGACGCGGACTAACTCTTTGGCAGAAG-3'.
```

The methods described above were used, and the clones were screened by KpnI/SacI digestion, and BstXI digestion. The sequences were verified by dideoxy chain termination sequencing. Recombinant protein was produced as described above for the wildtype enzymes.

The reaction mixture consisted of 50 mM Tris-Cl pH 8.3, 2 mM $MgCl_2$, 200 mM C3 carbon source, 5 mM alpha-ketoglutarate, sodium salt, 0.05 mM pyridoxal phosphate, deaerated water to achieve a final volume of 0.5 mL after the addition of the enzymes, 3 mM potassium phosphate pH 7.5, 25 μg of crude recombinant *C. testosteroni* ProA aldolase as prepared in Example 2, 500 μg of crude L-aspartate aminotransferase (AspC) as prepared in Example 1, and solid tryptophan to afford a concentration of >60 mM (saturated; some undissolved throughout the reaction). The reaction mix was incubated at 30° C. for 30 minutes with mixing. Serine, alanine, and aspartate were supplied as 3-carbon sources. Assays were performed with and without secondary PLP enzymes (purified) capable of performing beta-elimination and beta-lyase reactions (tryptophanase (TNA), double mutant tryptophanase, β-tyrosinase (TPL)). The results of the LC/MS analyses of the reaction mixtures are shown in Table 4:

TABLE 4

Production of monatin utilizing alternative C3-carbon sources

| C3-carbon source | Additional PLP Enzyme | Relative Activity |
|---|---|---|
| none | None | 0% |
| pyruvate | None | 100% |
| serine | None | 3% |
| serine | 11 μg wildtype TNA (1 U) | 5.1% |
| serine | 80 μg double mutant TNA | 4.6% |
| alanine | None | 32% |
| alanine | 11 μg wildtype TNA | 41.7% |
| alanine | 80 μg mutant TNA | 43.9% |
| aspartate | 110 μg wildtype TNA (10 U) | 7.7% |
| aspartate | 5 U wildtype TPL (crude) | 5.1% |
| aspartate | 80 μg mutant TNA | 3.3% |

The monatin produced from alanine and serine as 3-carbon sources was verified by LC/MS/MS daughter scan analysis, and was identical to the characterized monatin produced in Example 3. Alanine was the best alternative tested, and was transaminated by the AspC enzyme. The amount of monatin produced was increased by addition of the tryptophanase, which has a transamination secondary activity. The amount of monatin produced with serine as a carbon source nearly doubled with the addition of the tryptophanase enzymes, even though only one-fifth of the amount of tryptophanase was added in comparison to the aminotransferase. AspC is capable of some amount of beta-elimination activity alone. The results with aspartate indicate that the tryptophanase activity on aspartate does not increase with the same site-directed mutations as previously suggested for β-tyrosinase. It is expected that the mutant β-tyrosinase will have higher activity for production of monatin.

Example 6

Detection of Monatin, MP, Tryptophan, and Glutamic Acid

This example describes methods used to detect the presence of monatin, or its precursor 2-hydroxy 2-(indol-3-ylm-ethyl)-4-keto glutaric acid, as well tryptophan and glutamic acid. It also describes a method for the separation and detection of the four stereoisomers of monatin.

LC/MS Analysis of Monatin, MP, and Tryptophan

Analyses of mixtures for monatin, MP, and/or tryptophan derived from in vitro or in vivo biochemical reactions were performed using a Waters/Micromass liquid chromatography-tandem mass spectrometry (LC/MS/MS) instrument including a Waters 2795 liquid chromatograph with a Waters 996 Photo-Diode Array (PDA) absorbance monitor placed in series between the chromatograph and a Micromass Quattro Ultima triple quadrupole mass spectrometer. LC separations were made using an Xterra MS $C_8$ reversed-phase chromatography column, 2.1 mm×250 mm, or a Supelco Discovery $C_{18}$ reversed phase chromatography column, 2.1 mm×150 mm at room temperature or at 40° C. The LC mobile phase consisted of A) water containing 0.05% (v/v) trifluoroacetic acid and B) methanol containing 0.05% (v/v) trifluoroacetic acid.

The gradient elution was linear from 5% B to 35% B, 0-4 min, linear from 35% B to 60% B, 4-6.5 min, linear from 60% B to 90% B, 6.5-7 min, isocratic at 90% B 7-11 min, linear from 90% B to 95% B, 11-12 min, linear from 95% B to 5% B, 12-13 min, with a 5 min re-equilibration period between runs. The flow rate was 0.25 mL/min, and PDA absorbance was monitored from 200 nm to 400 nm. All parameters of the ESI-MS were optimized and selected based on generation of protonated molecular ions ($[M+H]^+$) of the analytes of interest, and production of characteristic fragment ions.

The following instrumental parameters were used for LC/MS analysis of monatin: Capillary: 3.5 kV; Cone: 40 V; Hex 1: 20 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 15.0; High mass resolution (Q1): 15.0; Ion energy: 0.2; Entrance: 50V; Collision Energy: 2; Exit: 50V; Low mass resolution (Q2): 15; High mass resolution (Q2): 15; Ion energy (Q2): 3.5; Multiplier: 650. Uncertainties for reported mass/charge ratios (m/z) and molecular masses are ±0.01%. Initial detection of the alpha-keto acid form of monatin (MP) and monatin in the mixtures was accomplished by LC/MS monitoring with collection of mass spectra for the region m/z 150-400. Selected ion chromatograms for protonated molecular ions ($[M+H]^+$=292 for MP, $[M+H]^+$=293 for monatin, $[M+H]^+$= 205 for tryptophan) allowed direct identification of these analytes in the mixtures. Subsequent methods for monatin and MP detection used multiple reaction monitoring (MRM) LC/MS/MS methodology (see below).

LC/MS/MS Analysis for Monatin

LC/MS/MS daughter ion experiments were performed on monatin as follows. A daughter ion analysis involves transmission of the parent ion (e.g., m/z=293 for monatin) of interest from the first mass analyzer (Q1) into the collision cell of the mass spectrometer, where argon is introduced and chemically dissociates the parent into fragment (daughter) ions. These fragment ions are then detected with the second mass analyzer (Q2), and can be used to corroborate the structural assignment of the parent. Tryptophan was characterized and quantified in the same way via transmission and fragmentation of m/z=205.

The following instrumental parameters were used for LC/MS/MS analysis of monatin: Capillary: 3.5 kV; Cone: 40 V; Hex 1: 20 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 13.0; High mass resolution (Q1): 13.0; Ion energy: 0.2; Entrance: −5 V; Collision Energy: 14; Exit: 1V; Low mass resolution (Q2): 15; High mass resolution (Q2): 15; Ion energy (Q2): 3.5; Multiplier: 650.

LC/MS/MS Multiple Reaction Monitoring

To increase the sensitivity and selectivity of monatin detection, an LC/MS/MS method employing MRM measurements has been developed. LC separations were performed as described in previous sections. Instrumental parameters for EST-MS/MS were set up as described in the previous section, except that low and high mass resolution settings for Q1 and Q2 are set to 12.0 to maximize sensitivity. Five monatin-specific parent-to daughter transitions are used to specifically detect monatin in in vitro and in vivo reactions. The transitions are 293.1 to 158.3, 293.1 to 168.2, 293.1 to 211.2, 293.1 to 230.2, and 293.1 to 257.2.

High-Throughput Determination of Monatin, Tryptophan, and Glutamic Acid (Glutamate)

High-throughput analyses (<5 min/sample) of mixtures for monatin, tryptophan, and/or glutamic acid derived from in vitro or in vivo reactions were carried out using instrumentation described above, and the same MS parameters as described for LC/MS/MS Multiple Reaction Monitoring. LC separations were made using a 4.6 mm×50 mm Advanced Separation Technologies Chirobiotic T column at room temperature. The LC mobile phase consisted of A) water containing 0.25% acetic acid; B) Methanol containing 0.25% acetic acid. The isocratic elution was at 50% B, 0-5 min. The flow rate was 0.6 mL/min. All parameters of the ESI-MS/MS system were optimized and selected based on optimal in-source generation of the protonated molecular ions of tryptophan and monatin and the internal standard $^2H_5$-tryptophan or $^2H_3$-glutamic acid, as well as collision-induced production of analyte-specific fragment ions for multiple reaction monitoring (MRM) experiments (204.7 to 146.4 for tryptophan, 209.7 to 151.4 for $^2H_5$-tryptophan, 147.6 to 102.4 for glutamic acid, 150.6 to 105.4 for $^2H_3$-glutamic acid, monatin-specific transitions listed in the previous section).

Accurate Mass Measurement of Monatin.

High resolution MS analysis was carried out using an Applied Biosystems-Perkin Elmer Q-Star hybrid quadrupole/time-of-flight mass spectrometer. The measured mass for protonated monatin used tryptophan as an internal mass calibration standard. The calculated mass of protonated monatin, based on the elemental composition $C_{14}H_{17}N_2O_5$ is 293.1137. Monatin produced using the biocatalytic process described in Example 3 showed a measured mass of 293.1144. This is a mass measurement error of less than 2 parts per million (ppm), providing conclusive evidence of the elemental composition of monatin produced enzymatically.

Chiral LC/MS/MS (MRM) Measurement of Monatin

Determination of the stereoisomer distribution of monatin in in vitro and in vivo reactions was accomplished by derivitization with 1-fluoro-2-4-dinitrophenyl-5-L-alanine amide (FDAA), followed by reversed-phase LC/MS/MS MRM measurement.

Derivitization of Monatin with FDAA

To 50 μL of sample or standard was added 200 μL of a 1% solution of FDAA in acetone. Forty μL of 1.0 M Sodium bicarbonate was added, and the mixture incubated for 1 h at 40° C. with occasional mixing. The sample was removed and cooled, and neutralized with 20 μL of 2.0 M HCl (more HCl may be required to effect neutralization of a buffered biological mixture). After degassing is complete, samples were ready for analysis by LC/MS/MS.

LC/MS/MS Multiple Reaction Monitoring for the Determination of the Stereoisomer Distribution of Monatin in In Vitro and In Vivo Reactions.

Analyses were performed using the LC/MS/MS instrumentation described in previous sections. LC separations capable of separating all four stereoisomers of monatin (specifically FDAA-monatin) were performed on a Phenomenex Luna (5 μm) C18 reversed phase chromatography column at 40° C. The LC mobile phase consisted of A) water containing 0.05% (mass/volume) ammonium acetate and B) acetonitrile. The gradient elution was linear from 2% B to 34% B, 0-33 min, linear from 34% B to 90% B, 33-34 min, isocratic at 90% B 34-44 min, and linear from 90% B to 2% B, 44-46 min, with a 16 min re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]$^+$) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1: 10 V; Aperture: 0 V; Hex 2: 0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5V; Collision Energy: 20; Exit: 1V; Low mass resolution (Q2): 12; High mass resolution (Q2): 12; Ion energy (Q2): 3.0; Multiplier: 650. Three FDAA-monatin-specific parent-to daughter transitions are used to specifically detect FDAA-monatin in in vitro and in vivo reactions. The transitions are 543.6 to 268.2, 543.6 to 499.2, and 543.6 to 525.2. Identification of FDAA-monatin stereoisomers is based on chromatographic retention time as compared to purified monatin stereoisomers, and mass spectral data.

Liquid Chromatography-Post Column Fluorescence Detection of Amino Acids Including Glutamate Liquid chromatography with post-column fluorescence detection for the determination of glutamic acid in in vitro and in vivo reactions was performed on a Waters 2690 LC system or equivalent combined with a Waters 474 scanning fluorescence detector, and a Waters post-column reaction module. LC separations were performed on an Interaction-Sodium loaded ion exchange column at 60° C. Mobile phase A was Pickering Na 328 buffer (Pickering Laboratories, Inc.; Mountain View, Calif.). Mobile phase B was Pickering Na 740 buffer. The gradient elution was from 0% B to 100% B, 0-20 min, isocratic at 100% B, 20-30 min, and linear from 100% B to 0% B, 30-31 min, with a 20 min re-equilibration period between runs. The flow rate for the mobile phase was 0.5 mL/min. The flow rate for the OPA post-column derivitization solution was 0.5 mL/min. The fluorescence detector settings were EX 338 nm and Em 425 nm. Norleucine was employed as an internal standard for the analysis. Identification of amino acids was based on chromatographic retention time data for purified standards.

Example 7

Production of Monatin in Bacteria

This example describes methods used to produce monatin in *E. coli* cells. One skilled in the art will understand that similar methods can be used to produce monatin in other bacterial cells. In addition, vectors containing other genes in the monatin synthesis pathway (FIG. 2) can be used.

Production of Monatin in *E. coli* BL21(DE3)::proA/pET30 Xa/LIC Cells

Fresh plates of *E. coli* BL21(DE3)::*C. testosteroni* proA/pET30 Xa/LIC cells (as described in Example 2) were prepared on LB medium containing 50 μg/mL kanamycin. Overnight cultures (5 mL) were inoculated from a single colony and grown at 30° C. in LB medium with kanamycin. Typically, a 1 to 50 inoculum was used for induction in trp-1+ glucose medium containing 50 ρg/mL kanamycin.

Trp-1+glucose medium, a minimal medium that has been used for increased production of tryptophan in *E. coli* cells (Zeman et al. *Folia Microbiol*. 35:200-4, 1990), was prepared as follows. To 700 mL nanopure water the following reagents were added: 2 g $(NH_4)_2SO_4$, 13.6 g $KH_2PO_4$, 0.2 g $MgSO_4*7H_2O$, 0.01 g $CaCl_2*2H_2O$ and 0.5 mg $FeSO_4*7H_2O$. The pH was adjusted to 7.0, the volume was increased to 850 mL, and the medium was autoclaved. A 50% glucose solution was prepared separately, and sterile-filtered. Forty mL was added to the base medium (850 mL) for a 1 L final volume.

A 10 g/L L-tryptophan solution was prepared in 0.1 M sodium phosphate pH 7, and sterile-filtered. One-tenth volume was typically added to cultures as specified below. A 10% sodium pyruvate solution was also prepared and sterile-filtered. A 10 mL aliquot was typically used per liter of culture. Stocks of ampicillin (100 mg/mL), kanamycin (25 mg/mL) and IPTG (840 mM) were prepared, sterile-filtered, and stored at −20° C. before use. Tween 20 (polyoxyethylene 20-Sorbitan monolaurate) was utilized at a 0.2% (vol/vol)

final concentration. Ampicillin was used at non-lethal concentrations, typically 1-10 µg/mL final concentration.

Cells were grown at 37° C. and sampled every hour until an $OD_{600}$ of 0.35-0.8 was obtained. Cells were then induced with 0.1 mM IPTG, and the incubation temperature was reduced to 34° C. Samples (1 ml) were collected prior to induction (zero time point) and centrifuged at 5000×g. The supernatant was frozen at −20° C. for LC-MS analysis. Four hours post-induction, another 1 mL sample was collected and centrifuged to separate the broth from the cell pellet. Tryptophan, sodium pyruvate, ampicillin, and Tween were added as described above.

The cells were grown for 48 hours post-induction, and another 1 mL sample was taken and prepared as above. At 48 hours, another aliquot of tryptophan and pyruvate were added. The entire culture volume was centrifuged after approximately 70 hours of growth (post-induction), for 20 minutes at 4° C. and 3500 rpm. The supernatant was decanted and both the broth and the cells were frozen at −80° C. The broth fractions were filtered and analyzed by LC/MS. The heights and areas of the $[M+H]^+=293$ peaks were monitored as described in Example 6. The background level of the medium was subtracted. The data was also normalized for cell growth by plotting the height of the $[M+H]^+=293$ peak divided by the optical density of the culture at 600 nm.

Higher levels of monatin were produced when pyruvate, ampicillin, and Tween were added 4 hours post induction rather than at induction. Other additives such as PLP, additional phosphate, or additional $MgCl_2$ did not increase the production of monatin. Higher titers of monatin were obtained when tryptophan was utilized instead of indole-3-pyruvate, and when the tryptophan was added post-induction rather than at inoculation, or at induction. Prior to induction, and 4 hours post-induction (at time of substrate addition), there was typically no detectable level of monatin in the fermentation broth or cellular extracts. Negative controls were done utilizing cells with pET30a vector only, as well as cultures where tryptophan and pyruvate were not added. A parent MS scan demonstrated that the compound with $(m+1)/z=293$ was not derived from larger molecules, and daughter scans (performed as in Example 6) were similar to monatin made in vitro.

The effect of a non-ionic detergent (such as Tween, Trixon X-100 and dodecylammonium acetate) on monatin cell secretion was studied. In particular, the effect of Tween on the secretion of monatin was studied by utilizing 0, 0.2% (vol/vol), and 0.6% final concentrations of Tween-20. The highest amount of monatin produced by shake flasks was at 0.2% Tween. Other Tween types (for example, Tween-40, Tween-60, and Tween-80) were also tested in *E. coli* at this concentration, because in this host it is expected that many detergents will non-specifically increase the leakiness of the cell, although the growth of the cells is typically inhibited by Tween or other detergents. Tween 40 caused the least inhibition to growth, followed by Tween 60, Tween 80, and Tween 20. The final $OD_{600}$ of cells grown in Tween 20 was slightly over half of the cultures grown in the presence of Tween 40.

The ampicillin concentration was varied between 0 and 10 µg/mL. The amount of monatin in the cellular broth increased rapidly (2.5×) between 0 and 1 µg/mL, and increased 1.3× when the ampicillin concentration was increased from 1 to 10 µg/mL.

A time course experiment showing typical results is shown in FIG. 10. The amount of monatin secreted into the cell broth increased, even when the values are normalized for cell growth. By using the molar extinction coefficient of tryptophan, the amount of monatin in the broth was estimated to be less than 10 µg/mL. The same experiment was repeated with the cells containing vector without proA insert. Many of the numbers were negative, indicating the peak height at $(m+1)/z=293$ was less in these cultures than in the medium alone (FIG. 10). The numbers were consistently lower when tryptophan and pyruvate were absent, demonstrating that monatin production is a result of an enzymatic reaction catalyzed by the aldolase enzyme.

The in vivo production of monatin in bacterial cells was repeated in 800 mL shake flask experiments and in fermentors. A 250 mL sample of monatin (in cell-free broth) was purified by anion exchange chromatography and preparative reverse-phase liquid chromatography. This sample was evaporated, and submitted for high resolution mass analysis (described in Example 3). The high resolution MS indicated that the metabolite being produced is monatin.

Because the optimization experiments for the in vitro process suggested that higher concentrations of monatin could be produced when the aminotransferase concentration was several times higher than that of the aldolase (see Example 3), an operon was constructed for in vivo studies in which the aspC gene was expressed at a higher level than the proA gene.

Primers were designed to introduce *C. testosteroni* proA into an operon with aspC/pET30 Xa/LIC, as follows: 5' primer: ACTCGGATCCGAAGGAGATATACATATG-TACGAACTGGGACT (SEQ ID NO: 67) and 3' primer: CGGCTGTCGACCGTTAGTCAATATATTTCAGGC (SEQ ID NO: 68). The 5' primer contains a BamHI site, the 3' primer contains a SalI site for cloning. PCR was performed as described in Example 2 and the product was gel purified using a QIAquick® Gel Extraction Kit. The aspC/pET30 Xa/LIC construct and the PCR product were digested with BamHI and SalI. The digests were purified using a QIAquick® PCR Purification Kit, eluting from the spin columns with EB buffer. The proA PCR product was ligated with the vector using the Roche Rapid DNA Ligation kit (Indianapolis, Ind.) according to manufacturer's instructions. Chemical transformations were done using NovaBlue Singles (Novagen) as described in Example 1. Single colonies were used to inoculate LB medium containing 50 mg/L kanamycin (5 mL) and plasmid DNA was purified using the Qiagen QIAquick® Spin Miniprep Kit. The plasmid DNA was screened by restriction digest analysis and the sequence was confirmed by Seqwright (Houston, Tex.).

The intervening sequence between the two genes was shortened by 23 base pairs using a Stratagene QuikChange™ Site-Directed Mutagenesis Kit (LaJolla, Calif.). The following primers were designed and synthesized for the procedure: forward 5'-GAAGCGATTGTGGCAGTGCTGTAAG-GCTCTAACGGATCCGAAGGAGATAT ACATATGTAC (SEQ ID NO: 75); reverse 5'-GTACATATGTATCTCCG-GATCCGTTAGA-GCCTTACAGCACTGCCA-CAATCGCTTC (SEQ ID NO: 76). The manufacturer's protocol was followed for the temperature cycling, digestion, and transformation into XL10-Gold competent cells. Clones able to grow on LB plates containing 50 mg/L kanamycin were screened by restriction digest analysis and the sequences were confirmed by dideoxy chain termination DNA sequencing (SeqWright, Houston, Tex.). One mutation occurred in all sequenced clones in the proA gene (G642A) that changed the aldolase amino acid sequence from methionine to isoleucine at position 214. This construct was used without further modification. Constructs were subcloned into BLR(DE3), BLR(DE3)pLysS, BL21(DE3) and BL21(DE3)pLysS (Novagen). The proA/pET30 Xa/LIC construct was also transformed into BL21 (DE3)pLysS.

Initial comparisons of BLR(DE3) shake flask samples under the standard conditions described above analyzed by LC/MS as described in Example 6 demonstrated that the addition of the second gene (aspC) improved the amount of monatin produced by seven-fold. Because the growth rate is higher, BL21(DE3)-derived host strains were used for the following experiments. The proA clones and the two gene operon clones were induced in Trp-1 medium as above. Chloramphenicol (34 μg/mL) was added to the medium of cultures containing cells with the pLysS vector. Shake flask experiments were performed with and without the addition of 0.2% Tween-20 and 1 mg/L ampicillin. The amount of monatin in the broth was calculated using in vitro produced purified monatin as a standard. Lc/MS/MS analyses were performed as described in Example 6. Cells were sampled at zero, 4 hours, 24 hours, 48 hours, 72 hours, and 96 hours of growth.

The results are shown in Table 5 for the maximum amounts produced in the culture broths. In most instances, the two gene construct gave higher values than the corresponding proA construct. The host strains with the pLysS vector, which should have leakier cell envelopes, showed higher levels of monatin secretion, although these strains typically grow at a slower rate. The additions of Tween and ampicillin were beneficial for monatin secretion. It is expected that substitution of penicillin or other penicillin derivatives (such as carbenicillin) for ampicillin will give similar benefits.

TABLE 5

Amount of Monatin Produced by E. coli Bacteria

| Construct | Host | Tween + Amp | μg/mL monatin | time |
|---|---|---|---|---|
| proA | BL21(DE3) | − | 0.41 | 72 hr |
| proA | BL21(DE3) | + | 1.58 | 48 hr |
| proA | BL21(DE3)pLysS | − | 1.04 | 48 hr |
| proA | BL21(DE3)pLysS | + | 1.60 | 48 hr |
| aspC:proA | BL21(DE3) | − | 0.09 | 48 hr |
| aspC:proA | BL21(DE3) | + | 0.58 | 48 hr |
| aspC:proA | BL21(DE3)pLysS | − | 1.39 | 48 hr |
| aspC:proA | BL21(DE3)pLysS | + | 6.68 | 48 hr |

The affect of several detergent Tweens on the growth rate of E. coli BL21(DE3) was studied in shake flask experiments. Either Tween-20, -40, 60, or -80 was added at 0.2% in the presence of 10 μg/mL ampicillin and the growth was followed over 48 h. Tween-40 affected the growth rate the least. The rate of growth in the presence of Tween-20 was about half that was observed when the organism was grown in the presence of Tween-40. Tween-60 and -80 were intermediate in affect.

It is expected that, in addition to differentially affecting the growth rate of the E. coli host organism, the different Tween formulations will have different affects on the secretion of monatin.

Construction of aspCproApET32b

The aspCproA/pET30 Xa/LIC plasmid with the shortened intervening sequence (~7 μg) and pET32b (~6.6 μg) were digested with XbaI and SalI. The digestion of the pET32b vector with XbaI and SalI removes the amino-terminal thioredoxin-, His-, and S-tags while this digestion maintains the His-Tag that is upstream of the aspC sequence in the pET30 Xa/LIC plasmid. The 2.1 kB aspCproA band and the 5.4 kB pET32b band were purified from a 1%-TAE agarose gel using a QIAquick® Gel Extraction Kit. The digested DNA was ligated with the digested vector using the Roche Rapid DNA Ligation kit and the ligation mix was transformed into NovaBlue™ Singles (Novagen) as described above. Clones able to grow on LB plates containing 100 μg/mL of ampicillin or carbenicillin were screened by restriction digest analysis and the sequences were confirmed by dideoxy chain termination DNA sequencing (SeqWright, Houston, Tex.). E. coli BL21 (DE3) and BL21(DE3)pLysS cells were transformed with aspCproA/pET32 according to the Novagen protocol. Two clones from the BL21(DE3) transformation set able to grow on LB plates with 100 μg/mL ampicillin and two clones from the BL21(DE3)pLysS transformation set able to grow on LB plates with 100 μg/mL ampicillin plus 34 μg/mL chloramphenicol were tested for their ability to express the aldolase and aminotransferase genes. Fifty mL cultures of the constructs in LB with the appropriate antibiotics were grown at 37° C. with shaking to an $OD_{600}$ of between 0.5 and 0.75. The gene expression was induced by the addition of 0.1 mM IPTG and the cultures were incubated a further 3 h at 30° C. with shaking. The cells were harvested by centrifugation at 4000×g for 10 min, washed with 50 mM MOPS, pH 7 and centrifuged again. Cell extracts were prepared using Novagen BugBuster™ reagent with benzonase nuclease and Calbiochem protease inhibitor cocktail III according to the Novagen protocol. The level of protein expression in the cell extracts was analyzed by SDS-PAGE using 4-15% gradient gel (Bio-Rad, Hercules, Calif.). Both polypeptides expressed well; the aldolase polypeptide appeared to be 15-20% of the soluble protein fraction while the aminotransferase polypeptide appeared to be 20-30% of the soluble protein fraction in the BL21(DE3) host cultures. The level of expression in the BL21(DE3)pLysS cultures was lower.

Fresh plates of E. coli BL21(DE3)::aspCproA/pET32b were prepared on LB medium containing 100 μg/mL ampicillin. Overnight cultures (5 mL) were inoculated from a single colony and grown at 30° C. in LB medium with ampicillin. Typically, a 1 to 100 inoculum was used for induction in trp-1+glucose medium containing 100 mg/L ampicillin or carbenicillin. The inoculated cultures (100 mL) were incubated at 37° C. with shaking until the $OD_{600}$ reached 0.5. The gene expression was induced by the addition of 0.1 mM IPTG (final concentration) and the culture was incubated a further 4 h at 30° C. with shaking. Pyridoxine was also added to a final concentration of 0.5 mM when gene expression was induced. Four hours after induction, a 25-mL aliquot of trp-1 medium and 0.05 mL of 100 mg/mL carbenicillin (5 mg) were added to the culture and the incubation was continued at 30° C. with shaking. Eighteen hours after induction, 0.04 mM pyridoxal phosphate (final concentration) in potassium phosphate (50 mM, pH 7.2) was added. The culture was divided into two equal aliquots in sterile culture flasks. Solid tryptophan to a final concentration of 50 mM, Tween-20 to a final concentration of 0.2% (stock solution of 20%), and sodium pyruvate to a final concentration of 0.1% (stock solution of 10%) were added to the first aliquot. Solid tryptophan to a final concentration of 50 mM and Tween-20 to a final concentration of 0.2% were added to the second aliquot. The pH of both cultures was adjusted to 8.2-8.4 and the incubation at 30° C. was continued. Samples for analysis of monatin (0.5 mL) and protein production (5-10 mL) were withdrawn at 4, 18 (before additions), 19, 24, and 48 h after induction with IPTG. These samples were centrifuged to pellet the cells. Supernatants were filtered using Acrodisc® 13 mm syringe filters (0.45 um; Gelman Laboratory) before LC-MS analysis for monatin. The cell pellets were washed with 50 mM MOPS, pH 7, and frozen at −80° C. until cell extracts were prepared for analysis of protein production.

The concentration of monatin in the fermentation broth samples was measured by LC/MS or LC/MS/MS (described in Example 6). Monatin was detected in the 24 h fermentation broth sample at a concentration of 34 mg/L when tryptophan and Tween were added to the culture. The concentration fell to 4.4 mg/L 48 h after induction. Monatin was detected in the fermentation broth samples at a concentration of 130-150 mg/L from 19-48 h after induction when tryptophan, pyruvate and Tween were added to the culture.

Cell extracts were prepared using Novagen BugBuster™ reagent with benzonase nuclease and Calbiochem protease inhibitor cocktail III according to the Novagen protocol. The level of protein expression in the cell extracts was analyzed by SDS-PAGE using 4-15% gradient gel (Bio-Rad, Hercules, Calif.). The concentrations of the expressed proteins were at their highest in the cell extract samples from 18-24 h after induction. The aldolase polypeptide accounted for >10% of the soluble protein while the aminotransferase protein appeared to be >25% of the soluble protein.

Example 8

Production of Monatin in Yeast

This example describes methods used to produce monatin in eukaryotic cells. One skilled in the art will understand that similar methods can be used to produce monatin in any cell of interest. In addition, other genes can be used (e.g., those listed in FIG. 2) in addition to, or alternatively to, those described in this example.

The pESC Yeast Epitope Tagging Vector System (Stratagene, La Jolla, Calif.) was used to clone and express the *E. coli* aspC and *C. testosteroni* proA genes into *Saccharomyces cerevisiae*. The pESC vectors contain both the GAL1 and the GAL10 promoters on opposite strands, with two distinct multiple cloning sites, allowing for expression of two genes at the same time. The pESC-His vector also contains the His3 gene for complementation of histidine auxotrophy in the host (YPH500). The GAL1 and GAL10 promoters are repressed by glucose and induced by galactose; a Kozak sequence is needed for optimal expression in yeast. The pESC plasmids are shuttle vectors, allowing the initial constructs to be made in *E. coli* (with the bla gene for selection); however, no bacterial ribosome binding sites are present in the multiple cloning sites.

The following primers were designed for cloning into pESC-His (restriction sites are underlined, Kozak sequence is in bold): aspC (BamHI/SalI), GAL 1: 5'-CGC GGATCCATAATGGTTGAGAACATTACCG-3' (SEQ ID NO: 69) and 5'-ACGC GTCGACTTACAGCACTGCCACAATCG-3' (SEQ ID NO: 70). proA (EcoRI/NotI), GAL10: 5'-CCG GAATTCATAATGGTCGAACTGGGAGTTGT-3' (SEQ ID NO: 71) and 5'-GAAT GCGGCCGCTTAGTCAATATATTTCAGCC-3' (SEQ ID NO: 72).

The second codon for both mature proteins was changed from an aromatic amino acid to valine due to the introduction of the Kozak sequence. The genes of interest were amplified using pET30 Xa/LIC DNA) purified using a Qiagen QIAprep® Spin Miniprep Kit (Valencia, Calif.)) of the clones described in Examples 1 and 2 as template. PCR was performed using an Eppendorf Master cycler gradient thermocycler and the following protocol for a 50 µL reaction: 1.0 µL template, 1.0 µM of each primer, 0.4 mM each dNTP, 3.5 U Expand High Fidelity Polymerase (Roche, Indianapolis, Ind.), and 1× Expand™ buffer with Mg. The thermocycler program used consisted of a hot start at 94° C. for 5 minutes, followed by 29 repetitions of the following steps: 94° C. for 30 seconds, 50° C. for 1 minute 45 seconds, and 72° C. for 2 minutes 15 seconds. After the 29 repetitions the sample was maintained at 72° C. for 10 minutes and then stored at 4° C.

The PCR products were purified by separation on a 1% TAE-agarose gel followed by recovery using a QIAquick® Gel Extraction Kit (Qiagen).

The pESC-His vector DNA (2.7 µg) was digested with BamHI/SalI and gel-purified as described above. The aspC PCR product was digested with BamHI/SalI and purified with a QIAquick PCR Purification Kit (Qiagen). Ligations were performed with the Roche Rapid DNA Ligation Kit following the manufacturer's protocols. Desalted ligation mixtures were electroporated into 40 µl Electromax DH10B competent cells (Invitrogen; Carlsbad, Calif.) using a 0.2 cm Bio-Rad disposable cuvette with a BioRad Gene Pulser II system, according to the manufacturer's instructions. After 1 h of recovery in 1 mL of SOC medium, the transformants were plated on LB medium containing 100 µg/mL ampicillin. Single colonies were used to inoculate 5 mL cultures of LB containing 100 µg/mL ampicillin and these were incubated overnight at 37° C. Plasmid DNA was purified from the overnight cultures using QIAprep Spin Miniprep Kits. This DNA was screened by restriction digest and sequenced (Seqwright) for verification using primers designed for the vector.

The aspC/pESC-His clone and the proA PCR product were digested with EcoRI and NotI. The DNA was purified and the ligations were carried out as described above. The two gene construct was transformed into Electromax DH10B competent cells (Invitrogen) and screened by restriction digest and sequenced (Seqwright) for verification.

The two gene construct was transformed into *S. cerevisiae* strain YPH500 using the S.c. EasyComp™ Transformation Kit (Invitrogen). Transformation reactions were plated on SC-His minimal medium (Invitrogen pYES2 manual) containing 2% glucose. Individual yeast colonies were screened for the presence of the proA and aspC genes by colony PCR using the PCR primers listed above. Pelleted cells (2 µl) were suspended in 20 µL of Y-Lysis Buffer (Zymo Research; Orange, Calif.) containing 1 µl of zymolase and heated at 37° C. for 10 minutes. Four µL of this suspension was then used in a 50 µL PCR reaction using the PCR protocol described above.

Five mL cultures were grown overnight on SC-His+2% glucose at 30° C. and 225 rpm. The cells were gradually adjusted to growth on raffinose in order to minimize the lag period prior to induction with galactose. After approximately 12 hours of growth, absorbance measurements at 600 nm were taken and an appropriate volume of cells was spun down and resuspended to give an OD600 of 0.4 in the fresh SC-His medium. The following carbon sources were used sequentially: 1% raffinose+1% glucose, 0.5% glucose+1.5% raffinose, 2% raffinose, and finally 1% raffinose+2% galactose for induction.

After approximately 16 hours of growth in induction medium, the 50 mL cultures were divided into duplicate 25 mL cultures and the following were added to one of the cultures: (final concentrations) 1 g/L L-tryptophan, 5 mM sodium phosphate, pH 7.1, 1 g/L sodium pyruvate, 1 mM MgCl$_2$. Samples of broths and cell pellets from the non-induction medium and from the 16 h cultures (prior to addition of substrates for the monatin pathway) were saved as negative controls. In addition, constructs containing only a functional aspC gene (and a truncated nonfunctional proA gene) were utilized as another negative control. The cells were allowed to grow for a total of 69 hours post-induction. In some experiments the yeast cells were induced at a lower OD600 and only grown for 4 hours prior to addition of tryptophan and pyruvate. However, the monatin pathway substrates appear to inhibit growth and the addition at higher OD600 was more effective.

The cell pellets from the cultures were lysed with 5 mL of YeastBuster™+50 μl THP (Novagen) per gram of cells (wet weight) following manufacturer's protocols. In addition, Calbiochem protease inhibitor set III and benzonase nuclease (Novagen) was added to the reagent as described in previous examples for the preparation of bacterial cell extracts. The culture broth and cell extracts were filtered and analyzed by LC/MS/MS as described in Example 6. Using this method, no monatin was detected in the broth samples, indicating that the cells could not secrete monatin under these conditions (the proton motive force may be insufficient under these conditions or the general amino acid transporters may be saturated with tryptophan). Expression of the recombinant proteins was not at a level that allowed for detection of changes using SDS-PAGE.

Monatin was detectable (about 60 ng/mL) transiently in cell extracts generated from the cells expressing two functional genes when tryptophan and pyruvate were added to the medium. Monatin was not detected in any of the negative control cell extracts. In vitro assays for monatin were performed in duplicate with cell extracts containing 4.4 mg/mL of total protein (about double what is typically used for E. coli cell extracts) using the optimized assay described in Example 3. Other assays were performed with the addition of either 32 μg/mL C. testosteroni ProA aldolase or 400 μg/mL AspC aminotransferase to determine which enzyme was limiting in the yeast cell extracts. Negative controls were performed with no addition of enzyme or the addition of only AspC aminotransferase (the aldol condensation can occur at a low level non-enzymatically). Positive controls were performed with partially purified enzymes (30-40%), using 16 μg/mL aldolase and 400 μg/mL aminotransferase.

The in vitro assays were analyzed by SRM. The analysis of cell extracts showed that tryptophan was effectively transported into the cells when it was added to the medium post-induction, resulting in tryptophan levels two orders of magnitude higher than those in which no additional tryptophan was added. The results for in vitro monatin analysis are shown in Table 6 (numbers indicate ng/mL).

alone. This indicates that the recombinant AspC aminotransferase comprises approximately 1-2% of the yeast total protein. The cell extracts of uninduced cultures had a small amount of activity when assayed with added ProA aldolase due to the presence of native aminotransferases in the cells. When assayed with added AspC aminotransferase, the activity of the extracts from uninduced cells increased to the amount of monatin produced by the negative control with AspC (ca. 200 ng/ml). In contrast, the activity observed when assaying the two gene construct cell extract increases more when aminotransferase is supplemented than when aldolase is added. Since both genes should be expressed at the same level, this indicates that the amount of monatin produced is maximized when the level of aminotransferase is higher than that of aldolase.

The addition of pyruvate and tryptophan not only inhibits cellular growth, but apparently inhibits protein expression as well. The addition of the pESC-Trp plasmid can be used to correct for tryptophan auxotrophy of the YPH500 host cells, to provide a means of supplying tryptophan with fewer effects on growth, expression, and secretion. S. cerevisiae strain YPH500 was co-transformed with the aspCproA/pESC-His construct and pESC-trp using the S.c. EasyComp™ Transformation Kit (Invitrogen). Cultures were grown in a medium with both histidine and tryptophan omitted and induced as described above. Monatin was detected at low levels in cell extract samples (less than 8.7 ng/mL) from the YPH500:: aspCproA/pESC-His cultures to which no substrates (neither tryptophan nor pyruvate) were added to the growth medium after induction. In contrast no monatin was detected in cell extracts from cultures containing YPH500 cells transformed solely with the aspCproA/pESC-His construct.

Example 9

In vivo Production of Monatin in Wildtype Organisms

For some markets, it may be desirable to have a non-genetically modified organism as a production host for monatin. Genomics databases were searched for organisms known

TABLE 6

Monatin production with yeast cell extracts.

| | AspC yeast construct | +ProA aldolase | +AspC aminotransferase | two-gene yeast construct | +ProA aldolase | +AspC aminotransferase |
|---|---|---|---|---|---|---|
| repressed (glucose medium) | 0 | 888.3 | 173.5 | 0 | 465.2 | 829 |
| 24 hr post-induction | 0 | 2832.8 | 642.4 | 0 | 1375.6 | 9146.6 |
| 69 hr post-induction | 0 | 4937.3 | 340.3 | 71.9 | 1652.8 | 23693.5 |
| 69 hr post-induction + substrates | 0 | 556.9 | 659.1 | 21.9 | 755.6 | 16688.2 |
| positive control (purified enzymes) | 21853 | | | 21853 | | |
| negative control (no enzymes) | 0 | | 254.3 | 0 | | 254.3 |

Positive results were obtained with the full two-gene construct cell extracts from cultures with and without added substrate during growth. These results, when compared to the positive controls, indicate that the enzymes were expressed at levels of close to 1% of the total protein in yeast. The amount of monatin produced when the cell extracts from the aspC construct (with truncated proA) were assayed with aldolase was significantly greater than when cell extracts were assayed to have the 4-hydroxy 4-methyl 2-oxoglutarate aldolase, an enzyme that can be used for monatin production. Sinorhizobium meliloti, Comamonas testosteroni, and Pseudomonas straminea are known to contain this aldolase as well as aromatic aminotransferases. These organisms were grown under various conditions to induce production of monatin. Classical mutagenesis techniques could be utilized to improve the titer of monatin produced by these organisms.

Materials

Unless otherwise specified all reagents were of media-grade purity or higher. TY medium contained (per L) 6 g tryptone, 3 g yeast extract, 9 mM $CaCl_2$. The tryptone and yeast extract were dissolved in nanopure water, and the pH was adjusted to 7.2. The volume was adjusted to 991 ml, and the mixture was sterilized by autoclaving. One molar calcium chloride was prepared separately, filter-sterilized, and added to the freshly autoclaved medium.

Para-hydroxybenzoate (PHB) Medium was prepared as directed by ATCC (ATCC 1702). Solution A (990 ml) contained 3 g $(NH_4)_2SO_4$, 1.6 g $K_2HPO_4$, 2.5 g NaCl, 0.5 g yeast extract, and 3 g 4-hydroxybenzoate. Solution B (10 ml) contained 0.27 g $MgSO_4$-$7H_2O$. Solutions A and B were autoclaved separately and combined after cooling to prepare Solution C. To this freshly prepared Solution C, 1 ml of a solution was added that contained 0.05 g $Fe(NH_4)_2(SO_4)_2$-$6H_2O$ (filter-sterilized prior to use). The pH of the final medium was adjusted to 7.0 with 6N NaOH.

A 10 g/L L-tryptophan solution was prepared in 0.1 M sodium phosphate pH 7, and sterile-filtered. One-tenth volume was typically added to cultures as specified below. A 10% sodium pyruvate solution was also prepared and sterile-filtered. A 10 ml aliquot was typically used per liter of culture.

M9 minimal medium plates were prepared as described in Sambrook et al. (ed.), Molecular Cloning: A Laboratory Manual 2nd ed., vol. 1-3, Cold Spring Harbor Laboratory Press, Cold Spring Harbor, N.Y., 1989 and *Rhizobium* minimal medium plates were prepared as follows. Each liter of media contained 15 g agar, 0.1 g yeast extract, 1 g $(NH_4)_2SO_4$, 7 g $K_2HPO_4$, 2 g $KH_2PO_4$, 0.1 g MgSO4-7H20, 0.02 g $ZnSO_4$-$7H_2O$, 0.0025 g $NiCl_2$-$6H_2O$, and 4 mL 1 M $CaCl_2$ (filter sterilized, added after autoclaving). Carbon sources and casamino acids were added at various concentrations described in the text below.

Methods

*Sinorhizobium meliloti* 1021 (ATCC 51124) was inoculated in TY medium, while *Comamonas testosteroni* (ATCC 49249) and *Pseudomonas straminea* (ATCC 33636) were grown in Nutrient Broth (Difco). All strains were cultured at 26° C. After two days growth, 2 mL of culture were used to inoculate 100 mL of freshly prepared PHB media. After 1 hour of growth with PHB as the sole carbon and energy source, which can induce the aldolase-containing pathway in *C. testosteroni*, 10 mL of tryptophan and 1 mL pyruvate were added. Cells were grown for 60 h, and all cultures had a final pH of 8-9.

The absorbance at 600 nm was recorded after 60 h as follows: *S. meliloti*, 3.35; *P. straminea*, 1.28; and *C. testosteroni*, 1.93.

Cells were centrifuged for 20 minutes at 3500 rpm at 4° C. Pellets were frozen at −80° C. until processed. Supernatants (fermentation broth) were filtered for LC/MS analysis. Results were normalized to account for differences in amount of biomass. The cell pellets were treated with BugBuster reagent (Novagen) as described in Example 1, and the resulting cell extracts were analyzed by SDS-PAGE and filtered for LC/MS. Due to differences in efficiencies of lysis, the results were normalized by absorbance at 280 nm, an indication of the relative amounts of cellular protein. Similar cell extracts were prepared for cells grown on PHB without addition of tryptophan and pyruvate, and in one case (*S. meliloti*), the cells were grown on TY medium rather than PHB.

After several days of growth, no bands at expected sizes for aldolase dominated on SDS-PAGE. These cell extracts were desalted on a PD10 column and assayed for in vitro production of monatin or monatin precursor from indole-3-pyruvate, pyruvate, and glutamate. The assay mixture contained, in 1 mL, 100 mM Tris-HCl (pH 7), 2 mM $MgCl_2$, 1 mM potassium phosphate (pH 8), 0.05 mM PLP, enzyme (cell extract), and 6 mM each of indole-3-pyruvate (prepared in ethanol), glutamate, and sodium pyruvate. The reactions were started by adding 0.5 mL of desalted cellular extracts and were incubated at 37° C. for 30 minutes, filtered, and frozen at −80° C. prior to LC/MS analysis.

Detection on LC/MS was done as described in Example 6. For the in vitro assays, negative controls were done with no cell extracts supplied to determine the baseline amount of monatin or MP that was produced from the reaction of the substrates with magnesium and phosphate. The results are shown in Tables 7-9. The numbers reflect Electrospray peak heights from LC-MS analysis, due to difficulties integrating the area in some cases. These numbers are roughly proportional to monatin concentration and were used to look for qualitative trends.

TABLE 7

In vivo results: Fermentation broth analysis

| Sample | MP | monatin | monatin normalized by $OD_{600}$ |
|---|---|---|---|
| *S. meliloti* at 60 hr | 0 | $1.7 \times 10^6$ | $0.5 \times 10^6$ |
| *P. straminea* at 60 hr | 0 | $1.1 \times 10^6$ | $0.85 \times 10^6$ |
| *C. testosteroni* at 60 hr | 0 | $1 \times 10^6$ | $0.5 \times 10^6$ |

Analysis of the LC/MS chromatograms indicated that the *C. testosteroni* strain may have metabolized a larger percentage of the tryptophan feed than the other two organisms, although it did not appear to increase the level of monatin detected. These results may suggest that the cells were not efficient at secreting monatin. Therefore, the cellular extracts also were analyzed by LC/MS (Table 8).

TABLE 8

Cell Extract analysis

| Sample | monatin | $OD_{280}$ of CE | normalized monatin |
|---|---|---|---|
| *S. meliloti* | | | |
| PHB + tryptophan + pyruvate | low but detectable | 0.137 | |
| PHB alone | $3 \times 10^5$ | 0.029 | $1.03 \times 10^7$ |
| TY media alone | $1.3 \times 10^5$ | 0.047 | $2.77 \times 10^6$ |
| *P. straminea* | | | |
| PHB + tryptophan + pyruvate | Low but detectable | 0.195 | |
| PHB alone | $2 \times 10^5$ | 0.061 | $3.2 \times 10^6$ |
| *C. testosteroni* | | | |
| PHB + tryptophan + pyruvate | $2 \times 10^5$ | 0.144 | $1.38 \times 10^6$ |
| PHB alone | $2.4 \times 10^5$ | 0.282 | $8.5 \times 10^5$ |

The absence of detectable levels of MP in both the broth and the cell extracts indicated that the MP was not stable in this particular matrix. Any effect of additional tryptophan and pyruvate was not detectable, except in the case of *Comamonas*, where a benefit was noted. Later experiments have suggested that the timing of the addition of tryptophan and pyruvate is very important, addition at the incorrect time can adversely affect the growth of the cultures. It is not known whether tryptophan and pyruvate are efficiently taken up in these wildtype organisms, or what changes in gene expression occur as a result of adding large concentrations of these substrates to the medium. While the parahydroxybenzoate substrate is only known to induce the aldolase in *Comamonas*, it appears to have improved the level of monatin produced in *S. meliloti* as well.

To confirm the presence enzymes capable of producing monatin from indole-3-pyruvate in the cellular extracts of *S. meliloti* and *C. testosteroni*, in vitro assays were performed as described above. The cell extracts were desalted to remove any residual monatin left from the culture. The culture condition for the cells is shown on the left of Table 9, while the MS peak height for monatin is shown in the right column.

TABLE 9

In vitro results with cell extracts

| Growth medium | monatin MS peak height |
|---|---|
| *S. meliloti* | |
| PHB + tryptophan + pyruvate | $2.8 \times 10^6$ |
| PHB alone | $8.3 \times 10^5$ |
| TY media alone | $4.8 \times 10^6$ |
| *C. testosteroni* | |
| PHB + tryptophan + pyruvate | $2.58 \times 10^6$ |
| PHB alone | $3.5 \times 10^6$ |
| MgCl$_2$ - no enzyme | $6.5 \times 10^5$ |

The results shown in Table 9 qualitatively demonstrate that monatin is formed by these filtered cell extracts, in comparison to the negative control. The negative control on the last line of the table is indicative of chemically induced aldol condensation. The cells grown on PHB without excess tryptophan had very low signal to noise ratios for monatin, suggesting that addition of tryptophan may induce the expression of native aromatic aminotransferases. The *S. meliloti* cell extracts from cells grown on TY appear to have at least one other contaminant that is interfering with the quantitation as the mass spectra and UV spectra show distinct differences from the positive controls and other samples. The daughter fragments and UV spectra of the *S. meliloti* 293 monatin peak are consistent with monatin produced from purified aldolase/transaminase mixtures, although there was an indication of larger molecular mass-species. Parent scans, however, did not indicate that the larger molecules were related to the 293 peaks.

Further growth experiments were done with *S. meliloti* and *C. testosteroni*. *S. meliloti* was grown in TY and PHB media with and without tryptophan and pyruvate. Additionally, Tween and ampicillin were added to one of the PHB+tryptophan+pyruvate flasks to permeabilize the cells. *C. testosteroni* was grown in NB or PHB media, with and without added tryptophan. TY media was used as a negative control in LC/MS analyses. In both organisms tested, the peak heights corresponding to monatin molecular mass were higher for cells grown in PHB medium versus the rich TY medium, and increased for both cell types upon addition of tryptophan and pyruvate. The addition of Tween and ampicillin greatly reduced the growth rate of the *Sinorhizobium* cells, but did appear to improve the level of monatin in the broth when normalized by OD$_{600}$. In PHB medium, the LC/MS signal level corresponding to monatin was 2-3× higher in the broth samples than the negative control.

Samples from the *S. meliloti* PHB experiments were evaporated and partially purified by cation exchange chromatography. The elution profile looked similar to other enzymatically produced samples of monatin.

Plate Assays Using Monatin as the Main Carbon and Energy Source

Organisms that can synthesize monatin can be detected by screening for growth on plates in which monatin (or the monatin precursor (MP)) is the main carbon and energy source. Screening by this method requires (1) that the synthetic pathway be reversible, allowing the product, monatin, to be metabolized by this route and (2) that the organism has a transport system that is able to import monatin or MP. *S. meliloti, P. straminea*, and *C. testosteroni* were tested for their ability to grow on minimal medium plates which contained monatin as the primary carbon and energy source.

Experimental Methods and Results

Plates containing M9 minimal medium or *Rhizobium* minimal medium were prepared with 0.01% casamino acids and 0.1-0.2% carbon source (glucose or purified monatin). Negative control plates contained casamino acids but no additional carbon source. *S. meliloti, P. straminea*, and *C. testosteroni* were grown in rich media to OD 2.1-2.7 and diluted 1000-fold with sterile 1× phosphate-buffered saline (PBS). A volume of 1-10 µL was used for plating. The plates were incubated at 26° C. for several days. *S. meliloti* grown on M9 medium+monatin exhibited better growth than the other strains tested, while there was no growth on the M9 medium alone. The experiments were repeated and *C. testosteroni* was grown in both NB as well as PHB media prior to induction. Again using M9 media for plating, the *S. meliloti* appeared to grow better with monatin as the carbon source than the other organisms. The *C. testosteroni* also exhibited some growth. Using the *Rhizobium* minimal medium, the *C. testosteroni* grew better with monatin as the carbon and energy source than it did with glucose. In addition, at the higher dilution ($10^{-6}$), the use of PHB-grown inoculum increased the number and size of colonies obtained compared to the NB-grown inoculum.

To ensure that contamination had not occurred, four colonies from various *C. testosteroni* plates were analyzed by colony-PCR using the primers for the HMG aldolase gene. All four colonies gave PCR products at about 750 bp (the correct size), while the negative control contained no product. The colonies were also restreaked on PHB plates and were again found to be capable of growth. The plating experiment for *C. testosteroni* using PHB-grown liquid cultures and M9 plates was repeated, and the cells were spun down, washed with 1×PBS, and resuspended in 1×PBS prior to plating. The number of colonies obtained was comparable to the glucose plate, while the negative control contained no colonies.

These results, along with the fact that *Sinorhizobium* and several Pseudomonads contain the aldolase genes for the in vitro production of monatin, suggest that these organisms are capable of producing monatin without introduction of heterologous genes. It is clear that the growth medium, addition of substrates such as tryptophan and pyruvate, and the addition of components that affect the cell wall are important factors for increasing the level of monatin produced by these wild-type organisms. Understanding the expression of the aldolase and aromatic aminotransferase genes in the organisms and influencing that expression will lead to improved monatin production. It is expected that classical mutagenesis techniques could be used to improve productivity.

Other Experiments Using Different Feeding Strategies

The shake flask experiments of *P. straminea, C. testosteroni* and *S. meliloti* cultures were repeated with experimental improvements using a different feeding strategy for substrates and cofactors and analyzed using LC/MS/MS MRM.

Methods

*Pseudomonas straminea* and *Comamonas testosteroni* were grown in PHB medium. *Sinorhizobium meliloti* was grown in PHB medium as described above and supplemented with 3.75 ml of 20% yeast extract and 2 ml of 50% glucose. Starter cultures were grown up and inoculated into 250 ml medium in 1 L shake flasks. All cultures were incubated at 29° C. overnight, shaking at 250 rpm to an $OD_{600}$ of ~0.5-1.1.

A feeding strategy for addition of substrates, cofactors and agents (Component list in Tables 10 and 11) to assist with monatin efflux, was implemented as follows per 250 ml of culture:

TABLE 10

| | Day 2: Additions | | |
|---|---|---|---|
| Component | Control | Experimental 1 | Experimental 2 |
| 50 mM pyridoxine HCl | 2.5 ml | 2.5 ml | 2.5 ml |
| 0.1 M $NaPO_4$ buffer | 25 ml | — | — |
| 1% L-tryptophan in 0.1 M $NaPO_4$ buffer | — | 25 ml | 25 ml |
| Distilled water | 5 ml | 2.5 ml | — |
| 10% sodium pyruvate | — | 2.5 ml | 2.5 ml |
| 100 mg/ml ampicillin | — | — | 2.5 µl |
| 20% Tween 20 | — | — | 2.5 ml |

Following day 2 additions cultures were incubated at 25° C. with shaking at 90-100 rpm.

TABLE 11

| | Day 3: Additions | | |
|---|---|---|---|
| Component | Control | Experimental 1 | Experimental 2 |
| 10% sodium pyruvate | — | 2.5 ml | 2.5 ml |
| L-tryptophan (solid) | — | 1 g | 1 g |
| 20 mM PLP | — | 500 µl | 500 µl |
| Distilled water | 2.5 ml | — | — |

Following day 3 additions, cultures were grown for ~8 hours after which culture was centrifuged to separate the cells. Supernatants were filtered and analyzed by LC/MS/MS analysis for monatin (see Example 6). Cell extracts were prepared from cell pellets as follows: pellets were resuspended in 1× phosphate buffered saline and suspensions were passed twice through the French press (~20,000 psi) and then centrifuged to remove cell debris.

TABLE 12

| | Results: Monatin Formation (ppb) | | |
|---|---|---|---|
| Bacterial strain | Control | Experimental 1 | Experimental 2 |
| *Pseudomonas stramininea* (secreted) | Not detected | Detected trace amount, unable to integrate | 84 ppb |
| *Comamonas testosteroni* (secreted) | Not detected | 200 ppb | 355 ppb |
| *Sinorhizobium meliloti* (secreted) | Not detected | Not detected | Not detected |
| *Sinorhizobium meliloti* (cell extracts) | Not detected | Not analyzed | 168 ppb |

Analyses of the filtered fermentation broth samples using the LC/MS/MS MRM method definitively demonstrated that monatin was produced by *C. testosteroni* and *P. straminea* (see Table 12). Using the FDAA derivitization method described in Example 6, S,S monatin formation was confirmed in *C. testosteroni* samples.

Analysis of the filtered cell extracts from Experimental 2 condition demonstrated that monatin was produced intracellularly by *S. meliloti* as well. No monatin was detected in the fermentation broth of *S. meliloti*, indicating that this organism was not secreting monatin. However, when cell extracts of this culture from Experimental 2 condition were examined, multiple monatin isomers were identified using reverse phase LC/MS/MS. The isomers were identified as S,S or R,R and S,R or R,S monatin. These analyses suggest that at least two isomers of monatin are produced by *S. meliloti*. Organisms that produce multiple isomers of monatin can be used as a source of enzymes for production of specific stereoisomers of monatin in vitro.

Taken together, the results above clearly demonstrated the potential of *Pseudomonas straminea, Comamonas testosteroni* and *Sinorhizobium meliloti* to prodeu monatin or serve as asource of genes in the monatin operon that can be expressed in heterologous hosts.

Selection Method for Screening of Pyruvate Aldolases in Recombinant *E. coli*

Strains of *Escherichia coli* that require pyruvate supplementation when grown on M9 minimal medium with ribose as the carbon source have been described previously (J. Bacteriol. 1995. 177:5719-5722). The genotype of the strain is: ΔpykA ΔpykF. The double knockout can be generated by the method of Datsenko and Wanner (PNAS. 2000. 97:6640-6645). These strains can form a basis for a pyruvate-generating aldolase screen and to screen for aldolases that are more active on a specific stereoisomer of monatin, a particular stereoisomer of monatin precursor, or an analog of monatin or monatin precursor. An analog of monatin precursor includes compounds that have been identified as substrates for ProA aldolases or KHG aldolases such as 4-hydroxy-4-methyl-2-oxoglutarate, 4-carboxy-4-hydroxy-2-oxoadipate, 4-hydroxy-4-methyl-2-oxoadipate, or other carboxyl rich compounds that are converted to pyruvate in an aldol reaction. An example of an analog of monatin that can be used is 4-hydroxy-4-methyl glutamic acid, which can be easily transaminated to 4-hydroxy-4-methyl-2-oxoglutarate (a substrate of ProA) by native aminotransferases in a test cell.

Cloning

The following primers were used to generate the pykA knockout:

```
                                        (SEQ ID NO: 85)
5'-ATGTCCAGAAGGCTTCGCAGAACAAAAATCGTTACCACGTTAGGTGT
AGGCTGGAGCTGCTTC-3'
and
                                        (SEQ ID NO: 86)
5'-CTCTACCGTTAAAATACGCGTGGTCTTAGTAGAACCCACGGTACCAT
ATGAATATCCTCCTTAG-3'.
```

The following primers were used to generate the pykF knockout:

```
                                        (SEQ ID NO: 87)
5'-AGGACGTGAACAGATGCGGTGTTAGTAGTGCCGCTCGGTACCAGCAT
ATGAATATCCTCCTTAG-3'
and
                                        (SEQ ID NO: 88)
5'-ATGAAAAAGACCAAAATTGTTTGCACCATCGGACCGAAAACCGGTGT
AGGCTGGAGCTGCTTC-3'.
```

A PCR reaction was performed with either pKD3 or pKD4 as template using standard protocols. The PCR product was electroporated into a strain of *E. coli* that expresses the lambda red homologous recombination system. The PCR product had homology to pykA or pykF and recombined into the chromosome at those sites. When the double crossover occurred the resulting progeny carried a deleted pykA or pykF gene and an antibiotic resistance marker. The deleted genes with the antibiotic resistance markers were transduced into an E. coli strain (MG1655) using standard P1 transduction techniques.

Strain Analyses

The double knockout was tested for growth on minimal medium (M9 salts (Difco) supplemented with Balch's vitamin solution, Balch's modified trace element solution (Balch, W. E., G. E. Fox, L. J. Magrum, C. R. Woese, and R. S. Wolfe. 1979. Methanogens: reevaluation of a unique biological group. Microbiol. Rev. 43:260-296), 0.4% D-ribose). No growth was seen for the double mutant unless 5 mM pyruvate was also included in the media. Wild-type MG1655 grew on the above media both in the presence and absence of pyruvate. The double knockout was tested for growth on the minimal medium described above supplemented with 0.4% glucose rather than ribose. Growth on this medium was similar to that seen with the wild-type strain. With this medium pyruvate can be generated from glucose via the ptsI gene product (the enzyme of the phosphotransferase system that makes pyruvate from phosphoenolpyruvate and transfers the phosphate to glucose). The double knockout strain was also tested for growth using the medium as described above supplemented with 0.4% L-arabinose or 0.4% D-xylose rather than ribose. Pyruvate is not generated from growth on these 5-carbon containing (non-PTS) substrates. The double knockout did not grow under these conditions unless it was supplemented with 5 mM pyruvate, while the wild-type strain grew normally both in the presence and absence of pyruvate.

The proA aldolase gene from *Comomonas testosteroni* (described in Example 2 cloned in pET30 Xa/LIC) and the aspC/proA genes described in Example 3 (cloned in pET30 Xa/LIC and pET32) were sub-cloned into pBAD-TOPO using the pBAD TOPO TA expression kit (Invitrogen). Expression of the gene(s), in these constructs, is regulated by the inducible araBAD promoter. In the presence of arabinose (for example 0.4%) and IPTG the gene(s) are expressed. Unless supplemented with pyruvate or a source of pyruvate, the strain will not grow on minimal medium. The medium can be supplemented with monatin, monatin precursor, or an analog of monatin or monatin precursor. Typical ranges of substrate used in literature are 0.5-5 mM. The ProA aldolase can, for example, convert the monatin precursor into pyruvate and indole-3-pyruvate providing the strain a source of pyruvate and allowing growth on minimal medium with 0.4% arabinose. The construct expressing both the proA and the aspC genes can convert monatin into the monatin precursor and the monatin precursor into pyruvate and indole-3-pyruvate. This system can be used to screen for aldolases and to screen for aldolases that are more active on a specific stereoisomer of monatin, a specific stereoisomer of monatin precursor, or an analog of monatin or monatin precursor. For example, if directed evolution is performed on any of the aldolases mentioned in Example 2, a plate assay can utilize media containing either R or S monatin precursor to measure the enantiospecificity of the resulting mutant enzyme. If growth occurs on the plates containing R-monatin precursor and little or no growth occurs on the plate containing S-monatin precursor, the aldolase has a specificity for substrates containing the R-chirality at the reaction site.

M9 minimal medium plates were made containing 1× Balch's vitamin solution and Balch's modified trace element solution (Balch, W. E., G. E. Fox, L. J. Magrum, C. R. Woese, and R. S. Wolfe. 1979. Methanogens: reevaluation of a unique biological group. Microbiol. Rev. 43:260-296). Glucose or arabinose was included as the carbon source (0.4% w/v) and plates were supplemented with either 5 mM monatin (R,R; S,S racemic mixture) that had been dissolved in 20 mM potassium phosphate buffer (pH 8.0) or an equal volume of potassium phosphate buffer without monatin. Growth is summarized in Table 13 below:

TABLE 13

|  | Glucose | Glucose monatin | Arabinose | Arabinose monatin |
| --- | --- | --- | --- | --- |
| MG1655 | ++++ | ++++ | ++++ | ++++ |
| MG1655 ΔpykA ΔpykF | ++++ | ++++ | + | + |
| MG1655 ΔpykA ΔpykF + aspCproA/ pBAD-TOPO | ++++ | ++++ | + | ++ |

It is expected that the screen could be optimized by controlling the levels of ProA and AspC, increasing uptake of monatin, using monatin precursor in the place of monatin (in this case the aminotransferase would not need to be present), or using a less hydrophobic analog of monatin such as those described above. Methods for increasing the uptake of monatin include addition of amino acid mixtures, addition of specific amino acids, and the use of detergents, antibiotics, antibiotic analogs, or enzymes that help to permeabilize the cell wall. Polymyxin B nonapeptide (Dixon and Chopra. 1986. Antimicrobial Agents and Chemotherapy. 29:781-788) and microcystin RR (Dixon, Al-Nazawi, and Alderson. FEMS Microbiology Letters. 2004. 230:167-170) have been described as agents that permeabilize the outer membrane of *E. coli*.

It is expected that other promoter systems/plasmids can be used in this screening system with equivalent results. Examples include T7 promoter systems, and IPTG inducible promoters such as taq and lac.

Synthesis of Monatin and Monatin Precursor (MP) Analogs

The monatin precursor (MP) analog 4-hydroxy-4-methyl-2-oxoglutarate is synthesized using the method of Shannon and Marcus (1962) or Prey et al (1955) or Waldmann et al (1954). The monatin precursor (MP) analog 4-carboxy-4-hydroxy-2-oxoadipate is synthesized by the method of Tack et al (1972) or the method of Martius (1943).

The monatin analog 4-hydroxy-4-methyl glutamic acid is biosynthesized from 4-hydroxy-4-methyl-2-oxoglutarate by reaction with aspC aminotransferase in the presence of the amino donor glutamate as described in the Transamination Activity section of Example 4.

Example 10

Increased Production of Pyruvate in *Escherichia coli* by Knockout of Lipoate Biosynthetic Gene Interruption of the lipoate biosynthesis pathway can increase pyruvate productivity in *E. coli*, which can be advantageous for in vivo monatin production. If little or no lipoate is available to serve as a cofactor for pyruvate dehydrogenase, the formation of acetyl-CoA from pyruvate is limited. A DE3 strain can be used for expression of the monatin operon from the T7 promoter in pET30 Xa/LIC. A BW25113ΔlipA::cam strain was used as a donor strain for P1 transduction of the lipA knockout (with chloramphenicol insertion) into *E. coli*

7692, a tryptophan overproducing strain. Both the *E. coli* 7692ΔlipA and BW25113ΔlipA mutants were lysogenized for T7 expression.

Strains

*E. coli* strain BW25113 and *E. coli* CGSC 7692 were obtained from the Genetic Stock Center (Yale University). *E. coli* CGSC 7692 has the following genotype: W3110tnaA2trpEFBR19 (Doolittle and Yanofsky, *J. Bacteriol.*, (1968) 95:1283-1294; and Yanofsky et al., *J. Bacteriol.*, (1984) 158:1018-1024). This strain has a feedback resistant anthranilate synthase gene (trpE), which is a key branchpoint and regulatory point for the biosynthesis of tryptophan.

The BW25113 ΔlipA::cam construct was provided by Dr. Hans Liao (WO02085293 A).

Materials and Methods

P1 phage was purchased from ATCC (Manassas, Va.) catalog #25404-B 1. The lambda (DE3) lysogenization kit was purchased from Novagen (Madison, Wis.). Unless otherwise stated, all reagents were of media grade or higher.

Pyruvate overproduction medium was used that contained the following: 50 g/L glucose (added after autoclaving); 10 g/L $(NH_4)_2SO_4$; 4 g/L peptone (Fisher); 1 g/L $K_2HPO_4$; 2 g/l NaCl; 0.5 g/L $MgSO_4\text{-}7H_2O$; 14.7 mg/L $CaCl_2\text{-}2H_2O$ (added after autoclaving); and 1 µg per liter lipoate (added after autoclaving). The pyruvate overproduction medium was adjusted to a pH of 8 with NaOH.

Genetic Manipulation of *E. coli* Strains

P1 transduction was performed using the method of Miller (Miller, J. H., "A short course in bacterial genetics": Cold Spring Harbor Laboratory, Cold Spring Harbor, N.Y., 1992). P1 lysates were created using *E. coli* BW25113 ΔlipA::cam cells. The P1 phage isolated was then used to transduce *E. coli* CGSC 7692. The clones of interest were selected by growth on LB plates containing 34 µg/ml chloramphenicol and 10 nM lipoate. The lipoate synthase deletion was confirmed by growth comparison on plates with and without lipoate and by PCR screening and analysis of the PCR product for correct size and restriction pattern.

The λDE3 lysogenization of *E. coli* strains CGSC 7692, 7692ΔlipA, and BW25113ΔlipA was performed using the Novagen λDE3 Lysogenization Kit following the manufacturer's protocol. The presence of DE3 phage was verified by utilization of the T7 Tester phage (4107) which cannot form plaques in the absence of the T7 RNA polymerase. Lysogenization was further verified by expression studies using the aspC/pET30 Xa/LIC construct.

Detection of Pyruvic Acid

Samples from in vitro or in vivo biochemical reaction experiments to be analyzed for pyruvic acid were treated with formic acid to reduce the pH to less than 3 and then filtered through 0.45 µm Nylon syringe filters prior subjecting to LC/MS analysis. Identification of pyruvic acid was based on retention time and mass selective detection. LC separations were made using Waters 2690 liquid chromatography system and a 2.1 mm×250 mm Phenomenex Aqua $C_{18}$ reversed-phase chromatography column with isocratic elution at 40° C. The LC mobile phase was 1% methanol in water containing 0.1% (v/v) formic acid with a flow rate of 0.18 mL/min.

The detection system for analysis of pyruvic acid includes a Waters 996 Photo-Diode Array (PDA) detector and a Waters Micromass ZQ quadrupole mass spectrometer. The PDA, operating at 195 to 225 nm for monitoring chromatographic profile, was placed in series between the chromatography system and the mass spectrometer. To enhance the stability of pyruvic acid's $[M-H]^-$ ion, an in-line post column additive of 1% (v/v) $NH_4OH$ in iso-propanol and water was added at the rate of 0.025 mL/min prior to the mass spectrometer.

Parameters for the Micromass ZQ quadrupole mass spectrometer operating in negative electrospray ionization mode (−ESI) were set as the following; Capillary: 2.0 kV; Cone: 30 V; Extractor: 4 V; RF lens: 1 V; Source temperature: 120° C.; Desolvation temperature: 380° C.; Desolvation gas: 600 L/h; Cone gas: Off; Low mass resolution: 15.0; High mass resolution: 15.0; Ion energy: 0.2; Multiplier: 650. Single ion monitoring MS experiment was set up to allow selectively detect m/z 87, which was the deprotonated molecular $[M-H]^-$ ion of pyruvic acid.

Growth Experiments

Twenty mL cultures of BW25113, BW25113ΔlipA, BW25113ΔlipA(DE3), CGSC 7692, 7692ΔlipA, 7692(DE3), and 7692ΔlipA(DE3) were grown in 125 mL shake flasks containing 2YT medium (Sambrook et al.) with 10 nM lipoate. After 24 hours, a sample of fermentation broth was removed for analysis and 20 g/L of glucose was added. The culture was allowed to grow for another 24 hours, at which time the cells were harvested and the fermentation broths were filtered and analyzed by LC/MS as described above. The benefit of the genetic knockout of lipoate biosynthesis is shown in FIG. 14 as both the 7692ΔlipA and BW25113ΔlipA cells are clearly capable of producing more pyruvate than the CGSC 7692 and BW25113 cells that contain the lipA gene. The experiment was repeated in pyruvate overproduction media (Yokota et al., (1997). *J. Ferment. Bioeng.*, 83:132-138) containing 50 g/L glucose. Samples of broth were removed after 24, 48, and 72 hours of growth and analyzed by LC/MS for pyruvate. The results are shown in FIG. 15, confirming the results of FIG. 14 using a different medium. The 7692 constructs appear to have higher productivity in 2YT media. It is expected that similar genetic mutations in other microorganisms will have similar effects.

Example 11

Production of Monatin in *Escherichia coli* Constructs Lacking the Lipoate Synthase Gene In Example 10, pyruvate production was increased in *E. coli* constructs in which the lipA gene was deleted. The DE3 strains of the lipA knockouts were transformed with the monatin operon (aspC proA/pET32b construct described in Example 7) and were evaluated for their ability to express the induced proteins and to produce monatin. The *E. coli* BW25113ΔlipA(DE3) construct, transformed with the monatin operon, produced 8-9 ng/mL biomonatin when tryptophan was added to the culture several hours after induction. The tryptophan overproducing strain *E. coli* 7692ΔlipA (DE3), transformed with the monatin operon, produced about 2 ng/mL monatin without a tryptophan feed. The *E. coli* 7692(DE3) construct, transformed with the monatin operon but containing the lipA gene, did not produce any detectable monatin.

Preparation of Electrocompetent Cells of *E. coli* 7692(DE3), 7692ΔlipA(DE3), and BW25113ΔlipA(DE3)

Two hundred milliliter cultures of *E. coli* 7692(DE3), 7692ΔlipA(DE3), and BW25113ΔlipA(DE3) in LB medium (containing 12.5 µg/mL chloramphenicol and 10 nM alpha-lipoic acid if ΔlipA) were grown at 37° C. with shaking to an $OD_{650}$ of 0.45-0.5. After cooling in an ice bath, the cultures were centrifuged at 4,000×g for 10 min at 4° C. The supernatants were decanted, and the cell pellets were each suspended in 200 mL of sterile ice cold water. The centrifugation was repeated, and the cell pellets were each suspended in 20 mL of sterile ice cold water. After a third centrifugation, the cell pellets were each suspended in 2 mL ice cold 10% glycerol. The cell pellets resulting from a fourth centrifugation were suspended in 0.15 mL ice cold 10% glycerol, and the suspensions were dispensed into 40 μL aliquots and frozen at −80° C.

E. coli 7692(DE3), 7692ΔlipA(DE3), and BW25113ΔlipA (DE3) electrocompetent cells were transformed with the monatin operon construct (aspC proA/pET32) by electroporation under standard conditions described in the Bio-Rad electroporation manual using a Bio-Rad Gene Pulsar II apparatus. Clones able to grow on LB plates containing 100 μg/mL of ampicillin (and 20 nM alpha lipoic acid if ΔlipA) were analyzed for their ability to express the aldolase and aminotransferase genes.

Fifty mL cultures of two 7692(DE3) clones in LB with 100 μg/mL ampicillin were grown at 37° C. with shaking to an $OD_{650}$ of between 0.5 and 0.9. In addition, fifty mL cultures of one 7692DlipA(DE3) clone and one BW25113ΔlipA(DE3) clone in LB with 100 μg/mL ampicillin and 10 nM alpha lipoic acid were grown at 37° C. with shaking to an $OD_{650}$ of between 0.5 and 0.9. The gene expression was induced by the addition of 0.1 mM IPTG, and the cultures were incubated a further 4 h at 30° C. with shaking. The cells were harvested by centrifugation at 4,000 rpm for 10 min and washed with 50 mM MOPS, pH 7 buffer and centrifuged again. Cell extracts were prepared using Novagen BugBuster™ reagent with benzonase nuclease and Calbiochem protease inhibitor cocktail III according to the manufacturer's protocol. The level of protein expression in the cell extracts was analyzed by SDS-PAGE using a 4-15% gradient gel (Bio-Rad, Hercules, Calif.). Both the aldolase and aminotransferase expressed well in all the hosts, and the levels were similar to those seen in the E. coli BL21(DE3) host when grown on LB medium.

Production of Monatin in E. coli 7692(DE3), 7692ΔlipA (DE3), and BW25113ΔlipA (DE3) Cells Transformed with aspCproApET32

In these experiments the E. coli strains transformed with aspCproA/pET32 were grown and induced as described above. To these cultures were added both tryptophan and pyruvate and intracellular and extracellular samples were analyzed for production of monatin.

Fresh plates of E. coli 7692(DE3), 7692ΔlipA(DE3), and BW25113ΔlipA(DE3) cells transformed with aspC proA/pET32 were prepared on LB medium containing 100 μg/mL ampicillin. The plates used for the ΔlipA strains also contained 10 nM alpha lipoic acid. Overnight cultures (5 mL) were inoculated from a single colony and grown at 37° C. in LB medium with 100 μg/mL ampicillin and 10 nM alpha lipoic acid. One mL of the overnight culture was used as an inoculum in 100 mL of trp-1 medium containing 100 μg/mL carbenicillin and 10 nM alpha lipoic acid. The cultures were incubated at 37° C. with shaking until the $OD_{650}$ reached about 0.5. The gene expression was induced by the addition of 0.1 mM IPTG, and the cultures were incubated a further 4 h at 30° C. with shaking. When gene expression was induced, pyridoxine was added to a final concentration of 0.5 mM, as well as 1 nmole of alpha lipoic acid. Four hours after induction, a 25 mL aliquot of trp-1 medium and 0.05 mL of 100 mg/mL carbenicillin (5 mg) were added to the cultures, and the incubation was continued at 30° C. with shaking. Eighteen hours after induction, 0.04 mM pyridoxal phosphate in potassium phosphate (50 mM, pH 7.2) was added to all cultures. The E. coli 7692(DE3) and 7692 ΔlipA(DE3) cultures which had been transformed with aspC proA/pET32 received glucose (0.2 g) and Tween-20 to a final concentration of 0.2%. The E. coli BW25113ΔlipA(DE3) construct culture received solid tryptophan to final concentration of 50 mM and Tween-20 to final concentration of 0.2%. The pH of all 3 cultures was adjusted to 8.2-8.4, and the incubation at 30° C. was continued. Samples for analysis of monatin (0.5 mL) and protein production (5-10 mL) were withdrawn at 0, 4, 18 (before additions), 19, 24, 48, and 72 h after induction with IPTG.

The concentration of monatin in the fermentation broth samples was measured by LC/MS or LC/MS/MS as described in Example 6.

Monatin was detected in the fermentation broth at a concentration of ~2 ng/mL in the 18 h sample from the aspC proA/pET32 transformed E. coli 7692ΔlipA(DE3) culture. No monatin was detected in the samples withdrawn between 24 and 72 h. No monatin was detected in any of the samples from the aspC proA/pET32 transformed E. coli 7692(DE3) culture. Monatin was detected, however, in the 48 and 72 h fermentation broth samples of the aspC proA/pET32 transformed E. coli BW25113ΔlipA(DE3) culture at a concentration of 8-9 ng/mL.

Cell extracts were prepared using Novagen BugBuster™ reagent with benzonase nuclease and Calbiochem protease inhibitor cocktail III according to Novagen's protocol. The level of protein expression in the cell extracts was analyzed by SDS-PAGE using a 4-15% gradient gel (Bio-Rad, Hercules, Calif.). The concentrations of the expressed proteins were at the highest level in the 24 h cell extract sample for the aspC proA/pET32 transformed E. coli 7692(DE3) samples. The concentrations of the expressed proteins were at their highest in the 4 and 18 h samples for the aspC proA/pET32 transformed E. coli 7692 ΔlipA(DE3) cell extract samples. The aldolase polypeptide accounted for about 15% of the soluble protein, while the aminotransferase polypeptide appeared to be >30% of the soluble protein in these samples. The two polypeptides did not express as well in the aspC proA/pET32 transformed E. coli BW25113 ΔlipA(DE3) culture grown in the trp-1 medium. The highest levels appeared in the 18 and 24 h cell extract samples, however, neither polypeptide was greater than 10-15% of the total soluble protein.

These results show that the proteins were produced in all the strains transformed with aspC proA/pET32 after induction with IPTG. The two strains in which the lipA gene was deleted (E. coli BW25113ΔlipA (DE3) and 7692ΔlipA (DE3)) and were transformed with aspC proA/pET32 produced monatin without a pyruvate feed. This shows that the lipA gene knockout is beneficial for in vivo production of monatin. The tryptophan overproducing strain E. coli 7692ΔlipA(DE3) produced monatin without the addition of tryptophan or pyruvate. The level of monatin production was much less, however, than the amounts produced and secreted in E. coli constructs that were fed both tryptophan and pyruvate (For example, see Table 5 of Example 7).

Example 12

Production of Monatin in Escherichia coli Constructs that Overproduce Tryptophan and Pyruvate Escherichia coli tryptophan overproducing strains, NRRL 12264 lacking a lipA gene were evaluated for the ability to produce monatin when transformed with a plasmid containing the aspC and proA genes as well as a second operon containing a tryptophan operon. Both monatin and tryptophan were measured after induction of gene expression.

Strains

In Example 15, three strains cited in U.S. Pat. No. 4,371,614 as tryptophan overproducers were examined for their ability to produce tryptophan in two media formulations. One strain, NRRL B-12262, (also called AGX15 with the cited genotype serB⁻, trpΔED, tnaA2⁻, tetS, tyrA⁻, pheA⁻) carries a plasmid called pGX44 that is derived from pBR322 (Roeder and Somerville, *Molec. Gen. Genet.*, 1979, 176: 361-368) and contains the serB gene and the tryptophan operon. Another strain, NRRL B-12264 (also called AGX6 with the cited genotype serB⁻, trpΔED, tnaA2⁻, aroP⁻) contains a plasmid called pGX50 derived from pBR322 and contains the serB gene, a tryptophan operon, which was derived from cells that are resistant to 5-methyltryptophan, and an ampicillin resistance gene. These two strains were subjected to the following genetic manipulations and the strain derived from NRRL B-12264 was analyzed for monatin production.

Genetic Manipulations

The P1 transductions to delete the lipA gene and the λDE3 lysogenization of *E. coli* NRRL strains 12262 and 12264 were carried out as described in Example 10. The lipoate synthase deletion was confirmed by growth comparison on plates with and without lipoate and by PCR screening and analysis of the PCR product for correct size and restriction pattern. The presence of DE3 phage was verified by utilization of the T7 Tester phage and the ability to express the aspC gene when transformed with aspCpET30 (Xa/LIC). The plasmid pGX44 was cured from strain 12262 and the plasmid pGX50 was cured from strain 12264 by repeated passages on rich media containing serine and tryptophan and without ampicillin. The curing was verified in strain 12264 by the loss of the ability to grow in the presence of ampicillin.

Preparation of Electrocompetent Cells of *E. coli* 12262ΔlipA (DE3) and 12264ΔlipA (DE3)

Electrocompetent cells of *E. coli* 12264ΔlipA(DE3) and 12262ΔlipA(DE3) were prepared as described in Example 10. After the final wash and re-suspension in ice cold 10% glycerol the cells were dispensed into 40 μL aliquots and frozen at −80° C.

Construction of Plasmids Containing Tryptophan Operons

The plasmid pGX44 was purified from strain 12262 and the plasmid pGX50 was purified from strain 12264 using a Qiagen QIAprep® Spin Miniprep Kit. *Escherichia coli* genomic DNA was isolated from strain *E. coli* DH10B (Invitrogen; Carlsbad, Calif.) as described in Example 1.

Primers were designed to clone the tryptophan operon of plasmid pGX44, pGX50 and genomic DNA from *E. coli* strain DH10B into the pPRONco plasmid using the KpnI and BamHI restriction sites. This plasmid is a derivative of the pPROLar.A122 vector (BD Biosciences Clontech, Palo Alto, Calif.) in which one of the NcoI sites was removed by mutation T1538C. The tryptophan operon (Genbank Accession No.: NC_000913.2 GI:49175990 1320970-1314440) contains the open reading frames of the following genes: trpE, trpD, trpC, trpB and trpA. The GenBank Accession numbers for the gene products are as follows: trpE, GenBank Accession No.: NP_415780.1 GI:16129225; trpD, GenBank Accession No.: NP_415779.1 GI:16129224; trpC, GenBank Accession No.: NP_415778.1 GI:16129223; trpB, GenBank Accession No.: NP_415777.1 GI:16129222; trpA GenBank Accession No.: NP_415776.1 GI:16129221.

(SEQ ID NO: 79)
N term: 5'-CGGGGTACCCATGCAAACACAAAAACCGACTCTCGAAC-TG-3'

The following PCR protocol was used for gene amplification: In a 50 μL reaction, 100-300 ng DNA template, 1.0 μM of each primer, 0.2 mM each dNTP, 0.75 U pfuUltra HF Polymerase (Stratagene; LaJolla, Calif.), 2.5 U Expand High Fidelity™ Polymerase (Roche Molecular Biochemicals, Indianapolis, Ind.), and 1× Expand™ buffer with Mg were added. The thermocycler program utilized a hot start of 94° C. for 5 minutes; followed by 30 cycles of a denaturing step at 94° C. (30 sec), an annealing step at 61.5° C. (1 min), and an extension step at 72° C. (8 min); and finally a finishing step at 72° C. (7 min). The amplified DNA was purified from a 1% agarose gel using a Qiagen QIAquick® Gel Extraction Kit (Valencia, Calif.).

The PCR products and the pPRONco vector were sequentially digested with BamHI and then KpnI purchased from NEB (Beverly, Mass.) and following the manufacturer's protocols. After both digests the DNA purified from the protein and buffer salts using a Qiagen QIAquick PCR Clean-up Kit. The vector was also treated with shrimp alkaline phosphatase (Roche Molecular Biochemicals, Indianapolis, Ind.) according to the manufacturer's recommendations before the second clean-up step. The purified DNA was quantified by measuring the absorbance at 260 nm and ligated using T4 ligase (NEB) at a ratio of insert to vector of >8 to 1. Transformation of the ligation mixtures into electrocompetent *E. coli* DH10B cells was performed under standard conditions using a 0.1 cm cuvette and a Bio-Rad Gene Pulser II system as described in the Bio-Rad electroporation manual. Clones containing a tryptophan operon were identified by restriction analysis and confirmed by DNA sequencing. The nucleic acid sequence of the tryptophan operon genes from *E. coli* DH10B and pGX44 (*E. coli* strain 12262) were identical and in agreement with the NCBI database (see accession numbers listed above) while the tryptophan operon from pGX50 (*E. coli* strain 12264) showed 15 mutations in the trpE gene but was identical to the DH10B and pGX44 sequences in the trpD, trpC, trpB and trpA genes. The mutations in the trpE gene of pGX44 are as follows: G30A(silent), T61C(silent), C63G (silent), G160A(silent), T189A(silent), C210T(silent), C211A(Gln72Lys), A217G(silent), C218T(silent), T220A (silent), C229T(silent); C232T(silent), C241G(silent), G281A(Ser94Asn), C349T(silent). SEQ ID NOS.: 81 and 82 set forth the nucleic acid and amino acid sequences, respectively, of the trpE gene from pGX50.

Transformation of *E. coli* Strains 12262ΔlipA (DE3) and 12264ΔlipA(DE3)

*E. coli* 12264ΔlipA(DE3), and 12262ΔlipA(DE3) electrocompetent cells were transformed with aspC proApET32 (described in Example 10) or co-transformed with aspCproApET32 and one of the tryptophan operon constructs described above by electroporation under standard conditions described in the Bio-Rad electroporation manual using a Bio-Rad Gene Pulsar II apparatus. Clones able to grow on LB plates containing either ampicillin at 100 mg/L and 20 nM alpha lipoic acid (aspCpro ApET32 transformed strains) or ampicillin at 100 mg/L, kanamycin at 50 mg/L, and 20 mM alpha lipoic acid (aspC proApET32 and tryptophan operon transformed strains) were chosen for further analysis.

Production of Monatin in *E. coli* Strain 12264ΔlipA(DE3) Transformed with Plasmids Containing the aspC and proA Genes and a Tryptophan Operon Fresh plates of *E. coli* 12264ΔlipA(DE3) transformed with aspC proA/pET32, or aspC proA/pET32 and DH10trpoperon/pPRONco, or with aspC proA/pET32 and pGX44trpoperon/pPRONco, or with aspC proA/pET32 and pGX50trpoperon/pPRONco were prepared on LB medium containing the appropriate antibiotics and 20 nM alpha lipoic acid. Overnight cultures (5 mL) were inoculated from a single colony and grown at 37° C. in LB medium or trp-1 medium (described in Examples 1 and 7) containing the appropriate antibiotics and 20 nM alpha lipoic acid. The strain carrying aspC proA/pET32 and pGX50trpoperon/pPRONco did not grow in liquid culture in either trp-1 or LB and was not did not grow and was not used further. One to two mL of each of the overnight cultures were used as inocula for 100 mL of trp-1 medium containing the appropriate antibiotics, 0.4% casamino acids, 0.1% Balch's vitamin solution, and 20 nM alpha lipoic acid. Balch's vitamin solution contains the following: p-aminobenzoic acid (5.0 mg), folic acid (2.0 mg), biotin (2.0 mg), nicotinic acid (5.0 mg), calcium pantothenate (5.0 mg), riboflavin (5.0 mg), thiamin-HCl (5.0 mg), pyridoxine-HCl (10.0 mg), cyanocobalamin (0.1 mg), and alpha lipoic acid (0.1 mg) in 1 L. The pH is adjusted to 7.0 with NaOH and the solution is filtered sterilized before use.

The strains were incubated at 37° C. with shaking. The strain carrying only the aspC proA/pET32 vector showed no increase in OD at 600 nm through 8 h and was not incubated further. The other cultures were incubated until the OD600 reached about 0.5 (approximately 8 h). The gene expression was induced by the addition of 0.2 mM IPTG and 0.5% arabinose. Pyridoxine at 0.5 mM and biotin at 1 mg/mL were also added to each culture flask. Five hours after induction, 0.04 mM pyridoxal phosphate, 0.5% sodium pyruvate, 0.2% Tween-20 and 10 µg/mL ampicillin were added to each culture flask and the incubation was continued at 30° C. Samples for analysis of monatin (0.5 mL) and protein production (5-10 mL) were withdrawn at 0, 4, 16, 24, 40, 49 and 67 h after induction with IPTG. The concentrations of monatin and tryptophan in the fermentation broth samples were measured by LC-MS/MS MRM. The results are shown in the following tables. The concentration of both tryptophan and monatin was highest in the fermentation broth samples withdrawn 16 to 24 h after induction, as shown in Tables 14 and 15.

TABLE 14

Monatin and tryptophan production in *E. coli* 12264ΔlipA(DE3) transformed with aspCproA/pET32 and DH10trpoperon/pPRONco Fermentation broth samples

| Time after induction | [monatin]; ng/mL | [tryptophan]; ng/mL |
| --- | --- | --- |
| 4 | 12.4 | 2992.5 |
| 16 | 140.1 | 6986.1 |
| 24 | 179.1 | 7599.3 |
| 40 | 169.6 | 5993.2 |
| 49 | 150.7 | 5033.8 |
| 67 | 152.2 | 3854.4 |

TABLE 15

Monatin and tryptophan production in *E. coli* 12264ΔlipA(DE3) transformed with aspCproA/pET32 and pGX44trpoperon/pPRONco Fermentation broth samples

| Time after induction | [monatin]; ng/mL | [tryptophan]; ng/mL |
| --- | --- | --- |
| 4 | 9.4 | 1959.1 |
| 16 | 91.6 | 5231.2 |
| 24 | 119.3 | 5611.8 |
| 40 | 116.1 | 4470.2 |
| 49 | 112.4 | 3973.9 |
| 67 | 114.0 | 2947.3 |

Cell extracts were prepared using Novagen BugBuster™ reagent with benzonase nuclease, r-Lysozyme and Calbiochem protease inhibitor cocktail III according to Novagen's protocol. The level of protein expression in the cell extracts was analyzed by SDS-PAGE using a 4-15% gradient gel (Bio-Rad, Hercules, Calif.). The proteins expressed efficiently in the cell extracts prepared from samples harvested 4-24 h after induction. Proteins with a molecular mass of 55 to 59 kD (trpD and trpE gene products) and 48 to 50 kD (trpC and $HIS_6$aspC gene products) (6×HIS tag disclosed as SEQ ID NO: 90) showed high levels of expression. The cell extract samples were diluted 5-fold, filtered and analyzed by LC/MS/MS MRM. Tryptophan but not monatin was detected in the cell extract samples. The highest concentrations of tryptophan were measured in the samples withdrawn 16 to 24 h after induction and decreased in later time points. It is expected that more concentrated cell extract samples will show monatin concentrations at detectable levels.

Example 13

Production of Monatin in Recombinant Gram Positive Bacteria

This example describes methods that can be used to produce monatin in Gram positive bacteria such as *Corynebacterium* cells. One skilled in the art will understand that similar methods can be used to produce monatin in other bacterial cells. In addition, vectors can contain other genes for increased production of monatin.

Methods and Materials

*Corynebacterium glutamicum* ATCC 21847 was obtained from the American Type Culture Collection. This strain is known to be resistant to a variety of aromatic amino acid analogs and requires phenylalanine and tyrosine for growth.

All restriction enzymes were purchased from New England BioLabs (Beverly, Mass.). Primers were synthesized by Integrated DNA Technologies, Inc (Coralville, Iowa) unless noted otherwise. The *Corynebacterium/E. coli* shuttle vector, pEKEX-2, was obtained from Dr. Lothar Eggeling, Institute of Biotechnology 1, Forschungszentrum Jülich GmbH, 52425 Jülich Germany (Eikmanns et al., (1991) *Gene* 102(1):93-8)).

Construction of aspCproApEKEX-2

Recombinant DNA techniques for PCR, purification of DNA, ligations and transformations were carried out according to established procedures (Sambrook, Fritsch, Maniatis et al., 1989). The monatin operon containing the aspC and proA genes was cloned into the pEKEX-2 vector using the aspCproApET32b construct as the template. Primers for the synthesis of the operon with a KpnI restriction 5' of the aspC ATG start codon and 3' of the proA stop codon were designed for PCR amplification. The forward primer was designed to include a ribosomal binding site 5' of the aspC sequence and to exclude the His-tag sequence present in the pET32 construct. Forward primer: 5'-CGGGGTACCAGAAG-GAGAGATGCACGAT-GTTTGAGAACATTACCGC-CGCT-3'; Reverse primer: 5'-CGGGGTACCGCTTAGTCAAT-ATATTTCAGGC-3' (SEQ ID NOS: 83 and 84).

The following PCR protocol was used to amplify the monatin operon. In a 50 µL reaction, 50 ng template, 1.0 µM of each primer, 0.2 mM each dNTP, 0.5 U Pfuturbo DNA polymerase (Stratagene, LaJolla, Calif.), 2.8 U Expand High Fidelity™ Polymerase, and 1× Expand™ buffer with Mg were added (Roche, Indianapolis, Ind.). The thermocycler program used included a hot start at 96° C. for 5 min; 10 repetitions of the following steps: 94° C. for 30 sec, 59-59° C. for 1 min, 45 sec (gradient thermocycler), and 72° C. for 1 min, 30 sec; 15 repetitions of the following steps: 94° C. for 30 sec, 59-59° C. for 1 min, 45 sec, and 72° C. for 1 min, 30 sec increasing 5 sec each cycle; 10 repetitions of the following steps: 94° C. for 30 sec, 59-59° C. for 1 min, 45 sec, and 72° C. for 2 min, 45 sec. After the 35 cycles, the sample was incubated at 72° C. for 7 min and then stored at 4° C. The PCR product was purified using the QIAQuick PCR Clean-up kit (Valencia, Calif.) and was quantified by measuring the absorbance at 260 nm.

The pEKEX-2 plasmid was digested with KpnI for 2 h at 37° C. and then treated with shrimp alkaline phosphatase for 15 min (Roche Molecular Biochemicals; Indianapolis, Ind.). The PCR product was digested with KpnI in an overnight reaction at 37° C., and both digests were purified using a QIAQuick PCR Clean-up kit. The ligation reaction was carried out using the Roche Rapid DNA Ligation kit (Indianapolis, Ind.) with 84 ng of plasmid and 130 ng of PCR product, and the resulting ligation mixture was transformed into E. coli DH10B ElectroMAX cells (Invitrogen, Carlsbad, Calif.) using the manufacturer's recommended procedure for transformation of E. coli cells with 0.2 cm micro-electroporation cuvettes and a Bio-Rad Gene Pulser II system (Hercules, Calif.). After recovery in SOC medium, the transformation mixture was plated on LB plates containing kanamycin at 50 µg/mL. Plasmid DNA was isolated from liquid cultures (5 mL 2× YT medium+kanamycin (50 µg/mL) grown overnight at 37° C.) of colonies picked from the LB+kanamycin plates and purified using a QIAprep® Spin Miniprep kit (Qiagen). The plasmids were then screened by restriction digestion for inserts with the correct orientation and size, and the sequences were verified by dideoxynucleotide chain-termination DNA sequencing (SeqWright, Houston, Tex.).

Two clones with the correct sequence and orientation were tested for their ability to express the aldolase and aminotransferase genes. Fifty mL cultures of the constructs in LB with 50 µg/mL kanamycin were grown at 37° C. with shaking to an $OD_{600}$ of about 0.3. The gene expression was induced by the addition of 0.1 mM IPTG, and the cultures were incubated a further 15 h at 30° C. with shaking. Samples (10 mL) were withdrawn at 0, 2, and 15 h after induction. The cells were harvested by centrifugation at 4000×g for 10 min, washed with 50 mM MOPS, pH 7, and centrifuged again. Cell extracts were prepared using Novagen BugBuster™ reagent with benzonase nuclease and Calbiochem protease inhibitor cocktail III according to the Novagen's protocol. The level of protein expression in the cell extracts was analyzed by SDS-PAGE using 4-15% gradient gel (Bio-Rad, Hercules, Calif.). Both polypeptides were expressed. The proA aldolase polypeptide was 5-10% of the soluble protein fraction 15 h after induction, while the aspC aminotransferase polypeptide appeared to be 20-30% of the soluble protein fraction in the 15 h sample.

Preparation of *Corynebacterium glutamicum* Competent Cells for Electroporation

Electrocompetent *C. glutamicum* cells were prepared using a method that combined the protocols of Tauch et al. (*Current Microbiology*, (2002) 45:362-367) and Koffas et al. (*Metabolic Engineering*, (2003) 5:32-41). *C. glutamicum* cells were grown overnight and inoculated the next day into 200 mL of MB medium (with an initial absorbance at 600 nm of 0.1). MB medium contains 5 g/L yeast extract, 15 g/L tryptone, 5 g/L soytone, and 5 g/L sodium chloride. The cells were then grown to a final absorbance at 600 nm of 0.7 with shaking at 200 rpm. The cells were collected by centrifugation (4000×g for 20 min at 4° C.), and the cell pellet was washed 3 times with 40 mL of ice-cold buffer (20 mM HEPES, pH 7.2, containing 5% glycerol). The thrice washed pellet was washed two more times with 20 mL ice-cold 10% v/v glycerol. After centrifugation at 4000×g for 10 min at 4° C., the cell pellet was suspended in 1.0 mL 10% v/v glycerol, divided into 0.15 mL aliquots, and stored at −80° C.

Transformation of *Corynebacterium glutamicum* with aspCproApEKEX-2

Transformations in *C. glutamicum* cells (strain 21847) were carried out using a method that combined the procedures of Tauch et al. (*Current Microbiology*, (2002) 45:362-367) and Koffas et al. (*Metabolic Engineering*, (2003) 5:32-41). The electrocompetent *C. glutamicum* cells were thawed on ice. The aspCproApEKEX-2 DNA was added (1 µg), and the mixture incubated on ice for 5 minutes before transfer to a chilled 0.2 cm electroporation cuvette. Prior to the electric pulse, 0.8 mL of ice-cold 10% v/v glycerol was put on the cell suspension very gently to avoid mixing the two liquid layers. The electroporation conditions were 200 ohms, 25 µFd, and 12.5 kV/cm. Following exposure to the single electric pulse, the cell suspension was immediately transferred into 4 mL of pre-warmed (46° C.) MB medium and incubated at 46° C. for 6 min without shaking. Subsequently, the cells were incubated with shaking at 200 rpm for 50 min at 30° C. Portions of the cells were spread on selective MB plates containing 25 µg/mL kanamycin to recover transformants. Clones able to grow on the selective MB plates containing 25 µg/mL kanamycin were screened by PCR to confirm transformation.

Production of Monatin in *Corynebacterium* Cells Transformed with aspCproApEKEX-2

Fresh plates of *C. glutamicum*::aspC proA/pEKEX-2 (strain 21847) were prepared on MB medium containing 25 µg/mL kanamycin. Overnight cultures (5 mL) were inoculated from a single colony and grown at 30° C. in MB containing 25 µg/mL kanamycin. The culture was centrifuged, and the cells suspended in 1 mL of the production medium. An aliquot of the suspension (0.5 mL) was used to inoculate 100 mL of production medium. The production medium was similar to that used by Koffas et al. (*Metabolic Engineering*, (2003) 5:32-41) for the production of lysine with the following modifications. The amino acid additions were tyrosine and phenylalanine at final concentrations of 200 µg/mL; kanamycin was added at 25 µg/mL; threonine, methionine, and leucine were not added. The inoculated cultures (100 mL) were incubated at 30° C. with shaking until the $OD_{600}$ reaches 0.2-0.4. The gene expression was induced by the addition of 1.0 mM IPTG (final concentration), and the culture was incubated at 30° C. with shaking. Pyridoxine was added to a final concentration of 0.5 mM when gene expression was induced. The incubation was continued at 30° C. with shaking overnight.

Sixteen hours after induction, 0.04 mM pyridoxal phosphate (final concentration) in potassium phosphate (50 mM, pH 7.2), sodium pyruvate (0.1%), and Tween-20 (0.2%) was added. The incubation at 30° C. was continued. Samples for analysis of monatin and protein production (5 mL) were withdrawn at several time points from 0 to 112 hours after the induction with IPTG. The samples were centrifuged, and the separated supernatant and pellet fractions were frozen at −80° C. until analysis.

The concentration of monatin in the fermentation broth samples was measured by LC-MS/MS (described in Example 6). Monatin (from 3 to 12 ng/mL) was detected in broth samples withdrawn 66 to 112 hours after induction. Cultures producing more tryptophan also produced more monatin. For example, when the concentration of tryptophan in a broth sample withdrawn at 40 hours after induction was 70 µg/mL, the monatin concentration was 11-12 ng/mL in samples withdrawn 66 to 112 hours after induction. In contrast, a culture that produced less tryptophan (51 µg/mL at 40 hours) only secreted 3 ng/mL of monatin.

Production of Monatin in *C. glutamicum* (ATCC 13058), a Glutamate Overproducer

Methods and Materials

*Corynebacterium glutamicum* ATCC 13058 was obtained from the American Type Culture Collection. This strain is known to produce and secrete glutamate.

Preparation of *Corynebacterium glutamicum* (ATCC 13058) Competent Cells for Electroporation and Transformation with aspCproApEKEX-2

Electrocompetent *C. glutamicum* (ATCC 13058) cells were prepared as described for ATCC strain 21847. After the final wash and re-suspension in 10% glycerol, 0.15 mL aliquots were stored at −80° C. The cells also were transformed with aspCproApEKEX-2 and pEKEX-2 as described for ATCC strain 21847.

Production of Monatin in *Corynebacterium* (ATCC 13058) Cells Transformed with aspCproApEKEX-2

Fresh plates of 2 isolates of *C. glutamicum*::aspCproA/pEKEX-2 (ATCC 13058) and 1 isolate of *C. glutamicum*:: pEKEX-2 (ATCC 13058) were prepared on MB medium containing 25 μg/mL kanamycin. Overnight cultures (5 mL) were inoculated from a single colony and grown at 30° C. in MB containing 25 μg/mL kanamycin. The cultures were centrifuged, and the cells suspended in 1 mL of the *C. glutamicum* fermentation medium. This medium contains the following in 1 L: glucose (100 g), $(NH_4)_2SO_4$ (2 g), $K_2HPO_4$ (1 g), $KH_2PO_4$ (1 g), $MgSO_4\text{-}7H_2O$ (0.25 g), $FeSO_4\text{-}7H_2O$ (0.01 g), $MnSO_4\text{-}4H_2O$ (0.01 g), biotin (2.5 μg). (Small aliquots 10% urea are added to the cultures at intervals of 4-6 h to maintain the pH for long fermentations.) An aliquot of each suspension (0.5 mL) was used to inoculate 2×100-mL of the medium. The inoculated cultures (100 mL) were incubated at 30° C. with shaking until the $OD_{600}$ reached ~0.4. The gene expression was induced by the addition of 1.0 mM IPTG (final concentration), and the culture was incubated at 30° C. with shaking. Pyridoxine was added to a final concentration of 0.5 mM when gene expression was induced. The incubation was continued at 30° C. with shaking overnight.

Nine hours after induction, 0.04 mM pyridoxal phosphate (final concentration) in potassium phosphate (50 mM, pH 7.2), sodium pyruvate (0.1%), and Tween-20 (0.2%) were added to one culture flask for each construct. The Tween-20 was omitted from the second flask of each culture. The incubation at 30° C. was continued. Samples for analysis of monatin and protein production (5 mL) were withdrawn at several time points from 0 to 68 hours after the induction with IPTG. The samples were centrifuged, and the separated supernatant and pellet fractions were frozen at −80° C. until analysis.

Results

The concentration of monatin in the fermentation broth samples was measured by LC-MS/MS. Monatin was detected in broth samples withdrawn 30 to 68 hours after induction. At 45 h after induction the monatin concentration was highest in the cultures transformed with aspCproApEKEX-2 to which Tween-20 had been added—between 240 and 330 ng/mL. The level of monatin in the cultures without Tween-20 ranged from 50 to 66 ng/mL. Surprisingly, monatin was also observed in detectable but not quantifiable levels in the control cultures.

Production of Monatin in *Corynebacterium* (ATCC 13058) Cells Transformed with aspCproApEKEX-2 (con't)

The shake flask experiments were repeated with *C. glutamicum* 13058::aspC proA/pEKEX-2 and *C. glutamicum* 13058::pEKEX-2 using a different feed regimen and were analyzed by LC/MS/MS MRM as described in Example 6.

The following starter cultures were grown in LB with kanamycin at 50 mg/L at 30° C. with shaking at 250 rpm overnight:
  *C. glutamicum* 13058::aspCproA/pEKEX-2-1 (monatin operon)
  *C. glutamicum* 13058::pEKEX-2-1 (vector control)

The 5 ml starter cultures were transferred to 100 ml of *C. glutamicum* fermentation medium containing kanamycin at 50 mg/L. Cultures were incubated at 30° C. with shaking at 250 rpm to $OD_{600}$ of ~0.5. At this time the following additions were made to each flask to induce gene expression: 1 μl IPTG (840 mM stock), 10 ml pyridoxine HCl (50 mM stock), and 200 μl PLP (20 mM stock). Cultures were incubated at 30° C. with shaking at 250 rpm for 3 hours (OD600~0.5) following induction with IPTG. The cultures were divided into two flasks by removal of 55 ml (half) volume to new flasks. Each flask was subjected to one of the two treatments described below. Additions were made as described in Table 16:

TABLE 16

| Sterile stock solutions | Treatment: substrates | Treatment: substrates + Tween, Ampicillin |
|---|---|---|
| L-tryptophan (1% in 0.1 M $NaPO_4$ buffer) | 5 mL | 5 mL |
| 10% sodium pyruvate | 5 mL | 5 mL |
| Distilled water | 3 mL | — |
| 20% Tween 40 | — | 1 mL |
| 10% Tween 60 | — | 2 mL |
| 100 mg/mL ampicillin | — | 50 μl |

After the additions, cultures were incubated at 30° C. with shaking at 250 rpm for 48 hours. Ten ml culture broth from each flask was removed for dry cell weight determination. The remaining culture volume was centrifuged and supernatants were filtered and used for glutamate and monatin analysis.

The results for culture broths are tabulated below in Table 17.

TABLE 17

| Description | Dry cell weight (DCW) (mg/ml) | Monatin (ng/ml) | Monatin (ng/mg DCW) | Glutamate (mg/mL) | Glutamate (mg/mg DCW) |
|---|---|---|---|---|---|
| *C. glutamicum* 13058 (PEKEX2-1) + substrates | 1.64 | 293 | 179 | 7.4 | 4.5 |
| *C. glutamicum* 13058 (PEKEX2-1) + substrates + Tween, Amp | 0.52 | 67 | 129 | 616.0 | 1185 |
| *C. glutamicum* 13058 (monatin operon) + substrates | 0.86 | 248 | 288 | 5.4 | 6.3 |
| *C. glutamicum* 13058 (monatin operon) + substrates + Tween, Amp | 0.28 | 164 | 586 | 166.4 | 594.3 |

As observed above there was a definite increase in monatin production in *C. glutamicum* 13058 cells expressing the aspC and proA genes when compared to cells transformed with the vector pEKEX-2. However, monatin is clearly being formed in cells that were not transformed with the vector containing the aspC and proA genes indicating that wildtype *Corynebac-*

*terium glutamicum* strains are capable of making monatin. A further increase in monatin efflux was also observed upon addition of Tween-40, Tween-60 and ampicillin to the cultures. In addition chiral analysis using the FDAA derivatization method of Example 6 of a *C. glutamicum* 13058 supernatant sample transformed with vector alone demonstrated the presence of both S,S monatin and trace amounts of R,R monatin (seen transiently). In a separate experiment, LC/MS/MS MRM analysis showed the presence of multiple monatin peaks, indicating the presence of either S,R or R,S and RR, or SS monatin.

*C. glutamicum* 13032::aspCproA/PEKEX-2 was also grown in shake flask experiments using the same protocol as used with *C. glutamicum* 13058::aspCproA/PEKEX-2. At 21 hours following induction, *C. glutamicum* 13032::aspCproA/PEKEX-2 produced 1059 ppb of monatin when the cultures were treated with Tween and ampicillin in addition to substrates as shown in Table 16. *C. glutamicum* 13032::aspCproA/PEKEX-2 produced 428 ppb of monatin in the absence of Tween and ampicillin treatment at the corresponding time point of 21 hours following induction with IPTG. A control experiment with *C. glutamicum* 13032::PEKEX-2 produced 45-58 ppb of monatin with or without Tween and ampicillin at 21 hours following induction with IPTG. *C. glutamicum* 13032 represents an additional production host for monatin production.

Taken together, the results above clearly demonstrated the potential of *Corynebacterium glutamicum* and other members of the genus *Corynebacterium*, to produce monatin or serve as a source of genes in the monatin operon that can be expressed in heterologous hosts.

Example 14

Increased Production of Tryptophan in vivo Using Mutations which Relieve Regulation in *Escherichia coli*

The tryptophan biosynthetic pathway is highly regulated in *Escherichia coli*. Relief of the regulatory points can increase the flux towards tryptophan biosynthesis. Regulation can occur either by feedback inhibition of the enzymes, as well as repression of the synthesis of enzymes in the pathway. As tryptophan is an intermediate in monatin production, improvement of the levels of tryptophan can improve the levels of monatin produced. The regulatory genes described below are only a few of the regulatory points in the trytophan pathway and those skilled in the art know that other tryptophan overproduction strategies can also increase monatin yields in *E. coli*.

One skilled in the art can use analogs to select for resistant mutants that can overproduce tryptophan. Relief of regulatory points in the trytophan pathway can result in an increase in the levels of monatin produced by bacteria such as *E. coli*. One approach towards altering control points of feedback inhibition is to select mutants that are resistant to analog compounds. Examples of such compounds include, but are not limited to, 5-fluorotryptophan, 3-fluorophenylalanine, beta-2-thienylalanine, 6-fluorotryptophan, tryptophanhydroxamate, p-fluorophenylalanine, p-aminophenylalanine, tyrosinehydroxamate, and phenylalaninehydroxate (Azuma et al., *Appl. Microbiol. Biotechnol.*, 1993, 39: 471-476; and Duda and Sasvari-Szekely, *Acta Biochim. Biophys. Acad. Sci. Hung.*, 1973, 8: 81-90).

*E. coli* strains such as 7692 and *E. coli* 7692ΔlipA DE3 (described in Example 10) can be grown on fresh LB plates. Individual colonies can be used to inoculate shake flasks with M9 medium plus glucose and other required vitamins or cofactors. After 24 hours of incubation at 37° C. with 250 rpm shaking, small aliquots of *E. coli* culture can be removed and plated on M9 medium plates that contain various concentrations of analogs (e.g., 1 mg/mL p-fluoropheynlalanine). Resistant colonies can be picked and grown in 5 mL cultures of LB at 37° C. with shaking to screen for increased tryptophan production. Increased tolerance to the analogs on the plates can be affected by gradually increasing the analog concentration. This could also be carried out in continuous culture.

These analogs can, for example, affect a key branchpoint at the start of aromatic amino acid synthesis, 3-deoxy-D-arabino-heptulosonate 7-phosphate synthase. In *E. coli*, this is coded for by three isozymes aroF, aroG, and aroH, each of which are feedback inhibited by an amino acid of the pathway, namely tyrosine, phenylalanine, and tryptophan, respectively. Mutants resistant to the analogs described above will show relief of this feedback inhibition.

Another key branchpoint is anthranilate synthase and feedback resistant mutations in this gene can also improve tryptophan production. Also, the effects of the one regulatory mutation (e.g., the feedback resistant anthranilate synthase) can be masked by a backup of an intermediate in the pathway. Thus, those skilled in the art will combine tryptophan pathway mutations to improve monatin production. Other examples of mutations in the tryptophan pathway and aromatic biosynthetic pathway that can be used to improve monatin production include, but are not limited to, any of the enzymes specific to tryptophan biosynthesis which are made resistant to feedback inhibition by tryptophan, and relief of repression altering trpR or its binding site, as well as relief of the attenuation control of operon expression (Kim et al., *J. Microbiol. Biotechnol.*, 2000, 10: 789-796; Jossek et al., *FEMS Microbiol. Lett.*, 2001, 202: 145-148; Bongaerts et al., *Metabol. Eng.*, 2001, 3: 289-300; Azuma et al., *Appl. Microbiol. Biotechnol.*, 1993, 39: 471-476; Flores et al., *Nature Biotechnol.*, 1996, 14: 620-623; Tribe and Pittard, *Appl. Environ. Microbiol.*, 1979, 38: 181-190; Yanofsky et al., *J. Bacteriol.*, 1984, 158: 1018-1024; Gosset et al., *J. Indus. Microbiol.*, 1996, 17: 47-52).

Besides genetic alteration of strains to enhance tryptophan and monatin production, growth conditions such as medium ingredients as well as altered process conditions such as pH, temperature and mixing can improve synthesis of tryptophan and monatin by a host microorganism. Thus, suitable medium such as those containing growth factors can be used to increase tryptophan production from *E. coli*. For example, the concentration of growth factors such as pyrimidines, trace elements, and biotin can impact production and excretion of intermediates (Jensen, (1993) *J. Bacteriol.*, 175:3401-3407).

Example 15

Increased Production of Tryptophan in *E. coli* Using an Overexpression Strategy Another strategy to increase the levels of tryptophan in *E. coli* is to increase the number of copies of the trytophan biosynthetic genes in the cell. This can be accomplished by cloning the genes into a vector and transforming the vector into cells. One skilled in the art will recognize that increasing the copy number of the genes can also be accomplished by cloning the genes into the chromosomal DNA, or altering the native promoter region.

Three strains cited in U.S. Pat. No. 4,371,614 were obtained from the U.S.D.A. Peoria culture collection. The first host strain, NRRL B-4574, is also called KB3100 and is ΔaroP. The second strain, NRRL B-12262, is also called AGX15 and has the genotype serB⁻, trpΔED, tnaA2⁻, tetS, tyrA⁻, pheA⁻. It contains a plasmid called pGX44. pGX44 is derived from pBR322 (Roeder and Somerville, *Molec. Gen. Genet.*, 1979, 176: 361-368) and contains the serB gene and the tryptophan operon. The third strain, NRRL B-12264, is also called AGX6 and has the genotype serB⁻, trpΔED, tnaA2⁻, aroP⁻. It contains a plasmid called pGX50. pGX50 is derived from pBR322 and contains the serB gene and a tryptophan operon which was derived from cells that are resistant to 5-methyltryptophan.

Strains NRRL B-12262 and B-12264 have the serB gene deleted, which results in serine being needed for host strain growth. The plasmids pGX44 (in B12262) and pGX50 (in B-12264) each contain the serB gene, thus the serine auxotrophy is a selection pressure for retaining the plasmid. A medium that lacks serine can be used to maintain the plasmid even in the presence of high concentrations of tryptophan produced by these organisms. The plasmid carrying strains, 12262 and 12264, when cultured in medium without serine must maintain multiple copies of the plasmid to survive and grow and, therefore, carry multiple copies of a tryptophan operon. The NRRL B-4574 strain does not carry either of these plasmids, and thus, only has one copy of a tryptophan operon (on the genome). All growth media and fermentation media used for NRRL B-12264 contained 50 μg/mL ampicillin as the pGX50 vector contains an ampicillin resistance gene.

The strains were grown in LB broth and Trp Production medium. Trp production medium contains, per liter: 30 g of Glucose, 10 g of $(NH_4)_2 SO_4$, 1.0 g of $KH_2PO_4$, 1.0 g of $MgSO_4$-$7H_2O$, 0.01 g of $FeSO_4$-$7H_2O$, 0.01 g of $MnCl_2$-$4H_2$), 4 g of Casamino acids, and 40 g of $CaCO_3$. The inoculum for the shake flasks was grown in LB broth. Three milliliters of inoculum culture was used to inoculate 50 mL of media in a 250 mL baffled shake flask. The shake flasks were incubated at 30° C. with moderate shaking (200 rpm). Tryptophan was measured as described in Example 6. The shake flasks were sampled periodically for glucose and $OD_{550}$. The results are presented in Table 18.

TABLE 18

Tryptophan production by *E. coli* strains containing multiple copies of the tryptophan operon

| *E. coli* strain | μg/mL Tryptophan |
| --- | --- |
| NRRL B-4574 Trp Production Medium | 6 |
| NRRL B-4574 LB Broth | 44 |
| NRRL B-12262 Trp Production Medium | 417 |
| NRRL B-12262 LB Broth | 568 |
| NRRL B-12264 Trp Production Medium | 104 |
| NRRL B-12264 LB Broth | 2 |
| Trp Production Medium Blank | 0.01 |
| LB Broth Medium Blank | 60 |

Multiple copies of the tryptophan operon appear to increase the production of tryptophan by *E. coli*. Strains that contain some of the same genetic modifications but no extra copies of the tryptophan operon produced less tryptophan under similar experimental conditions. For example, *E. coli* SR 250 (Rothman and Kirsch, 2003) is a tyrA- and pheA- strain, but it produced only approximately 0.1 μg/mL when tested under similar conditions. These data suggest that a host strain with multiple copies of tryptophan biosynthetic genes, particularly ones with pheA disrupted, can be used to obtain increased monatin production.

Example 16

Production of Tryptophan in Fermentors

Fermentors can be used to achieve economically efficient monatin production. With the use of fermentation equipment, parameters such as pH, oxygen, and mixing are easily controlled so that a fermentation reaction can be optimized.

Three *E. coli* strains, NRRL B-4575, NRRL B-12262 and NRRL B-12264 were obtained from the U.S.D.A. laboratory in Peoria, Ill. The latter two strains both contain the tryptophan operon on plasmids. These strains are described in more detail in Example 15. Infors fermentors with 300 ml of medium was used for the fermentation study. The tryptophan production medium was described in Example 15.

The bacterial inoculum was taken from freshly streaked LB plates. One loopful was inoculated into 50 mL of Trp Production medium in 250 mL shake flask, and the culture grown overnight at 37° C. 15 mL from the seed flask was inoculated into each duplicate Infor 300 mL fermentor vessel containing 250 mL of Trp Production medium. Agitation was started at 500 rpm and allowed to increase to 1000 rpm. Air was sparged in at 1 vvm and increased to 5 vvm by 4 hours. The pH was maintained at 7.0 with 1N sodium hydroxide.

Samples were taken periodically and analyzed for glucose and $OD_{550}$. After 3 days, the fermentation broth was spun down at 15,000 rpm for 2 minutes, filtered, and frozen until tryptophan analysis.

As shown in Example 15, NRRL B-12262 produces about 4-fold more tryptophan than NRRL B-12264 in shake flasks using the Trp production medium. As seen in Table 19, NRRL B-12262 produces considerably less tryptophan in fermentors than in shake flasks, which could be due to unoptimized scale-up stress on the microorganism. A similar stress of strain NRRL B-12264 could explain its lack of production of detectable tryptophan in fermentors. It is expected that those skilled in the art will be able to improve tryptophan production in fermentors by both NRRL B-12262 and NRRL B-12264 strains.

TABLE 19

| *E. coli* strain | μg/mL Tryptophan |
| --- | --- |
| NRRL B-4574 | 0.03 |
| NRRL B-12262 | 221 |
| NRRL B-12264 | 0.03 |
| Tryptophan Production Medium Blank | 0.04 |

Example 17

Increased Production of Tryptophan by Mutants of *Corynebacterium*

*Corynebacterium glutamicum* ATCC 21847 was obtained from the American Type Culture Collection. This strain is resistant to a variety of analogs and has genetic mutations that create phenylalanine and tyrosine auxotrophy. *C. glutamicum* 21850 and 21851 are different strains that were created similarly using analogs such as 6 fluoro-tryptophan, 4 aminophenylalanine, tryptophan hydroxamate and 4 methyl tryptophan.

A fresh colony of ATCC 21847 from a nutrient agar plate was inoculated into a 5 mL tube of seed which contains glucose, 2%, peptone, 1%, yeast extract, 1%, and NaCl, 0.3%. After overnight culture at 30° C. with shaking, 2 mL of the tube was inoculated into 50 mL of media in a shake flask. Two media were used. The first medium (Medium 1) is composed of: glucose, 10%, $KH_2PO_4$, 0.05%, $K_2HPO_4$, 0.05%, $MgSO_4$-$7H_2O$, 0.025%, $(NH_4)_2SO_4$, 2%, NZ-amine, 0.5%, biotin, 30 µg/mL, and $CaCO_3$, 2%. The pH was adjusted to 7.2. The second medium (Medium 2) is composed of per liter: Molasses, 100 g based on glucose, $KH_2PO_4$, 0.5 g, $K_2HPO_4$, 0.5 g, $MgSO_4$, 0.25 g, $NH_4SO_4$, 0.25 g, Corn Steep Liquor, 10 g, $CaCO_3$, 20 g, tyrosine, 38 mL of 4 mg/mL stock solution, and phenylalanine, 12 mL of a 25 mg/mL stock solution (U.S. Pat. No. 3,849,251). The pH was adjusted to 7.2.

The flasks were incubated at 30° C. in Innova shakers at 250 rpm for four days, and tryptophan levels were measured as described in Example 6.

The results are shown in Table 20. The analog resistant mutant of *Corynebacterium* produced tryptophan (Table 20) at higher levels than other *C. glutamicum* strains. The higher levels observed with Medium 2 are likely a reflection of the rich medium components, such as the Corn Steep Liquor and molasses. Similarly, ATCC 21851 produced 300-370 µg/mL tryptophan in Medium 2, and only 1-2 µg/mL tryptophan in Medium 1. ATCC 21850 was not tested in the optimal medium (Medium 2), but is expected to behave similarly to 21851. These results demonstrate that *Corynebacterium* host strains can be economical producers of monatin. In addition, strategies similar to those described herein for increasing tryptophan production in *E. coli* (See, e.g., Examples 14-17) can be used in *Corynebacterium* to improve its properties as a host production microbial strain for monatin (Shiio et al., *Agr. Biol. Chem.*, 1975, 39: 627-635; Hagino and Nakayama, *Agr. Biol. Chem.*, 1975, 39: 343-349; Shiio et al., *Agr. Biol. Chem.*, 1984, 48: 2073-2080; Heery et al., *Biochem. Biophys. Res. Commun.*, 1994, 201: 1255-1262; Heery and Dunican, *Appl. Environ. Microbiol.*, 1993, 59:791-799; and Katsumata and Ikeda, *Bio/Technol.*, 1993, 11:921-925).

TABLE 20

Production of tryptophan by *Corynebacterium* ATCC 21847

| Medium | Tryptophan (µg/mL) |
|---|---|
| Medium 1 | 80.8 |
| Medium 1 | 119 |
| Medium 2 | 2517 |
| Medium 2 | 2535 |
| Medium 1 Blank | 37.2 |
| Medium 2 Blank | 1.0 |

Example 18

Glutamate Production in *Corynebacterium glutamicum*

Part A: Physical Methods for Improving Yields of Glutamate in the Broth

One important limitation for economical amino acid production is the excretion of the amino acid out of the cell. Microbial cells typically have mechanisms for transporting amino acids into the cell, but the mechanisms of export of high levels of amino acids is not known in many cases. Physical means, such as use of detergents and modifications of the medium, can be used to effect glutamate efflux. Since both glutamate and monatin are dicarboxylic acids, one skilled in the art could use the techniques described below for glutamate to improve monatin release into the medium.

*Corynebacterium glutamicum* ATCC 13058, 13655, and 13689 were obtained from the American Type Culture Collection. These strains are cited as producers of glutamate (U.S. Pat. Nos. 3,002,889 and 3,128,237).

The strains were grown in shake flasks in medium containing per liter: $KH_2PO_4$, 1.0 g, soy peptone, 2.0 g, $MgSO_4 7H_2O$, 0.4 g, $FeSO_4$, 0.01 g, $MnSO_4$, 0.01 g, glucose, 100 g, urea, 5 g, biotin, 4 µg, thiamine, 200 µg. The pH of the medium was adjusted to 6.0 and urea, glucose, biotin, and thiamine were all sterilized separately. The cultures were incubated at 30° C. for 72 hours with shaking. At 18 hr, 1.8% urea was added to the flasks.

All three strains produced glutamate and secreted some of it in the medium, as shown in Table 21. Cells were recovered from the flasks by centrifugation and were split and treated by either of two methods: a detergent-enzyme method using BugBuster® with Lysonase™ (Novagen) and osmotic shock. Osmotic shock was performed by diluting cells 1:20 with cold deionized water. These treatments are expected to partially, but not completely, disrupt the cell envelope of a gram positive organism (such as *Corynebacterium glutamicum*) and, thus, should facilitate release of intracellular metabolites. Glutamate was analyzed by the high throughput method described in Example 6.

The data show that an equivalent amount of glutamate to that secreted was retained in the cell and that various physical treatments were able to release it. In addition to these treatments, other physical treatments would also be expected to release glutamate from the cell and these techniques could also be employed to facilitate the liberation of monatin.

TABLE 21

Glutamate concentration in medium (secreted) and glutamate released from *C. glutamicum* by physical treatment

| TREATMENT | Excreted µg/mL* | Bug Buster µg/mL | Osmotic µg/mL |
|---|---|---|---|
| ATCC 13869 | 300 | 198.5 | 318.5 |
| ATCC 13655 | 275.5 | 221.5 | 137 |
| ATCC 13058 | 253 | 207 | 200.5 |

*values are presented as µg of glutamate produced per mL of fermentation broth.

Part B: Additional factors for Improvement of Glutamate Production

Glutamate excretion can be affected by a variety of factors including antibiotics, surfactants, temperature, osmotic stress, pH and biotin concentration. This example elucidates factors involved in glutamate production and/or secretion.

*Corynebacterium glutamicum* ATCC 13058 and ATCC 13655 were obtained from the American Type Culture Collection. These strains are known producers of glutamate.

A series of statistical, factorial designs were done to investigate various factors in glutamate production in *C. glutamicum* ATCC strains 13058 and 13655. A colony of each strain was used to inoculate 5 mL of modified MCGC medium for an overnight culture at 30° C. Shake flasks with modified MCGC medium were inoculated with 0.5-1.0 mL of the seed cultures. The modified MCGC medium contains (per L): 3 g $Na_2HPO_4$, 6 g $KH_2PO_4$, 2 g NaCl, 8 g $(NH_4)_2SO_4$, 0.5 g Soytone, 60 g glucose, 3.9 mg $FeCl_3$, 0.9 mg $ZnSO_4$-$7H_2O$, 0.56 mg $CuSO_4$-$5H_2O$, 3.9 mg $MnSO_4$-$7H_2O$, 0.1 mg $(NH_4)_6Mo_7O_4$-$4H_2O$, 0.3 mg $Na_2B_4O_7$-$10H_2O$, 84 mg $CaCl_2$-$2H_2O$, 2 g betaine. Treatments included (per liter) 100 mmol MOPS or MES, 50 or 400 mg $MgSO_4$-$7H_2O$, 4 or 20 mg thiamin, and 4 or 20 ug biotin. At 16 hours, Tween 40 or 60 were added to 3 mls per liter, ampicillin to 0 or 10 ug/mL, and temperature increased to 40° C. for flasks requiring higher temperature treatment. The flasks were incubated at 250 rpm and 30° C., unless otherwise noted, for 2-3 days.

Samples were taken periodically and analyzed for glucose concentration (g/L), cell density ($OD_{600}$) and pH. After 2-3 days, samples were centrifuged and supernatant was filtered and frozen until glutamate analysis by HPLC as in Example 6 for the fluorescence detection method.

Factors studied for glutamate production/excretion included ampicillin, Tween, temperature, initial pH, biotin, magnesium, and thiamine. For *C. glutamicum* ATCC 13058, statistically significant factors in glutamate production included biotin, initial pH and an interaction between biotin and pH. Analysis of variance (ANOVA), a statistical method to test hypotheses about differences between two or more means, was used to analyze the results. The predictive model was significant at the α level of <0.0001 with an adjusted $R^2$ of 0.96. An initial pH of 8.0 was better for glutamate production than pH 7.6 or 6.5. The lowest biotin concentration, 4 ug/L, resulted in greater production of glutamate. This result is consistent with other research showing that a limiting concentration of biotin from 2 to 5 ug/L (micrograms/L) affects the fluidity of the cell membrane and enhances glutamate efflux (Eggeling L and Sahm H (1999) "Amino-acid production: principles of metabolic engineering" in Metabolic Engineering (Ed: Lee S Y, Papoutsakis E T); Marcel Dekker, Inc, NY, N.Y. Thus, in one embodiment, culture medium for a microorganism comprises 5 ug/L or less biotin.

Both the low and high levels of biotin (4 ug/L and 20 ug/L) resulted in higher glutamate at pH 8.0 than at pH 7.6. Tween 40 and Tween 60 worked equally well, although, there was a possible interaction between magnesium concentration and Tween type that affected glutamate production. In the presence of Tween, ampicillin addition decreased glutamate production. The supernatant glutamate concentration ranges for ATCC 13058 and ATCC 13655 were 0-13.3 mM and 0-11.3 mM, respectively.

These results show that glutamate production/excretion can be manipulated with the significant factors above. It is predicted that the same factors will be useful in monatin production/excretion based on the dicarboxylic acid structure that it shares with glutamate. (Delaunay S., et al, 1999, Enzyme and Microbial Technology, 25, 762-768).

Part C: Improvement of Glutamate Production with Kramer's Medium and Increased Temperature This example demonstrates an improved glutamate production with a different strain, temperature, and medium.

*Corynebacterium glutamicum* strains ATCC 13032 and ATCC 13058 were obtained from the American Type Culture Collection.

A study with both strains was carried out at 30° and 37° C. in Kramer's A medium. A colony of each strain was used to inoculate 5 mL of Kramer's A medium for an overnight culture at 30° C. Shake flasks with Kramer's A medium were inoculated with 0.5-1.0 mL of the seed cultures. Kramer's A medium contains (per L): 5 g $(NH_4)_2SO_4$, 5.0 g urea, 2.0 g $KH_2PO_4$, 1.53 g $K_2HPO_4$, 1 mole $MgSO_4\cdot7H_2O$, 50 g glucose, 0.01 g $FeSO_4\cdot7H_2O$, 0.01 g $MnSO_4\cdot7H_2O$, 0.01 g $CaCl_2\cdot2H_2O$, 0.03 mg $ZnSO_4\cdot7H_2O$, 0.1 mg as Mo from $(NH_4)_6Mo_7O_{24}\cdot4H_2O$, 0.10 mg $H_3BO_3$, 0.07 mg $CoCl_2\cdot6H_2O$, 0.01 mg $NiCl_2\cdot2H_2O$, 0.03 mg $CuCl_2\cdot2H_2O$ and 1 ug biotin. The pH is adjusted to 7.0 with 5M NaOH. Tween and ampicillin were not added in this experiment. The flasks were incubated at 250 rpm and 30° C. or 37° C. for 24 hours. Glutamate was analyzed by the high throughput method described in Example 6.

Results for the experiment with ATCC 13032 and ATCC 13058 at 30° and 37° C. are listed in Table 22.

TABLE 22

Glutamate concentration in Kramer's A medium at two temperatures

| ATCC Strain | Temperature (° C.) | Glutamate (mM) |
|---|---|---|
| 13032 | 30 | 40.7 |
| 13032 | 37 | 39.4 |
| 13058 | 30 | 40.5 |
| 13058 | 37 | 54.2 |

*Corynebacterium glutamicum* ATCC 13058 produced more glutamate (54 mM) at 37° C. while *C. glutamicum* 13032 produced similar amounts (~40 mM) at both temperatures. These results again show that glutamate production/excretion can be manipulated by varying the temperature and medium components. It is predicted that the same factors will be useful in monatin production/excretion based on the dicarboxylic acid backbone that it shares with glutamate. (Hoischen C. and Kramer R., 1989, Arch Microbiol, 151:342-347).

Example 19

Cloning of Tryptophanase Gene (tna) from *Escherichia coli*

Tryptophanase Polypeptides (EC 4.1.99.1) Catalyze the Following Reversible Reaction:

L-Tryptophan+$H_2O$⇌Indole+Pyruvate+$NH_3$

In some instances, the gene encoding tryptophanase is deleted from host strains to prevent hydrolytic breakdown of tryptophan. However, if an excess of indole, pyruvate, and ammonium are supplied to cells, this enzyme can be overexpressed to aid in the synthesis of tryptophan. This approach is particularly useful when no deregulation of the host biosynthetic pathway of tryptophan has been performed. The tryptophanase gene from *Escherichia coli* DH10B was cloned into a pPROLAR derived vector that is compatible with pET vectors containing monatin biosynthetic pathway genes and supplementary genes.

Isolation of Genomic DNA for Cloning

*Escherichia coli* genomic DNA was isolated from strain DH10B (Invitrogen) and prepared using the Qiagen Genomic-tip™ (500/G) kit. From 30 mL of this strain grown in LB to an $OD_{650}$ of 1.87, 0.3 mg of purified DNA was obtained. The purified DNA was dissolved in Qiagen elution buffer (EB) at a concentration of 0.37 μg/μL.

Polymerase Chain Reaction Protocol

Primers were designed for molecular cloning in pPRO-Lar.A122 (Clontech Laboratories, Inc.) in which the NcoI recognition site in the kanamycin gene was mutated (herein referred to as pPRONco). The sequence of the pPRONco primers was as follows:

```
                                    (SEQ ID NOS: 77 and 78)
forward: 5'-TGCCATGGAAAACTTTA-AACATCT-3';

reverse: 5'-CCAAGCTTTTAAACTTCTTTAAGTTTTG-3'.
```

PCR was performed using the following PCR protocol. In a 50 μL reaction, 0.1-0.5 μg template, 1.5 μM of each primer, 0.4 mM each dNTP, 3.5 U Expand High Fidelity Polymerase (Roche, Indianapolis, Ind.), and 1× Expand™ buffer with Mg were used. The thermocycler program used included a hot start at 96° C. for 5 minutes, followed by 29 repetitions of the following steps: 94° C. for 30 seconds, 50° C. for 1.75 minutes, and 72° C. for 2.25 minutes. After the 29 repetitions, the sample was maintained at 72° C. for 10 minutes and then stored at 4° C. This PCR protocol produced a product of about 1500 bp.

Cloning

The PCR products were gel purified from 0.8 or 1% TAE-agarose gels using the Qiagen gel extraction kit (Valencia, Calif.). The tna gene was inserted in the pPRONco vector by insertion between the NcoI and HindIII restriction sites in the multiple cloning site. Cloning in pPRONde was accomplished by insertion between the NdeI and HindIII sites.

The ligation mixture was transformed into DH10B cells using electroporation. Cells were plated on LB plates containing 50 mg/L kanamycin for selection. Plasmid DNA was purified using the Qiagen spin miniprep kit and screened for the correct inserts by restriction digest. The sequences of plasmids that appeared to have the correct insert were verified by dideoxy chain termination DNA sequencing. Chemically competent *E. coli* BL21(DE3) cells were co-transformed with aspC proA/pET32 and tna/pPRONco or transformed with tna/pPRONco alone according to the manufacturer's protocol (Novagen, Madison, Wis.).

Production of Monatin and Tryptophan in *E. coli* BL21(DE3) Cells Transformed with aspC proApET32 and tna/pPRONco Cultures of *E. coli* BL21(DE3) transformed with tna/pPRONco or transformed with both aspC proA/pET32 and tna/pPRONco were grown in trp-1 medium with 0.4% glucose and Balch's vitamin solution at 37° C. with shaking (duplicate cultures for each construct). The tna/pPRONco cultures also contained 50 µg/mL kanamycin while the cultures containing BL21(DE3) transformed with both plasmids also contained 50 µg/mL kanamycin and 100 µg/mL ampicillin. (see Examples 1, 7 and 11 for recipes). When the $OD_{600}$ reached between 0.5 to 0.7 the cultures were induced with 1.0 mM IPTG and 0.5% L-arabinose and the incubation was continue at 30° C. In addition, 0.5 mM pyridoxine was added at the time of induction. Five hours after induction, 0.04 mM pyridoxal phosphate, 0.5% sodium pyruvate, and 0.6% ammonium chloride were added to each culture flask, the pH of each was adjusted to 7.5-7.6, and then 5 mM indole (from a stock of 50 mM indole in aqueous 2% TritonX-100) was added to each flask. The incubation was continued at 30° C. Samples for analysis of tryptophan and monatin (0.5 mL) and protein induction (1 mL) were withdrawn at 0, 5, 7.5, 20, 30, 48, and 74 h after induction with IPTG. Samples for dry cell weight (DCW) analysis were withdrawn 7.5, 20, 30, and 48 h after induction. The concentrations of monatin and tryptophan in the fermentation broth samples was measured by LC-MS/MS MRM as described in Example 6.

The results are shown in Tables 23 and 24 below. The concentration of tryptophan in the fermentation broth reached about 1.1 g/L 20 h after induction in the cultures expressing the tna gene alone and increased to approximately 1.3 g/L by 74 h. Monatin could not be detected in any of the samples withdrawn from the cultures expressing only the tna gene. The concentration of tryptophan in the cultures expressing both tna and aspCproA genes was about 10% that of the cultures expressing the tna gene alone. In these cultures, however, monatin was produced. The highest concentration was measured at 48 h after induction (263 ng/mL).

TABLE 23

Tryptophan production in *E. coli* BL21(DE3) transformed with tna/pPRONco Fermentation broth samples

| Time after induction | [tryptophan]; µg/mL | [tryptophan]; µg/mg DCW |
|---|---|---|
| 0 | 0 | 0 |
| 5 | 0 | 0 |
| 7.5 | 223.8 | 19.7 |
| 20 | 1188.5 | 134.6 |
| 28 | 872.2 | 95.2 |
| 48 | 1137 | 170.5 |
| 74 | 1300.8 | |

TABLE 24

Monatin and tryptophan production in *E. coli* BL21(DE3) transformed with tna/pPRONco and aspCproA/pET32a Fermentation broth samples

| Time after induction | [tryptophan]; µg/mL | [tryptophan]; µg/mgDCW | [monatin]; ng/mL | [monatin]; ng/mgDCW |
|---|---|---|---|---|
| 0 | 0 | 0 | 0 | 0 |
| 5 | 0 | 0 | 0 | 0 |
| 7.5 | 29.2 | 3.7 | 0 | 0 |
| 20 | 109.3 | 20.0 | 80.5 | 12.8 |
| 28 | 79.2 | 12.9 | 145.5 | 23.3 |
| 48 | 104.1 | 19.2 | 262.6 | 49.2 |
| 74 | 110.1 | | 187.3 | |

Example 20

Increasing Flux to Aromatic Pathways by Overexpression of Phosphoenolpyruvate Synthase (EC 2.7.9.2) and Related Genes Engineering central metabolism to increase the flux of carbon from glucose or pyruvate to the aromatic pathways can increase the amount of tryptophan, and therefore the amount of monatin produced during fermentation. Different approaches have been taken, one of which is to recycle the pyruvate formed by either the PTS or pyruvate kinases back to PEP by enhancing expression of PEP synthase (Pps) (Patnaik and Liao, (1994), *Appl. Env. Microbiol.*, 60:3903-3908; Patnaik et al., (1995), *Biotechnol. Bioeng.*, 46, 361-370; Yi et al., (2002), *Biotechnol. Prog.*, 18, 1141-1148; U.S. Pat. No. 6,489,100; U.S. Pat. No. 5,985,617; and U.S. Pat. No. 5,906,925). PEP synthase converts ATP and pyruvate to AMP, phosphoenolpyruvate, and phosphate in the presence of water. Increased PEP levels cause an increase in DAHP production, which is an important precursor to shikimate, chorismate, and to aromatic amino acid production. The ppsA gene is highly ubiquitous and can be readily isolated and overexpressed in a production host such as *E. coli*. Recombinant PpsA can be introduced into the chromosome of a host organism or on a plasmid. A plasmid containing the ppsA gene could be co-expressed with the monatin operon described in Example 7 or could be added to the monatin operon. The transketolase (tkt) gene can be co-expressed to further increase aromatic amino acid precursor molecules. It is expected that such genetic constructs would improve monatin production.

Example 21

Production of Biosynthetic Genes in Fermentors

Example 3 describes a process utilizing two enzymes, an aminotransferase and an aldolase to produce monatin from tryptophan and pyruvate. The aldolase (ProA aldolase, proA gene) from *Comamonas testosteroni* and the L-aspartate aminotransferase encoded by the *E. coli* aspC gene have been cloned, expressed, and purified as described in previous examples. Fermentation processes were developed to increase production of the enzymes so they can be used in an in vitro process for the production of monatin.

Batch Fermentation for the Production of L-aspartate Aminotransferase

An *E. coli* aspC/pET30/BL21(DE3) (L-aspartate aminotransferase producer) strain was grown in batch in a 3 L fermentor using a medium containing per liter: 2 g $(NH_4)_2SO_4$, 1.6 g $KH_2PO_4$, 9.9 g $Na_2HPO_4*7H_2O$, 0.65 g sodium citrate $MgSO_4$, 20 g NZ Amine A, 20 g glucose, and 25 mg kanamycin. The pH was controlled at 7.0 with NaOH, the temperature was maintained at 37° C. before induction and lowered to 34° C. at the time of induction. The culture was maintained aerobic throughout the fermentation by increasing the agitation rate. Enzyme expression was induced with 0.1 to 0.4 mM IPTG. The cells were induced at an $OD_{600}$ of 3 (between 3 and 4 h after inoculation) or 10 (between 5 and 6 h after inoculation). The best results were obtained when the cells were induced at $OD_{600}$ of 3 with 0.1 mM IPTG. Under these conditions, cell biomass concentration reached 7.2 g/L, with about 20-40% of the total soluble protein being the aminotransferase. The overall amount of enzyme (0.8 grams of aminotransferase polypeptide per liter of culture) was 6 times greater than was obtained in shake flask cultures experiments carried out as described in Example 3.

Fed-Batch Fermentation for the Production of ProA Aldolase

An *E. coli* proA/pET30/BL21(DE3) (aldolase producer) was grown in a 3 liter fermentor in fed-batch mode. A defined medium was used containing, per liter: 2 g $(NH_4)_2SO_4$, 8 g $KH_2PO_4$, 2 g NaCl, 1 g Na Citrate, 0.01 g $FeSO_4*7H_2O$, 2 g $MgSO_4*7H_2O$, 0.05 g $CaSO_4*2H_2O$, 7.5 mg EDTA, 2.5 mg $MnSO_4*H_2O$, 0.5 mg $CoCl_2*6H_2O$, 0.5 mg $ZnSO_4*7H_2O$, 0.05 mg $CuSO_4*5H_2O$, 0.05 mg $H_3BO_3$, 50 mg p-aminobenzoic acid, 20 mg folic acid, 20 mg biotin, 20 mg nicotinic acid, 50 mg calcium pantothenate, 50 mg riboflavin, 50 mg thiamine hydrochloride, and 100 mg of pyridoxine hydrochloride. The initial glucose concentration was 2 g/L, and glucose was fed exponentially to maintain a growth rate between 0.15 and 0.25 $hour^{-1}$. Nitrogen was provided on demand through pH control with $NH_4OH$. The cultures were induced with 1 mM IPTG when an $OD_{600}$ of 25 (17 h after inoculation) or 35 (21 h after inoculation) was reached. The better protein expression was obtained when the cells were induced at the lower cell density. Enzyme expression was very high at 20-30% of the total soluble protein, and even though specific enzyme activity was reduced compared with cells grown in flasks, the overall enzyme activity per L of medium was 9 times greater than that measured in shake flask experiments carried out as described in Example 3. A total of 1.8 grams of aldolase polypeptide was measured per liter of culture. Different cell concentrations were obtained depending on the growth rate, with a maximum of 26.3 g/L of dry cell weight.

Both fermentation processes can be applied to produce any of these enzymes. The fed-batch protocol in which glucose is fed exponentially to maintain a growth rate between 0.15 and 0.25 $hour^{-1}$ is a better method to obtain high cell density with high enzyme concentration and can be further optimized to increase the specific enzyme activity in each case. Alternative feeding protocols for the fed-batch fermentation could also be utilized, such as constant feeding-rate or intermittent feeding.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing monatin or salt thereof, wherein the method comprises:
   (a) culturing a microorganism selected from the group consisting of *Sinorhizobium meliloti, Comamonas testosteroni, Pseudomonas straminea*, and *Corynebacterium glutamicum* under conditions which result in the production of monatin in a culture medium comprising tryptophan, pyruvic acid, a non-ionic detergent, penicillin, a penicillin derivative or a combination thereof; and
   (b) extracting monatin or salt thereof from the culture medium or the cultured microorganism.

2. The method of claim 1, wherein the microorganism secretes monatin or salt thereof.

3. The method of claim 1, wherein the microorganism is cultured in a fermentor.

* * * * *

SEQUENCE LISTING

```
<160> NUMBER OF SEQ ID NOS: 110

<210> SEQ ID NO 1
<211> LENGTH: 1170
<212> TYPE: DNA
<213> ORGANISM: Sinorhizobium meliloti

<400> SEQUENCE: 1
atgttcgacg ccctcgcccg ccaagccgac gatcccttgc ttttcctgat cggcctgttc      60
aggaaggatg agcgccccgg aaaggtcgat ctcggcgtag gagtctatcg cgacgagacc     120
ggacgcacgc cgatcttccg ggccgtcaag gcggcggaaa agcggcttct cgaaacacag     180
gacagcaagg cctatatcgg ccccgaaggg gacctcgtct ttctcgatcg gctctgggaa     240
ctcgtcggcg gcgacacgat cgagcggagc catgttgcgg gcgtccagac gcccggcggc     300
tccggcgcgc tccgtttggc ggcggacctc atcgcccgca tgggcggccg aggcatctgg     360
ctcgggctgc cgagctggcc gaaccacgcg ccgatcttca aggcggccgg gctcgatatc     420
gccacctacg acttcttcga cattccgtcg cagtcggtca tcttcgataa tctggtgagc     480
gcgctggaag gcgccgcatc cggcgatgcg gtgctgctgc atgcaagctg ccacaacccg     540 accggcgcg tcctgagcga agcacaatgg atggagatcg ccgcgctggt ggccgagcgc     600
ggcctgctgc cgctcgtcga tctcgcctat caggggttcg gccgcggcct cgaccaggat     660
```

```
gtcgcgggcc tccggcatct tctcggcgtg gtcccggaag cgctcgtcgc ggtttcctgc    720
tcgaagtcct tcgggcttta tcgcgagcgc gcgggcgcga tcttcgcgcg gaccagctcg    780
actgcctcgg cggacagggt gcgctcaaac ctcgcgggcc tcgcacgcac cagctattcc    840
atgccgccga tcacggcgc agccgtcgtc cggacgatcc ttgacgaccc ggaactcagg    900
cgcgactgga cggaggagct cgagacgatg cggctcagga tgacgggcct ccggcggtcg    960
cttgccgagg gactccgcac ccgctggcag agcctcggcg cagtcgccga tcaggagggc   1020
atgttctcca tgctgccgct ttccgaagcg gaggttatgc ggctcaggac cgagcacggc   1080
atctatatgc cggcatccgg ccgcatcaac atcgccgggc tgaagacggc ggaagccgcc   1140
gagattgccg gcaagttcac cagtctctga                                    1170

<210> SEQ ID NO 2
<211> LENGTH: 389
<212> TYPE: PRT
<213> ORGANISM: Sinorhizobium meliloti

<400> SEQUENCE: 2

Met Phe Asp Ala Leu Ala Arg Gln Ala Asp Pro Leu Leu Phe Leu
 1               5                  10                  15

Ile Gly Leu Phe Arg Lys Asp Glu Arg Pro Gly Lys Val Asp Leu Gly
            20                  25                  30

Val Gly Val Tyr Arg Asp Glu Thr Gly Arg Thr Pro Ile Phe Arg Ala
        35                  40                  45

Val Lys Ala Ala Glu Lys Arg Leu Leu Glu Thr Gln Asp Ser Lys Ala
    50                  55                  60

Tyr Ile Gly Pro Glu Gly Asp Leu Val Phe Leu Asp Arg Leu Trp Glu
65                  70                  75                  80

Leu Val Gly Gly Asp Thr Ile Glu Arg Ser His Val Ala Gly Val Gln
                85                  90                  95

Thr Pro Gly Gly Ser Gly Ala Leu Arg Leu Ala Ala Asp Leu Ile Ala
            100                 105                 110

Arg Met Gly Gly Arg Gly Ile Trp Leu Gly Leu Pro Ser Trp Pro Asn
        115                 120                 125

His Ala Pro Ile Phe Lys Ala Ala Gly Leu Asp Ile Ala Thr Tyr Asp
    130                 135                 140

Phe Phe Asp Ile Pro Ser Gln Ser Val Ile Phe Asp Asn Leu Val Ser
145                 150                 155                 160

Ala Leu Glu Gly Ala Ala Ser Gly Asp Ala Val Leu Leu His Ala Ser
                165                 170                 175

Cys His Asn Pro Thr Gly Gly Val Leu Ser Glu Ala Gln Trp Met Glu
            180                 185                 190

Ile Ala Ala Leu Val Ala Glu Arg Gly Leu Leu Pro Leu Val Asp Leu
        195                 200                 205

Ala Tyr Gln Gly Phe Gly Arg Gly Leu Asp Gln Asp Val Ala Gly Leu
    210                 215                 220

Arg His Leu Leu Gly Val Val Pro Glu Ala Leu Val Ala Val Ser Cys
225                 230                 235                 240

Ser Lys Ser Phe Gly Leu Tyr Arg Glu Arg Ala Gly Ala Ile Phe Ala
                245                 250                 255

Arg Thr Ser Ser Thr Ala Ser Ala Asp Arg Val Arg Ser Asn Leu Ala
            260                 265                 270

Gly Leu Ala Arg Thr Ser Tyr Ser Met Pro Pro Asp His Gly Ala Ala
        275                 280                 285
```

Val Val Arg Thr Ile Leu Asp Asp Pro Glu Leu Arg Arg Asp Trp Thr
                290                 295                 300

Glu Glu Leu Glu Thr Met Arg Leu Arg Met Thr Gly Leu Arg Arg Ser
305                 310                 315                 320

Leu Ala Glu Gly Leu Arg Thr Arg Trp Gln Ser Leu Gly Ala Val Ala
                325                 330                 335

Asp Gln Glu Gly Met Phe Ser Met Leu Pro Leu Ser Glu Ala Glu Val
                340                 345                 350

Met Arg Leu Arg Thr Glu His Gly Ile Tyr Met Pro Ala Ser Gly Arg
                355                 360                 365

Ile Asn Ile Ala Gly Leu Lys Thr Ala Glu Ala Ala Glu Ile Ala Gly
                370                 375                 380

Lys Phe Thr Ser Leu
385

<210> SEQ ID NO 3
<211> LENGTH: 1260
<212> TYPE: DNA
<213> ORGANISM: Rhodobacter sphaeroides

<400> SEQUENCE: 3
atgcgctcta cgacggctcc tggtccgagt ggggcatgta tgacgatctc aaggtcgcga      60
aaggatgacg aaggaatgct gaccgccctg aagccgcagc ccgcggacaa gatcctgcaa     120
ctgatccaga tgttccgcga ggatgcgcgc gcggacaaga tcgatctggg cgtgggcgtc     180
tacaaggacc cgaccgggct caccccggtc atgcgggccg tgaaggcggc cgagaagcgg     240
ctctgggagg tcgagaccac caagacctac accggccttg ccgacgagcc ggcctacaat     300
gccgcgatgg cgaagctgat cctcgcgggc gcggtcccgg ccgaccgggt ggcctcggtc     360
gccaccccgg cggcacgggc gcggtgcgt caggcgctcg agctgatccg catggcctcg     420
cccgaggcca ccgtctggat ctcgaacccg acctggccga accatctgtc gatcgtgaaa     480
tatctcggca tcccgatgcg ggaataccgc tatttcgacg ccgagaccgg cgccgtcgat     540
gccgagggca tgatggagga tctggcccag gtgaaggcgg cgacgtggt gctgctgcac     600 ggctgctgcc acaacccgac cggcgccaac ccgaacccgg tgcagtggct ggccatctgc     660
gagagcctgg cccggacagg cgcggtgccg ctgatcgacc tcgcctatca gggcttcggc     720
gacgggctcg agatggatgc ggcggcgacg cggcttctgg ccaccagact gcccgaggtg     780
ctgatcgcgg cctcctgctc gaagaacttc ggcatctacc gcgagcgcac gggcatcctg     840
atcgccatcg gcgaggcggc gggccggggc acggtgcagg ccaacctcaa cttcctgaac     900
cggcagaact actccttccc gccggaccat ggcgcgcggc tcgtgaccat gatcctcgag     960
gacgagacgc tgagcgccga ctggaaggcg gaactcgagg aggtgcggct caacatgctg    1020
acactgcgcc gccagcttgc cgatgcgctg caggccgaga ccggctcgaa ccgcttcggc    1080
ttcgtggccg agcatcgcgg catgttctcg cgcctcggga tcacgcccgc cgaggtggag    1140
cggctgcgga ccgagcacgg ggtctacatg gtgggcgatt cgcggctgaa catcgcgggg    1200
ctgaaccgga cgaccgtgcc ggtgctggcg cgcgcggtgg ccaaggtgct gcgcggctga    1260

<210> SEQ ID NO 4
<211> LENGTH: 419
<212> TYPE: PRT
<213> ORGANISM: Rhodobacter sphaeroides

<400> SEQUENCE: 4

Met Arg Ser Thr Thr Ala Pro Gly Pro Ser Gly Ala Cys Met Thr Ile

```
                1               5                  10                 15
         Ser Arg Ser Arg Lys Asp Asp Glu Gly Met Leu Thr Ala Leu Lys Pro
                         20                  25                  30

Gln Pro Ala Asp Lys Ile Leu Gln Leu Ile Gln Met Phe Arg Glu Asp
                         35                  40                  45

Ala Arg Ala Asp Lys Ile Asp Leu Gly Val Gly Val Tyr Lys Asp Pro
                         50                  55                  60

Thr Gly Leu Thr Pro Val Met Arg Ala Val Lys Ala Ala Glu Lys Arg
          65                  70                  75                  80

Leu Trp Glu Val Glu Thr Thr Lys Thr Tyr Thr Gly Leu Ala Asp Glu
                                 85                  90                  95

Pro Ala Tyr Asn Ala Ala Met Ala Lys Leu Ile Leu Ala Gly Ala Val
                         100                 105                 110

Pro Ala Asp Arg Val Ala Ser Val Ala Thr Pro Gly Gly Thr Gly Ala
                         115                 120                 125

Val Arg Gln Ala Leu Glu Leu Ile Arg Met Ala Ser Pro Glu Ala Thr
                         130                 135                 140

Val Trp Ile Ser Asn Pro Thr Trp Pro Asn His Leu Ser Ile Val Lys
         145                 150                 155                 160

Tyr Leu Gly Ile Pro Met Arg Glu Tyr Arg Tyr Phe Asp Ala Glu Thr
                         165                 170                 175

Gly Ala Val Asp Ala Glu Gly Met Met Glu Asp Leu Ala Gln Val Lys
                         180                 185                 190

Ala Gly Asp Val Val Leu Leu His Gly Cys Cys His Asn Pro Thr Gly
                         195                 200                 205

Ala Asn Pro Asn Pro Val Gln Trp Leu Ala Ile Cys Glu Ser Leu Ala
                         210                 215                 220

Arg Thr Gly Ala Val Pro Leu Ile Asp Leu Ala Tyr Gln Gly Phe Gly
         225                 230                 235                 240

Asp Gly Leu Glu Met Asp Ala Ala Ala Thr Arg Leu Leu Ala Thr Arg
                         245                 250                 255

Leu Pro Glu Val Leu Ile Ala Ala Ser Cys Ser Lys Asn Phe Gly Ile
                         260                 265                 270

Tyr Arg Glu Arg Thr Gly Ile Leu Ile Ala Ile Gly Glu Ala Ala Gly
                         275                 280                 285

Arg Gly Thr Val Gln Ala Asn Leu Asn Phe Leu Asn Arg Gln Asn Tyr
                         290                 295                 300

Ser Phe Pro Pro Asp His Gly Ala Arg Leu Val Thr Met Ile Leu Glu
         305                 310                 315                 320

Asp Glu Thr Leu Ser Ala Asp Trp Lys Ala Glu Leu Glu Glu Val Arg
                         325                 330                 335

Leu Asn Met Leu Thr Leu Arg Arg Gln Leu Ala Asp Ala Leu Gln Ala
                         340                 345                 350

Glu Thr Gly Ser Asn Arg Phe Gly Phe Val Ala Glu His Arg Gly Met
                         355                 360                 365

Phe Ser Arg Leu Gly Ile Thr Pro Ala Glu Val Glu Arg Leu Arg Thr
                         370                 375                 380

Glu His Gly Val Tyr Met Val Gly Asp Ser Arg Leu Asn Ile Ala Gly
         385                 390                 395                 400

Leu Asn Arg Thr Thr Val Pro Val Leu Ala Arg Ala Val Ala Lys Val
                         405                 410                 415

Leu Arg Gly
```

<210> SEQ ID NO 5
<211> LENGTH: 1260
<212> TYPE: DNA
<213> ORGANISM: Rhodobacter sphaeroides

<400> SEQUENCE: 5

```
atgcgctcta cgacggctcc tggtccgagt ggggcatgta tgacgatctc aaggtcgcga     60
aaggatgacg aaggaatgct gaccgccctg aagccgcagc ccgcggacaa gatcctgcaa    120
ctgatccaga tgttccgcga ggatgcgcgc gcggacaaga tcgatctggg cgtgggcgtc    180
tacaaggacc cgaccgggct caccccggtc atgcgggccg tgaaggccgc cgagaagcgg    240
ctctgggagg tcgagaccac caagacctac accggccttg ccggcgagcc cgcctacaat    300
gccgcgatgg cgaagctgat cctcgcaggc gcggtcccgg ccgaccgggt ggcctcggtc    360
gccaccccg gcggcacggg cgcggtgcgt caggcgctcg agctgatccg catggcctcg    420
cccgaggcca ctgtctggat ctcgaacccg acctggccga accatctgtc gatcgtgaaa    480
tatctcggca tcccgatgcg ggaataccgc tatttcgacg ccgagaccgg cgccgtcgat    540
gccgagggct tgatggagga tctggcccag gtgaaggcgg gcgacgtggt gctgctgcac    600
ggctgctgcc acaaccccga cggcgccaac ccgaacccgg tgcagtggct ggccgtctgc    660
gagagcctgg cccggacagg cgcggtgccg ctgatcgacc tcgcctatca gggcttcggc    720
gacgggctcg agatggatgc ggcggcgacg cggcttctgg ccaccagact gcccgaggtg    780
ctgatcgcgg cctcctgctc gaagaacttc ggcatctacc gcgagcgaac gggcatcctg    840
atcgccatcg cgaggcggc gggccggggc acggtgcagg ccaacctcaa cttcctgaac    900
cggcagaact actccttccc gccggaccat ggcgcgcggc tcgtgaccat gatcctcgag    960
gacgagacgc tgagcgccga ctggaaggcg gaactcgagg aggtgcggct caacatgctg   1020
acgctgcgcc gccagcttgc cgatgcgctg caggccgaga ccggctcgaa ccgcttcggc   1080
ttcgtggccg agcatcgcgg catgttctcg cgcctcggga tcacgcccgc cgaggtggag   1140
cggctgcgga ccgagcacgg ggtctacatg gtgggcgatt cgcggctgaa catcgcgggg   1200
ctgaaccgga cgaccgtgcc ggtgctggcg cgcgcggtgg ccaaggtgct gcgcggctga   1260
```

<210> SEQ ID NO 6
<211> LENGTH: 419
<212> TYPE: PRT
<213> ORGANISM: Rhodobacter sphaeroides

<400> SEQUENCE: 6

Met Arg Ser Thr Thr Ala Pro Gly Pro Ser Gly Ala Cys Met Thr Ile
 1               5                  10                  15

Ser Arg Ser Arg Lys Asp Asp Glu Gly Met Leu Thr Ala Leu Lys Pro
            20                  25                  30

Gln Pro Ala Asp Lys Ile Leu Gln Leu Ile Gln Met Phe Arg Glu Asp
        35                  40                  45

Ala Arg Ala Asp Lys Ile Asp Leu Gly Val Gly Val Tyr Lys Asp Pro
    50                  55                  60

Thr Gly Leu Thr Pro Val Met Arg Ala Val Lys Ala Ala Glu Lys Arg
65                  70                  75                  80

Leu Trp Glu Val Glu Thr Thr Lys Thr Tyr Thr Gly Leu Ala Gly Glu
                85                  90                  95

Pro Ala Tyr Asn Ala Ala Met Ala Lys Leu Ile Leu Ala Gly Ala Val
            100                 105                 110

Pro Ala Asp Arg Val Ala Ser Val Ala Thr Pro Gly Gly Thr Gly Ala
        115                 120                 125

```
Val Arg Gln Ala Leu Glu Leu Ile Arg Met Ala Ser Pro Glu Ala Thr
    130                 135                 140

Val Trp Ile Ser Asn Pro Thr Trp Pro Asn His Leu Ser Ile Val Lys
145                 150                 155                 160

Tyr Leu Gly Ile Pro Met Arg Glu Tyr Arg Tyr Phe Asp Ala Glu Thr
                165                 170                 175

Gly Ala Val Asp Ala Glu Gly Leu Met Glu Asp Leu Ala Gln Val Lys
            180                 185                 190

Ala Gly Asp Val Val Leu Leu His Gly Cys Cys His Asn Pro Thr Gly
        195                 200                 205

Ala Asn Pro Asn Pro Val Gln Trp Leu Ala Val Cys Glu Ser Leu Ala
210                 215                 220

Arg Thr Gly Ala Val Pro Leu Ile Asp Leu Ala Tyr Gln Gly Phe Gly
225                 230                 235                 240

Asp Gly Leu Glu Met Asp Ala Ala Ala Thr Arg Leu Leu Ala Thr Arg
                245                 250                 255

Leu Pro Glu Val Leu Ile Ala Ala Ser Cys Ser Lys Asn Phe Gly Ile
            260                 265                 270

Tyr Arg Glu Arg Thr Gly Ile Leu Ile Ala Ile Gly Glu Ala Ala Gly
        275                 280                 285

Arg Gly Thr Val Gln Ala Asn Leu Asn Phe Leu Asn Arg Gln Asn Tyr
290                 295                 300

Ser Phe Pro Pro Asp His Gly Ala Arg Leu Val Thr Met Ile Leu Glu
305                 310                 315                 320

Asp Glu Thr Leu Ser Ala Asp Trp Lys Ala Glu Leu Glu Glu Val Arg
                325                 330                 335

Leu Asn Met Leu Thr Leu Arg Arg Gln Leu Ala Asp Ala Leu Gln Ala
            340                 345                 350

Glu Thr Gly Ser Asn Arg Phe Gly Phe Val Ala Glu His Arg Gly Met
        355                 360                 365

Phe Ser Arg Leu Gly Ile Thr Pro Ala Glu Val Glu Arg Leu Arg Thr
370                 375                 380

Glu His Gly Val Tyr Met Val Gly Asp Ser Arg Leu Asn Ile Ala Gly
385                 390                 395                 400

Leu Asn Arg Thr Thr Val Pro Val Leu Ala Arg Ala Val Ala Lys Val
                405                 410                 415

Leu Arg Gly

<210> SEQ ID NO 7
<211> LENGTH: 1239
<212> TYPE: DNA
<213> ORGANISM: Leishmania major

<400> SEQUENCE: 7
atgtccatgc aggcggccat gaccacggcg gagcgctggc agaagattca ggcacaagct      60
cccgatgtca tcttcgatct cgcaaaacgc gccgccgctg ccaagggccc caaggccaac     120
ctcgtcattg gtgcctaccg cgacgagcag ggccgtccct atccgctacg cgtggtccgc     180
aaggctgagc agcttctctt ggacatgaat ctcgactacg agtacctacc catctcgggc     240
taccagccct tcatcgatga ggcggtaaag attatctacg caataccgt cgagctggag      300 aacctggttg cggtgcagac gctgagcggg accggtgctg tctctctcgg ggcgaagctg     360
ctgactcgcg tcttcgacgc tgagacgacg cccatctacc tttccgaccc cacgtggccc     420
aaccactacg gcgtcgtgaa ggctgctggc tggaagaaca tctgcacgta cgcctactac     480
```

```
gaccccaaga cggtcagcct gaatttcgag ggcatgaaga aagacattct ggcggcgccg      540
gacggctccg tgttcattct gcaccagtgc gcgcacaacc ccaccggcgt ggacccgtcg      600
caggagcagt ggaacgagat cgcgtcactg atgctggcca agcaccatca ggtgttcttc      660
gactccgcct accaaggcta tgcgagcggc agcctcgaca cggacgcgta tgctgcccgc      720
ctgtttgccc ccgcggcat cgaggtactg ctggcgcagt cgttctccaa gaacatgggc       780
ttgtacagcg agcgtgcagg cacgctgtcg ctgctcctca aggacaagac gaagcgcgcg      840
gatgtaaaga gcgtgatgga ttcgctgatc cgtgaggagt acacgtgccc cccagcccac      900
ggtgcccgct tagcccacct aatcctgagc aacaacgaac tgcgaaagga gtgggaggca      960
gagctatcag ccatggcaga gcgcatccgt acgatgcgcc gcaccgtgta cgacgagctg     1020
ctgcgcctgc agacgcccgg gagctgggaa catgtcatta ccagattgg catgttttcc     1080 ttcctcgggc tgtcaaaggc gcagtgcgaa tactgccaaa accacaacat cttcatcaca     1140
gtgtcgggcc gcgctaacat ggcaggtctg acgcatgaga cggcgctgat gctagcacag     1200
acgatcaacg atgctgtgcg caatgtgaat cgtgagtga                            1239
```

<210> SEQ ID NO 8
<211> LENGTH: 412
<212> TYPE: PRT
<213> ORGANISM: Leishmania major

<400> SEQUENCE: 8

```
Met Ser Met Gln Ala Ala Met Thr Thr Ala Glu Arg Trp Gln Lys Ile
  1               5                  10                  15

Gln Ala Gln Ala Pro Asp Val Ile Phe Asp Leu Ala Lys Arg Ala Ala
                 20                  25                  30

Ala Ala Lys Gly Pro Lys Ala Asn Leu Val Ile Gly Ala Tyr Arg Asp
             35                  40                  45

Glu Gln Gly Arg Pro Tyr Pro Leu Arg Val Val Arg Lys Ala Glu Gln
         50                  55                  60

Leu Leu Leu Asp Met Asn Leu Asp Tyr Glu Tyr Leu Pro Ile Ser Gly
 65                  70                  75                  80

Tyr Gln Pro Phe Ile Asp Glu Ala Val Lys Ile Ile Tyr Gly Asn Thr
                 85                  90                  95

Val Glu Leu Glu Asn Leu Val Ala Val Gln Thr Leu Ser Gly Thr Gly
            100                 105                 110

Ala Val Ser Leu Gly Ala Lys Leu Leu Thr Arg Val Phe Asp Ala Glu
        115                 120                 125

Thr Thr Pro Ile Tyr Leu Ser Asp Pro Thr Trp Pro Asn His Tyr Gly
    130                 135                 140

Val Val Lys Ala Ala Gly Trp Lys Asn Ile Cys Thr Tyr Ala Tyr Tyr
145                 150                 155                 160

Asp Pro Lys Thr Val Ser Leu Asn Phe Glu Gly Met Lys Lys Asp Ile
                165                 170                 175

Leu Ala Ala Pro Asp Gly Ser Val Phe Ile Leu His Gln Cys Ala His
            180                 185                 190

Asn Pro Thr Gly Val Asp Pro Ser Gln Glu Gln Trp Asn Glu Ile Ala
        195                 200                 205

Ser Leu Met Leu Ala Lys His His Gln Val Phe Phe Asp Ser Ala Tyr
    210                 215                 220

Gln Gly Tyr Ala Ser Gly Ser Leu Asp Thr Asp Ala Tyr Ala Ala Arg
225                 230                 235                 240
```

```
Leu Phe Ala Arg Arg Gly Ile Glu Val Leu Leu Ala Gln Ser Phe Ser
                245                 250                 255

Lys Asn Met Gly Leu Tyr Ser Glu Arg Ala Gly Thr Leu Ser Leu Leu
            260                 265                 270

Leu Lys Asp Lys Thr Lys Arg Ala Asp Val Lys Ser Val Met Asp Ser
        275                 280                 285

Leu Ile Arg Glu Glu Tyr Thr Cys Pro Pro Ala His Gly Ala Arg Leu
    290                 295                 300

Ala His Leu Ile Leu Ser Asn Asn Glu Leu Arg Lys Glu Trp Glu Ala
305                 310                 315                 320

Glu Leu Ser Ala Met Ala Glu Arg Ile Arg Thr Met Arg Arg Thr Val
                325                 330                 335

Tyr Asp Glu Leu Leu Arg Leu Gln Thr Pro Gly Ser Trp Glu His Val
            340                 345                 350

Ile Asn Gln Ile Gly Met Phe Ser Phe Leu Gly Leu Ser Lys Ala Gln
        355                 360                 365

Cys Glu Tyr Cys Gln Asn His Asn Ile Phe Ile Thr Val Ser Gly Arg
    370                 375                 380

Ala Asn Met Ala Gly Leu Thr His Glu Thr Ala Leu Met Leu Ala Gln
385                 390                 395                 400

Thr Ile Asn Asp Ala Val Arg Asn Val Asn Arg Glu
                405                 410

<210> SEQ ID NO 9
<211> LENGTH: 1182
<212> TYPE: DNA
<213> ORGANISM: Bacillus subtilis

<400> SEQUENCE: 9
atggaacatt tgctgaatcc gaaagcaaga gagatcgaaa tttcaggaat acgcaaattc      60
tcgaatcttg tagcccaaca cgaagacgtc atttcactta caatcggcca gcctgatttt     120
ttcacaccgc atcatgtgaa agctgccgca aaaaaagcca ttgatgaaaa cgtgacgtca     180
tatactccga atgccggcta cctggagctg agacaagctg tgcagcttta tatgaagaaa     240
aaagcggatt tcaactatga tgctgaatct gaaattatca tcacaacagg cgcaagccaa     300
gccattgatg ctgcattccg gacgatttta tctcccggtg atgaagtcat tatgccaggg     360
cctatttatc cgggctatga acctattatc aatttgtgcg gggccaagcc tgtcattgtt     420
gatactacgt cacacggctt taagcttacc gcccggctga ttgaagatgc tctgacaccc     480
aacaccaagt gtgtcgtgct tccttatccg tcaaaaccct accggcgtga tttatctgaa     540
gaagaactga aaagcatcgc agctctctta aaaggcagaa atgtcttcgt attgtctgat     600
gaaatataca gtgaattaac atatgacaga ccgcattact ccatcgcaac ctatttgcgg     660
gatcaaacga ttgtcattaa cgggttgtca aaatcacaca gcatgaccgg ttggagaatt     720
ggatttttat ttgcaccgaa agacattgca aagcacattt taaaggttca tcaatacaat     780
gtgtcgtgcg cctcatccat ttctcaaaaa gccgcgcttg aagctgtcac aaacggcttt     840
gacgatgcat tgattatgag agaacaatac aaaaaacgtc tggactatgt ttatgaccgt     900
cttgttccca tgggacttga cgtagttaaa ccgtccggtg cgtttttata cttcccttct     960
attaaatcat ttggaatgac ttcatttgat tttagtatgg ctcttttgga agacgctggc    1020
gtggcactcg tgccgggcag ctcgttctca acatatggtg aaggatatgt aaggctgtct    1080
tttgcatgct caatggacac gctgagagaa ggcctagacc gtttagaatt atttgtatta    1140
aaaaaacgtg aagcaatgca gacgataaac aacggcgttt aa                       1182
```

<210> SEQ ID NO 10
<211> LENGTH: 393
<212> TYPE: PRT
<213> ORGANISM: Bacillus subtilis

<400> SEQUENCE: 10

Met Glu His Leu Leu Asn Pro Lys Ala Arg Glu Ile Glu Ile Ser Gly
1               5                   10                  15

Ile Arg Lys Phe Ser Asn Leu Val Ala Gln His Glu Asp Val Ile Ser
            20                  25                  30

Leu Thr Ile Gly Gln Pro Asp Phe Phe Thr Pro His His Val Lys Ala
        35                  40                  45

Ala Ala Lys Lys Ala Ile Asp Glu Asn Val Thr Ser Tyr Thr Pro Asn
    50                  55                  60

Ala Gly Tyr Leu Glu Leu Arg Gln Ala Val Gln Leu Tyr Met Lys Lys
65                  70                  75                  80

Lys Ala Asp Phe Asn Tyr Asp Ala Glu Ser Glu Ile Ile Ile Thr Thr
                85                  90                  95

Gly Ala Ser Gln Ala Ile Asp Ala Ala Phe Arg Thr Ile Leu Ser Pro
            100                 105                 110

Gly Asp Glu Val Ile Met Pro Gly Pro Ile Tyr Pro Gly Tyr Glu Pro
        115                 120                 125

Ile Ile Asn Leu Cys Gly Ala Lys Pro Val Ile Val Asp Thr Thr Ser
    130                 135                 140

His Gly Phe Lys Leu Thr Ala Arg Leu Ile Glu Asp Ala Leu Thr Pro
145                 150                 155                 160

Asn Thr Lys Cys Val Val Leu Pro Tyr Pro Ser Asn Pro Thr Gly Val
                165                 170                 175

Thr Leu Ser Glu Glu Glu Leu Lys Ser Ile Ala Ala Leu Leu Lys Gly
            180                 185                 190

Arg Asn Val Phe Val Leu Ser Asp Glu Ile Tyr Ser Glu Leu Thr Tyr
        195                 200                 205

Asp Arg Pro His Tyr Ser Ile Ala Thr Tyr Leu Arg Asp Gln Thr Ile
    210                 215                 220

Val Ile Asn Gly Leu Ser Lys Ser His Ser Met Thr Gly Trp Arg Ile
225                 230                 235                 240

Gly Phe Leu Phe Ala Pro Lys Asp Ile Ala Lys His Ile Leu Lys Val
                245                 250                 255

His Gln Tyr Asn Val Ser Cys Ala Ser Ser Ile Ser Gln Lys Ala Ala
            260                 265                 270

Leu Glu Ala Val Thr Asn Gly Phe Asp Asp Ala Leu Ile Met Arg Glu
        275                 280                 285

Gln Tyr Lys Lys Arg Leu Asp Tyr Val Tyr Asp Arg Leu Val Ser Met
    290                 295                 300

Gly Leu Asp Val Val Lys Pro Ser Gly Ala Phe Tyr Ile Phe Pro Ser
305                 310                 315                 320

Ile Lys Ser Phe Gly Met Thr Ser Phe Asp Phe Ser Met Ala Leu Leu
                325                 330                 335

Glu Asp Ala Gly Val Ala Leu Val Pro Gly Ser Ser Phe Ser Thr Tyr
            340                 345                 350

Gly Glu Gly Tyr Val Arg Leu Ser Phe Ala Cys Ser Met Asp Thr Leu
        355                 360                 365

Arg Glu Gly Leu Asp Arg Leu Glu Leu Phe Val Leu Lys Lys Arg Glu
    370                 375                 380

Ala Met Gln Thr Ile Asn Asn Gly Val
385             390

<210> SEQ ID NO 11
<211> LENGTH: 1176
<212> TYPE: DNA
<213> ORGANISM: Lactobacillus amylovorus

<400> SEQUENCE: 11

| | | | | | |
|---|---|---|---|---|---|
| atgccagaat | tagctaatga | tttaggatta | agcaaaaaga | tcactgatgt | aaaagcttca | 60 |
| ggaattagaa | tctttgataa | caaagtttca | gctattcctg | cattatcaa | attgactttg | 120 |
| ggtgaaccag | atatgaatac | tcctgagcat | gttaagcaag | cggctattaa | gaatattgca | 180 |
| gataatgatt | cacactatgc | tccacaaaag | ggaaagcttg | aattaagaaa | agctatcagt | 240 |
| aaatatttga | aaaagattac | tggaattgaa | tatgatccag | aaacagaaat | cgtagtaaca | 300 |
| gttggtgcaa | ctgaagcaat | taacgctacc | ttgtttgcta | ttactaatcc | gggtgacaag | 360 |
| gttgcaattc | ctacgccagt | cttttctcta | tattggcccg | tggctacact | tgctgatgcc | 420 |
| gattatgttt | tgatgaatac | tgcagaagat | ggttttaagt | taacacctaa | gaagttagaa | 480 |
| gaaactatca | agaaaatcc | aacaattaaa | gcagtaattt | tgaattatcc | aactaaccca | 540 |
| actggtgttg | aatatagcga | agatgaaatt | aaagctttgg | ctaaggtaat | taagataat | 600 |
| catctgtacg | taattaccga | tgaaatttac | agtactttga | cttacggtgt | aaaacacttt | 660 |
| tcaattgcca | gcttaattcc | agaaagagca | atttatatct | ctggtttatc | taaatcacat | 720 |
| gcgatgactg | gttatcgttt | aggctatgtt | gccggacctg | caaaaattat | ggcagaaatt | 780 |
| ggtaaagttc | atggcccttat | ggtgacgact | acgacggatt | catcacaagc | tgccgcaatt | 840 |
| gaagcacttg | aacacggact | tgatgaccct | gagaaatata | gggaagttta | tgaaaagcgt | 900 |
| cgtgactatg | ttttaaagga | attagccgag | atagagatgc | aagcagttaa | gccgaaggt | 960 |
| gcattttata | tctttgctaa | aattccagct | aagtatggca | aagacgatat | gaaatttgcc | 1020 |
| ttggatttag | cttttaaaga | aaaagtgggt | atcactccag | gtagtgcatt | tggtcctggt | 1080 |
| ggtgaaggtc | atattagatt | atcttatgca | tcaagtgatg | aaaacttgca | tgaggcaatg | 1140 |
| aagcgaatga | agaaagtttt | acaagaggac | gaataa | | | 1176 |

<210> SEQ ID NO 12
<211> LENGTH: 391
<212> TYPE: PRT
<213> ORGANISM: Lactobacillus amylovorus

<400> SEQUENCE: 12

Met Pro Glu Leu Ala Asn Asp Leu Gly Leu Ser Lys Lys Ile Thr Asp
1               5                   10                  15

Val Lys Ala Ser Gly Ile Arg Ile Phe Asp Asn Lys Val Ser Ala Ile
                20                  25                  30

Pro Gly Ile Ile Lys Leu Thr Leu Gly Glu Pro Asp Met Asn Thr Pro
            35                  40                  45

Glu His Val Lys Gln Ala Ala Ile Lys Asn Ile Ala Asp Asn Asp Ser
        50                  55                  60

His Tyr Ala Pro Gln Lys Gly Lys Leu Glu Leu Arg Lys Ala Ile Ser
65                  70                  75                  80

Lys Tyr Leu Lys Lys Ile Thr Gly Ile Glu Tyr Asp Pro Glu Thr Glu
                85                  90                  95

Ile Val Val Thr Val Gly Ala Thr Glu Ala Ile Asn Ala Thr Leu Phe
            100                 105                 110

```
Ala Ile Thr Asn Pro Gly Asp Lys Val Ala Ile Pro Thr Pro Val Phe
        115                 120                 125

Ser Leu Tyr Trp Pro Val Ala Thr Leu Ala Asp Ala Asp Tyr Val Leu
130                 135                 140

Met Asn Thr Ala Glu Asp Gly Phe Lys Leu Thr Pro Lys Leu Glu
145                 150                 155                 160

Glu Thr Ile Lys Glu Asn Pro Thr Ile Lys Ala Val Ile Leu Asn Tyr
                165                 170                 175

Pro Thr Asn Pro Thr Gly Val Glu Tyr Ser Glu Asp Glu Ile Lys Ala
            180                 185                 190

Leu Ala Lys Val Ile Lys Asp Asn His Leu Tyr Val Ile Thr Asp Glu
        195                 200                 205

Ile Tyr Ser Thr Leu Thr Tyr Gly Val Lys His Phe Ser Ile Ala Ser
    210                 215                 220

Leu Ile Pro Glu Arg Ala Ile Tyr Ile Ser Gly Leu Ser Lys Ser His
225                 230                 235                 240

Ala Met Thr Gly Tyr Arg Leu Gly Tyr Val Ala Gly Pro Ala Lys Ile
                245                 250                 255

Met Ala Glu Ile Gly Lys Val His Gly Leu Met Val Thr Thr Thr Thr
            260                 265                 270

Asp Ser Ser Gln Ala Ala Ile Glu Ala Leu Glu His Gly Leu Asp
        275                 280                 285

Asp Pro Glu Lys Tyr Arg Glu Val Tyr Glu Lys Arg Arg Asp Tyr Val
290                 295                 300

Leu Lys Glu Leu Ala Glu Ile Glu Met Gln Ala Val Lys Pro Glu Gly
305                 310                 315                 320

Ala Phe Tyr Ile Phe Ala Lys Ile Pro Ala Lys Tyr Gly Lys Asp Asp
                325                 330                 335

Met Lys Phe Ala Leu Asp Leu Ala Phe Lys Glu Lys Val Gly Ile Thr
            340                 345                 350

Pro Gly Ser Ala Phe Gly Pro Gly Gly Glu Gly His Ile Arg Leu Ser
        355                 360                 365

Tyr Ala Ser Ser Asp Glu Asn Leu His Glu Ala Met Lys Arg Met Lys
    370                 375                 380

Lys Val Leu Gln Glu Asp Glu
385                 390

<210> SEQ ID NO 13
<211> LENGTH: 1413
<212> TYPE: DNA
<213> ORGANISM: R. sphaeroides

<400> SEQUENCE: 13
atgcgcgagc ctcttgccct cgagatcgac ccgggccacg gcggcccgct gttcctcgcc      60
atcgccgagg cgatcaccct cgacatcacc cgcgggcggc tgaggcccgg agcgagactg     120
cccggcacac gcgcgctggc gcgggcgctc ggcgtgcatc gcaacaccgg ggatgccgcc     180
tatcaggagt tgctgaccca gggctggctg caggccgagc ccgcgcgggg caccttcgtg     240
gcgcaggatc tgccgcaggg gatgctggtg cacaggcccg cgcccgcgcc ggtcgagccg     300
gtcgcgatgc gcgcggggct cgccttctcc gatggcgcgc cggaccccga gctggtgccc     360
gacaaggcgc tggcgcgggc ctttcgccgg cgctcctgt cgcccgcctt ccgcgccgga     420
gcggattacg gcgatgcccg cggcaccctcc tcgctgcggg aggcgctggc agcctatctc     480
gcctcggacc ggggcgtggt cgcggatcct gcgcggctgc tgatcgcgcg gggcagccag     540
```

```
atggcgctgt tcctggtagc ccgggcggcg ctggcgccgg agagggcgat cgcggtcgag    600
gagccgggct atccgctggc ctgggaggcg ttccgcgcag cgggagcgga ggtgcgcggc    660
gtgccggtgg atggcggcgg cctcaggatc gacgcgctcg aggccgcgct ggcccgggat    720
ccgcgaatcc gggcggtcta tgtcacgccc catcaccagt atccgacgac cgtcaccatg    780
ggcgcggcgc ggcggttgca gcttctggaa ctggcagagc gccaccggct cgcgctgatc    840
gaggacgact acgaccacga ataccgcttc gagggccgtc cggtgctgcc gctggctgcc    900
cgcgcgccgg aaggtctgcc gctgatctat gtgggctcgc tgtcgaaact gctctcgccc    960
ggtatccggc tgggatacgc gctggcgccc gagcggctgc tgacccgcat ggccgcggcg    1020
cgcgccgcca tcgaccggca gggcgacgcg ccgctcgagg cggcgctggc cgagctgatc    1080
cgcgacggcg atctgggccg tcatgcccgc aaggcgcgca gggtctaccg ggcgcggcgg    1140
gatctgctgg cggagcgtct cacggcgcag ctggccgggc gcgccgcctt cgatctgccg    1200
gccgggggcc tcgcgctgtg gctgcgctgc gcggcgtct cggccgagac ctgggccgaa    1260
gccgcagggc aggcggggct cgccctgctg ccgggcacgc gcttcgcgct ggagagcccg    1320
gcgccgcagg ccttccggct gggctatgcg gcgctggacg aggggcagat cgcccgggcg    1380
gtggagatcc tcgcccggag cttccccggc tga                                1413
```

<210> SEQ ID NO 14
<211> LENGTH: 470
<212> TYPE: PRT
<213> ORGANISM: R. sphaeroides

<400> SEQUENCE: 14

```
Met Arg Glu Pro Leu Ala Leu Glu Ile Asp Pro Gly His Gly Pro
  1               5                  10                  15

Leu Phe Leu Ala Ile Ala Glu Ala Ile Thr Leu Asp Ile Thr Arg Gly
                 20                  25                  30

Arg Leu Arg Pro Gly Ala Arg Leu Pro Gly Thr Arg Ala Leu Ala Arg
             35                  40                  45

Ala Leu Gly Val His Arg Asn Thr Val Asp Ala Ala Tyr Gln Glu Leu
         50                  55                  60

Leu Thr Gln Gly Trp Leu Gln Ala Glu Pro Ala Arg Gly Thr Phe Val
 65                  70                  75                  80

Ala Gln Asp Leu Pro Gln Gly Met Leu Val His Arg Pro Ala Pro Ala
                 85                  90                  95

Pro Val Glu Pro Val Ala Met Arg Ala Gly Leu Ala Phe Ser Asp Gly
            100                 105                 110

Ala Pro Asp Pro Glu Leu Val Pro Asp Lys Ala Leu Ala Arg Ala Phe
        115                 120                 125

Arg Arg Ala Leu Leu Ser Pro Ala Phe Arg Ala Gly Ala Asp Tyr Gly
    130                 135                 140

Asp Ala Arg Gly Thr Ser Ser Leu Arg Glu Ala Leu Ala Ala Tyr Leu
145                 150                 155                 160

Ala Ser Asp Arg Gly Val Val Ala Asp Pro Ala Arg Leu Leu Ile Ala
                165                 170                 175

Arg Gly Ser Gln Met Ala Leu Phe Leu Val Ala Arg Ala Leu Ala
            180                 185                 190

Pro Gly Glu Ala Ile Ala Val Glu Glu Pro Gly Tyr Pro Leu Ala Trp
        195                 200                 205

Glu Ala Phe Arg Ala Ala Gly Ala Glu Val Arg Gly Val Pro Val Asp
    210                 215                 220
```

Gly Gly Gly Leu Arg Ile Asp Ala Leu Glu Ala Ala Leu Ala Arg Asp
225                 230                 235                 240

Pro Arg Ile Arg Ala Val Tyr Val Thr Pro His His Gln Tyr Pro Thr
            245                 250                 255

Thr Val Thr Met Gly Ala Ala Arg Arg Leu Gln Leu Leu Glu Leu Ala
        260                 265                 270

Glu Arg His Arg Leu Ala Leu Ile Glu Asp Asp Tyr Asp His Glu Tyr
    275                 280                 285

Arg Phe Glu Gly Arg Pro Val Leu Pro Leu Ala Arg Ala Pro Glu
290                 295                 300

Gly Leu Pro Leu Ile Tyr Val Gly Ser Leu Ser Lys Leu Leu Ser Pro
305                 310                 315                 320

Gly Ile Arg Leu Gly Tyr Ala Leu Ala Pro Glu Arg Leu Leu Thr Arg
                325                 330                 335

Met Ala Ala Ala Arg Ala Ala Ile Asp Arg Gln Gly Asp Ala Pro Leu
            340                 345                 350

Glu Ala Ala Leu Ala Glu Leu Ile Arg Asp Gly Asp Leu Gly Arg His
        355                 360                 365

Ala Arg Lys Ala Arg Arg Val Tyr Arg Ala Arg Arg Asp Leu Leu Ala
    370                 375                 380

Glu Arg Leu Thr Ala Gln Leu Ala Gly Arg Ala Ala Phe Asp Leu Pro
385                 390                 395                 400

Ala Gly Gly Leu Ala Leu Trp Leu Arg Cys Ala Gly Val Ser Ala Glu
                405                 410                 415

Thr Trp Ala Glu Ala Ala Gly Gln Ala Gly Leu Ala Leu Leu Pro Gly
            420                 425                 430

Thr Arg Phe Ala Leu Glu Ser Pro Ala Pro Gln Ala Phe Arg Leu Gly
        435                 440                 445

Tyr Ala Ala Leu Asp Glu Gly Gln Ile Ala Arg Ala Val Glu Ile Leu
    450                 455                 460

Ala Arg Ser Phe Pro Gly
465                 470

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
ggtattgagg gtcgcatgaa ggttttagtc aatgg                         35

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
agaggagagt tagagcctta tgaaatgcta gcagcct                       37

<210> SEQ ID NO 17
<211> LENGTH: 35
<212> TYPE: DNA
<213> ORGANISM: Artificial Sequence
<220> FEATURE:
<223> OTHER INFORMATION: Primer

<400> SEQUENCE: 17
ggtattgagg gtcgcatgtt cgacgccctc gcccg                          35

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
agaggagagt tagagcctca gagactggtg aacttgc                        37

<210> SEQ ID NO 19
<211> LENGTH: 35
<212> TYPE: DNA
<213> ORGANISM: Artificial Sequence
<220> FEATURE:
<223> OTHER INFORMATION: Primer

<400> SEQUENCE: 19
ggtattgagg gtcgcatgga acatttgctg aatcc                          35

<210> SEQ ID NO 20
<211> LENGTH: 37
<212> TYPE: DNA
<213> ORGANISM: Artificial Sequence
<220> FEATURE:
<223> OTHER INFORMATION: Primer

<400> SEQUENCE: 20
agaggagagt tagagcctta aacgccgttg tttatcg                        37

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
ggtattgagg gtcgcatgcg cgagcctctt gccct                          35

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
agaggagagt tagagcctca gccggggaag ctccggg                        37

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23
ggtattgagg gtcgcatgtc cacgcaggcg gccat                          35

<210> SEQ ID NO 24
<211> LENGTH: 37

```
<212> TYPE: DNA
<213> ORGANISM: Artificial Sequence
<220> FEATURE:
<223> OTHER INFORMATION: Primer

<400> SEQUENCE: 24
agaggagagt tagagcctca ctcacgattc acattgc                              37

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
ggtattgagg gtcgcatgcc agaattagct aatga                                35

<210> SEQ ID NO 26
<211> LENGTH: 37
<212> TYPE: DNA
<213> ORGANISM: Artificial Sequence
<220> FEATURE:
<223> OTHER INFORMATION: Primer

<400> SEQUENCE: 26
agaggagagt tagagcctta ttcgtcctct tgtaaaa                              37

<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
ggtattgagg gtcgcatgcg ctctacgacg gctcc                                35

<210> SEQ ID NO 28
<211> LENGTH: 37
<212> TYPE: DNA
<213> ORGANISM: Artificial Sequence
<220> FEATURE:
<223> OTHER INFORMATION: Primer

<400> SEQUENCE: 28
agaggagagt tagagcctca gccgcgcagc accttgg                              37

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
ggtattgagg gtcgcatgtt tgagaacatt accgc                                35

<210> SEQ ID NO 30
<211> LENGTH: 37
<212> TYPE: DNA
<213> ORGANISM: Artificial Sequence
<220> FEATURE:
<223> OTHER INFORMATION: Primer

<400> SEQUENCE: 30
agaggagagt tagagcctta cagcactgcc acaatcg                              37
```

<210> SEQ ID NO 31
<211> LENGTH: 1194
<212> TYPE: DNA
<213> ORGANISM: E. coli

<400> SEQUENCE: 31

```
gtgtttcaaa aagttgacgc ctacgctggc gacccgattc ttacgcttat ggagcgtttt      60
aaagaagacc ctcgcagcga caaagtgaat ttaagtatcg gtctgtacta caacgaagac     120
ggaattattc cacaactgca agccgtggcg gaggcggaag cgcgcctgaa tgcgcagcct     180
catggcgctt cgctttattt accgatggaa gggcttaact gctatcgcca tgccattgcg     240
ccgctgctgt ttggtgcgga ccatccggta ctgaaacaac agcgcgtagc aaccattcaa     300
acccttggcg gctccggggc attgaaagtg gcgcgcgatt tcctgaaacg ctacttcccg     360
gaatcaggcg tctgggtcag cgatcctacc tgggaaaacc gcgtagcaat attcgccggg     420
gctggattcg aagtgagtac ttaccccctgg tatgacgaag cgactaacgg cgtgcgcttt     480
aatgacctgt tggcgacgct gaaaacatta cctgcccgca gtattgtgtt gctgcatcca     540
tgttgccaca acccaacggg tgccgatctc actaatgatc agtgggatgc ggtgattgaa     600
attctcaaag cccgcgagct tattccattc ctcgatattg cctatcaagg atttggtgcc     660
ggtatggaag aggatgccta cgctattcgc gccattgcca cgctggatt acccgctctg     720
gtgagcaatt cgttctcgaa aattttctcc ctttacggcg agcgcgtcgg cggacttctt     780
gttatgtgtg aagatgccga agccgctggc cgcgtactgg ggcaattgaa agcaacagtt     840
cgccgcaact actccagccc gccgaatttt ggtgcgcagg tggtggctgc agtgctgaat     900
gacgaggcat tgaaagccag ctggctggcg gaagtagaag agatgcgtac tcgcattctg     960
gcaatgcgtc aggaattggt gaaggtatta agcacagaga tgccagaacg caatttcgat    1020
tatctgctta atcagcgcgg catgttcagt tataccggtt taagtgccgc tcaggttgac    1080
cgactacgtg aagaatttgg tgtctatctc atcgccagcg gtcgcatgtg tgtcgccggg    1140
ttaaatacgg caaatgtaca acgtgtggca aaggcgtttg ctgcggtgat gtaa          1194
```

<210> SEQ ID NO 32
<211> LENGTH: 397
<212> TYPE: PRT
<213> ORGANISM: E. coli

<400> SEQUENCE: 32

```
Val Phe Gln Lys Val Asp Ala Tyr Ala Gly Asp Pro Ile Leu Thr Leu
  1               5                  10                  15

Met Glu Arg Phe Lys Glu Asp Pro Arg Ser Asp Lys Val Asn Leu Ser
                 20                  25                  30

Ile Gly Leu Tyr Tyr Asn Glu Asp Gly Ile Ile Pro Gln Leu Gln Ala
             35                  40                  45

Val Ala Glu Ala Glu Ala Arg Leu Asn Ala Gln Pro His Gly Ala Ser
         50                  55                  60

Leu Tyr Leu Pro Met Glu Gly Leu Asn Cys Tyr Arg His Ala Ile Ala
 65                  70                  75                  80

Pro Leu Leu Phe Gly Ala Asp His Pro Val Leu Lys Gln Gln Arg Val
                 85                  90                  95

Ala Thr Ile Gln Thr Leu Gly Gly Ser Gly Ala Leu Lys Val Gly Ala
            100                 105                 110

Asp Phe Leu Lys Arg Tyr Phe Pro Glu Ser Gly Val Trp Val Ser Asp
        115                 120                 125
```

```
Pro Thr Trp Glu Asn Arg Val Ala Ile Phe Ala Gly Ala Gly Phe Glu
    130                 135                 140

Val Ser Thr Tyr Pro Trp Tyr Asp Glu Ala Thr Asn Gly Val Arg Phe
145                 150                 155                 160

Asn Asp Leu Leu Ala Thr Leu Lys Thr Leu Pro Ala Arg Ser Ile Val
                165                 170                 175

Leu Leu His Pro Cys Cys His Asn Pro Thr Gly Ala Asp Leu Thr Asn
            180                 185                 190

Asp Gln Trp Asp Ala Val Ile Glu Ile Leu Lys Ala Arg Glu Leu Ile
        195                 200                 205

Pro Phe Leu Asp Ile Ala Tyr Gln Gly Phe Gly Ala Gly Met Glu Glu
    210                 215                 220

Asp Ala Tyr Ala Ile Arg Ala Ile Ala Ser Ala Gly Leu Pro Ala Leu
225                 230                 235                 240

Val Ser Asn Ser Phe Ser Lys Ile Phe Ser Leu Tyr Gly Glu Arg Val
                245                 250                 255

Gly Gly Leu Ser Val Met Cys Glu Asp Ala Glu Ala Ala Gly Arg Val
            260                 265                 270

Leu Gly Gln Leu Lys Ala Thr Val Arg Arg Asn Tyr Ser Pro Pro
        275                 280                 285

Asn Phe Gly Ala Gln Val Val Ala Ala Val Leu Asn Asp Glu Ala Leu
    290                 295                 300

Lys Ala Ser Trp Leu Ala Glu Val Glu Met Arg Thr Arg Ile Leu
305                 310                 315                 320

Ala Met Arg Gln Glu Leu Val Lys Val Leu Ser Thr Glu Met Pro Glu
                325                 330                 335

Arg Asn Phe Asp Tyr Leu Leu Asn Gln Arg Gly Met Phe Ser Tyr Thr
            340                 345                 350

Gly Leu Ser Ala Ala Gln Val Asp Arg Leu Arg Glu Glu Phe Gly Val
        355                 360                 365

Tyr Leu Ile Ala Ser Gly Arg Met Cys Val Ala Gly Leu Asn Thr Ala
    370                 375                 380

Asn Val Gln Arg Val Ala Lys Ala Phe Ala Ala Val Met
385                 390                 395

<210> SEQ ID NO 33
<211> LENGTH: 35
<212> TYPE: DNA
<213> ORGANISM: Artificial Sequence
<220> FEATURE:
<223> OTHER INFORMATION: Primer

<400> SEQUENCE: 33
ggtattgagg gtcgcgtgtt tcaaaaagtt gacgc                            35

<210> SEQ ID NO 34
<211> LENGTH: 37
<212> TYPE: DNA
<213> ORGANISM: Artificial Sequence
<220> FEATURE:
<223> OTHER INFORMATION: Primer

<400> SEQUENCE: 34
agaggagagt tagagcctta catcaccgca gcaaacg                          37

<210> SEQ ID NO 35
<211> LENGTH: 35
<212> TYPE: DNA
```

<213> ORGANISM: Artificial Sequence
<220> FEATURE:
<223> OTHER INFORMATION: Primer

<400> SEQUENCE: 35
ggtattgagg gtcgcatgga gtccaaagtc gttga          35

<210> SEQ ID NO 36
<211> LENGTH: 37
<212> TYPE: DNA
<213> ORGANISM: Artificial Sequence
<220> FEATURE:
<223> OTHER INFORMATION: Primer

<400> SEQUENCE: 36
agaggagagt tagagcctta cacttggaaa acagcct          37

<210> SEQ ID NO 37
<211> LENGTH: 35
<212> TYPE: DNA
<213> ORGANISM: Artificial Sequence
<220> FEATURE:
<223> OTHER INFORMATION: Primer

<400> SEQUENCE: 37
ggtattgagg gtcgcatgaa aaactggaaa acaag          35

<210> SEQ ID NO 38
<211> LENGTH: 37
<212> TYPE: DNA
<213> ORGANISM: Artificial Sequence
<220> FEATURE:
<223> OTHER INFORMATION: Primer

<400> SEQUENCE: 38
agaggagagt tagagcctta cagcttagcg ccttcta          37

<210> SEQ ID NO 39
<211> LENGTH: 35
<212> TYPE: DNA
<213> ORGANISM: Artificial Sequence
<220> FEATURE:
<223> OTHER INFORMATION: Primer

<400> SEQUENCE: 39
ggtattgagg gtcgcatgcg agggcatta ttcaa          35

<210> SEQ ID NO 40
<211> LENGTH: 36
<212> TYPE: DNA
<213> ORGANISM: Artificial Sequence
<220> FEATURE:
<223> OTHER INFORMATION: Primer

<400> SEQUENCE: 40
agaggagagt tagagcctca gcccttgagc gcgaag          36

<210> SEQ ID NO 41
<211> LENGTH: 1416
<212> TYPE: DNA
<213> ORGANISM: E. coli

<400> SEQUENCE: 41
atggaaaact ttaaacatct ccctgaaccg ttccgcattc gtgttattga gccagtaaaa          60
cgtaccaccc gcgcttatcg tgaagaggca attattaaat ccggtatgaa cccgttcctg          120

```
ctggatagcg aagatgtttt tatcgattta ctgaccgaca gcggcaccgg ggcggtgacg      180
cagagcatgc aggctgcgat gatgcgcggc gacgaagcct acagcggcag tcgtagctac      240
tatgcgttag ccgagtcagt gaaaaatatc tttggttatc aatacaccat tccgactcac      300
cagggccgtg cgcagagcca aatctatatt ccggtactga ttaaaaaacg cgagcaggaa      360
aaaggcctgg atcgcagcaa aatggtggcg ttctctaact atttctttga taccacgcag      420
ggccatagcc agatcaacgg ctgtaccgtg cgtaacgtct atatcaaaga agccttcgat      480
acgggcgtgc gttacgactt taaaggcaac tttgaccttg agggattaga acgcggtatt      540
gaagaagttg gtccgaataa cgtgccgtat atcgttgcaa ccatcaccag taactctgca      600
ggtggtcagc cggtttcact ggcaaactta aaagcgatgt acagcatcgc gaagaaatac      660
gatattccgg tggtaatgga ctccgcgcgc tttgctgaaa acgcctattt catcaagcag      720
cgtgaagcag aatacaaaga ctggaccatc gagcagatca cccgcgaaac ctacaaatat      780
gccgatatgc tggcgatgtc cgccaagaaa gatgcgatgg tgccgatggg cggcctgctg      840
tgcatgaaag acgacagctt ctttgatgtg tacaccgagt gcagaaccct tgcgtggtg      900 caggaaggct tcccgacata tggcggcctg gaaggcggcg cgatggagcg tctggcggta      960
ggtctgtatg acggcatgaa tctcgactgg ctggcttatc gtatcgcgca ggtacagtat     1020
ctggtcgatg gtctggaaga gattggcgtt gtctgccagc aggcgggcgg tcacgcggca     1080
ttcgttgatg ccggtaaact gttgccgcat atcccggcag accagttccc ggcacaggcg     1140
ctggcctgcg agctgtataa agtcgccggt atccgtgcgg tagaaattgg ctctttcctg     1200
ttaggccgcg atccgaaaac cggtaaacaa ctgccatgcc cggctgaact gctgcgttta     1260
accattccgc gcgcaacata tactcaaaca catatggact tcattattga agcctttaaa     1320
catgtgaaag agaacgcggc gaatattaaa ggattaacct ttacgtacga accgaaagta     1380
ttgcgtcact tcaccgcaaa acttaaagaa gtttaa                              1416
```

<210> SEQ ID NO 42
<211> LENGTH: 1371
<212> TYPE: DNA
<213> ORGANISM: Citrobacter freundii

<400> SEQUENCE: 42

```
atgaattatc cggcagaacc cttccgtatt aaaagcgttg aaactgtatc tatgatcccg       60
cgtgatgaac gcctcaagaa aatgcaggaa gcgggttaca atactttcct gttaaattcg      120
aaagatattt atattgacct gctgacagac agtggcacta acgcaatgag cgacaagcag      180
tgggccggaa tgatgatggg tgatgaagcg tacgcgggca gcgaaaactt ctatcatctg      240
gaaagaaccg tgcaggaact gtttggcttt aaacatattg ttccgactca ccaggggcgt      300
ggcgcagaaa acctgttatc gcagctggct attaaacctg gcaatatgt tgccgggaat       360 atgtatttca ctaccacccg ttatcaccag gaaaaaatg gtgcgtgtt tgtcgatatc        420 gttcgtgacg aagcgcacga tgccggtctg aatattgcgt ttaaaggtga tatcgatctt      480
aaaaaattac aaaagctgat tgatgaaaaa ggcgcagaga atattgcgta tatctgcctg      540
gcggtgacgg ttaacctcgc gggcggccaa ccggtctcga tggctaacat gcgtgcggtg      600
cgtgaactga cagaagcgca tggcattaaa gtgttctacg acgctacccg ctgcgtagaa      660
aacgcctact ttatcaaaga gcaagagcag ggctttgaga acaagagcat cgccgagatc      720
gtgcatgaga tgttcagcta cgccgacggt gtaccatga tggtaaaaaa agactgtctg       780
gtgaacatcg gcggcttcct gtgcatgaac gatgacgaaa tgttctcttc tgccaaagag      840
```

```
ttagtcgtgg tctacgaagg gatgccatct tacggcggcc tggccggacg tgatatggaa    900
gcgatggcga ttggcctgcg tgaagccatg cagtacgaat atattgagca ccgcgtgaag    960
caggttcgct acctgggcga taagctgaaa ccgctggcg taccgattgt tgaaccggta    1020
ggcggtcacg cggtattcct cgatgcgcgt cgcttctgcg agcatctgac gcaagatgag    1080
ttcccggcac aaagtctggc tgccagcatc tatgtggaaa ccggcgtgcg cagtatggag    1140
cgcggaatta tctctgcggg ccgtaataac gtgaccggtg aacaccacag accgaaactg    1200
gaaaccgtgc gtctgactat tccacgtcgt gtttatacct acgcacatat ggatgttgtg    1260
gctgacggta ttattaaact ttaccagcac aaagaagata ttcgcgggct gaagtttatt    1320
tacgagccga agcagttgcg tttctttact gcacgctttg attacatcta a            1371
```

<210> SEQ ID NO 43
<211> LENGTH: 35
<212> TYPE: DNA
<213> ORGANISM: Artificial Sequence
<220> FEATURE:
<223> OTHER INFORMATION: Primer

<400> SEQUENCE: 43
ggtattgagg gtcgcatgga aaactttaaa catct                              35

<210> SEQ ID NO 44
<211> LENGTH: 37
<212> TYPE: DNA
<213> ORGANISM: Artificial Sequence
<220> FEATURE:
<223> OTHER INFORMATION: Primer

<400> SEQUENCE: 44
agaggagagt tagagcctta aacttcttta agttttg                            37

<210> SEQ ID NO 45
<211> LENGTH: 35
<212> TYPE: DNA
<213> ORGANISM: Artificial Sequence
<220> FEATURE:
<223> OTHER INFORMATION: Primer

<400> SEQUENCE: 45
ggtattgagg gtcgcatgaa ttatccggca gaacc                              35

<210> SEQ ID NO 46
<211> LENGTH: 37
<212> TYPE: DNA
<213> ORGANISM: Artificial Sequence
<220> FEATURE:
<223> OTHER INFORMATION: Primer

<400> SEQUENCE: 46
agaggagagt tagagcctta gatgtaatca aagcgtg                            37

<210> SEQ ID NO 47
<211> LENGTH: 31
<212> TYPE: DNA
<213> ORGANISM: Artificial Sequence
<220> FEATURE:
<223> OTHER INFORMATION: Primer

<400> SEQUENCE: 47
ccagggcacc ggcgcagagc aaatctatat t                                  31

<210> SEQ ID NO 48

```
<211> LENGTH: 30
<212> TYPE: DNA
<213> ORGANISM: Artificial Sequence
<220> FEATURE:
<223> OTHER INFORMATION: Primer

<400> SEQUENCE: 48
tgcgccggtg ccctggtgag tcggaatggt                                    30

<210> SEQ ID NO 49
<211> LENGTH: 32
<212> TYPE: DNA
<213> ORGANISM: Artificial Sequence
<220> FEATURE:
<223> OTHER INFORMATION: Primer

<400> SEQUENCE: 49
tcctgcacgc ggcaaagggt tctgcactcg gt                                 32

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
ctttgccgcg tgcaggaagg cttcccgaca                                    30

<210> SEQ ID NO 51
<211> LENGTH: 29
<212> TYPE: DNA
<213> ORGANISM: Artificial Sequence
<220> FEATURE:
<223> OTHER INFORMATION: Primer

<400> SEQUENCE: 51
aggggaccgg cgcagaaaac ctgttatcg                                     29

<210> SEQ ID NO 52
<211> LENGTH: 32
<212> TYPE: DNA
<213> ORGANISM: Artificial Sequence
<220> FEATURE:
<223> OTHER INFORMATION: Primer

<400> SEQUENCE: 52
tctgcgccgg tcccctggtg agtcggaaca at                                 32

<210> SEQ ID NO 53
<211> LENGTH: 29
<212> TYPE: DNA
<213> ORGANISM: Artificial Sequence
<220> FEATURE:
<223> OTHER INFORMATION: Primer

<400> SEQUENCE: 53
gttagtccgc gtctacgaag ggatgccat                                     29

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
```
gtagacgcgg actaactctt tggcagaag                                              29

<210> SEQ ID NO 55
<211> LENGTH: 35
<212> TYPE: DNA
<213> ORGANISM: Artificial Sequence
<220> FEATURE:
<223> OTHER INFORMATION: Primer

<400> SEQUENCE: 55
ggtattgagg gtcgcatgta cgaactggga gttgt                                       35

<210> SEQ ID NO 56
<211> LENGTH: 37
<212> TYPE: DNA
<213> ORGANISM: Artificial Sequence
<220> FEATURE:
<223> OTHER INFORMATION: Primer

<400> SEQUENCE: 56
agaggagagt tagagcctta gtcaatatat ttcaggc                                     37

<210> SEQ ID NO 57
<211> LENGTH: 35
<212> TYPE: DNA
<213> ORGANISM: Artificial Sequence
<220> FEATURE:
<223> OTHER INFORMATION: Primer

<400> SEQUENCE: 57
ggtattgagg gtcgcatgtc cggcatcgtt gtcca                                       35

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
agaggagagt tagagcctca gacatatttc agtccca                                     37

<210> SEQ ID NO 59
<211> LENGTH: 35
<212> TYPE: DNA
<213> ORGANISM: Artificial Sequence
<220> FEATURE:
<223> OTHER INFORMATION: Primer

<400> SEQUENCE: 59
ggtattgagg gtcgcatgcg actgaacaac ctcgg                                       35

<210> SEQ ID NO 60
<211> LENGTH: 37
<212> TYPE: DNA
<213> ORGANISM: Artificial Sequence
<220> FEATURE:
<223> OTHER INFORMATION: Primer

<400> SEQUENCE: 60
agaggagagt tagagcctca gttctccacg tattcca                                     37

<210> SEQ ID NO 61
<211> LENGTH: 35
<212> TYPE: DNA
<213> ORGANISM: Artificial Sequence
<220> FEATURE:

<223> OTHER INFORMATION: Primer

<400> SEQUENCE: 61
ggtattgagg gtcgcatgag cgtggttcac cggaa    35

<210> SEQ ID NO 62
<211> LENGTH: 37
<212> TYPE: DNA
<213> ORGANISM: Artificial Sequence
<220> FEATURE:
<223> OTHER INFORMATION: Primer

<400> SEQUENCE: 62
agaggagagt tagagcctca atcgatatat ttcagtc    37

<210> SEQ ID NO 63
<211> LENGTH: 35
<212> TYPE: DNA
<213> ORGANISM: Artificial Sequence
<220> FEATURE:
<223> OTHER INFORMATION: Primer

<400> SEQUENCE: 63
ggtattgagg gtcgcatgag cctggttaat atgaa    35

<210> SEQ ID NO 64
<211> LENGTH: 37
<212> TYPE: DNA
<213> ORGANISM: Artificial Sequence
<220> FEATURE:
<223> OTHER INFORMATION: Primer

<400> SEQUENCE: 64
agaggagagt tagagcctta tgactttaac gcgttga    37

<210> SEQ ID NO 65
<211> LENGTH: 684
<212> TYPE: DNA
<213> ORGANISM: C. testosteroni

<400> SEQUENCE: 65
atgtacgaac tgggagttgt ctaccgcaat atccagcgcg ccgaccgcgc tgctgctgac    60
ggcctggccg ccctgggctc cgccaccgtg cacgaggcca tgggccgcgt cggtctgctc    120
aagcccctata tgcgccccat ctatgccggc aagcaggtct cgggcaccgc cgtcacggtg    180
ctgctgcagc ccggcgacaa ctggatgatg catgtggctg ccgagcagat tcagcccggc    240
gacatcgtgg tcgcagccgt caccgcagag tgcaccgacg gctacttcgg cgatctgctg    300
gccaccagct tccaggcgcg cggcgcacgt gcgctgatca tcgatgccgg cgtgcgcgac    360
gtgaagacgc tgcaggagat ggactttccg gtctggagca aggccatctc ttccaagggc    420
acgatcaagg ccaccctggg ctcggtcaac atccccatcg tctgcgccgg catgctggtc    480
acgcccggtg acgtgatcgt ggccgacgac gacggcgtgg tctgcgtgcc cgccgcgcgt    540
gccgtggaag tgctggccgc cgcccagaag cgtgaaagct cgaaggcga aaagcgcgcc    600
aagctggcct cgggcatcct cggcctggat atgtacaaga tgcgcgagcc cctggaaaag    660
gccggcctga atatattga ctaa    684

<210> SEQ ID NO 66
<211> LENGTH: 227
<212> TYPE: PRT
<213> ORGANISM: C. testosteroni -continued

<400> SEQUENCE: 66

Met Tyr Glu Leu Gly Val Val Tyr Arg Asn Ile Gln Arg Ala Asp Arg
1               5                   10                  15

Ala Ala Ala Asp Gly Leu Ala Ala Leu Gly Ser Ala Thr Val His Glu
            20                  25                  30

Ala Met Gly Arg Val Gly Leu Leu Lys Pro Tyr Met Arg Pro Ile Tyr
        35                  40                  45

Ala Gly Lys Gln Val Ser Gly Thr Ala Val Thr Val Leu Leu Gln Pro
    50                  55                  60

Gly Asp Asn Trp Met Met His Val Ala Ala Glu Gln Ile Gln Pro Gly
65                  70                  75                  80

Asp Ile Val Val Ala Val Thr Ala Glu Cys Thr Asp Gly Tyr Phe
                85                  90                  95

Gly Asp Leu Leu Ala Thr Ser Phe Gln Ala Arg Gly Ala Arg Ala Leu
            100                 105                 110

Ile Ile Asp Ala Gly Val Arg Asp Val Lys Thr Leu Gln Glu Met Asp
        115                 120                 125

Phe Pro Val Trp Ser Lys Ala Ile Ser Ser Lys Gly Thr Ile Lys Ala
130                 135                 140

Thr Leu Gly Ser Val Asn Ile Pro Ile Val Cys Ala Gly Met Leu Val
145                 150                 155                 160

Thr Pro Gly Asp Val Ile Val Ala Asp Asp Gly Val Val Cys Val
                165                 170                 175

Pro Ala Ala Arg Ala Val Glu Val Leu Ala Ala Gln Lys Arg Glu
            180                 185                 190

Ser Phe Glu Gly Glu Lys Arg Ala Lys Leu Ala Ser Gly Ile Leu Gly
        195                 200                 205

Leu Asp Met Tyr Lys Met Arg Glu Pro Leu Glu Lys Ala Gly Leu Lys
    210                 215                 220

Tyr Ile Asp
225

<210> SEQ ID NO 67
<211> LENGTH: 42
<212> TYPE: DNA
<213> ORGANISM: Artificial Sequence
<220> FEATURE:
<223> OTHER INFORMATION: Primer

<400> SEQUENCE: 67
actcggatcc gaaggagata tacatatgta cgaactggga ct                    42

<210> SEQ ID NO 68
<211> LENGTH: 33
<212> TYPE: DNA
<213> ORGANISM: Artificial Sequence
<220> FEATURE:
<223> OTHER INFORMATION: Primer

<400> SEQUENCE: 68
cggctgtcga ccgttagtca atatatttca ggc                              33

<210> SEQ ID NO 69
<211> LENGTH: 31
<212> TYPE: DNA
<213> ORGANISM: Artificial Sequence
<220> FEATURE:
<223> OTHER INFORMATION: Primer

<400> SEQUENCE: 69
cgcggatcca taatggttga gaacattacc g                            31

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
acgcgtcgac ttacagcact gccacaatcg                              30

<210> SEQ ID NO 71
<211> LENGTH: 32
<212> TYPE: DNA
<213> ORGANISM: Artificial Sequence
<220> FEATURE:
<223> OTHER INFORMATION: Primer

<400> SEQUENCE: 71
ccggaattca taatggtcga actgggagtt gt                           32

<210> SEQ ID NO 72
<211> LENGTH: 33
<212> TYPE: DNA
<213> ORGANISM: Artificial Sequence
<220> FEATURE:
<223> OTHER INFORMATION: Primer

<400> SEQUENCE: 72
gaatgcggcc gcttagtcaa tatatttcag gcc                          33

<210> SEQ ID NO 73
<211> LENGTH: 15
<212> TYPE: DNA
<213> ORGANISM: Artificial Sequence
<220> FEATURE:
<223> OTHER INFORMATION: Primer

<400> SEQUENCE: 73
ggtattgagg gtcgc                                              15

<210> SEQ ID NO 74
<211> LENGTH: 17
<212> TYPE: DNA
<213> ORGANISM: Artificial Sequence
<220> FEATURE:
<223> OTHER INFORMATION: Primer

<400> SEQUENCE: 74
agaggagagt tagagcc                                            17

<210> SEQ ID NO 75
<211> LENGTH: 60
<212> TYPE: DNA
<213> ORGANISM: Artificial Sequence
<220> FEATURE:
<223> OTHER INFORMATION: Primer

<400> SEQUENCE: 75
gaagcgattg tggcagtgct gtaaggctct aacggatccg aaggagatat acatatgtac    60

<210> SEQ ID NO 76
<211> LENGTH: 57
<212> TYPE: DNA
<213> ORGANISM: Artificial Sequence
<220> FEATURE:
<223> OTHER INFORMATION: Primer

<400> SEQUENCE: 76
gtacatatgt atatctccgg atccgttaga gccttacagc actgccacaa tcgcttc    57

<210> SEQ ID NO 77
<211> LENGTH: 24
<212> TYPE: DNA
<213> ORGANISM: Artificial Sequence
<220> FEATURE:
<223> OTHER INFORMATION: Primer

<400> SEQUENCE: 77
tgccatggaa aactttaaac atct    24

<210> SEQ ID NO 78
<211> LENGTH: 28
<212> TYPE: DNA
<213> ORGANISM: Artificial Sequence
<220> FEATURE:
<223> OTHER INFORMATION: Primer

<400> SEQUENCE: 78
ccaagctttt aaacttcttt aagttttg    28

<210> SEQ ID NO 79
<211> LENGTH: 40
<212> TYPE: DNA
<213> ORGANISM: Artificial Sequence
<220> FEATURE:
<223> OTHER INFORMATION: Primer

<400> SEQUENCE: 79
cggggtaccc atgcaaacac aaaaaccgac tctcgaactg    40

<210> SEQ ID NO 80
<211> LENGTH: 33
<212> TYPE: DNA
<213> ORGANISM: Artificial Sequence
<220> FEATURE:
<223> OTHER INFORMATION: Primer

<400> SEQUENCE: 80
cgcggatcct taactgcgcg tcgccgcttt cat    33

<210> SEQ ID NO 81
<211> LENGTH: 1563
<212> TYPE: DNA
<213> ORGANISM: Artificial Sequence
<220> FEATURE:
<223> OTHER INFORMATION: Synthetic Construct

<400> SEQUENCE: 81
atgcaaacac aaaaaccgac tctcgaacta ctaacctgcg aaggcgctta tcgcgacaac    60
ccgaccgcgc tttttcacca gttgtgtggg gatcgtccgg caacgctgct gctggaatcc    120
gcagatatcg acagcaaaga tgatttaaaa agcctgctac tggtagacag tgcgctgcgc    180
attacagcat taggtgacac tgtcacaatt aaggcgttat ccggcaatgg tgaagccctg    240
ctggcactac tggataacgc cctgcctgcg ggtgtggaaa atgaacaatc accaaactgc    300
cgtgtgctgc gcttcccccc tgtcagtcca ctgctggatg aagacgctcg cttatgctcc    360
ctttcggttt ttgacgcttt ccgtttattg cagaatctgt tgaatgtacc gaaggaagaa    420
cgagaagcca tgttcttcgg cggcctgttc tcttatgacc ttgtggcggg atttgaagat    480

```
ttaccgcaac tgtcagcgga aaataactgc cctgattct gttttatct cgctgaaacg      540 ctgatggtga ttgaccatca gaaaaaaagc accgtattc aggccagcct gtttgctccg      600
aatgaagaag aaaacaacg tctcactgct cgcctgaacg aactacgtca gcaactgacc      660
gaagccgcgc cgccgctgcc agtggtttcc gtgccgcata tgcgttgtga atgtaatcag      720
agcgatgaag agttcggtgg cgtagtgcgt ttgttgcaaa aagcgattcg cgctggagaa      780
attttccagg tggtgccatc tcgccgtttc tctctgccct gcccgtcacc gctggcggcc      840
tattacgtgc tgaaaaagag taatcccagc ccgtacatgt tttttatgca ggataatgat      900
ttcaccctat ttggcgcgtc gccggaaagc tcgctcaagt atgatgccac cagccgccag      960
attgagatct acccgattgc cggaacacgc ccacgcggtc gtcgcgccga tggttcactg     1020
gacagagatc tcgacagccg tattgaactg gaaatgcgta ccgatcataa agagctgtct     1080
gaacatctga tgctggttga tctcgcccgt aatgatctgg cacgcatttg caccccggc      1140 agccgctacg tcgccgatct caccaaagtt gaccgttatt cctatgtgat gcacctcgtc     1200
tctcgcgtag tcggcgaact gcgtcacgat cttgacgccc tgcacgctta tcgcgcctgt     1260
atgaatatgg ggacgttaag cggtgcgccg aaagtacgcg ctatgcagtt aattgccgag     1320
gcggaaggtc gtcgccgcgg cagctacggc ggcgcggtag gttatttcac cgcgcatggc     1380
gatctcgaca cctgcattgt gatccgctcg gcgctggtgg aaaacggtat cgccaccgtg     1440
caagcgggtg ctggtgtagt ccttgattct gttccgcagt cggaagccga cgaaacccgt     1500
aacaaagccc gcgctgtact gcgcgctatt gccaccgcgc atcatgcaca ggagactttc     1560
tga                                                                   1563
```

<210> SEQ ID NO 82
<211> LENGTH: 520
<212> TYPE: PRT
<213> ORGANISM: Artificial Sequence
<220> FEATURE:
<223> OTHER INFORMATION: Synthetic Construct

<400> SEQUENCE: 82

```
Met Gln Thr Gln Lys Pro Thr Leu Glu Leu Leu Thr Cys Glu Gly Ala
 1               5                  10                  15

Tyr Arg Asp Asn Pro Thr Ala Leu Phe His Gln Leu Cys Gly Asp Arg
            20                  25                  30

Pro Ala Thr Leu Leu Glu Ser Ala Ile Asp Ser Lys Asp Asp
        35                  40                  45

Leu Lys Ser Leu Leu Leu Val Asp Ser Ala Leu Arg Ile Thr Ala Leu
    50                  55                  60

Gly Asp Thr Val Thr Ile Lys Ala Leu Ser Gly Asn Gly Glu Ala Leu
65                  70                  75                  80

Leu Ala Leu Leu Asp Asn Ala Leu Pro Ala Gly Val Glu Asn Glu Gln
                85                  90                  95

Ser Pro Asn Cys Arg Val Leu Arg Phe Pro Val Ser Pro Leu Leu
            100                 105                 110

Asp Glu Asp Ala Arg Leu Cys Ser Leu Ser Val Phe Asp Ala Phe Arg
        115                 120                 125

Leu Leu Gln Asn Leu Leu Asn Val Pro Lys Glu Glu Arg Glu Ala Met
    130                 135                 140

Phe Phe Gly Gly Leu Phe Ser Tyr Asp Leu Val Ala Gly Phe Glu Asp
145                 150                 155                 160

Leu Pro Gln Leu Ser Ala Glu Asn Asn Cys Pro Asp Phe Cys Phe Tyr
```

```
            165                 170                 175
Leu Ala Glu Thr Leu Met Val Ile Asp His Gln Lys Lys Ser Thr Arg
        180                 185                 190

Ile Gln Ala Ser Leu Phe Ala Pro Asn Glu Glu Lys Gln Arg Leu
        195                 200                 205

Thr Ala Arg Leu Asn Glu Leu Arg Gln Gln Leu Thr Glu Ala Ala Pro
        210                 215                 220

Pro Leu Pro Val Val Ser Val Pro His Met Arg Cys Glu Cys Asn Gln
225                 230                 235                 240

Ser Asp Glu Glu Phe Gly Gly Val Val Arg Leu Leu Gln Lys Ala Ile
                245                 250                 255

Arg Ala Gly Glu Ile Phe Gln Val Val Pro Ser Arg Arg Phe Ser Leu
                260                 265                 270

Pro Cys Pro Ser Pro Leu Ala Ala Tyr Tyr Val Leu Lys Lys Ser Asn
            275                 280                 285

Pro Ser Pro Tyr Met Phe Phe Met Gln Asp Asn Asp Phe Thr Leu Phe
        290                 295                 300

Gly Ala Ser Pro Glu Ser Ser Leu Lys Tyr Asp Ala Thr Ser Arg Gln
305                 310                 315                 320

Ile Glu Ile Tyr Pro Ile Ala Gly Thr Arg Pro Arg Gly Arg Arg Ala
                325                 330                 335

Asp Gly Ser Leu Asp Arg Asp Leu Asp Ser Arg Ile Glu Leu Glu Met
                340                 345                 350

Arg Thr Asp His Lys Glu Leu Ser Glu His Leu Met Leu Val Asp Leu
                355                 360                 365

Ala Arg Asn Asp Leu Ala Arg Ile Cys Thr Pro Gly Ser Arg Tyr Val
            370                 375                 380

Ala Asp Leu Thr Lys Val Asp Arg Tyr Ser Tyr Val Met His Leu Val
385                 390                 395                 400

Ser Arg Val Val Gly Glu Leu Arg His Asp Leu Asp Ala Leu His Ala
                405                 410                 415

Tyr Arg Ala Cys Met Asn Met Gly Thr Leu Ser Gly Ala Pro Lys Val
            420                 425                 430

Arg Ala Met Gln Leu Ile Ala Glu Ala Glu Gly Arg Arg Arg Gly Ser
        435                 440                 445

Tyr Gly Gly Ala Val Gly Tyr Phe Thr Ala His Gly Asp Leu Asp Thr
        450                 455                 460

Cys Ile Val Ile Arg Ser Ala Leu Val Glu Asn Gly Ile Ala Thr Val
465                 470                 475                 480

Gln Ala Gly Ala Gly Val Val Leu Asp Ser Val Pro Gln Ser Glu Ala
                485                 490                 495

Asp Glu Thr Arg Asn Lys Ala Arg Ala Val Leu Arg Ala Ile Ala Thr
            500                 505                 510

Ala His His Ala Gln Glu Thr Phe
            515                 520

<210> SEQ ID NO 83
<211> LENGTH: 50
<212> TYPE: DNA
<213> ORGANISM: Artificial Sequence
<220> FEATURE:
<223> OTHER INFORMATION: Primer

<400> SEQUENCE: 83
cggggtacca gaaggagaga tgcacgatgt ttgagaacat taccgccgct            50
```

```
<210> SEQ ID NO 84
<211> LENGTH: 31
<212> TYPE: DNA
<213> ORGANISM: Artificial Sequence
<220> FEATURE:
<223> OTHER INFORMATION: Primer

<400> SEQUENCE: 84
cggggtaccg cttagtcaat atatttcagg c                              31

<210> SEQ ID NO 85
<211> LENGTH: 63
<212> TYPE: DNA
<213> ORGANISM: Artificial Sequence
<220> FEATURE:
<223> OTHER INFORMATION: Primer

<400> SEQUENCE: 85
atgtccagaa ggcttcgcag aacaaaaatc gttaccacgt taggtgtagg ctggagctgc    60
ttc                                                                 63

<210> SEQ ID NO 86
<211> LENGTH: 64
<212> TYPE: DNA
<213> ORGANISM: Artificial Sequence
<220> FEATURE:
<223> OTHER INFORMATION: Primer

<400> SEQUENCE: 86
ctctaccgtt aaaatacgcg tggtattagt agaacccacg gtaccatatg aatatcctcc    60
ttag                                                                64

<210> SEQ ID NO 87
<211> LENGTH: 64
<212> TYPE: DNA
<213> ORGANISM: Artificial Sequence
<220> FEATURE:
<223> OTHER INFORMATION: Primer

<400> SEQUENCE: 87
aggacgtgaa cagatgcggt gttagtagtg ccgctcggta ccagcatatg aatatcctcc    60
ttag                                                                64

<210> SEQ ID NO 88
<211> LENGTH: 63
<212> TYPE: DNA
<213> ORGANISM: Artificial Sequence
<220> FEATURE:
<223> OTHER INFORMATION: Primer

<400> SEQUENCE: 88
atgaaaaaga ccaaaattgt ttgcaccatc ggaccgaaaa ccggtgtagg ctggagctgc    60
ttc                                                                 63

<210> SEQ ID NO 89
<211> LENGTH: 10
<212> TYPE: PRT
<213> ORGANISM: Lactobacillus amylovorus

<400> SEQUENCE: 89

Met Pro Glu Leu Ala Asn Asp Leu Gly Leu
 1               5                  10
```

<210> SEQ ID NO 90
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 90

His His His His His His
 1               5

<210> SEQ ID NO 91
<211> LENGTH: 682
<212> TYPE: DNA
<213> ORGANISM: Sinorhizobium meliloti

<400> SEQUENCE: 91

```
atgagcgtgg ttcaccggaa tatcgagcgc accgatagaa gcctcgcaga cgccctggcg      60
gagtgcggcg ttgcgacggt gcacgaggcg atgggccgta ccggcctgat gcagtcctat     120
atgcggcccg tctggcgcgg ggcgcgcgtg gcgggtacgc cggtaacggt ctcgataccg     180
cctgccgaca actggatgat ccatgtagcg gtcgagcaat gccgcgaagg cgacattctc     240
gttgtcgcac cgacctcacc ttgcgacgcc ggctatttcg gcgaattgct tgcgacctcc     300
ctcatggtgc gtggcgtgcg cggactgatc atcgaggccg gggtacggga cgtcagcgaa     360
ttggaggaaa tcggctttcc cgtctggtcg cggttcgtct cggcacaggg aacggtgaag     420
gcgacgcttg gttcggtcaa cgtgccgatc gtctgcgcag cgccaccgt ggcacccggc      480 gatgtcgtca tcgccgacga cgacggggtc atggtcgtgc cgaaagcgca ggccgaacaa     540
gcggtcgcgg cctcgcgcgc ccggctcgag aaggagcgca agacgcgtga gcggctggcc     600
gccggcgaac tgggactgga catctacgac atgcgcggcg cactggccgc caaaggactg     660
aaatatatcg attgagcggg ag                                              682
```

<210> SEQ ID NO 92
<211> LENGTH: 224
<212> TYPE: PRT
<213> ORGANISM: Sinorhizobium meliloti

<400> SEQUENCE: 92

Met Ser Val Val His Arg Asn Ile Glu Arg Thr Asp Arg Ser Leu Ala
 1               5                  10                  15

Asp Ala Leu Ala Glu Cys Gly Val Ala Thr Val His Glu Ala Met Gly
             20                  25                  30

Arg Thr Gly Leu Met Gln Ser Tyr Met Arg Pro Val Trp Arg Gly Ala
         35                  40                  45

Arg Val Ala Gly Thr Ala Val Thr Val Ser Ile Pro Pro Ala Asp Asn
     50                  55                  60

Trp Met Ile His Val Ala Val Glu Gln Cys Arg Glu Gly Asp Ile Leu
 65                  70                  75                  80

Val Val Ala Pro Thr Ser Pro Cys Asp Ala Gly Tyr Phe Gly Glu Leu
                 85                  90                  95

Leu Ala Thr Ser Leu Met Val Arg Gly Val Arg Gly Leu Ile Ile Glu
            100                 105                 110

Ala Gly Val Arg Asp Val Ser Glu Leu Glu Ile Gly Phe Pro Val
            115                 120                 125

Trp Ser Arg Phe Val Ser Ala Gln Gly Thr Val Lys Ala Thr Leu Gly
        130                 135                 140

Ser Val Asn Val Pro Ile Val Cys Ala Gly Ala Thr Val Ala Pro Gly

```
                145                 150                 155                 160
Asp Val Val Ile Ala Asp Asp Gly Val Met Val Val Pro Lys Ala
                    165                 170                 175

Gln Ala Glu Gln Ala Val Ala Ala Ser Arg Ala Arg Leu Lys Glu
                    180                 185                 190

Arg Lys Thr Arg Glu Arg Leu Ala Ala Gly Glu Leu Gly Leu Asp Ile
                    195                 200                 205

Tyr Asp Met Arg Gly Ala Leu Ala Ala Lys Gly Leu Lys Tyr Ile Asp
                    210                 215                 220

<210> SEQ ID NO 93
<211> LENGTH: 693
<212> TYPE: DNA
<213> ORGANISM: Arthrobacter keyseri

<400> SEQUENCE: 93
atgcgactga caacctcgg catcgtccgc accaacatcg aacgtccgga ccccgcggac      60
gtcaaacggc tttcgcagtt cggcgtcgcc actatccatg aggcgatggg gcgagtgggg     120
ctcctgcgcc cctacatcag gccggcctac acaggcgcta agctctgtgg tccggcagta    180
accgtgctgc tgcagcctgg tgacaactgg atgttccacg tcgccgccga gcaggtgcag    240
gaaggcgatg tgatcgtcgc cggctgcacc accgaaagcg aggacggctt cttcggtgag    300
ctgctcgcca cctcgctgac cgcccgcggc tgcaagggcc tggtcatcga cggtggtgtc    360
cgcgacgtcg ccgatctgga aagatggat ttcccggtgt tctcccgcgc cgtcaacgcc    420
aaaggcacgg tcaaggccac cctcggatcg gtgaacatcc ccgtagtggt cgcgaacgcg    480
gtggtgaatc ccggcgacgt ggtggtggcc gacgtcgacg gcgttgtggt tgtcccgcgc    540
gagcttgtcg agcggtggc agacgccagc cagaagcgcg aggataacga ggaagccaaa    600
cgcgtgaagt tccgcgaggg cgtcttgggc ctggatgtct acggcatgcg cgggcctctc    660
gccaaggctg gcctggaata cgtggagaac tga                                 693

<210> SEQ ID NO 94
<211> LENGTH: 230
<212> TYPE: PRT
<213> ORGANISM: Arthrobacter keyseri

<400> SEQUENCE: 94

Met Arg Leu Asn Asn Leu Gly Ile Val Arg Thr Asn Ile Glu Arg Pro
  1               5                  10                  15

Asp Pro Ala Asp Val Lys Arg Leu Ser Gln Phe Gly Val Ala Thr Ile
                    20                  25                  30

His Glu Ala Met Gly Arg Val Gly Leu Leu Arg Pro Tyr Ile Arg Pro
                35                  40                  45

Ala Tyr Thr Gly Ala Lys Leu Cys Gly Pro Ala Val Thr Val Leu Leu
            50                  55                  60

Gln Pro Gly Asp Asn Trp Met Phe His Val Ala Ala Glu Gln Val Gln
 65                  70                  75                  80

Glu Gly Asp Val Ile Val Ala Gly Cys Thr Thr Glu Ser Glu Asp Gly
                    85                  90                  95

Phe Phe Gly Glu Leu Leu Ala Thr Ser Leu Thr Ala Arg Gly Cys Lys
                100                 105                 110

Gly Leu Val Ile Asp Gly Gly Val Arg Asp Val Ala Asp Leu Glu Lys
            115                 120                 125

Met Asp Phe Pro Val Phe Ser Arg Ala Val Asn Ala Lys Gly Thr Val
        130                 135                 140
```

```
Lys Ala Thr Leu Gly Ser Val Asn Ile Pro Val Val Ala Asn Ala
145                 150                 155                 160

Val Val Asn Pro Gly Asp Val Val Ala Asp Val Asp Gly Val Val
                165                 170                 175

Val Val Pro Arg Glu Leu Val Gly Ala Val Ala Asp Ala Ser Gln Lys
            180                 185                 190

Arg Glu Asp Asn Glu Glu Ala Lys Arg Val Lys Phe Arg Glu Gly Val
        195                 200                 205

Leu Gly Leu Asp Val Tyr Gly Met Arg Gly Pro Leu Ala Lys Ala Gly
    210                 215                 220

Leu Glu Tyr Val Glu Asn
225                 230
```

<210> SEQ ID NO 95
<211> LENGTH: 591
<212> TYPE: DNA
<213> ORGANISM: Bacillus subtilis

<400> SEQUENCE: 95

```
atggagtcca aagtcgttga aaaccgtctg aaagaagcaa agctgattgc agtcattcgt    60
tcaaaggata agcaggaggc ctgtcagcag attgagagtt tattagataa agggattcgt   120
gcagttgaag tgacgtatac gaccccggg catcagata ttatcgaatc cttccgtaat    180
agggaagata tttttaattgg cgcgggtacg gtcatcagcg cgcagcaagc tggggaagct   240
gctaaggctg gcgcgcagtt tattgtcagt ccgggttttt cagctgatct tgctgaacat   300
ctatcttttg taaagacaca ttatatcccc ggcgtcttga ctccgagcga aattatggaa   360
gcgctgacat tcggttttac gacattaaag ctgttcccaa gcggtgtgtt tggcattccg   420
tttatgaaaa atttagcggg tccttttccg caggtgaccct tattccgac aggcgggata   480
catccgtctg aagtgcctga ttggcttaga gccggagctg cgccgtcgg agtcggcagc   540
cagttgggca gctgttcaaa agaggatttg caggctgttt tccaagtgta a            591
```

<210> SEQ ID NO 96
<211> LENGTH: 196
<212> TYPE: PRT
<213> ORGANISM: Bacillus subtilis

<400> SEQUENCE: 96

```
Met Glu Ser Lys Val Val Glu Asn Arg Leu Lys Glu Ala Lys Leu Ile
1               5                   10                  15

Ala Val Ile Arg Ser Lys Asp Lys Gln Glu Ala Cys Gln Gln Ile Glu
            20                  25                  30

Ser Leu Leu Asp Lys Gly Ile Arg Ala Val Glu Val Thr Tyr Thr Thr
        35                  40                  45

Pro Gly Ala Ser Asp Ile Ile Glu Ser Phe Arg Asn Arg Glu Asp Ile
    50                  55                  60

Leu Ile Gly Ala Gly Thr Val Ile Ser Ala Gln Gln Ala Gly Glu Ala
65                  70                  75                  80

Ala Lys Ala Gly Ala Gln Phe Ile Val Ser Pro Gly Phe Ser Ala Asp
                85                  90                  95

Leu Ala Glu His Leu Ser Phe Val Lys Thr His Tyr Ile Pro Gly Val
                100                 105                 110

Leu Thr Pro Ser Glu Ile Met Glu Ala Leu Thr Phe Gly Phe Thr Thr
            115                 120                 125

Leu Lys Leu Phe Pro Ser Gly Val Phe Gly Ile Pro Phe Met Lys Asn
```

```
                130                 135                 140
Leu Ala Gly Pro Phe Pro Gln Val Thr Phe Ile Pro Thr Gly Gly Ile
145                 150                 155                 160

His Pro Ser Glu Val Pro Asp Trp Leu Arg Ala Gly Ala Gly Ala Val
                165                 170                 175

Gly Val Gly Ser Gln Leu Gly Ser Cys Ser Lys Glu Asp Leu Gln Ala
                180                 185                 190

Val Phe Gln Val
        195

<210> SEQ ID NO 97
<211> LENGTH: 714
<212> TYPE: DNA
<213> ORGANISM: Yersinia pestis

<400> SEQUENCE: 97
atgagcctgg ttaatatgaa aggggtcgtg gtcacaaaca ttgaacgagc tgaactagcc      60
ctgttacaac gtttcgctga atatggcgtg gcaacagtgc atgaagctca actgcggcag     120
ggactattgg atgagcgaat taaacctatt cagcaagggc gctgtattgc tggcaatgcg     180
gtgacggtat tggttacacc cggagataac tggatgttcc atgttgccgt agagcagtgt     240
cagcctggcg atgtgttgct cgttgcgccg acctccgaat gccatgatgg cttttttggt     300
gacctgctcg cgacctcact gctggcgcgc ggcgtggtgg cattggttgg agatatcggg     360
atccgagata gccagacgct cgcgaaatg aatttccctg tgtggtcgcg tgcggtttgg     420
gcacaaggta cggtgaaagc ctcgcttggc tcggtcaatg tgccggtgat ctgcgcgggt     480
cagttggtca accccggcga tattgtggtg gcagacgatg atggcgtagt cattgtgcca     540
agagaacaag ccaccgcgat tgctgatgcg gcacagacac gggtagatct tgaaacgagc     600
aaacgtcagc gtctggctaa tggcgagctc gggctggata tctatcaaat gcgtgcccct     660
ctggcgaaaa aagggctgcg ttacgtcaat agtctcaacg cgttaaagtc ataa            714

<210> SEQ ID NO 98
<211> LENGTH: 237
<212> TYPE: PRT
<213> ORGANISM: Yersinia pestis

<400> SEQUENCE: 98

Met Ser Leu Val Asn Met Lys Gly Val Val Thr Asn Ile Glu Arg
 1               5                  10                  15

Ala Glu Leu Ala Leu Leu Gln Arg Phe Ala Glu Tyr Gly Val Ala Thr
                20                  25                  30

Val His Glu Ala Gln Leu Arg Gln Gly Leu Leu Asp Glu Arg Ile Lys
            35                  40                  45

Pro Ile Gln Gln Gly Arg Cys Ile Ala Gly Asn Ala Val Thr Val Leu
        50                  55                  60

Val Thr Pro Gly Asp Asn Trp Met Phe His Val Ala Val Glu Gln Cys
65                  70                  75                  80

Gln Pro Gly Asp Val Leu Leu Val Ala Pro Thr Ser Glu Cys His Asp
                85                  90                  95

Gly Phe Phe Gly Asp Leu Leu Ala Thr Ser Leu Leu Ala Arg Gly Val
                100                 105                 110

Val Ala Leu Val Gly Asp Ile Gly Ile Arg Asp Ser Gln Thr Leu Arg
            115                 120                 125

Glu Met Asn Phe Pro Val Trp Ser Arg Ala Val Trp Ala Gln Gly Thr
        130                 135                 140
```

```
Val Lys Ala Ser Leu Gly Ser Val Asn Val Pro Val Ile Cys Ala Gly
145                 150                 155                 160

Gln Leu Val Asn Pro Gly Asp Ile Val Val Ala Asp Asp Gly Val
            165                 170                 175

Val Ile Val Pro Arg Glu Gln Ala Thr Ala Ile Ala Asp Ala Ala Gln
            180                 185                 190

Thr Arg Val Asp Leu Glu Thr Ser Lys Arg Gln Arg Leu Ala Asn Gly
        195                 200                 205

Glu Leu Gly Leu Asp Ile Tyr Gln Met Arg Ala Pro Leu Ala Lys Lys
    210                 215                 220

Gly Leu Arg Tyr Val Asn Ser Leu Asn Ala Leu Lys Ser
225                 230                 235
```

<210> SEQ ID NO 99
<211> LENGTH: 642
<212> TYPE: DNA
<213> ORGANISM: E. coli

<400> SEQUENCE: 99

```
atgaaaaact ggaaaacaag tgcagaatca atcctgacca ccggcccggt tgtaccggtt    60
atcgtggtaa aaaaactgga acacgcggtg ccgatggcaa aagcgttggt tgctggtggg   120
gtgcgcgttc tggaagtgac tctgcgtacc gagtgtgcag ttgacgctat ccgtgctatc   180
gccaaagaag tgcctgaagc gattgtgggt gccggtacgg tgctgaatcc acagcagctg   240
gcagaagtca ctgaagcggg tgcacagttc gcaattagcc cgggtctgac cgagccgctg   300
ctgaaagctg ctaccgaagg gactattcct ctgattccgg ggatcagcac tgtttccgaa   360
ctgatgctgg gtatggacta cggttttgaaa gagttcaaat tcttcccggc tgaagctaac   420
ggcggcgtga aagccctgca ggcgatcgcg ggtccgttct cccaggtccg tttctgcccg   480
acgggtggta tttctccggc taactaccgt gactacctgg cgctgaaaag cgtgctgtgc   540
atcggtggtt cctggctggt tccggcagat gcgctggaag cgggcgatta cgaccgcatt   600
actaagctgg cgcgtgaagc tgtagaaggc gctaagctgt aa                      642
```

<210> SEQ ID NO 100
<211> LENGTH: 213
<212> TYPE: PRT
<213> ORGANISM: E. coli

<400> SEQUENCE: 100

```
Met Lys Asn Trp Lys Thr Ser Ala Glu Ser Ile Leu Thr Thr Gly Pro
  1               5                  10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125
```

Leu Lys Glu Phe Lys Phe Pro Ala Glu Ala Asn Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Asp Ala Leu
                180                 185                 190

Glu Ala Gly Asp Tyr Asp Arg Ile Thr Lys Leu Ala Arg Glu Ala Val
            195                 200                 205

Glu Gly Ala Lys Leu
        210

<210> SEQ ID NO 101
<211> LENGTH: 675
<212> TYPE: DNA
<213> ORGANISM: Sphingomonas sp.

<400> SEQUENCE: 101
atgtccggca tcgttgtcca gaatatcgaa cgggcgagcc tttccgttgt cgacggcctt    60
gcgaaatgcg gcgtcgccac cgtacatgag gcgcagggcc gcacgggcct gctggccccc   120
accatgcgcc cgatctacac cggcgcgagg atcgcgggca gcgcggtcac gatttcggcg   180
cctccgggtg acaactggat ggtccatgtg gcgatcgagc aactgaagga aggcgatgtc   240
ctcctgctcg cgccgaccag tccctgcacc gatggctatt tcggcgatct ctggcgacc   300
tcggcgcagg cacgcggctg ccgtggcctg atcatcgatg ccggtgtacg cgacgtgcgg   360
gatttgaagc agatgaactt ccccgtctgg tcgaaggcca tccacgcgca gggcacgatc   420
aaggcgacgc tgggcagcgt caatatcccg gtcgtctgcg ccaatgcgct ggtcaatccc   480
ggcgacgtgg tgatcgcgga cgatgacggc gtgtgcgtcg taccgcgcgc gaatgctgcc   540
gcggtgctgg agaaggcgca ggcccgggag gctgcggagg aagccaagcg cgtgcgtctg   600
gcttcagggg aactgggcct cgacatctac aatatgcgcc gcgccttga ggaaatggga    660
ctgaaatatg tctga                                                    675

<210> SEQ ID NO 102
<211> LENGTH: 224
<212> TYPE: PRT
<213> ORGANISM: Sphingomonas sp.

<400> SEQUENCE: 102

Met Ser Gly Ile Val Val Gln Asn Ile Glu Arg Ala Ser Leu Ser Val
1               5                   10                  15

Val Asp Gly Leu Ala Lys Cys Gly Val Ala Thr Val His Glu Ala Gln
            20                  25                  30

Gly Arg Thr Gly Leu Leu Ala Pro Thr Met Arg Pro Ile Tyr Thr Gly
        35                  40                  45

Ala Arg Ile Ala Gly Ser Ala Val Thr Ile Ser Ala Pro Pro Gly Asp
    50                  55                  60

Asn Trp Met Val His Val Ala Ile Glu Gln Leu Lys Glu Gly Asp Val
65                  70                  75                  80

Leu Leu Leu Ala Pro Thr Ser Pro Cys Thr Asp Gly Tyr Phe Gly Asp
                85                  90                  95

Leu Leu Ala Thr Ser Ala Gln Ala Arg Gly Cys Arg Gly Leu Ile Ile
                100                 105                 110

```
Asp Ala Gly Val Arg Asp Val Arg Asp Leu Lys Gln Met Asn Phe Pro
        115                 120                 125

Val Trp Ser Lys Ala Ile His Ala Gln Gly Thr Ile Lys Ala Thr Leu
    130                 135                 140

Gly Ser Val Asn Ile Pro Val Val Cys Ala Asn Ala Leu Val Asn Pro
145                 150                 155                 160

Gly Asp Val Val Ile Ala Asp Asp Gly Val Cys Val Val Pro Arg
                165                 170                 175

Ala Asn Ala Ala Ala Val Leu Glu Lys Ala Gln Ala Arg Glu Ala Ala
                180                 185                 190

Glu Glu Ala Lys Arg Val Arg Leu Ala Ser Gly Glu Leu Gly Leu Asp
        195                 200                 205

Ile Tyr Asn Met Arg Pro Arg Leu Glu Glu Met Gly Leu Lys Tyr Val
    210                 215                 220

<210> SEQ ID NO 103
<211> LENGTH: 639
<212> TYPE: DNA
<213> ORGANISM: S. meliloti

<400> SEQUENCE: 103
atgagcgcga aaacggacaa gcttctctcc atcctcaagc tgcagccggt ggttccggtc    60
ttggtgatcg atgatgcggg gtcggcggta ccgctcgcgc gggcgctggt cgccggaggc   120
ctcaaggcga tcgagatcac cttgcgcacg ccggccgcgc tggaggcgat ccgtgccgtc   180
gcgaatgagg ttgagggcgc cgttgccggt gccggcacca tcctcaatgc tgcccagttc   240
gaagaggccg tcgcggccgg gtcgcagttc atcgtcagcc ccggcacgac gcaggaactg   300
atcgacgtcg ccaacgatca cgaggtgccg ctgctaccgg gtgcggcgac ggcgagcgag   360
gtcatggggc tgcgcgaaga gggctacgat gtgatgaagt tcttcccggc cgagcaggcc   420
ggaggcgctg cctatctgaa atcgctgtcg tcgccgctcg caggcaccat gttctgcccg   480
accggcggaa tctcgcttgc caatgcgcgc gactacctga cgcttccgaa cgtcgtttgc   540 gtcggcgggct cctgggttgc gccgaaggac ctggtcgtca ggggcgactg ggccggcatc   600
accaagcttg cggccgaggc cttcgcgctc aagggctga                         639

<210> SEQ ID NO 104
<211> LENGTH: 212
<212> TYPE: PRT
<213> ORGANISM: S. meliloti

<400> SEQUENCE: 104

Met Ser Ala Lys Thr Asp Lys Leu Leu Ser Ile Leu Lys Leu Gln Pro
1               5                   10                  15

Val Val Pro Val Leu Val Ile Asp Asp Ala Gly Ser Ala Val Pro Leu
            20                  25                  30

Ala Arg Ala Leu Val Ala Gly Gly Leu Lys Ala Ile Glu Ile Thr Leu
        35                  40                  45

Arg Thr Pro Ala Ala Leu Glu Ala Ile Arg Ala Val Ala Asn Glu Val
    50                  55                  60

Glu Gly Ala Val Ala Gly Ala Gly Thr Ile Leu Asn Ala Ala Gln Phe
65                  70                  75                  80

Glu Glu Ala Val Ala Ala Gly Ser Gln Phe Ile Val Ser Pro Gly Thr
                85                  90                  95

Thr Gln Glu Leu Ile Asp Val Ala Asn Asp His Glu Val Pro Leu Leu
            100                 105                 110
```

```
Pro Gly Ala Ala Thr Ala Ser Glu Val Met Gly Leu Arg Glu Glu Gly
        115                 120                 125

Tyr Asp Val Met Lys Phe Phe Pro Ala Glu Gln Ala Gly Gly Ala Ala
        130                 135                 140

Tyr Leu Lys Ser Leu Ser Ser Pro Leu Ala Gly Thr Met Phe Cys Pro
145                 150                 155                 160

Thr Gly Gly Ile Ser Leu Ala Asn Ala Arg Asp Tyr Leu Thr Leu Pro
                165                 170                 175

Asn Val Val Cys Val Gly Gly Ser Trp Val Ala Pro Lys Asp Leu Val
                180                 185                 190

Val Arg Gly Asp Trp Ala Gly Ile Thr Lys Leu Ala Ala Glu Ala Phe
            195                 200                 205

Ala Leu Lys Gly
        210

<210> SEQ ID NO 105
<211> LENGTH: 849
<212> TYPE: DNA
<213> ORGANISM: B. subtilis subsp. subtilis

<400> SEQUENCE: 105
atgaaggttt tagtcaatgg ccggctgatt gggcgcagtg aagcatcaat cgatttggaa      60
gatcgcggtt atcagtttgg tgacggcatc tatgaagtga tcagggtgta caaggagta     120
ttgttcggct acgtgagca tgcagagcgt ttttcagaa gtgctgctga atcggaatt      180
tcactgccat tcagtataga agatctcgag tgggacctgc aaaagcttgt acaggaaaat    240
gcggtcagtg agggagcggt atacattcag acaacaagag gtgtggcccc gcgaaaacac    300
cagtatgaag ccggcctcga gccgcagact actgcctata cgtttacggt gaaaaaaccg    360
gagcaagagc aggcatacgg agtggcggcc attacagatg aggatcttcg ctggttaaga    420
tgtgatatca aaagtctgaa tttactgtat aatgtcatga cgaagcaaag ggcctatgaa    480
gccggagcat ttgaagccat tttacttagg gacggcgttg ttacggaggg tacatcctct    540
aacgtttatg ccgttatcaa cggcacagtg cgaacacatc cggctaatcg gctcattctc    600
aatggaatta cacggatgaa tattttagga ctgattgaga gaatgggat caaactggat     660
gagactcctg tcagtgaaga agagttgaaa caggcggaag agatctttat ttcgtcaacg    720
acggcagaaa ttattccggt cgtgacgctc gatggacaat cgatcggaag cgggaaaccc    780
ggaccggtga ccaaacagct tcaggctgct tttcaagaaa gcattcaaca ggctgctagc    840
atttcataa                                                           849

<210> SEQ ID NO 106
<211> LENGTH: 282
<212> TYPE: PRT
<213> ORGANISM: B. subtilis subsp. subtilis

<400> SEQUENCE: 106

Met Lys Val Leu Val Asn Gly Arg Leu Ile Gly Arg Ser Glu Ala Ser
1               5                   10                  15

Ile Asp Leu Glu Asp Arg Gly Tyr Gln Phe Gly Asp Gly Ile Tyr Glu
            20                  25                  30

Val Ile Arg Val Tyr Lys Gly Val Leu Phe Gly Leu Arg Glu His Ala
        35                  40                  45

Glu Arg Phe Phe Arg Ser Ala Ala Glu Ile Gly Ile Ser Leu Pro Phe
    50                  55                  60

Ser Ile Glu Asp Leu Glu Trp Asp Leu Gln Lys Leu Val Gln Glu Asn
```

```
              65                  70                  75                  80
Ala Val Ser Glu Gly Ala Val Tyr Ile Gln Thr Thr Arg Gly Val Ala
                 85                  90                  95

Pro Arg Lys His Gln Tyr Glu Ala Gly Leu Glu Pro Gln Thr Thr Ala
                100                 105                 110

Tyr Thr Phe Thr Val Lys Lys Pro Glu Gln Glu Gln Ala Tyr Gly Val
                115                 120                 125

Ala Ala Ile Thr Asp Glu Asp Leu Arg Trp Leu Arg Cys Asp Ile Lys
            130                 135                 140

Ser Leu Asn Leu Leu Tyr Asn Val Met Thr Lys Gln Arg Ala Tyr Glu
145                 150                 155                 160

Ala Gly Ala Phe Glu Ala Ile Leu Leu Arg Asp Gly Val Val Thr Glu
                165                 170                 175

Gly Thr Ser Ser Asn Val Tyr Ala Val Ile Asn Gly Thr Val Arg Thr
                180                 185                 190

His Pro Ala Asn Arg Leu Ile Leu Asn Gly Ile Thr Arg Met Asn Ile
            195                 200                 205

Leu Gly Leu Ile Glu Lys Asn Gly Ile Lys Leu Asp Glu Thr Pro Val
210                 215                 220

Ser Glu Glu Leu Lys Gln Ala Glu Ile Phe Ile Ser Ser Thr
225                 230                 235                 240

Thr Ala Glu Ile Ile Pro Val Val Thr Leu Asp Gly Gln Ser Ile Gly
                245                 250                 255

Ser Gly Lys Pro Gly Pro Val Thr Lys Gln Leu Gln Ala Ala Phe Gln
                260                 265                 270

Glu Ser Ile Gln Gln Ala Ala Ser Ile Ser
            275                 280

<210> SEQ ID NO 107
<211> LENGTH: 1413
<212> TYPE: DNA
<213> ORGANISM: R. sphaeroides

<400> SEQUENCE: 107
atgcgcgagc tccttgccct cgagatcgac ccgggccacg gcggcccgct gttcctcacc      60
atcgccgagg cgatcaccct cgacatcacc cgcgggcggc tgaggcccgg agcgagactg     120
cccggcacgc gcgcgctggc acgcgcgctc ggggtgcacc gcaacacggt ggatgccgcc     180
tatcaggagt tgctgaccca gggctggctg caggcggaac ccgcgcgggg caccttcgtg     240
gcgcaggatc tgccgcaggg gatgctggtg cgcaggcccg cgcccgcgcc ggtcgagccg     300
gtcgcgatgc gcgcggggct cgccttctcc gacggcgcgc cggaccccga gctggtgccc     360
gacaaggcgc tggcgcgggc ctttcgccgg gcgctcctgt cgcccgcctt ccgcgccgga     420
gcggattacg gcgatgcccg cggcaccctc tcgctgcggg aggcgctggc agcctatctc     480
gcctcggacc gcggcgtggt cgcggatcct gcgcggctgc tgatcgcgcg gggcagccag     540
atggcgctct cctggccgc ccgggcggcg ctggcgccgg cgaggcgat cgcggtcgag     600 gagccgggct atccgctggc ctgggaggcg ttccgcgcag cgggagcgga ggtgcggggc     660
gtgccggtgg atggcggcgg actcaggatc gacgcgctcg aggccgcgct gtcccgggat     720
ccgtgcctcc gggcggtcta tgtcacgccg caccaccagt atccgacgac cgtcaccatg     780
ggcgccgcac ggcggttgca gcttctggaa ctggcagagc ccacgggct cgcgctgatc     840 gaggacgatt acgaccacga ataccgtttc gagggccgcc cggtgctgcc gctggccgcc     900
cgcgcgcccg aaggcctgcc gctgatctat gtgggctcgc tgtcgaagct gctctcgccc     960
```

```
ggtatccggc tgggctatgc gctggcgccc gagcggctgc tgacccgcat ggccgcggcg    1020
cgcgccgcca tcgaccggca gggcgacgcg ccgctcgagg cggcgctggc cgagctgatc    1080
cgcgacggcg atctggggccg ccatgcccgc aaggcgcgca gggtctaccg cgcgcggcgg    1140
```

```
ggtatccggc tgggctatgc gctggcgccc gagcggctgc tgacccgcat ggccgcggcg    1020
cgcgccgcca tcgaccggca gggcgacgcg ccgctcgagg cggcgctggc cgagctgatc    1080
cgcgacggcg atctgggccg ccatgcccgc aaggcgcgca gggtctaccg cgcgcggcgg    1140
gatctgctgg cggagcgtct cacggcgcag ctggccgggc gcgccgcctt cgatctgccg    1200
gccgggggcc tcgcgctgtg gctgcgctgc acgggcgtct cggccgagac ctgggccgaa    1260
gccgcagggc aggcggggct cgccctgctg ccgggcacgc gcttcgcgct ggagagcccg    1320
gcgccgcagg ccttccggct gggctatgcg gcgctggacg aggggcagat cgcccgggcg    1380
gtggagatcc tcgcccggag cttccccggc tga                                 1413
```

<210> SEQ ID NO 108
<211> LENGTH: 470
<212> TYPE: PRT
<213> ORGANISM: R. sphaeroides

<400> SEQUENCE: 108

```
Met Arg Glu Pro Leu Ala Leu Glu Ile Asp Pro Gly His Gly Gly Pro
  1               5                  10                  15

Leu Phe Leu Thr Ile Ala Glu Ala Ile Thr Leu Asp Ile Thr Arg Gly
             20                  25                  30

Arg Leu Arg Pro Gly Ala Arg Leu Pro Gly Thr Arg Ala Leu Ala Arg
         35                  40                  45

Ala Leu Gly Val His Arg Asn Thr Val Asp Ala Ala Tyr Gln Glu Leu
     50                  55                  60

Leu Thr Gln Gly Trp Leu Gln Ala Glu Pro Ala Arg Gly Thr Phe Val
 65                  70                  75                  80

Ala Gln Asp Leu Pro Gln Gly Met Leu Val Arg Arg Pro Ala Pro Ala
                 85                  90                  95

Pro Val Glu Pro Val Ala Met Arg Ala Gly Leu Ala Phe Ser Asp Gly
            100                 105                 110

Ala Pro Asp Pro Glu Leu Val Pro Asp Lys Ala Leu Ala Arg Ala Phe
        115                 120                 125

Arg Arg Ala Leu Leu Ser Pro Ala Phe Arg Ala Gly Ala Asp Tyr Gly
    130                 135                 140

Asp Ala Arg Gly Thr Ser Ser Leu Arg Glu Ala Leu Ala Ala Tyr Leu
145                 150                 155                 160

Ala Ser Asp Arg Gly Val Val Ala Asp Pro Ala Arg Leu Leu Ile Ala
                165                 170                 175

Arg Gly Ser Gln Met Ala Leu Phe Leu Ala Ala Arg Ala Ala Leu Ala
            180                 185                 190

Pro Gly Glu Ala Ile Ala Val Glu Pro Gly Tyr Pro Leu Ala Trp
        195                 200                 205

Glu Ala Phe Arg Ala Ala Gly Ala Glu Val Arg Gly Val Pro Val Asp
    210                 215                 220

Gly Gly Gly Leu Arg Ile Asp Ala Leu Glu Ala Leu Ser Arg Asp
225                 230                 235                 240

Pro Cys Leu Arg Ala Val Tyr Val Thr Pro His His Gln Tyr Pro Thr
                245                 250                 255

Thr Val Thr Met Gly Ala Ala Arg Arg Leu Gln Leu Leu Glu Leu Ala
            260                 265                 270

Glu Arg His Gly Leu Ala Leu Ile Glu Asp Asp Tyr Asp His Glu Tyr
        275                 280                 285

Arg Phe Glu Gly Arg Pro Val Leu Pro Leu Ala Ala Arg Ala Pro Glu
```

```
                    290                 295                 300
Gly Leu Pro Leu Ile Tyr Val Gly Ser Leu Ser Lys Leu Leu Ser Pro
305                 310                 315                 320

Gly Ile Arg Leu Gly Tyr Ala Leu Ala Pro Glu Arg Leu Leu Thr Arg
            325                 330                 335

Met Ala Ala Arg Ala Ala Ile Asp Arg Gln Gly Asp Ala Pro Leu
            340                 345                 350

Glu Ala Ala Leu Ala Glu Leu Ile Arg Asp Gly Asp Leu Gly Arg His
            355                 360                 365

Ala Arg Lys Ala Arg Arg Val Tyr Arg Ala Arg Asp Leu Leu Ala
            370                 375                 380

Glu Arg Leu Thr Ala Gln Leu Ala Gly Arg Ala Ala Phe Asp Leu Pro
385                 390                 395                 400

Ala Gly Gly Leu Ala Leu Trp Leu Arg Cys Thr Gly Val Ser Ala Glu
                405                 410                 415

Thr Trp Ala Glu Ala Ala Gly Gln Ala Gly Leu Ala Leu Leu Pro Gly
                420                 425                 430

Thr Arg Phe Ala Leu Glu Ser Pro Ala Pro Gln Ala Phe Arg Leu Gly
                435                 440                 445

Tyr Ala Ala Leu Asp Glu Gly Gln Ile Ala Arg Ala Val Glu Ile Leu
                450                 455                 460

Ala Arg Ser Phe Pro Gly
465                 470

<210> SEQ ID NO 109
<211> LENGTH: 1191
<212> TYPE: DNA
<213> ORGANISM: E.coli

<400> SEQUENCE: 109
atgtttgaga acattaccgc cgctcctgcc gacccgattc tgggcctggc cgatctgttt     60
cgtgccgatg aacgtcccgg caaaattaac ctcgggattg gtgtctataa agatgagacg    120
ggcaaaaccc cggtactgac cagcgtgaaa aaggctgaac agtatctgct cgaaaatgaa    180
accaccaaaa attacctcgg cattgacggc atccctgaat ttggtcgctg cactcaggaa    240
ctgctgtttg gtaaaggtag cgccctgatc aatgacaaac gtgctcgcac ggcacagact    300
ccggggggca ctggcgcact acgcgtggct gccgatttcc tggcaaaaaa taccagcgtt    360
aagcgtgtgt gggtgagcaa cccaagctgg ccgaaccata agagcgtctt taactctgca    420
ggtctggaag ttcgtgaata cgcttattat gatgcggaaa tcacactctc tgacttcgat    480
gcactgatta acagcctgaa tgaagctcag gctggcgacg tagtgctgtt ccatggctgc    540
tgccataacc caaccggtat cgaccctacg ctggaacaat ggcaaacact ggcacaactc    600
tccgttgaga aaggctggtt accgctgttt gacttcgctt accagggttt tgcccgtggt    660
ctggaagaag atgctgaagg actgcgcgct ttcgcggcta tgcataaaga gctgattgtt    720
gccagttcct actctaaaaa ctttggcctg tacaacgagc gtgttggcgc ttgtactctg    780
gttgctgccg acagtgaaac cgttgatcgc gcattcagcc aaatgaaagc ggcgattcgc    840
gctaactact ctaacccacc agcacacggc gcttctgttg ttgccaccat cctgagcaac    900
gatgcgttac gtgcgatttg gaacaagagc tgactgata tgcgccagcg tattcagcgt    960
atgcgtcagt tgttcgtcaa tacgctgcag gaaaaaggcg caaccgcga cttcagcttt   1020 atcatcaaac agaacggcat gttctccttc agtggcctga caaagaaca gtgctgcgt   1080 ctgcgcgaag agtttggcgt atatgcggtt gcttctggtc gcgtaaatgt ggccgggatg   1140
```
acaccagata acatggctcc gctgtgcgaa gcgattgtgg cagtgctgta a      1191

<210> SEQ ID NO 110
<211> LENGTH: 396
<212> TYPE: PRT
<213> ORGANISM: E.coli

<400> SEQUENCE: 110

```
Met Phe Glu Asn Ile Thr Ala Ala Pro Ala Asp Pro Ile Leu Gly Leu
 1               5                  10                  15

Ala Asp Leu Phe Arg Ala Asp Glu Arg Pro Gly Lys Ile Asn Leu Gly
             20                  25                  30

Ile Gly Val Tyr Lys Asp Glu Thr Gly Lys Thr Pro Val Leu Thr Ser
         35                  40                  45

Val Lys Lys Ala Glu Gln Tyr Leu Leu Glu Asn Glu Thr Thr Lys Asn
     50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                 85                  90                  95

Thr Ala Gln Thr Pro Gly Gly Thr Gly Ala Leu Arg Val Ala Ala Asp
            100                 105                 110

Phe Leu Ala Lys Asn Thr Ser Val Lys Arg Val Trp Val Ser Asn Pro
        115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
    210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270

Ser Gln Met Lys Ala Ala Ile Arg Ala Asn Tyr Ser Asn Pro Pro Ala
        275                 280                 285

His Gly Ala Ser Val Val Ala Thr Ile Leu Ser Asn Asp Ala Leu Arg
    290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365
```

```
Ala Val Ala Ser Gly Arg Val Asn Val Ala Gly Met Thr Pro Asp Asn
        370             375             380

Met Ala Pro Leu Cys Glu Ala Ile Val Ala Val Leu
385                 390             395
```